(12) United States Patent
Miyazaki et al.

(10) Patent No.: US 11,046,710 B2
(45) Date of Patent: Jun. 29, 2021

(54) SULFONAMIDE COMPOUNDS

(71) Applicants: DAIICHI SANKYO COMPANY, LIMITED, Tokyo (JP); SANFORD BURNHAM PREBYS MEDICAL DISCOVERY INSTITUTE, La Jolla, CA (US)

(72) Inventors: Shojiro Miyazaki, Tokyo (JP); Masaharu Inui, Tokyo (JP); Yasunobu Kurosaki, Tokyo (JP); Yuko Yamamoto, Tokyo (JP); Masanori Izumi, Tokyo (JP); Kaori Soma, Tokyo (JP); Anthony Pinkerton, La Jolla, CA (US); Masamichi Kishida, Tokyo (JP)

(73) Assignees: Daiichi Sankyo Company, Limited, Toyko (JP); Sanford Burnham Prebys Medical Discovery Institute, LaJolla, CA (US)

( * ) Notice: Subject to any disclaimer, the term of this patent is extended or adjusted under 35 U.S.C. 154(b) by 0 days.

(21) Appl. No.: 16/472,109

(22) PCT Filed: Dec. 22, 2017

(86) PCT No.: PCT/US2017/068314
§ 371 (c)(1),
(2) Date: Jun. 20, 2019

(87) PCT Pub. No.: WO2018/119444
PCT Pub. Date: Jun. 28, 2018

(65) Prior Publication Data
US 2020/0087321 A1 Mar. 19, 2020

Related U.S. Application Data

(60) Provisional application No. 62/438,722, filed on Dec. 23, 2016.

(51) Int. Cl.
| | | |
|---|---|---|
| *C07D 498/14* | (2006.01) | |
| *A61K 31/553* | (2006.01) | |
| *A61P 17/00* | (2006.01) | |
| *A61P 19/00* | (2006.01) | |

(52) U.S. Cl.
CPC .................. *C07D 498/14* (2013.01)

(58) Field of Classification Search
CPC ..... C07D 498/14; A61K 31/553; A61P 17/00; A61P 19/00
See application file for complete search history.

(56) References Cited

FOREIGN PATENT DOCUMENTS

| | | |
|---|---|---|
| CN | 1207098 A | 2/1999 |
| CN | 104334527 A | 2/2015 |
| CN | 106132954 A | 11/2016 |
| WO | 97/17344 A | 5/1997 |
| WO | 2009/017863 A2 | 2/2009 |
| WO | 2012068096 A2 | 5/2012 |
| WO | 2012109165 A1 | 8/2012 |
| WO | 2013/126608 A1 | 8/2013 |
| WO | 2017/007943 A1 | 1/2017 |

OTHER PUBLICATIONS

International Preliminary Report on Patentability dated Jun. 25, 2019, issued in corresponding International Application No. PCT/US2017/068314, filed Dec. 22, 2017, 7 pages.
Dahl, R., et al., "Discovery and Validation of a Series of Aryl Sulfonamides as Selective Inhibitors of Tissue-Nonspecific Alkaline Phosphatase (TNAP)," Journal of Medicinal Chemistry 52:6919-6925, 2009.
Jono, S., et al., "Vascular Calcification in Chronic Kidney Disease," Journal of Bone and Mineral Metabolism 24:176-181, 2006.
Kiu Weber, C.I., et al., "Cardiovascular Risk Markers Associated With Arterial Calcification in Patients With Chronic Kidney Disease Stages 3 and 4," Clinical Kidney Journal 7:176-173, 2014.
Lomashvili, K.A., et al., "Phosphate-Induced Vascular Calcification: Role of Pyrophosphate and Osteopontin," Journal of the American Society of Nephrology 15:1392-1401, 2004.
Lanzer, P., et al., "Medial Vascular Calcification Revisited: Review and Perspectives," European Heart Journal 35:1515-1525, 2014.
Miao, D., and A. Scutt, "Histochemical Localization of Alkaline Phosphatase Activity in Decalcified Bone and Cartilage," Journal of Histochemistry & Cytochemistry 50(3):333-340, 2002.
Narisawa, S., et al., "In Vivo Overexpression of Tissue-Nonspecific Alkaline Phosphatase Increases Skeletal Mineralization and Affects the Phosphorylation Status of Osteopontin," Journal of Bone and Mineral Research 28(7):1587-1598, Jul. 2013. (Author Manuscript provided, PMCID: PMC3688694, available in PMC Jul. 1, 2014, 21 pages).
Niarisawa, S., et al., "Novel Inhibitors of Alkaline Phosphatase Suppress Vascular Smooth Muscle Cell Calcification," Journal of Bone and Mineral Research 22(11):1700-1710, 2007.

(Continued)

*Primary Examiner* — Bruck Kifle
(74) *Attorney, Agent, or Firm* — Christensen O'Connor Johnson Kindness PLLC

(57) ABSTRACT

The present invention relates to a compound or a pharmacologically acceptable salt thereof having excellent tissue non-specific alkaline phosphatase inhibitory activity. The present invention provides a compound represented by the formula (I) or a pharmacologically acceptable salt thereof.

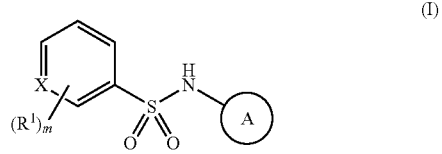

(I)

25 Claims, No Drawings

(56) References Cited

OTHER PUBLICATIONS

Ossareh, S., "Clinical and Economic Aspects of Sevelamer Therapy in End-Stage Renal Disease Patients," International Journal of Nephrology and Renovascular Disease 7:161-168, 2014.

Sheen, C.R., et al., "Pathophysiological Role of Vascular Smooth Muscle Alkaline Phosphatase in Medial Artery Calcification," Journal of Bone and Mineral Research 30(5):824-836, May 2015. (Author Manuscript provided, PMCID: PMC4406354, available in PMC May 1, 2015, 26 pages.).

Sidique, S., et al., "Design and Synthesis of Pyrazole Derivatives as Potent and Selective Inhibitors of Tissue-Nonspecific Alkaline Phosphatase (TNAP)," Bioorganic & Medicinal Chemistry Letters 19:222-225, 2009.

International Search Report dated Mar. 20, 2018, issued in corresponding International Application No. PCT/US2017/068314, filed Dec. 22, 2017, 3 pages Witten Opinion dated Mar. 20, 2018, issued in corresponding International Application No. PCT/US2017/068314, filed Dec. 22, 2017, 3 pages.

Indian Office Action dated Mar. 9, 2020, issued in corresponding Indian Application No. 201917023211, filed Jun. 12, 2019, 7 pages.

"Pyridine Compounds," Specification of Indian Application No. 201727026465 (International Application No. WO2017/007943), Daiichi Sankyo Company, Limited, and Sanford Burnham Prebys Medical Discovery Institute, 241 pages.

Debray, J., et al., "Inhibitors of tissue-nonspecific alkaline phosphatase: Design, Synthesis, Kinetics, Biomineralization and Cellular Tests," Elsevier: Bioorganic & Medicinal Chemistry 21: 7981-7987, 2013.

Office Action dated Apr. 30, 2021 from CN Applicaiton No. 201780078954.6, filed Dec. 22, 2017, 8 pages (see Search Report at p. 7 of Office Action).

SULFONAMIDE COMPOUNDS

CROSS-REFERENCE TO RELATED APPLICATION

This application claims the benefit of U.S. Application No. 62/438,722, filed Dec. 23, 2016, expressly incorporated herein by reference in its entirety.

FIELD OF THE INVENTION

The present invention relates to a novel sulfonamide compound or a pharmacologically acceptable salt thereof which has excellent tissue non-specific alkaline phosphatase (hereinafter, referred to as TNAP) inhibitory activity.

The present invention also relates to a therapeutic agent and/or prophylactic agent (preferably a therapeutic agent) for pseudoxanthoma elasticum (PXE), generalized arterial calcification of infancy (GACI), craniometaphyseal dysplasia (CMD), ossification of the yellow ligament (OYL), ossification of ligamentum flavum, arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL) ossification of the anterior longitudinal ligament (OALL), diffuse idiopathic skeletal hyperostosis (DISH), meniscal calcification, or peritoneal calcification, comprising the compound or the pharmacologically acceptable salt thereof as an active ingredient.

The present invention further relates to a composition for the treatment or prophylaxis of the aforementioned diseases, comprising the compound or the pharmacologically acceptable salt thereof as an active ingredient, use of the compound or the pharmacologically acceptable salt thereof for manufacturing a pharmaceutical for the treatment or prophylaxis of the disease, and a method for the treatment or prophylaxis of the disease, comprising administering a pharmacologically effective amount of the compound or the pharmacologically acceptable salt thereof to a mammal (preferably a human).

DESCRIPTION OF THE RELATED ART

In vivo calcification is strictly regulated by the balance of activation between osteoblasts and osteoclasts, phosphorus and calcium concentrations in plasma, and parathyroid hormone or vitamin D secreted in order to maintain the homeostasis of these concentrations (Non Patent Literature 1). Ectopic calcification is found in diseases, for example, pseudoxanthoma elasticum (PXE), generalized arterial calcification of infancy (GACI), craniometaphyseal dysplasia (CMD), ossification of the yellow ligament (OYL), ossification of ligamentum flavum, arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL) ossification of the anterior longitudinal ligament (OALL), diffuse idiopathic skeletal hyperostosis (DISH), meniscal calcification, and peritoneal calcification. In these pathological conditions, calcification in tissues (blood vessels, soft tissues, etc.) that are usually not calcified is caused by the failure of the regulatory mechanism mentioned above, and is known to bring about significantly reduced quality of life (QOL) due to the limitation of activity and an increased cardiovascular risk (Non Patent Literatures 2 and 3). No existing therapeutic agent is effective for ectopic calcification. Thus, there are very high unmet medical needs for this disease (Non Patent Literature 4).

TNAP, one of alkaline phosphatases, includes membrane-bound and secretory forms. TNAP is expressed in the bone, the liver, and the kidney and highly expressed particularly in the matrix vesicles of chondrocytes and osteoblasts. This enzyme is known to play an important role in in vivo calcification via the degradation of pyrophosphate, which is an endogenous anti-calcification factor (Non Patent Literature 5). A large number of reports show the increased expression level or elevated activity of TNAP at lesion sites of ectopic calcification, and ectopic calcification also occurs in mice which overexpress human TNAP, suggesting the importance of TNAP for ectopic calcification (Non Patent Literatures 6 and 7). Thus, the inhibition of TNAP is considered to elevate pyrophosphate concentrations in blood and in tissues and suppress ectopic calcification (Non Patent Literature 8).

Some compounds are known to have TNAP inhibitory activity (see e.g., Patent Literatures 1 and 2 and, Non Patent Literatures 9 to 12). Among them, compounds partially having a common skeleton are disclosed. Nonetheless, a compound having a 7-membered ring condensed with a pyridine ring has not yet been disclosed.

PATENT LITERATURE

[Patent Literature 1] International Publication No. WO 2009/017863 (PCT/US2008/063106)
[Patent Literature 2] International Publication No. WO 2013/126608 (U.S. Patent Publication No. 2015-0011551)

NON PATENT LITERATURE

[Non Patent Literature 1] J. Bone Miner Res, 2006, vol. 24, p. 176-181
[Non Patent Literature 2] Clin. Kidery. J., 2014, vol. 7, p. 167-173
[Non Patent Literature 3] Eur. Heart. J., 2014, vol. 35, p. 1515-1525.
[Non Patent Literature 4] Int. J. Nephrol. Renovasc. Dis., 2014, vol. 7, p. 161-168
[Non Patent Literature 5] J. Histochem. Cytochem., 2002, vol. 50, p. 333-340
[Non Patent Literature 6] J. Am. Soc. Nephrol., 2004, vol. 15, p. 1392-1401
[Non Patent Literature 7] J. Bone Miner Res, 2013, vol. 7, p. 1587-1598
[Non Patent Literature 8] J. Bone Miner Res, 2007, vol. 22, p. 1700-1710
[Non Patent Literature 9] Bioorg. Med. Chem. Lett., 2009, vol. 19, p. 222-225
[Non Patent Literature 10] J. Med. Chem., 2009, vol. 52, p. 6919-6925
[Non Patent Literature 11] Bioorg. Med. Chem., 2013, vol. 21, p. 7981-7987
[Non Patent Literature 12] J. Bone Miner Res, 2015, vol. 30, p. 824-836

SUMMARY OF THE INVENTION

The present inventors have conducted diligent studies and consequently found that a compound represented by the formula (I) mentioned later has excellent TNAP inhibitory activity based on its specific chemical structure, further has excellent properties in terms of the physicochemical properties (e.g., stability) of a pharmaceutical, and serves as a safe and useful pharmaceutical as a prophylactic or therapeutic agent for a pathological condition or a disease associated with ectopic calcification. On the basis of these findings, the present invention has been completed.

Specifically, the compound of the present invention has excellent properties in terms of TNAP inhibitory activity, solubility, cell membrane permeability, oral absorbability, concentration in blood, metabolic stability, tissue penetration, bioavailability (hereinafter, also referred to as BA), in vitro activity, in vivo activity, ex vivo activity, quick onset of drug efficacy, persistence of drug efficacy, physical stability, drug interaction, safety (e.g., cardiotoxicity or hepatotoxicity), etc., and is useful as a pharmaceutical [particularly, a pharmaceutical for the treatment or prophylaxis (preferably treatment) of pseudoxanthoma elasticum (PXE), generalized arterial calcification of infancy (GACI), craniometaphyseal dysplasia (CMD), ossification of the yellow ligament (OYL), ossification of ligamentum flavum, arterial calcification due to deficiency of CD73 (ACDC), calcification of joints and arteries (CALJA), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, idiopathic basal ganglia calcification (IBGC), heterotopic ossification (HO), calcific aortic valve disease (aortic valve stenosis), calcific tendinitis, ossification of the posterior longitudinal ligament (OPLL) ossification of the anterior longitudinal ligament (OALL), diffuse idiopathic skeletal hyperostosis (DISH), meniscal calcification, or peritoneal calcification].

The present invention provides:
(1) a compound represented by formula (I):

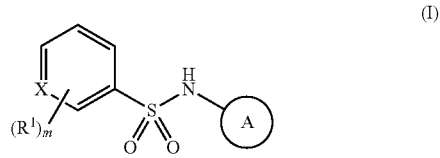

wherein
X represents —CH═, —C(—R$^1$)═, or —N═,
each substituent R$^1$ may be the same or different and may be each represent
a C1-6 alkyl group (wherein the alkyl group is optionally substituted by one to three groups, which may be the same or different, selected from substituent group A$^B$),
a C1-6 alkoxy group (wherein the alkoxy group is optionally substituted by one to three groups, which may be the same or different, selected from substituent group A$^B$),
a halogeno group,
a C6-10 aryl group (wherein the aryl group is optionally substituted by one or two groups, which may be the same or different, selected from substituent group A$^C$),
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group A$^C$),
a hydroxy group,
an amino group (wherein the amino group is optionally substituted by one or two groups, which may be the same or different C1-6 alkyl groups each optionally substituted by one to three groups, which may be the same or different, selected from substituent group A$^D$), a carboxyl group,
a C1-6 alkoxycarbonyl group (wherein the alkoxycarbonyl group is optionally substituted by one to three groups, which may be the same or different, selected from substituent group A$^D$),
an aminocarbonyl group (wherein the aminocarbonyl group is optionally substituted by one or two groups, which may be the same or different C1-6 alkyl groups each optionally substituted by one to three groups, which may be the same or different, selected from substituent group A$^D$), or
a cyano group,
m represents an integer selected from 1 to 4,
A represented by one of formula (IIa) to (IIh)

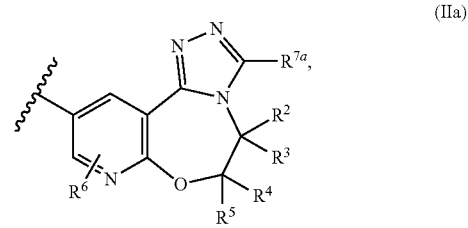

-continued

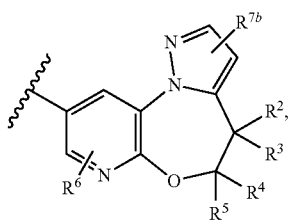
(IIb)

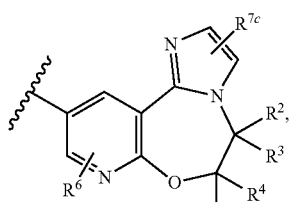
(IIc)

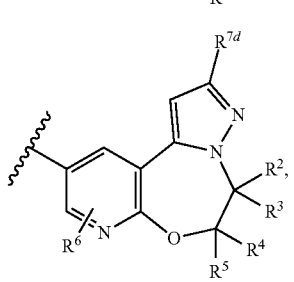
(IId)

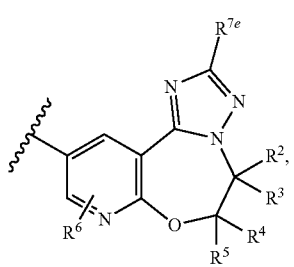
(IIe)

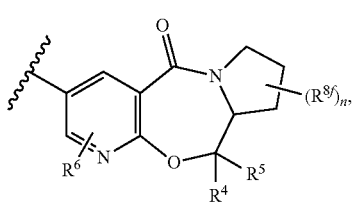
(IIf)

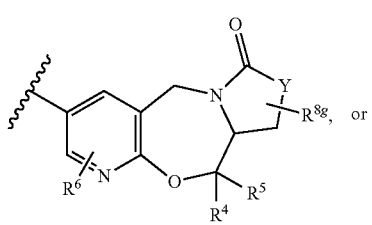
(IIg)

-continued

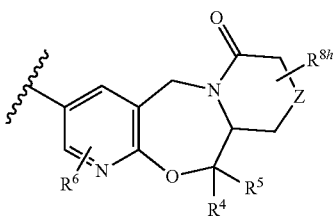
(IIh)

Y represents —CH$_2$—, —CH(—R$^{8g}$)—, —O—, or —N(—R$^{8g}$)—,

Z represents —CH$_2$—, —CH(—R$^{8h}$)—, —O—, or —N(—R$^{8h}$)—,

R$^2$ and R$^3$ are the same or different and each represent
a hydrogen atom,
a C1-6 alkyl group (wherein the alkyl group is optionally substituted by one to three groups, which may be the same or different, selected from the following substituents:
a hydroxy group,
a C1-6 alkoxy group optionally substituted by one group selected from substituent group A$^E$,
a C3-8 cycloalkyl group optionally substituted by one group selected from substituent group A$^E$,
a C6-10 aryl group optionally substituted by one or two groups selected from substituent group A$^E$,
a 3- to 10-membered heterocyclyl group containing one to four heteroatoms, which may be the same or different, selected from nitrogen, oxygen, and sulfur and optionally substituted by one or two groups selected from substituent group A$^E$,
a carboxyl group,
a C1-6 alkylcarbonyl group,
a C1-6 alkoxycarbonyl group, an amino group optionally substituted by one or two groups, which may be the same or different C1-6 alkyl groups,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group),
a C6-10 aryl group (wherein the aryl group is optionally substituted by one or two groups, which may be the same or different, selected from the following substituents:
a hydroxy group,
a C1-6 alkoxy group optionally substituted by one to three groups, which may be the same or different halogeno groups,
a C1-6 alkyl group optionally substituted by one group selected from substituent group A$^G$,
a C3-8 cycloalkyl group optionally substituted by one group selected from substituent group A$^G$,
a C6-10 aryl group optionally substituted by one group selected from substituent group A$^G$,
a 3- to 10-membered heterocyclyl group containing one to four heteroatoms, which may be the same or different, selected from nitrogen, oxygen, and sulfur and optionally substituted by one group selected from substituent group $A^G$,
an amino group optionally substituted by one or two groups, which may be the same or different C1-6 alkyl groups,
a carboxyl group,
a C1-6 alkylcarbonyl group,
a C1-6 alkoxycarbonyl group,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group),
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from the following substituents:
a hydroxy group,
a C1-6 alkoxy group optionally substituted by one to three groups, which may be the same or different halogeno groups,
a C1-6 alkyl group optionally substituted by one group selected from substituent group $A^G$,
a C3-8 cycloalkyl group optionally substituted by one group selected from substituent group $A^G$,
a C6-10 aryl group optionally substituted by one group selected from substituent group $A^G$,
a 3- to 10-membered heterocyclyl group containing one to four heteroatoms, which may be the same or different, selected from nitrogen, oxygen, and sulfur, and optionally substituted by one group selected from substituent group $A^G$,
an amino group optionally substituted by one or two groups, which may be the same or different C1-6 alkyl groups,
a carboxyl group,
a C1-6 alkylcarbonyl group,
a C1-6 alkoxycarbonyl group,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group),
a C1-6 alkylcarbonyl group (wherein the alkylcarbonyl group is optionally substituted by one to three groups, which may be the same or different, selected from substituent group $A^H$),
a C6-10 arylcarbonyl group (wherein the arylcarbonyl group is optionally substituted by one or two groups, which may be the same or different, selected from substituent group $A^H$ and a C1-6 halogenoalkyl group),
a 3- to 10-membered heterocyclylcarbonyl group containing one to four heteroatoms, which may be the same or different, selected from nitrogen, oxygen, and sulfur (wherein the heterocyclylcarbonyl group is optionally substituted by one or two groups, which may be the same or different, selected from substituent group $A^H$ and a C1-6 halogenoalkyl group),
a carboxyl group,
a C1-6 alkoxycarbonyl group (wherein the alkoxycarbonyl group is optionally substituted by one to three groups, which may be the same or different, selected from substituent group $A^J$),
an aminocarbonyl group (wherein the aminocarbonyl group is optionally substituted by one or two groups, which may be the same or different C1-6 alkyl groups each optionally substituted by one to three groups, which may be the same or different, selected from substituent group $A^J$),
a C6-10 arylaminocarbonyl group (wherein the arylaminocarbonyl group is optionally substituted by one or two groups, which may be the same or different, selected from substituent group $A^H$ and a C1-6 halogenoalkyl group),
a 4- to 7-membered saturated heterocyclylcarbonyl group containing one or two heteroatoms, which may be the same or different, selected from nitrogen, oxygen, and sulfur (wherein the heterocyclylcarbonyl group is optionally substituted by one to three groups, which may be the same or different, selected from substituent group $A^J$), or
a 3- to 10-membered heterocyclylaminocarbonyl group containing one to four heteroatoms, which may be the same or different, selected from nitrogen, oxygen, and sulfur (wherein the heterocyclylaminocarbonyl group is optionally substituted by one or two groups, which may be the same or different, selected from substituent group $A^H$ and a C1-6 halogenoalkyl group),
or
the C1-6 alkyl groups of $R^2$ and $R^3$ are optionally bonded to each other to form a 3- to 6-membered saturated carbocyclic ring or to form a 4- to 6-membered saturated heterocyclic ring via one nitrogen or oxygen atom (wherein one nitrogen atom in the 4- to 6-membered saturated heterocyclic ring is optionally replaced with a hydrogen atom, a C1-6 alkyl group, a C1-6 alkylcarbonyl group, a C1-6 alkoxycarbonyl group),
$R^4$ and $R^5$ are the same or different and each represent a hydrogen atom,
a C1-6 alkyl group (wherein the alkyl group is optionally substituted by one to three groups, which may be the same or different, selected from substituent group $A^C$),
a C6-10 aryl group (wherein the aryl group is optionally substituted by one or two groups, which may be the same or different, selected from substituent group $A^C$), or
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^C$),
$R^6$ represents
a hydrogen atom,
a C1-6 alkyl group ($R^6$ is a carbon substituent of the pyridinyl ring, not a nitrogen substituent) or
a hydroxy group, each substituent $R^{7a}$-$R^{7e}$ may be the same or different and may be each represent a hydrogen atom, a C1-6 alkyl group (wherein the alkyl group is optionally substituted by one to three groups, which may be the same or different, selected from substituent group $A^B$), a C6-10 aryl group (wherein the aryl group is optionally substituted by one or two groups, which may be the same or different, selected from substituent group $A^B$), a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^B$), or a hydroxy group, each substituent $R^{8f}$-$R^{8h}$ may be the same or different and may be each represent a hydrogen atom, a C1-6 alkyl group (wherein the alkyl group is optionally substituted by one to three groups, which may be the same or different, selected from substituent group $A^B$), a C3-8 cycloalkyl group (wherein the cycloalkyl group is optionally substituted by one group selected from substituent group A), a C6-10 aryl group (wherein the aryl group is optionally substituted by one or two groups, which may be the same or different, selected from substituent group $A^K$), a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^K$), a hydroxy group, a C1-6 alkoxy group (wherein the alkoxy group is optionally substituted by one group selected from substituent group $A^D$), a C3-8 cycloalkyloxy group (wherein the cycloalkyloxy group is optionally substituted by one group selected from substituent group $A^D$), a C6-10 aryloxy group (wherein the a C6-10 aryloxy group is optionally substituted by one or two groups selected from substituent group $A^D$), a carboxyl group, a C1-6 alkylcarbonyl group (wherein the alkylcarbonyl group is optionally substituted by one or two groups selected from substituent group $A^B$), a C1-6 alkoxycarbonyl group (wherein the alkylcarbonyl group is optionally substituted by one or two groups selected from substituent group $A^D$), an aminocarbonyl group (wherein the aminocarbonyl group is optionally substituted by one or two groups, which may be the same or different C1-6 alkyl groups), a 4- to 7-membered saturated heterocyclylcarbonyl group containing one or two heteroatoms, which may be the same or different, selected from nitrogen, oxygen, and sulfur, a C1-6 alkylcarbonyloxy group (wherein the alkylcarbonyloxy group is optionally substituted by one to three halogeno groups), an aminocarbonyloxy group (wherein the aminocarbonyloxy group is optionally substituted by one or two groups, which may be the same or different C1-6 alkyl groups), a 4- to 7-membered saturated heterocyclylcarbonyloxy group containing one or two heteroatoms, which may be the same or different, selected from nitrogen, oxygen, and sulfur, an amino group (wherein the amino group is optionally substituted by one or two groups, which may be the same or different, selected from the following substituents:

a C1-6 alkyl group optionally substituted by one to three groups, which may be the same or different, selected from substituent group $A^C$, a C3-8 cycloalkyl group optionally substituted by one group selected from substituent group $A^C$, a C6-10 aryl group optionally substituted by one or two groups, which may be the same or different, selected from substituent group $A^K$, a 3- to 10-membered heterocyclyl group containing one to four heteroatoms, which may be the same or different, selected from nitrogen, oxygen, and sulfur optionally substituted by one or two groups, which may be the same or different, selected from substituent group $A^K$, a C1-6 alkoxycarbonyl group optionally substituted by one or two groups, selected from substituent group $A^D$, an aminocarbonyl group optionally substituted by one or two groups, which may be the same or different C1-6 alkyl groups), a halogeno group, or a cyano group n represents an integer selected from 1 to 4, and the substituent groups represent $A^B$: a hydroxy group, a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a carboxyl group, a C1-6 alkoxycarbonyl group, an aminocarbonyl group (wherein the aminocarbonyl group is optionally substituted by one or two groups, which may be the same or different C1-6 alkyl groups), an amino group (wherein the amino group is optionally substituted by one or two groups, which may be the same or different C1-6 alkyl groups), a halogeno group, and a cyano group;

$A^C$: a hydroxy group, a C1-6 alkoxy group, an amino group (wherein the amino group is optionally substituted by one or two groups, which may be the same or different C1-6 alkyl groups), a halogeno group, and a cyano group;

$A^D$: a C1-6 alky group, a C1-6 alkoxy group, a carboxyl group, a C3-8 cycloalkyl group, a C6-10 aryl group, a 3- to 10-membered heterocyclyl group containing one to four heteroatoms, which may be the same or different, selected from nitrogen, oxygen, and sulfur, a carboxyl group, a C1-6 alkoxycarbonyl group, an aminocarbonyl group (wherein the aminocarbonyl group is optionally substituted by one or two groups, which may be the same or different C1-6 alkyl groups), a halogeno group, and
a cyano group;
$A^E$: a C6-10 aryl group,
a 3- to 10-membered heterocyclyl group containing one to four heteroatoms, which may be the same or different, selected from nitrogen, oxygen, and sulfur, and
a halogeno group;
$A^F$: a hydroxy group,
a C1-6 alkyl group (wherein the alkyl group is optionally substituted by one to three halogeno groups),
a C1-6 alkoxy group (wherein the alkoxy group is optionally substituted by one to three halogeno groups),
a halogeno group, an amino group, and
a cyano group;
$A^G$: a hydroxy group,
a C1-6 alkoxy group, an amino group,
a halogeno group, and
a cyano group;
$A^H$: a hydroxy group,
a C1-6 alkoxy group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
an amino group (wherein the amino group is optionally substituted by one or two groups, which may be the same or different C1-6 alkyl groups),
a halogeno group, and
a cyano group;
$A^J$: a C1-6 alkoxy group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
a halogeno group, and
a cyano group,
$A^K$: a hydroxy group,
a C1-6 alkyl group (wherein the alkyl group is optionally substituted by one to three halogeno groups),
a C1-6 alkoxy group (wherein the alkoxy group is optionally substituted by one to three halogeno groups),
a carboxyl group,
a C1-6 alkoxycarbonyl group,
an aminocarbonyl group (wherein the aminocarbonyl group is optionally substituted by one or two groups, which may be the same or different C1-6 alkyl groups), an amino group (wherein the amino group is optionally substituted by one or two groups, which may be the same or different C1-6 alkyl groups),
a halogeno group, and
a cyano group;
or a pharmacologically acceptable salt thereof;
(2) a compound represented by formula (I):

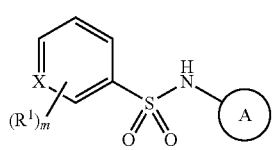

(I)

wherein
X represents —CH= or —N=,
each substituent $R^1$ may be the same or different and may represent a C1-6 alkoxy group or a halogeno group,
m represents an integer selected from 1 to 2,
A represented by one of formula (IIIa) to (IIId)

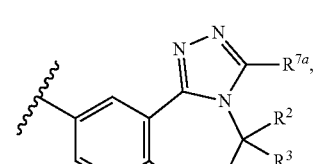

(IIIa)

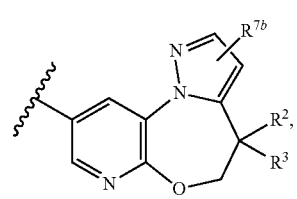

(IIIb)

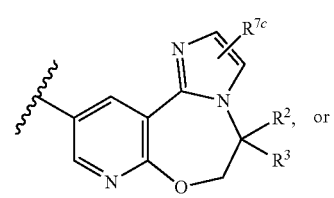

(IIIc)

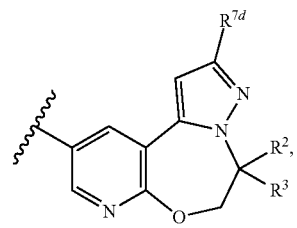

(IIId)

$R^2$ and $R^3$ are the same or different and each represent a hydrogen atom or a C1-6 alkyl group,
each substituent $R^{7a}$-$R^{7d}$ may be the same or different and may be each represent a hydrogen atom or a C1-6 alkoxy group;
or a pharmacologically acceptable salt thereof;
(3) the compound according to 2 above, wherein A is formula (IIId)

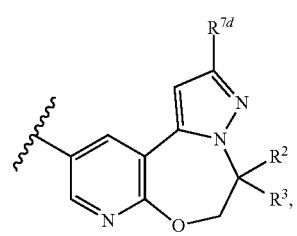

(IIId)

or a pharmacologically acceptable salt thereof;
(4) the compound according to 2 or 3 above, wherein each substituent $R^1$ may be the same or different and may represent an ethoxy group or a fluoro group, or a pharmacologically acceptable salt thereof;

(5) the compound according to 2 to 4 above, wherein $R^2$ and $R^3$ are the same or different and each represent a hydrogen atom or a methyl group, or a pharmacologically acceptable salt thereof;
(6) the compound according to 2 to 5 above, wherein $R^{7d}$ is a hydrogen atom, or a pharmacologically acceptable salt thereof;
(7) 5-chloro-N-(5,6-dihydropyrazolo[1,5-d]pyrido[3,2-f][1,4]oxazepin-10-yl)-2-methoxybenzenesulfonamide, 2-ethoxy-5-fluoro-N-[(5S)-5-methyl-5,6-dihydropyrazolo[1,5-d]pyrido[3,2-f][1,4]oxazepin-10-yl]benzenesulfonamide, 5-chloro-2-methoxy-N-[(5S)-5-methyl-5,6-dihydropyrazolo[1,5-d]pyrido[3,2-f][1,4]oxazepin-10-yl]pyridine-3-sulfonamide, or a pharmacologically acceptable salt thereof;
(8) 5-chloro-2-methoxy-N-(3-methyl-5,6-dihydropyrido[3,2-f][1,2,4]triazolo[4,3-d][1,4]oxazepin-10-yl)benzenesulfonamide, 5-chloro-N-(3-ethyl-5,6-dihydropyrido[3,2-f][1,2,4]triazolo[4,3-d][1,4]oxazepin-10-yl)-2-methoxybenzenesulfonamide, or a pharmacologically acceptable salt thereof;
(9) N-(5,6-dihydropyrazolo[1,5-d]pyrido[3,2-f][1,4]oxazepin-10-yl)-2-ethoxy-5-fluoropyridine-3-sulfonamide, or a pharmacologically acceptable salt thereof;
(10) N-(5,6-dihydropyrazolo[1,5-d]pyrido[3,2-f][1,4]oxazepin-10-yl)-2-ethoxy-5-fluorobenzenesulfonamide, or a pharmacologically acceptable salt thereof;
(11) 2-ethoxy-5-fluoro-N-[(5S)-5-methyl-5,6-dihydropyrazolo[1,5-d]pyrido[3,2-f][1,4]oxazepin-10-yl]pyridine-3-sulfonamide, or a pharmacologically acceptable salt thereof;
(12) 5-chloro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide, or a pharmacologically acceptable salt thereof;
(13) 5-chloro-N-[(8R,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide, or a pharmacologically acceptable salt thereof;
(14) a compound according to 1 to 13 above, wherein the pharmacologically acceptable salt is sodium salt;
(15) a compound according to 1 to 13 above, wherein the pharmacologically acceptable salt is potassium salt;
(16) a pharmaceutical composition comprising a compound according to 1 to 13 above, or a pharmacologically acceptable salt thereof, as an active ingredient;
(17) the pharmaceutical composition according to 16 above, wherein the pharmaceutical composition is intended for the treatment or prophylaxis of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), or aortic stenosis;
(18) a TNAP inhibitor comprising a compound according to 1 to 13 above, or a pharmacologically acceptable salt thereof, as an active ingredient;
(19) use of a compound according to 1 to 13 above, or a pharmacologically acceptable salt thereof, for the manufacturing a pharmaceutical composition;
(20) a method for the treatment or prophylaxis of a disease or condition selected from the group consisting of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis, comprising administering a therapeutically effective amount of a compound according to 1 to 13 above, or a pharmacologically acceptable salt thereof, to a subject in need thereof;
(21) a method according to 20 above, wherein the disease or condition is pseudoxanthoma elasticum (PXE);
(22) a method for inhibiting TNAP in a subject, comprising administering an effective amount of a compound according to 1 to 13 above, or a pharmacologically acceptable salt thereof, to the subject;
(23) a method according to 20 to 22 above, wherein the subject is a human;
(24) a compound according to 1 to 13 above, or a pharmacologically acceptable salt thereof, for use in the treatment of disease or condition selected from the group consisting of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis;
(25) a compound according to 1 to 13 above, or a pharmacologically acceptable salt thereof, for use in the treatment of pseudoxanthoma elastic (PXE); and
(26) a compound represented by formula (I):

$$(I)$$

wherein
X represents —CH═, —C(—$R^1$)═, or —N═,
each substituent $R^1$ may be the same or different and may be each represent
a C1-6 alkyl group (wherein the alkyl group is optionally substituted by one to three groups, which may be the same or different, selected from substituent group $A^B$),
a C1-6 alkoxy group (wherein the alkoxy group is optionally substituted by one to three groups, which may be the same or different, selected from substituent group $A^B$),
a halogeno group,
a C6-10 aryl group (wherein the aryl group is optionally substituted by one or two groups, which may be the same or different, selected from substituent group $A^C$),
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^C$),
a hydroxy group,
an amino group (wherein the amino group is optionally substituted by one or two groups, which may be the same or different C1-6 alkyl groups each optionally substituted by one to three groups, which may be the same or different, selected from substituent group $A^D$),
a carboxyl group,
a C1-6 alkoxycarbonyl group (wherein the alkoxycarbonyl group is optionally substituted by one to three groups, which may be the same or different, selected from substituent group $A^D$), an aminocarbonyl group (wherein the aminocarbonyl group is optionally substituted by one or two groups, which may be the same or different C1-6 alkyl groups each optionally substituted by one to three groups, which may be the same or different, selected from substituent group $A^D$), or
a cyano group,
m represents an integer selected from 1 to 4,
A represented by one of formula (IIa) to (IIe)

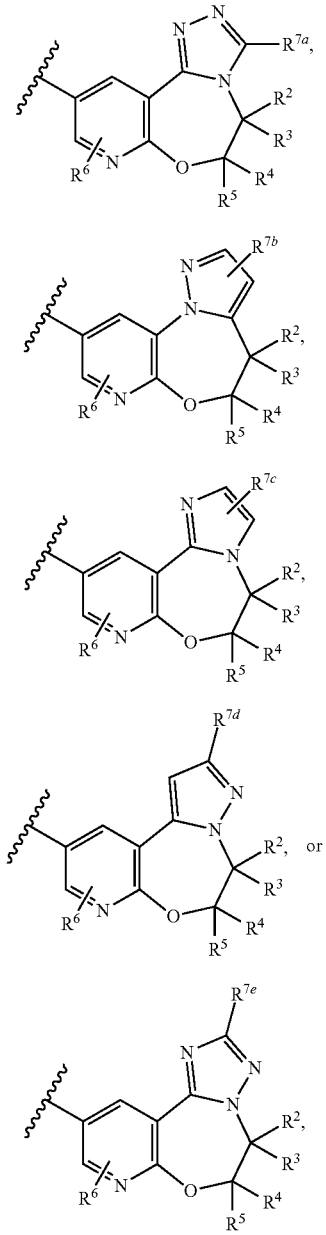

(IIa)

(IIb)

(IIc)

(IId)

(IIe)

$R^2$ and $R^3$ are the same or different and each represent
a hydrogen atom,
a C1-6 alkyl group (wherein the alkyl group is optionally substituted by one to three groups, which may be the same or different, selected from the following substituents:
a hydroxy group,
a C1-6 alkoxy group optionally substituted by one group selected from substituent group $A^E$, a C3-8 cycloalkyl group optionally substituted by one group selected from substituent group $A^F$,
a C6-10 aryl group optionally substituted by one or two groups selected from substituent group $A^F$,
a 3- to 10-membered heterocyclyl group containing one to four heteroatoms, which may be the same or different, selected from nitrogen, oxygen, and sulfur and optionally substituted by one or two groups selected from substituent group $A^F$,
a carboxyl group,
a C1-6 alkylcarbonyl group,
a C1-6 alkoxycarbonyl group,
an amino group optionally substituted by one or two groups, which may be the same or different C1-6 alkyl groups,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur,
an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group),
a C6-10 aryl group (wherein the aryl group is optionally substituted by one or two groups, which may be the same or different, selected from the following substituents:
a hydroxy group,
a C1-6 alkoxy group optionally substituted by one to three groups, which may be the same or different halogeno groups,
a C1-6 alkyl group optionally substituted by one group selected from substituent group $A^G$,
a C3-8 cycloalkyl group optionally substituted by one group selected from substituent group $A^G$,
a C6-10 aryl group optionally substituted by one group selected from substituent group $A^G$,
a 3- to 10-membered heterocyclyl group containing one to four heteroatoms, which may be the same or different, selected from nitrogen, oxygen, and sulfur and optionally substituted by one group selected from substituent group $A^G$,
an amino group optionally substituted by one or two groups, which may be the same or different C1-6 alkyl groups,
a carboxyl group,
a C1-6 alkylcarbonyl group,
a C1-6 alkoxycarbonyl group,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur,
an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group), a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from the following substituents:
a hydroxy group,
a C1-6 alkoxy group optionally substituted by one to three groups, which may be the same or different halogeno groups,
a C1-6 alkyl group optionally substituted by one group selected from substituent group $A^G$,
a C3-8 cycloalkyl group optionally substituted by one group selected from substituent group $A^G$,
a C6-10 aryl group optionally substituted by one group selected from substituent group $A^G$,
a 3- to 10-membered heterocyclyl group containing one to four heteroatoms, which may be the same or different, selected from nitrogen, oxygen, and sulfur, and optionally substituted by one group selected from substituent group $A^G$,
an amino group optionally substituted by one or two groups, which may be the same or different C1-6 alkyl groups,
a carboxyl group,
a C1-6 alkylcarbonyl group,
a C1-6 alkoxycarbonyl group,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur,
an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group),
a C1-6 alkylcarbonyl group (wherein the alkylcarbonyl group is optionally substituted by one to three groups, which may be the same or different, selected from substituent group $A^H$),
a C6-10 arylcarbonyl group (wherein the arylcarbonyl group is optionally substituted by one or two groups, which may be the same or different, selected from substituent group $A^H$ and
a C1-6 halogenoalkyl group),
a 3- to 10-membered heterocyclylcarbonyl group containing one to four heteroatoms, which may be the same or different, selected from nitrogen, oxygen, and sulfur (wherein the heterocyclylcarbonyl group is optionally substituted by one or two groups, which may be the same or different, selected from substituent group $A^H$ and
a C1-6 halogenoalkyl group),
a carboxyl group,
a C1-6 alkoxycarbonyl group (wherein the alkoxycarbonyl group is optionally substituted by one to three groups, which may be the same or different, selected from substituent group $A^J$),
an aminocarbonyl group (wherein the aminocarbonyl group is optionally substituted by one or two groups, which may be the same or different C1-6 alkyl groups each optionally substituted by one to three groups, which may be the same or different, selected from substituent group $A^J$),
a C6-10 arylaminocarbonyl group (wherein the arylaminocarbonyl group is optionally substituted by one or two groups, which may be the same or different, selected from substituent group $A^H$ and
a C1-6 halogenoalkyl group),
a 4- to 7-membered saturated heterocyclylcarbonyl group containing one or two heteroatoms, which may be the same or different, selected from nitrogen, oxygen, and sulfur (wherein the heterocyclylcarbonyl group is optionally substituted by one to three groups, which may be the same or different, selected from substituent group $A^J$), or
a 3- to 10-membered heterocyclylaminocarbonyl group containing one to four heteroatoms, which may be the same or different, selected from nitrogen, oxygen, and sulfur (wherein the heterocyclylaminocarbonyl group is optionally substituted by one or two groups, which may be the same or different, selected from substituent group $A^H$ and
a C1-6 halogenoalkyl group),
or
the C1-6 alkyl groups of $R^2$ and $R^3$ are optionally bonded to each other to form a 3- to 6-membered saturated carbocyclic ring or to form a 4- to 6-membered saturated heterocyclic ring via one nitrogen or oxygen atom (wherein one nitrogen atom in the 4- to 6-membered saturated heterocyclic ring is optionally replaced with a hydrogen atom, a C1-6 alkyl group, a C1-6 alkylcarbonyl group, a C1-6 alkoxycarbonyl group),
$R^4$ and $R^5$ are the same or different and each represent a hydrogen atom,
a C1-6 alkyl group (wherein the alkyl group is optionally substituted by one to three groups, which may be the same or different, selected from substituent group $A^C$),
a C6-10 aryl group (wherein the aryl group is optionally substituted by one or two groups, which may be the same or different, selected from substituent group $A^C$), or
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^C$),
$R^6$ represents
a hydrogen atom,
a C1-6 alkyl group ($R^6$ is a carbon substituent of the pyridinyl ring, not a nitrogen substituent) or
a hydroxy group,
each substituent $R^{7a}$~$R^{7e}$ may be the same or different and may be each represent
a hydrogen atom,
a C1-6 alkyl group (wherein the alkyl group is optionally substituted by one to three groups, which may be the same or different, selected from substituent group $A^B$),
a C6-10 aryl group (wherein the aryl group is optionally substituted by one or two groups, which may be the same or different, selected from substituent group $A^B$),
a 3- to 10-membered heterocyclyl group containing one to four heteroatoms, which may be the same or different, selected from nitrogen, oxygen, and sulfur (wherein the heterocyclyl group is optionally substituted by one or two groups, which may be the same or different, selected from substituent group $A^B$), or
a hydroxy group, and
the substituent groups represent
$A^B$: a hydroxy group,
a C1-6 alkoxy group,
a C3-8 cycloalkyl group,
a C6-10 aryl group, a 3- to 10-membered heterocyclyl group containing one to four heteroatoms, which may be the same or different, selected from nitrogen, oxygen, and sulfur,
a carboxyl group,
a C1-6 alkoxycarbonyl group,
an aminocarbonyl group (wherein the aminocarbonyl group is optionally substituted by one or two groups, which may be the same or different C1-6 alkyl groups),
an amino group (wherein the amino group is optionally substituted by one or two groups, which may be the same or different C1-6 alkyl groups),
a halogeno group, and
a cyano group;
$A^C$: a hydroxy group,
a C1-6 alkoxy group,
an amino group (wherein the amino group is optionally substituted by one or two groups, which may be the same or different C1-6 alkyl groups),
a halogeno group, and
a cyano group;
$A^D$: a C1-6 alkoxy group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
a carboxyl group,
a C1-6 alkoxycarbonyl group,
an aminocarbonyl group (wherein the aminocarbonyl group is optionally substituted by one or two groups, which may be the same or different C1-6 alkyl groups),
a halogeno group, and
a cyano group;
$A^E$: a C6-10 aryl group,
a 3- to 10-membered heterocyclyl group containing one to four heteroatoms, which may be the same or different, selected from nitrogen, oxygen, and sulfur, and
a halogeno group;
$A^F$: a hydroxy group,
a C1-6 alkyl group (wherein the alkyl group is optionally substituted by one to three halogeno groups),
a C1-6 alkoxy group (wherein the alkoxy group is optionally substituted by one to three halogeno groups),
a halogeno group,
an amino group, and
a cyano group;
$A^G$: a hydroxy group,
a C1-6 alkoxy group,
an amino group,
a halogeno group, and
a cyano group;
$A^H$: a hydroxy group,
a C1-6 alkoxy group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
an amino group (wherein the amino group is optionally substituted by one or two groups, which may be the same or different C1-6 alkyl groups),
a halogeno group, and
a cyano group;
$A^J$: a C1-6 alkoxy group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
a halogeno group, and
a cyano group,
or a pharmacologically acceptable salt thereof.

In the present invention, the "C1-6 alkyl group" refers to a linear or branched alkyl group having 1 to 6 carbon atoms. Examples thereof can include methyl, ethyl, n-propyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl groups. For $R^1$, $R^2$, $R^3$, $R^4$, $R^5$, $R^6$, $R^{7a}$~$R^{7e}$, $A^B$, $A^C$, $A^D$, $A^F$, or $A^G$, the C1-6 alkyl group is preferably an alkyl group having 1 to 3 carbon atoms, most preferably an ethyl or methyl group.

In the present invention, the "C1-6 alkylcarbonyl group" refers to the aforementioned "C1-6 alkyl group" bonded to a carbonyl group. Examples thereof can include methylcarbonyl, ethylcarbonyl, n-propylcarbonyl, n-butylcarbonyl, isobutylcarbonyl, s-butylcarbonyl, tert-butylcarbonyl, n-pentylcarbonyl, isopentylcarbonyl, 2-methylbutylcarbonyl, neopentylcarbonyl, 1-ethylpropylcarbonyl, n-hexylcarbonyl, isohexylcarbonyl, 4-methylpentylcarbonyl, 3-methylpentylcarbonyl, 2-methylpentylcarbonyl, 1-methylpentylcarbonyl, 3,3-dimethylbutylcarbonyl, 2,2-dimethylbutylcarbonyl, 1,1-dimethylbutylcarbonyl, 1,2-dimethylbutylcarbonyl, 1,3-dimethylbutylcarbonyl, 2,3-dimethylbutylcarbonyl, and 2-ethylbutylcarbonyl groups. For $R^2$ or $R^3$, the C1-6 alkylcarbonyl group is preferably an alkylcarbonyl group having 1 to 3 carbon atoms, most preferably a methylcarbonyl group.

In the present invention, the "C3-8 cycloalkyl group" refers to a 3- to 8-membered saturated cyclic hydrocarbon group. Examples thereof can include cyclopropyl, cyclobutyl, cyclopentyl, cyclohexyl, cycloheptyl, and cyclooctyl groups. For $R^2$, $R^3$, $A^B$, $A^D$, $A^H$, or $A^J$, the C3-8 cycloalkyl group is preferably a 3- to 6-membered saturated cyclic hydrocarbon group, more preferably a cyclopropyl, cyclobutyl, cyclopentyl, or cyclohexyl group.

In the present invention, the "C1-6 halogenoalkyl group" refers to the aforementioned "C1-6 alkyl group" substituted by one to six halogen atoms. Examples thereof can include linear or branched halogenoalkyl groups each having 1 to 6 carbon atoms, such as fluoromethyl, difluoromethyl, trifluoromethyl, 2,2,2-trifluoroethyl, 1,1,1,3,3,3-hexafluoro-2-propyl, chloromethyl, 2-chloroethyl, 3-chloro-n-propyl, 4-chloro-n-butyl, 5-chloro-n-pentyl, and 6-chloro-n-hexyl groups. For $R^2$ or $R^3$, the C6-10 halogenoalkyl group is preferably trifluoromethyl group.

In the present invention, the "C6-10 aryl group" refers to an aromatic hydrocarbon group having 6 to 10 carbon atoms. Examples thereof can include phenyl, indenyl, and naphthyl groups. For $R^1$, $R^2$, $R^3$, $R^4$, $R^5$, $R^{7a}$~$R^{7e}$, $A^B$, $A^D$, $A^E$, $A^H$, or $A^J$, the C6-10 aryl group is preferably a phenyl group.

In the present invention, the "C1-6 alkoxy group" refers to the aforementioned "C1-6 alkyl group" bonded to an oxygen atom. Examples thereof can include linear or branched alkoxy groups each having 1 to 6 carbon atoms, such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, and 2,3-dimethylbutoxy. For $R^1$, R², R³, Aᴮ, A^C, A^D, A^F, A^G, A^H, or A^J, the C1-6 alkoxy group is preferably a methoxy or ethoxy group.

In the present invention, the "C1-6 alkoxycarbonyl group" refers to the aforementioned "C1-6 alkoxy group" bonded to a carbonyl group. Examples thereof can include linear or branched alkoxycarbonyl groups each having 1 to 6 carbon atoms, such as methoxycarbonyl, ethoxycarbonyl, n-propoxycarbonyl, isopropoxycarbonyl, n-butoxycarbonyl, isobutoxycarbonyl, s-butoxycarbonyl, tert-butoxycarbonyl, n-pentoxycarbonyl, isopentoxycarbonyl, 2-methylbutoxycarbonyl, neopentoxycarbonyl, n-hexyloxycarbonyl, 4-methylpentoxycarbonyl, 3-methylpentoxycarbonyl, 2-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, and 2,3-dimethylbutoxycarbonyl. For R¹, R², R³, Aᴮ, or A^D, the C1-6 alkoxycarbonyl group is preferably a methoxycarbonyl or ethoxycarbonyl group.

In the present invention, the "4- to 7-membered saturated heterocyclyl group containing one or two heteroatoms, which may be the same or different, selected from nitrogen, oxygen, and sulfur" refers to a 4- to 7-membered saturated heterocyclic group containing one or two atoms of nitrogen, oxygen, and sulfur. Examples thereof can include oxetanyl, morpholinyl, thiomorpholinyl, pyrrolidinyl, pyrrolinyl, imidazolidinyl, imidazolinyl, pyrazolidinyl, pyrazolinyl, piperidinyl, piperazinyl, tetrahydrofuranyl, tetrahydropyranyl, and 5-oxo-4,5-dihydro-1,2,4-oxadiazolyl groups.

In the present invention, the "4- to 7-membered saturated heterocyclylcarbonyl group containing one or two heteroatoms, which may be the same or different, selected from nitrogen, oxygen, and sulfur" refers to the aforementioned "4- to 7-membered saturated heterocyclyl group containing one or two heteroatoms, which may be the same or different, selected from nitrogen, oxygen, and sulfur" bonded to a carbonyl group. Examples thereof can include morpholinylcarbonyl, thiomorpholinylcarbonyl, pyrrolidinylcarbonyl, pyrrolinylcarbonyl, piperidinylcarbonyl, piperazinylcarbonyl, tetrahydrofuranylcarbonyl, tetrahydropyranylcarbonyl, and 5-oxo-4,5-dihydro-1,2,4-oxadiazolylcarbonyl groups.

In the present invention, the "4- to 7-membered saturated heterocyclylcarbonyloxy group containing one or two heteroatoms, which may be the same or different, selected from nitrogen, oxygen, and sulfur" refers to the aforementioned "4- to 7-membered saturated heterocyclylcarbonyl group containing one or two heteroatoms, which may be the same or different, selected from nitrogen, oxygen, and sulfur" bonded to an oxygen atom. Examples thereof can include morpholinylcarbonyloxy, thiomorpholinylcarbonyloxy, pyrrolidinylcarbonyloxy, pyrrolinylcarbonyloxy, piperidinylcarbonyloxy, piperazinylcarbonyloxy, tetrahydrofuranylcarbonyloxy, tetrahydropyranylcarbonyloxy, and 5-oxo-4,5-dihydro-1,2,4-oxadiazolylcarbonyloxy groups.

In the present invention, the "3- to 10-membered heterocyclyl group containing one to four heteroatoms, which may be the same or different, selected from nitrogen, oxygen, and sulfur" refers to a 3- to 10-membered heterocyclic group containing one to four atoms of nitrogen, oxygen, and sulfur. Examples thereof can include the groups listed as the examples of the aforementioned "4- to 7-membered heterocyclyl group containing one or two heteroatoms, which may be the same or different, selected from nitrogen, oxygen, and sulfur", and aromatic heterocyclic groups such as furyl, thienyl, pyrrolyl, azepinyl, pyrazolyl, imidazolyl, oxazolyl, oxadiazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, and pyrazinyl. The "3- to 10-membered heterocyclic group" may be condensed with an additional cyclic group. Examples thereof can include benzofuranyl, chromenyl, indolizinyl, isoindolyl, indolyl, indazolyl, purinyl, quinolizinyl, isoquinolyl, quinolyl, phthalazinyl, naphthyridinyl, quinoxalinyl, quinazolinyl, isoindolinyl, 2,3-dihydro-1-benzofuranyl, 3,4-dihydro-1H-isochromenyl, 1,2,3,4-tetrahydroquinolinyl, and 1,2,3,4-tetrahydroisoquinolinyl groups.

In the present invention, the "3- to 10-membered heterocyclylcarbonyl group containing one to four heteroatoms, which may be the same or different, selected from nitrogen, oxygen, and sulfur" refers to the aforementioned "3- to 10-membered heterocyclyl group containing one to four heteroatoms, which may be the same or different, selected from nitrogen, oxygen, and sulfur" bonded to a carbonyl group. Examples thereof can include the groups listed as the examples of the aforementioned "4- to 7-membered saturated heterocyclylcarbonyl group containing one or two heteroatoms, which may be the same or different, selected from nitrogen, oxygen, and sulfur", bonded to a carbonyl group such as furylcarbonyl, thienylcarbonyl, pyrrolylcarbonyl, azepinylcarbonyl, pyrazolylcarbonyl, imidazolylcarbonyl, oxazolylcarbonyl, oxadiazolylcarbonyl, isoxazolylcarbonyl, thiazolylcarbonyl, isothiazolylcarbonyl, 1,2,3-oxadiazolylcarbonyl, triazolylcarbonyl, tetrazolylcarbonyl, thiadiazolylcarbonyl, pyranylcarbonyl, pyridylcarbonyl, pyridazinylcarbonyl, pyrimidinylcarbonyl, and pyrazinylcarbonyl groups.

In the present invention, the "3- to 10-membered heterocyclylaminocarbonyl group containing one or two heteroatoms, which may be the same or different, selected from nitrogen, oxygen, and sulfur" refers to the aforementioned "3- to 10-membered heterocyclyl group containing one to four heteroatoms, which may be the same or different, selected from nitrogen, oxygen, and sulfur" bonded to a carbonyl group via an amino group. Examples thereof can include such as furylaminocarbonyl, thienylaminocarbonyl, pyrrolylaminocarbonyl, azepinylaminocarbonyl, pyrazolylaminocarbonyl, imidazolylaminocarbonyl, oxazolylaminocarbonyl, oxadiazolylaminocarbonyl, isoxazolylaminocarbonyl, thiazolylaminocarbonyl, isothiazolylaminocarbonyl, 1,2,3-oxadiazolylaminocarbonyl, triazolylaminocarbonyl, tetrazolylaminocarbonyl, thiadiazolylaminocarbonyl, pyranylaminocarbonyl, pyridylaminocarbonyl, pyridazinylaminocarbonyl, pyrimidinylaminocarbonyl, and pyrazinylaminocarbonyl groups.

In the present invention, the "halogeno group" refers to a fluoro, chloro, bromo, or iodo group. For R¹, R², R³, Aᴮ, A^C, A^D, A^E, A^F, A^G, A^H, or A^J, the halogeno group is preferably a fluoro, chloro, or bromo group.

Preferably, each R¹ of the present invention, which may be the same or different, represents a C1-6 alkoxy group or a halogeno group.

Preferably, X of the present invention is —CH= or —N=.

Preferably, A of the invention is one of the following general formula (IIIa)(IIId)

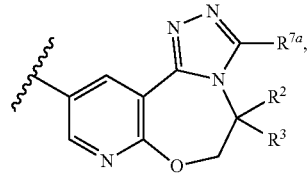

(IIIa)

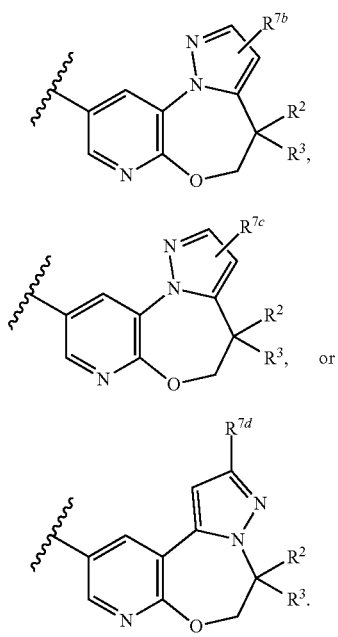

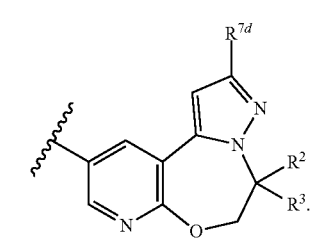

Preferably, $R^2$ and $R^3$ of the present invention are the same or different and each represent a hydrogen atom or a C1-6 alkyl group, or the C1-6 alkyl groups of $R^2$ and $R^3$ are bonded to each other to form a 3- to 6-membered saturated carbocyclic ring.

Preferably, each of $R^4$ and $R^5$ of the present invention is a hydrogen atom.

Preferably, $R^6$ of the present invention is a hydrogen atom.

Preferably, $R^7$ of the present invention is a hydrogen atom or a C1-6 alkyl group.

The compound represented by the general formula (I) of the present invention can form a salt with a base. Such a salt with a base is included in the scope of the present invention. Examples of the salt with a base can include: alkali metal salts such as lithium salt, sodium salt, potassium salt, and cesium salt; alkaline earth metal salts such as magnesium salt, calcium salt, and barium salt; inorganic nitrogen compound salts such as ammonium salt and hydrazine salt; primary amine salts such as methylamine salt, ethylamine salt, n-propylamine salt, isopropylamine salt, n-butylamine salt, 2-butylamine salt, isobutylamine salt, and tert-butylamine salt; secondary amine salts such as dimethylamine salt, diethylamine salt, diisopropylamine salt, pyrrolidine salt, piperidine salt, and morpholine salt; tertiary amine salts such as triethylamine salt and N-methylmorpholine salt; and aromatic amine salts such as pyridine salt, 4-(N,N-dimethylamino)pyridine salt, imidazole salt, and 1-methylimidazole salt. The salt is preferably an alkali metal salt, most preferably sodium salt or potassium salt. The compound represented by the general formula (I) of the present invention can form any ratio of a salt with a base. The respective salts with bases or mixtures thereof are included in the scope of the present invention.

The compound represented by the general formula (I) of the present invention can form an acid-addition salt, depending on its substituent. Such an acid-addition salt is included in the scope of the present invention. The compound represented by the general formula (I) of the present invention can form any ratio of an acid-addition salt, depending on its substituent. The respective acid addition salts (e.g., monoacid salt and hemi-acid salt) or mixtures thereof are included in the salt of the present invention.

The compound represented by the general formula (I) of the present invention or the pharmacologically acceptable salt thereof can form an anhydrate, a hydrate, or a solvate. The respective forms or mixtures thereof are included in the scope of the present invention.

When the compound represented by the general formula (I) of the present invention or the pharmacologically acceptable salt thereof has at least one asymmetric center, carbon-carbon double bond, axial chirality, tautomerism, or the like, optical isomers (including enantiomers and diastereomers), geometric isomers, rotational isomers, and tautomers may exist. These isomers and mixtures thereof are represented by a single formula such as the formula (I). The present invention encompasses these isomers and mixtures (including racemates) thereof at any ratio.

The compound represented by the general formula (I) of the present invention or the pharmacologically acceptable salt thereof can form an isotopic compound by the replacement of one or more atoms constituting the compound or the salt with isotopes at nonnatural ratios. The isotopes can be radioactive or nonradioactive. Examples thereof include deuterium ($^2$H; D), tritium ($^3$H; T), carbon-13 ($^{13}$C), carbon-14 ($^{14}$C), and iodine-125 ($^{125}$I). The radioactive or nonradioactive isotopic compound may be used as a pharmaceutical for the treatment or prophylaxis of a disease, a reagent for research (e.g., a reagent for assay), a diagnostic agent (e.g., a diagnostic imaging agent), or the like. The present invention encompasses these radioactive or nonradioactive isotopic compounds.

The compound represented by the general formula (I) of the present invention can be produced by, for example, the following method:

Method A

When A is represented by the general formula (IIa), the compound represented by the general formula (I) of the present invention can be produced by the method A.

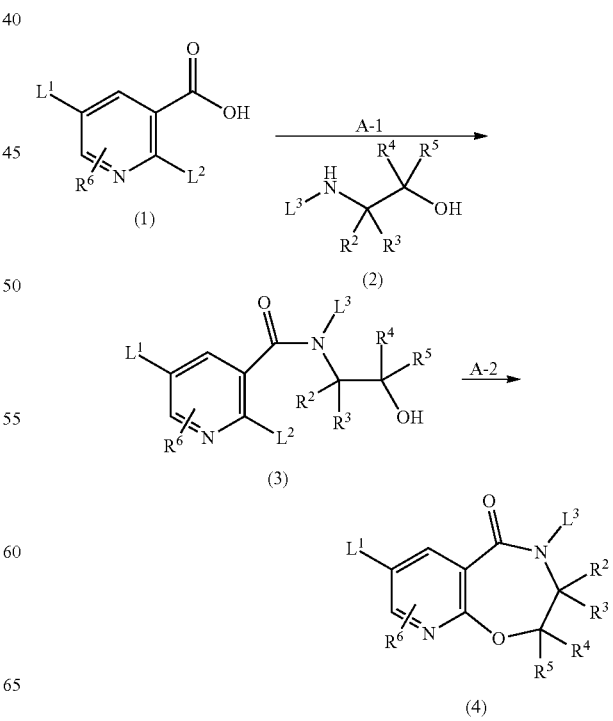

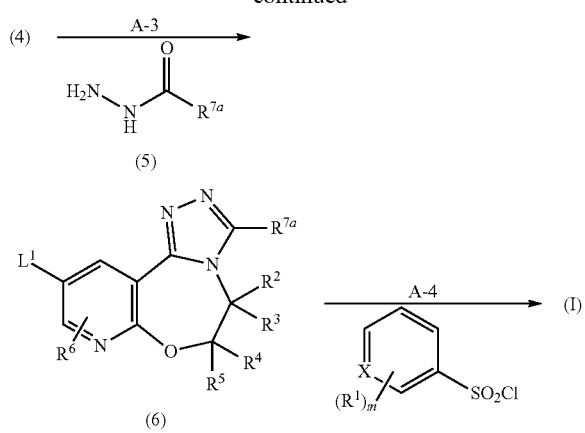

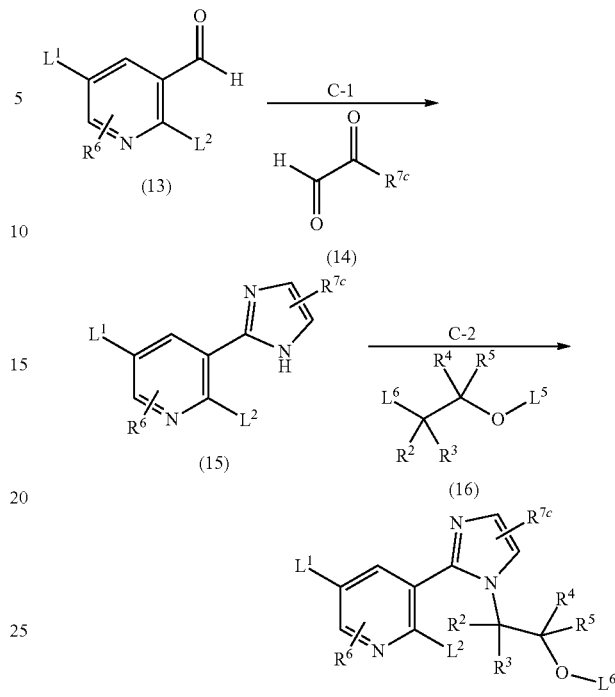

Method B

When A is represented by the general formula (IIb), the compound represented by the general formula (I) of the present invention can be produced by the method B.

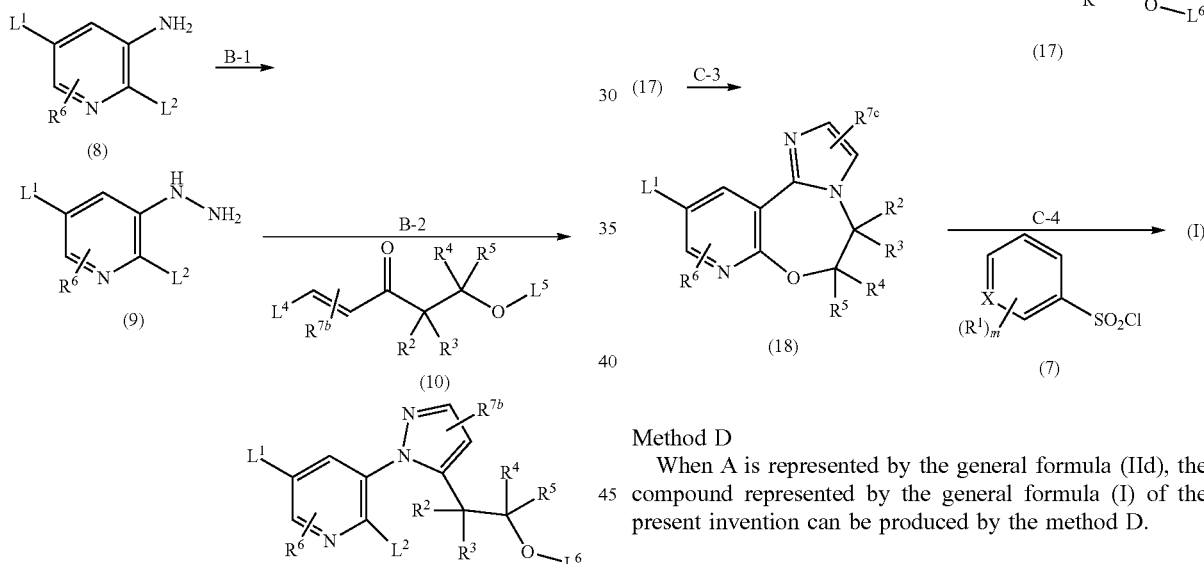

Method C

When A is represented by the general formula (IIc), the compound represented by the general formula (I) of the present invention can be produced by the method C.

Method D

When A is represented by the general formula (IId), the compound represented by the general formula (I) of the present invention can be produced by the method D.

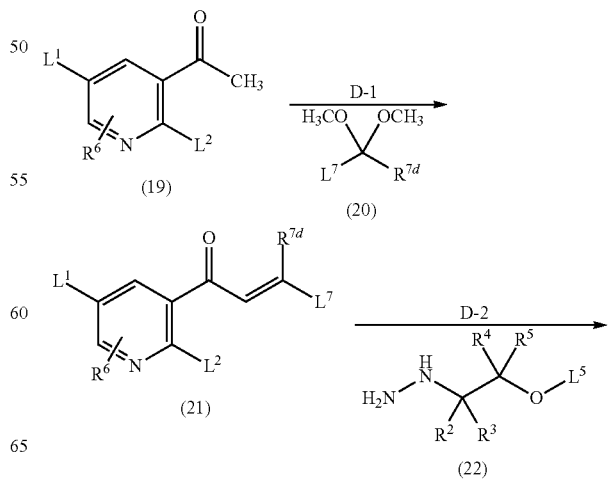

Method F

When A is represented by the general formula (IIf), the compound represented by the general formula (I) of the present invention can be produced by the method F.

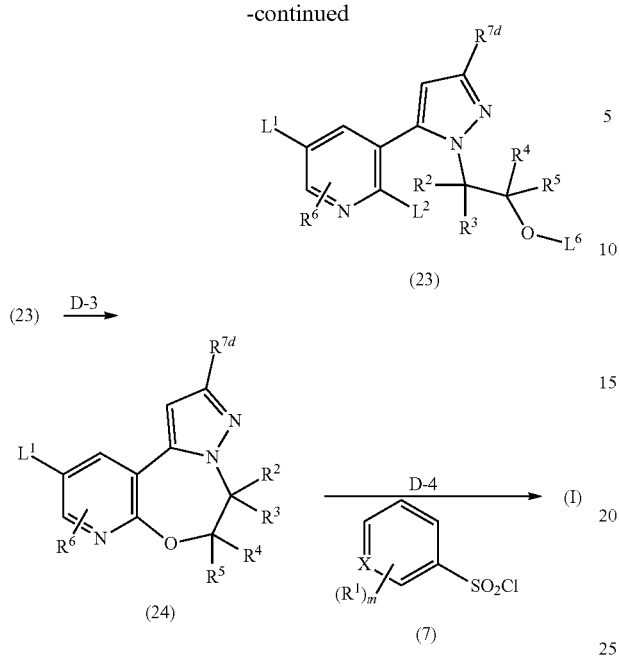

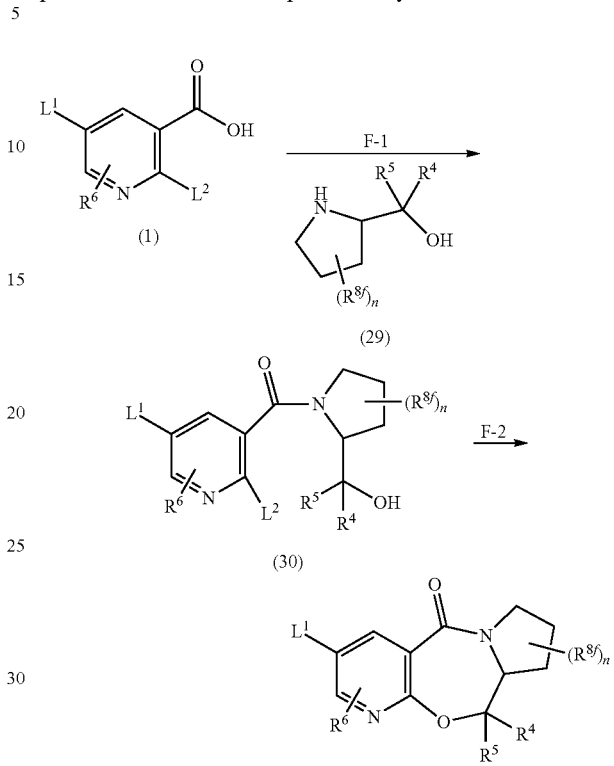

Method E

When A is represented by the general formula (IIe), the compound represented by the general formula (I) of the present invention can be produced by the method E.

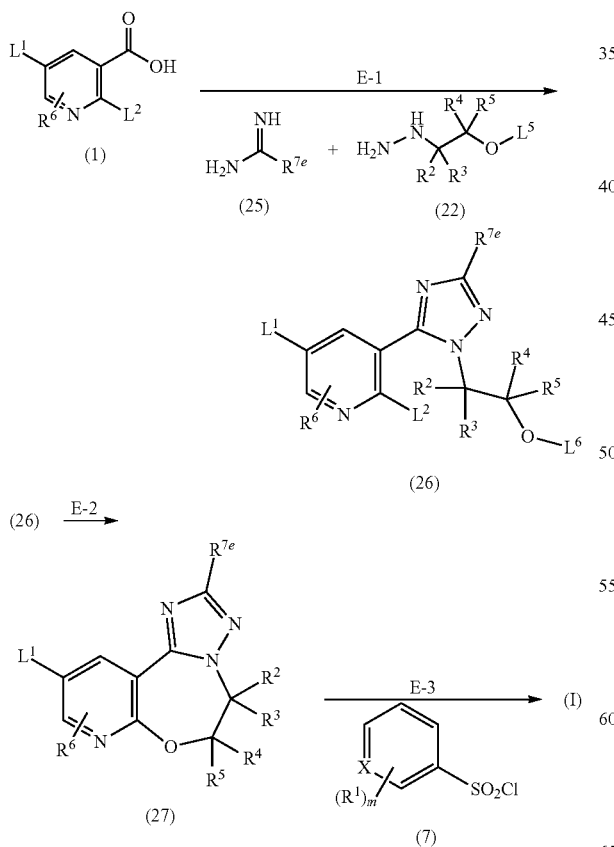

In the structural formulas of the compounds in the method A, method B, method C, method D, method E and method F, and the description below, $R^1$, $R^2$, $R^3$, $R^4$, $R^5$, $R^6$, $R^{7a-e}$, $R^{8f}$, m, n and X are as defined in the formula (I);

$L^1$ represents a nitro group, a halogeno group, or an amino group (wherein the amino group is optionally substituted by a C1-6 alkoxycarbonyl group), and is preferably a nitro group or a bromo group;

$L^2$ represents a halogeno group and is preferably a fluoro group or a chloro group;

$L^3$ represents a hydrogen atom or a C1-6 alkyl group (wherein the alkyl group is optionally substituted by an ethenyl group, a phenyl group, a 4-methoxyphenyl group or a 2,4-dimethoxyphenyl group), and is preferably a 2,4-dimethoxybenzyl group;

$L^4$ represents C1-6 alkoxy group, a halogeno group, or an amino group (wherein the amino group is optionally substituted by one or two groups, which may be the same or different C1-6 alkyl groups, or a C1-6 alkyl group and a C1-6 alkoxy group), and is preferably a dimethylamino group or a N,O-dimethylhydroxyamino group;

$L^5$ represents a hydrogen atom, a C1-6 alkyl group (wherein the alkyl group is optionally substituted by an ethenyl group, a phenyl group, or a 4-methoxyphenyl group) or a silyl group (wherein the silyl group is substituted by three groups, which may be the same or different C1-6 alkyl groups or phenyl groups), and is preferably tert-butyldimethylsilyl group or tert-butyldiphenylsilyl group;

$L^6$ represents a halogeno group or a sulfonate group (wherein the sulfonate group is substituted by a methyl group, a trifluoromethyl group, or a 4-methylphenyl groups), and is and is preferably a bromo group; and $L^7$ represents C1-6 alkoxy group, or an amino group (wherein the amino group is optionally substituted by one or two groups, which may be the same or different C1-6 alkyl groups, or a C1-6 alkyl group and a C1-6 alkoxy group), and is preferably a dimethylamino group or a N,O-dimethylhydroxyamino group.

When a compound serving as a reactive substrate in the reaction of each step in the method A, method B, method C, method D and method E has a group inhibiting the reaction of interest, such as an amino group, a hydroxy group, or a carbonyl group, an appropriate protective group may be introduced to the functional group and the introduced protective group may be removed, if necessary. Such a protective group is not particularly limited as long as the protective group is one usually used. The protective group can be a protective group described in, for example, T. W. Greene, P. G. M. Wuts, Protective Groups in Organic Synthesis, Fifth Edition, 2014, John Wiley & Sons, Inc. The reactions for the introduction and removal of these protective groups can be carried out according to routine methods such as methods described in the literature.

The solvent for use in the reaction of each step in the method A, method B, method C, method D and method E is not particularly limited as long as the solvent partially dissolves starting materials without inhibiting the reaction. The solvent is selected from, for example, the following solvent group: aliphatic hydrocarbons such as hexane, pentane, heptane, petroleum ether, and cyclohexane; aromatic hydrocarbons such as toluene, benzene, and xylene; halogenated hydrocarbons such as methylene chloride, chloroform, carbon tetrachloride, dichloroethane, chlorobenzene, and dichlorobenzene; ethers such as diethyl ether, diisopropyl ether, cyclopentylmethyl ether, t-butyl methyl ether, tetrahydrofuran, 1,4-dioxane, dimethoxyethane, and diethylene glycol dimethyl ether; ketones such as acetone, methyl ethyl ketone, methyl isobutyl ketone, and cyclohexanone; esters such as methyl acetate, ethyl acetate, propyl acetate, butyl acetate, and diethyl carbonate; nitriles such as acetonitrile, propionitrile, butyronitrile, and isobutyronitrile; organic acids such as formic acid, acetic acid, propionic acid, trifluoroacetic acid, and pentafluoropropionic acid; alcohols such as methanol, ethanol, 1-propanol, 2-propanol, 1-butanol, 2-butanol, 2-methyl-1-propanol, and 2-methyl-2-propanol; amides such as formamide, N,N-dimethylformamide, N,N-dimethylacetamide, N-methylpyrrolidone, N,N'-dimethylpropyleneurea, and hexamethylphosphortriamide; sulfoxides such as dimethyl sulfoxide and sulfolane; water; and mixtures thereof.

The acid for use in the reaction of each step in the method A, method B, method C, method D and method E mentioned below is not particularly limited as long as the acid does not inhibit the reaction. The acid is selected from the following acid group: inorganic acids such as hydrochloric acid, hydrobromic acid, hydroiodic acid, phosphoric acid, sulfuric acid, and nitric acid; organic acids such as formic acid, acetic acid, propionic acid, trifluoroacetic acid, and pentafluoropropionic acid; and organic sulfonic acids such as methanesulfonic acid, trifluoromethanesulfonic acid, p-toluenesulfonic acid, and camphorsulfonic acid.

The base for use in the reaction of each step in the method A, method B, method C, method D and method E mentioned below is not particularly limited as long as the base does not inhibit the reaction. The base is selected from the following base group: alkali metal carbonates such as lithium carbonate, sodium carbonate, potassium carbonate, and cesium carbonate; alkali metal bicarbonates such as lithium bicarbonate, sodium bicarbonate, and potassium bicarbonate; alkali metal hydroxides such as lithium hydroxide, sodium hydroxide, and potassium hydroxide; alkaline earth metal hydroxides such as calcium hydroxide and barium hydroxide; alkali metal phosphates such as sodium phosphate and potassium phosphate; alkali metal hydrides such as lithium hydride, sodium hydride, and potassium hydride; alkali metal amides such as lithium amide, sodium amide, and potassium amide; metal alkoxides such as lithium methoxide, sodium methoxide, sodium ethoxide, sodium tert-butoxide, and potassium tert-butoxide; lithium amides such as lithium diisopropylamide (LDA), lithium cyclohexylisopropylamide, and lithium tetramethylpiperazide; alkali metal silylamides such as lithium bistrimethylsilylamide, sodium bistrimethylsilylamide, and potassium bistrimethylsilylamide; alkyllithiums such as methyllithium, n-butyllithium, sec-butyllithium, and tert-butyllithium; alkyl magnesium halides such as methyl magnesium chloride, methyl magnesium bromide, methyl magnesium iodide, ethyl magnesium chloride, ethyl magnesium bromide, isopropyl magnesium chloride, isopropyl magnesium bromide, and isobutyl magnesium chloride; and organic amines such as triethylamine, tributylamine, diisopropylethylamine, diethylamine, diisopropylamine, N-methylpiperidine, N-methylmorpholine, N-ethylmorpholine, pyridine, picoline, 2,6-lutidine, 4-(N,N-dimethylamino)pyridine, N,N-dimethylaniline, N,N-diethylaniline, 1,5-diazabicyclo[4,3,0]non-5-ene, 1,4-diazabicyclo[2,2,2]octane (DABCO), and 1,8-diazabicyclo [5,4,0]-7-undecene (DBU).

In the reaction of each step in the method A, method B, method C, method D and method E mentioned below, the reaction temperature differs depending on solvents, starting materials, reagents, etc., and the reaction time differs depending on solvents, starting materials, reagents, etc.

After the completion of the reaction of each step in the method A, method B, method C, method D and method E mentioned below, the compound of interest of each step is isolated from the reaction mixture according to a routine method. The compound of interest is obtained, for example, by: (i) if necessary, filtering off insoluble matter such as a catalyst; (ii) adding water and a water-immiscible solvent (e.g., methylene chloride, chloroform, diethyl ether, ethyl acetate, or toluene) to the reaction mixture to extract the compound of interest; (iii) washing the organic layer with water, followed by drying using a desiccant such as anhydrous sodium sulfate or anhydrous magnesium sulfate; and (iv) distilling off the solvent. The obtained compound of interest can be further purified, if necessary, by a routine method, for example, recrystallization, reprecipitation, or silica gel column chromatography. Alternatively, the compound of interest of each step may be used directly in the next reaction without being purified.

In the reaction of each step in the method A, method B, method C, method D and method E mentioned below, optical isomers can be resolved by resolution using a chiral column.

Hereinafter, the reaction of each step in the method A, method B, method C, method D and method E will be described.

(Step A-1)

Step A-1 is the step of condensing compound (1) with compound (2) to produce compound (3). The compound (1) and (2) are known in the art or is easily obtained from a compound known in the art.

The method for condensing a carboxylic acid with an amine differs depending on the type of the carboxylic acid and can be generally carried out by a method well known in the techniques of organic synthetic chemistry, for example, a method described in Comprehensive Organic Transformations (Second Edition, 1999, John Wiley & Sons, Inc., pp. 1929-1930, 1941-1949, and 1953-1954). A preferred method involves converting the carboxylic acid to a corresponding acid halide, which is then condensed with a corresponding amine. Thus, step A-1 comprises:

(step A-1-1): the step of reacting compound (1) with a halogenating agent; and (step A-1-2): the step of reacting the compound obtained in the step A-1-1 with compound (2) in the presence of a base.

(Step A-1-1)

Examples of the halogenating agent used can include: thionyl chloride, phosphorus trichloride, phosphorus oxychloride, phosphorus pentachloride, phosphorus tribromide, phosphorus pentabromide, oxalyl chloride, carbon tetrachloride-triphenylphosphine, hexachloroethane-triphenylphosphine, N-chlorosuccinimide-triphenylphosphine, carbon tetrabromide-triphenylphosphine, and N-bromosuccinimide-triphenylphosphine; and combinations of these halogenating agents with additives such as N,N-dimethylformamide. The halogenating agent is preferably a combination of thionyl chloride with an additive or a combination of oxalyl chloride with an additive, more preferably a combination of oxalyl chloride with N,N-dimethylformamide.

Examples of the solvent used can include aliphatic hydrocarbons, aromatic hydrocarbons, halogenated hydrocarbons, ethers, and esters. The solvent is preferably a halogenated hydrocarbon or an ether, more preferably methylene chloride or tetrahydrofuran.

The reaction temperature is preferably 0° C. to 100° C., more preferably room temperature.

The reaction time is preferably 15 minutes to 6 hours.

(Step A-1-2)

Examples of the base used can include alkali metal carbonates, alkali metal bicarbonates, alkali metal hydrides, lithium amides, alkali metal silylamides, alkyllithiums, and organic amines. The base is preferably an organic amine, more preferably triethylamine or diisopropylethylamine.

Examples of the solvent used can include aliphatic hydrocarbons, aromatic hydrocarbons, halogenated hydrocarbons, ethers, esters, and amides. The solvent is preferably an ether or an amide, more preferably tetrahydrofuran or N,N-dimethylformamide.

The reaction temperature is preferably –78° C. to 100° C., more preferably –20° C. to room temperature.

The reaction time is preferably 15 minutes to 24 hours.

(Step A-2)

Step A-2 is the step of intramolecularly cyclizing the compound (3) obtained in the step A-1-2 in the presence of a base to produce compound (4). The compound (4) of interest of this step can also be converted, if necessary, to another compound (4) of interest through deprotection reaction. The method for converting the obtained compound (4) of interest to another compound (4) of interest by the removal of the protective group differs depending on the type of the protective group and can be generally carried out according to a routine method such as a method well known in the techniques of organic synthetic chemistry, for example, a method described in T. W. Greene, P. G. M. Wuts, Protective Groups in Organic Synthesis Fifth Edition, 2014, John Wiley & Sons, Inc.

When $L^3$ is a 2,4-dimethoxybenzyl group, the method is preferably a method using an acid in the presence of a cation scavenger. Thus, step A-2 comprises:

(step A-2-1): the step of intramolecularly cyclizing the compound (3) obtained in the step A-1-2 in the presence of a base to produce compound (4); and (step A-2-1): the step of deprotection reaction of the compound (4) of interest obtained in the step A-2-1 to produce another compound (4).

(Step A-2-1)

Examples of the base used can include alkali metal carbonates, alkali metal bicarbonates, alkali metal hydrides, alkali metal hydroxides, alkaline earth metal hydroxides, alkali metal alkoxides, lithium amides, alkali metal silylamides, and organic amines. The base is preferably an alkali metal hydride, an alkali metal carbonate, an alkali metal silylamide, or an organic amine, more preferably sodium bistrimethylsilylamide, sodium hydride, potassium carbonate, or cesium carbonate.

Examples of the solvent used can include aliphatic hydrocarbons, aromatic hydrocarbons, halogenated hydrocarbons, alcohols, ethers, esters, nitriles, ketones, and amides. The solvent is preferably an ether, a nitrile, or an amide, more preferably tetrahydrofuran, acetonitrile, or N,N-dimethylformamide.

The reaction temperature is preferably –78° C. to 100° C.

The reaction time is preferably 15 minutes to 24 hours.

(Step A-2-2)

Examples of the acid used can include inorganic acids, organic acids, organic sulfonic acids and mixtures thereof. The acid is preferably a mixture of an organic acid and an organic sulfonic acid, more preferably a mixture of trifluoroacetic acid and trifluoromethanesulfonic acid.

Examples of the cation scavenger used can include anisole, thioanisole, isoamylene, triethylsilane, triisopropylsilane, and triphenylphosphine. The cation scavenger is preferably anisole.

Examples of the solvent used can include aliphatic hydrocarbons, aromatic hydrocarbons, and halogenated hydrocarbons. The solvent is preferably a halogenated hydrocarbon, more preferably chloroform.

The reaction temperature is preferably –10° C. to 60° C.

The reaction time is preferably 30 minutes to 6 hours.

(Step A-3)

Step A-3 is the step of reacting the compound (4) obtained in step A-2-2 with compound (5) to produce compound (6). The compound (5) is known in the art or is easily obtained from a compound known in the art.

The method for triazole ring formation from an amide differs depending on the type of the amide and is not particularly limited as long as the reaction does not influence the other parts of the compound. This reaction can be carried out by, for example, a method involving converting the amide to a chloroimidate, which is then reacted with a corresponding hydrazide, described in L. Johan, J. Martin, Synthetic Communications, 36, 2217 (2006), and a method involving converting the amide to a thioimidate, which is then reacted with a corresponding hydrazide, described in K. D. Robarge, M. S. Dina, T. C. Somers, A. Lee, T. E. Rawson, A. G. Olivero, M. H. Tischler, R. R. Webb II, K. J. Weese, I. Aliagas, B. K. Blackburn, Bioorganic and Medicinal Chemistry, 6, 2345 (1998).

The method is preferably a method involving converting the amide to a thioimidate, which is then reacted with a corresponding hydrazide. Thus, step A-3 comprises:

(Step A-3-1): the step of reacting the compound (4) obtained in step A-2-2 with a sulfurizing agent to produce a thioamide;

(Step A-3-2): the step of reacting the thioamide obtained in step A-3-1 with an alkylating agent in the presence of base to produce a thioimidate; and (Step A-3-3): the step of reacting the thioimideate obtained in step A-3-2 with compound (5) in the presence or absence of an additive to produce compound (6).

(Step A-3-1)

The sulfurizing agent is preferably 2,4-bis(4-methoxyphenyl)-1,3,2,4-dithiadiphosphetane-2,4-disulfide (Lawesson's reagent).

Examples of the solvent used can include aliphatic hydrocarbons, aromatic hydrocarbons, halogenated hydrocarbons, ethers, and mixtures thereof. The solvent is preferably an ether, more preferably tetrahydrofuran.

The reaction temperature is preferably 0° C. to 65° C.

The reaction time is preferably 30 minutes to 24 hours.

(Step A-3-2)

Examples of the alkylating agent used can include methyl halides, ethyl halides, allyl halides, benzyl halids, methyl sulfonates, ethyl sulfonates trimethyloxisonium salts and triethyloxisonium salts. The alkylating agent is preferably methyl halides, and more preferably methyl iodide.

Examples of the base used can include alkali metal carbonates, alkali metal hydrides, lithium amides, and alkali metal silylamides. The base is preferably an alkali metal hydride, more preferably sodium hydride.

Examples of the solvent used can include aliphatic hydrocarbons, aromatic hydrocarbons, halogenated hydrocarbons, ethers, esters, nitriles, ketones, and amides. The solvent is preferably an ether or an amide, more preferably tetrahydrofuran or N,N-dimethylformamide.

The reaction temperature is preferably −20° C. to 60° C.

The reaction time is preferably 15 minutes to 6 hours.

(Step A-3-3)

Examples of the additive used can include inorganic acids, organic acids, organic sulfonic acids.

Alternatively, the additive may not be used. Preferably, the additive is not used.

Examples of the solvent used can include aliphatic hydrocarbons, aromatic hydrocarbons, halogenated hydrocarbons, alcohols, ethers and mixtures thereof. The solvent is preferably an alcohol, more preferably ethanol.

The reaction temperature is preferably room temperature to 100° C.

The reaction time is preferably 1 hour to 48 hours.

(Step A-4)

Step A-4 is the step of reacting the compound (6) obtained in the step A-3-3 with compound (7) in the presence of a base to produce compound (I). The compound (7) is known in the art or is easily obtained from a compound known in the art.

Hereinafter, this step is referred to as step A-4-1 when $L^1$ is a nitro group, as step A-4-2 when $L^1$ is an amino group, and as step A-3-3 when $L^1$ is a halogeno group.

(Step A-4-1)

When $L^1$ is a nitro group, step A-4-1 comprises:

(step A-4-1a): the step of selectively reducing the nitro group of the compound obtained in the step A-3-3 into an amino group; and (step A-4-1b): the step of reacting the compound obtained in the step A-4-1a with compound (7) in the presence of a base to produce compound (I).

(Step A-4-1a)

The method for selectively reducing the nitro group is not particularly limited as long as the method does not influence the other parts of the compound. This method can be generally carried out by a method well known in the techniques of organic synthetic chemistry, for example, a method described in Comprehensive Organic Transformations (Second Edition, 1999, John Wiley & Sons, Inc., pp. 821-828). The method is preferably a catalytic reduction method or a method using a combination of a reducing agent and an additive.

Examples of the metal catalyst for use in the catalytic reduction method can include: palladium catalysts such as palladium on carbon, palladium black, palladium hydroxide on carbon, and palladium on barium sulfate; platinum catalysts such as platinum oxide and platinum black, platinum on carbon; rhodium catalysts such as rhodium on aluminum oxide and chlorotris(triphenylphosphine)rhodium (I); and nickel catalysts such as Raney nickel. The metal catalyst is preferably a palladium catalyst, more preferably 10% palladium on carbon.

The hydrogen pressure in the catalytic reduction method is preferably 1 to 10 atm, more preferably 1 atm.

The solvent for use in the catalytic reduction method is not particularly limited as long as the solvent is inert to this reaction. Examples thereof can include aliphatic hydrocarbons, aromatic hydrocarbons, halogenated hydrocarbons, alcohols, ethers, esters, nitriles, ketones, amides, and mixtures thereof. The solvent is preferably an alcohol, an ether, an amide, or a mixture thereof, more preferably methanol or a mixture of tetrahydrofuran and ethanol.

The reaction temperature in the catalytic reduction method is preferably room temperature to 60° C.

The reaction time in the catalytic reduction method is preferably 1 hour to 24 hours.

The combination of the reagents for use in the reaction using the combination of the reducing agent and the additive is preferably a combination of sodium borohydride and nickel(II) chloride hexahydrate, a combination of zinc powder and acetic acid, a combination of iron powder and acetic acid, or a combination of tin(II) chloride and hydrochloric acid, more preferably a combination of sodium borohydride and nickel(II) chloride hexahydrate.

The solvent for use in the reaction using the combination of the reducing agent and the additive is preferably a mixture of an alcohol and an ether, more preferably a mixture of tetrahydrofuran and methanol.

The reaction temperature in the reaction using the combination of the reducing agent and the additive is preferably 0° C. to room temperature.

The reaction time in the reaction using the combination of the reducing agent and the additive is preferably 5 minutes to 2 hours.

(Step A-4-1b)

Examples of the base used can include alkali metal carbonates, alkali metal bicarbonates, alkali metal hydrides, alkali metal hydroxides, alkali metal alkoxides, lithium amides, alkali metal silylamides, and organic amines. The base is preferably an organic amine, more preferably pyridine.

Examples of the solvent used can include aliphatic hydrocarbons, aromatic hydrocarbons, halogenated hydrocarbons, ethers, esters, nitriles, ketones, and amides. Alternatively, the solvent may not be used. Preferably, the solvent is not used.

The reaction temperature is preferably 0° C. to 100° C., more preferably room temperature to 80° C.

The reaction time is preferably 5 minutes to 24 hours, more preferably 15 minutes to 3 hours.

The reaction for converting the obtained compound (I) of interest obtained in this step to another compound (I) of interest by the removal of the protective group is not particularly limited as long as the reaction does not influence the other parts of the compound. This reaction can be carried out according to a routine method, for example, a method described in T. W. Greene, P. G. M. Wuts, Protective Groups in Organic Synthesis, Fifth Edition, 2014, John Wiley & Sons, Inc.

(Step A-4-2)

When $L^1$ is an amino group, the compound (I) can be produced according to the step A-4-1b.

(Step A-4-3)

When $L^1$ is a halogeno group, step A-4-3 comprises:

(step A-4-3a): the step of converting the bromo group of the compound produced in the step A-3-3 to a N-Boc amide group using a metal catalyst in the presence of a base;

(step A-4-3b): the step of deprotecting the N-Boc group of the compound obtained in the step A-4-3a to form an amino group; and (step A-4-3c): the step of reacting the compound obtained in the step A-4-3b with compound (7) in the presence of a base to produce compound (I).

(Step A-4-3a)

The method for converting the bromo group on the aromatic ring to a N-Boc amide group is not particularly limited as long as the method does not influence the other parts of the compound. This method can be carried out according to a method well known in the techniques of organic synthetic chemistry, for example, a method described in A. P. Dishington, P. D. Johnson, J. G. Kettle, Tetrahedron Letters, 45, 3733 (2004) or S. Bhagwanth, A. G. Waterson, G. M. Adjabeng, K. R. Hornberger, Journal of Organic Chemistry, 74, 4634 (2009).

The metal catalyst used is preferably a combination of tris(dibenzylideneacetone)dipalladium(0) chloroform complex and 9,9-dimethyl-4,5-bis(diphenylphosphino)xanthene (Xantphos™) or a combination of tris(dibenzylideneacetone)dipalladium(0) chloroform complex and di-tert-butyl (2',4',6'-triisopropylbiphenyl-2-yl)phosphine (tBuXPhos™).

The base used is preferably an alkali metal carbonate, an alkali metal phosphate, or an alkali metal alkoxide, and more preferably potassium carbonate, cesium carbonate, potassium phosphate, or sodium tert-butoxide.

Examples of the solvent used can include aliphatic hydrocarbons, aromatic hydrocarbons, halogenated hydrocarbons, alcohols, ethers, esters, nitriles, ketones, amides, and mixtures thereof. The solvent is preferably an aromatic hydrocarbon, an ether, a nitrile, or an amide, more preferably toluene, 1,4-dioxane, acetonitrile, or N,N-dimethylformamide.

The reaction temperature is preferably room temperature to 100° C.

The reaction time is preferably 1 hour to 48 hours.

(Step A-4-3b)

The method for deprotecting the N-Boc group is not particularly limited as long as the method does not influence the other parts of the compound. This method can be carried out according to a routine method, for example, a method described in T. W. Greene, P. G. M. Wuts, Protective Groups in Organic Synthesis, Fifth Edition, 2014, John Wiley & Sons, Inc., pp. 930-946.

(Step A-4-3c)

The compound (I) can be produced according to the step A-4-1b.

When $L^1$ is a bromo group, the compound (I) can also be produced through the reaction of the compound (6) with the following compound (28):

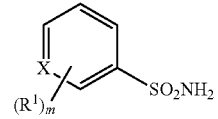

(28)

using a metal catalyst in the presence of a base.

The method for converting the bromo group on the aromatic ring to an arylsulfonamide group is not particularly limited as long as the method does not influence the other parts of the compound. This method can be carried out according to a method well known in the techniques of organic synthetic chemistry, for example, a method described in X. Wang, A. Guram, M. Ronk, J. E. Milne, J. S. Tedrow and M. M. Faul, Tetrahedron Letters, 53, 7 (2012), W. Deng, L. Liu, C. Zhang, M. Liu, and Q.-X. Guo, Tetrahedron Letters, 46, 7295 (2005), or D. K. Luci, J. B. Jameson, A. Yasgar, G. Diaz, N. Joshi, A. Kantz, K. Markham, S. Perry, N. Kuhn, J. Yeung, E. H. Kerns, L. Schultz, M. Holinstat, J. Nadler, D. A. Taylor-Fishwick, A. Jadhav, A. Simeonov, T. R. Holman and D. J. Maloney, Journal of Medicinal Chemistry, 57, 495 (2014).

The metal catalyst used is preferably a combination of copper(I) iodide and N-methyl-2-(methylamino)ethylamine, or a combination of copper(I) iodide and trans-N,N'-dimethylcyclohexane-1,2-diamine.

The base used is preferably an alkali metal carbonate, an alkali metal phosphate, or an alkali metal alkoxide, more preferably potassium carbonate, cesium carbonate, or potassium phosphate.

Examples of the solvent used can include aliphatic hydrocarbons, aromatic hydrocarbons, halogenated hydrocarbons, alcohols, ethers, esters, nitriles, ketones, amides, and mixtures thereof. The solvent is preferably an aromatic hydrocarbon, an ether, a nitrile, or an amide, more preferably xylene, 1,4-dioxane, acetonitrile, or N,N-dimethylformamide.

The reaction temperature is preferably room temperature to 100° C.

The reaction time is preferably 1 hour to 48 hours.

(Step B-1)

Step B-1 is the step of aminating compound (8) to produce compound (9).

The method for aminating a 3-aminopyridine to produce a 3-hydrazinopyridine is not particularly limited as long as the method does not influence the other parts of the compound. This method can be carried out according to a method well known in the techniques of organic synthetic chemistry, for example, a method described in D. Thomae, M. Jeanty, J. Coste, G. Guillaumet and F. Suzenet, European Journal of Organic Chemistry, 16, 3328 (2013), H. Y. Lo, C. C. Man, R. W. FlecK, N. A. Neil, R. H. Ingraham, A. Kukulka, J. R. Proudfoot, R. Betageri, T. Kirrane, U. Patel, R. Sharma, M. A. Hoermann, A. Kabcenell, and S. D. Lombaert, Bioorganic and Medicinal Chemistry Letters, 20, 6379 (2010), or N. Lachance, L.-P. Bonhomme-Beaulieu and P. Joly, Synthesis, 2009, 721.

(Step B-2)

Step B-2 is the step of reacting compound (9) obtained in the step B-1 with compound (10) in the presence or absence of an additive to produce compound (11). The compound (10) is known in the art or is easily obtained from a compound known in the art. The method for reacting a hydrazine with an α,β-unsaturated ketone to produce a pyrazole is not particularly limited as long as the method does not influence the other parts of the compound. This method can be carried out according to a method well known in the techniques of organic synthetic chemistry, for example, a method described in K. Y. Chang, S. H. Kim, G. Nam, J. H. Seo, J. H. Kim and D.-C. Ha, Bioorganic and Medicinal Chemistry Letters, 10, 1211 (2000).

Examples of the additive used can include: inorganic acids such as hydrochloric acid; organic acids such as acetic acid, trifluoroacetic acid; and organic sulfonic acids such as methanesulfonic acid, p-toluenesulfonic acid; alkali metal carbonates such as sodium carbonate, potassium carbonate, and cesium carbonate; alkali metal bicarbonates such as sodium bicarbonate; organic amines such as triethylamine, diisopropylethylamine, N-methylmorpholine, pyridine, 2,6-lutidine. Alternatively, the additive may not be used. The additive is preferably an alkali metal carbonate, more preferably sodium carbonate or potassium carbonate.

Examples of the solvent used can include aliphatic hydrocarbons, aromatic hydrocarbons, halogenated hydrocarbons, alcohols, ethers, water and mixtures thereof. The solvent is preferably an alcohol or a mixture of an alcohol and water, more preferably methanol or a mixture of methanol and water.

The reaction temperature is preferably room temperature to 65° C.

The reaction time is preferably 1 hour to 24 hours.

The compound (11) of interest of this step can also be converted, if necessary, to another compound (11) of interest through deprotection reaction. The method for converting the obtained compound (11) of interest to another compound (11) of interest by the removal of the protective group differs depending on the type of the protective group and can be generally carried out according to a routine method such as a method well known in the techniques of organic synthetic chemistry, for example, a method described in T. W. Greene, P. G. M. Wuts, Protective Groups in Organic Synthesis Fifth Edition, 2014, John Wiley & Sons, Inc.

(Step B-3)

Step B-3 is the step of cyclizing compound (11) obtained in the step B-2 in the presence of a base to produce compound (12).

When $L^5$ is a silyl group, the compound (12) can be produced by deprotection reaction of the silyl group. The method for deprotection reaction is preferably a method using a base.

Examples of the base used can include an alkali metal hydroxides, alkaline earth metal hydroxides, an alkali metal fluorides, or tetra(C1-6 alkyl)ammonium fluorides. The base is preferably a tetra(C1-6 alkyl)ammonium fluoride, and more preferably tetra-n-butylammonium fluoride.

The solvent used is preferably an ether, and more preferably tetrahydrofuran.

The reaction temperature is preferably room temperature to 65° C.

The reaction time is preferably 1 hour to 48 hours.

When $L^5$ is a hydrogen atom, the compound (12) can be produced according to the Step A-2-1.

(Step B-4)

Step B-4 is the step of reacting the compound (12) obtained in the step B-3 with compound (7) in the presence of a base to produce compound (I).

When $L^1$ is a nitro group, the compound (I) can be produced according to the step A-4-1.

When $L^1$ is an amino group, the compound (I) can be produced according to the step A-4-1b.

When $L^1$ is a halogeno group, the compound (I) can be produced according to the step A-4-3.

(Step C-1)

Step C-1 is the step of reacting compound (13) with compound (14) in the presence of an ammonium source to produce compound (15). The compound (14) is known in the art or is easily obtained from a compound known in the art.

The method for reacting an aldehyde with a 1,2-diketone in the presence of an ammonium source to produce an imidazole is not particularly limited as long as the method does not influence the other parts of the compound. This method can be carried out according to a method well known in the techniques of organic synthetic chemistry, for example, a method described in J. Chen, Z. Wang, C.-M. Li, Y. Lu, P. K. Vaddady, B. Meibohm, J. T. Dalton, D. D. Miller and W. Li, Journal of Medicinal Chemistry, 53, 7414 (2010) or M. A. Toledo, C. Pedregal, C. Lafuente, N. Diaz, M. A. Martinez-Grau, A. Jimenez, A. Benito, A. Torrado, C. Mateos, E. M. Joshi, S. D. Kahl, K. S. Rash, D. R. Mudra, V. N. Barth, D. B. Shaw, D. McKinzie, J. M. Witkin and M. A. Statnick, Journal of Medicinal Chemistry, 57, 3418 (2014).

The ammonium source used is preferably ammonia or ammonium acetate.

The solvent used is preferably an alcohol or a mixture of an alcohol and water, and more preferably a mixture of methanol and water or a mixture of isopropanol and water.

The reaction temperature is preferably 0 to 80° C.

The reaction time is preferably 1 hour to 4 days.

(Step C-2)

Step C-2 is the step of reacting compound (15) obtained in the step C-1 with compound (16) in the presence of a base to produce compound (17). The compound (16) is known in the art or is easily obtained from a compound known in the art.

Examples of the base used can include alkali metal carbonates, alkali metal hydrides, lithium amides, and alkali metal silylamides. The base is preferably an alkali metal carbonate, more preferably potassium carbonate or cesium carbonate.

Examples of the solvent used can include aliphatic hydrocarbons, aromatic hydrocarbons, halogenated hydrocarbons, ethers, esters, nitriles, ketones, and amides. The solvent is preferably an amide, more preferably N,N-dimethylformamide.

The reaction temperature is preferably 0° C. to 80° C.

The reaction time is preferably 15 minutes to 24 hours.

(Step C-3)

Step C-3 is the step of cyclizing compound (17) obtained in the step C-2 in the presence of a base to produce compound (18).

When $L^5$ is a silyl group, the compound (18) can be produced according to the Step B-3

When $L^5$ is a hydrogen atom, the compound (18) can be produced according to the Step A-2-1.

(Step C-4)

Step C-4 is the step of reacting the compound (18) obtained in the step C-3 with compound (7) in the presence of a base to produce compound (I).

When $L^1$ is a nitro group, the compound (I) can be produced according to the step A-4-1.

When $L^1$ is an amino group, the compound (I) can be produced according to the step A-4-1b.

When $L^1$ is a halogeno group, the compound (I) can be produced according to the step A-4-3.

(Step D-1)

Step D-1 is the step of condensing compound (19) with compound (20) to produce compound (21). The compound (20) is known in the art or is easily obtained from a compound known in the art.

The method for condensing a ketone with an acetal to produce α,β-unsaturated ketone is not particularly limited as long as the method does not influence the other parts of the compound. This method can be carried out according to a method well known in the techniques of organic synthetic chemistry, for example, a method described in D. W. Boykin, A. Kumar, M. Bajic, G. Xiao, W. D. Wilson, B. C. Bender, D. R. McCurdy, J. E. Hall and R. R. Tidwell, European Journal of Medicinal Chemistry, 32, 965 (1997) or I. M. El-Deeb, M. Ibrahim and S. H. Lee, Bioorganic and Medicinal Chemistry, 18, 3860(2010).

Examples of the solvent used can include aliphatic hydrocarbons, aromatic hydrocarbons, halogenated hydrocarbons, ethers, and amides. Alternatively, the solvent may not be used. Preferably, the solvent is not used.

The reaction temperature is preferably room temperature to 140° C.

The reaction time is preferably 30 minutes to 12 hours.

(Step D-2)

Step D-2 is the step of reacting compound (21) obtained in the step D-1 with compound (22) in the presence or absence of an additive to produce compound (23). The compound (22) is known in the art or is easily obtained from a compound known in the art. The compound (23) of interest of this step can also be converted, if necessary, to another compound (23) of interest through deprotection reaction. The method for converting the obtained compound (23) of interest to another compound (23) of interest by the removal of the protective group differs depending on the type of the protective group and can be generally carried out according to a routine method such as a method well known in the techniques of organic synthetic chemistry, for example, a method described in T. W. Greene, P. G. M. Wuts, Protective Groups in Organic Synthesis Fifth Edition, 2014, John Wiley & Sons, Inc.

Examples of the additive used can include: inorganic acids such as hydrochloric acid; organic acids such as acetic acid, trifluoroacetic acid; and organic sulfonic acids such as methanesulfonic acid, p-toluenesulfonic acid; alkali metal carbonates such as sodium carbonate, potassium carbonate, and cesium carbonate; alkali metal bicarbonates such as sodium bicarbonate; organic amines such as triethylamine, diisopropylethylamine, N-methylmorpholine, pyridine, 2,6-lutidine. Alternatively, the additive may not be used. The additive is preferably an organic acid, more preferably acetic acid.

Examples of the solvent used can include aliphatic hydrocarbons, aromatic hydrocarbons, halogenated hydrocarbons, alcohols, ethers, water and mixtures thereof. The solvent is preferably an alcohol or a mixture of an alcohol and water, more preferably ethanol or a mixture of ethanol and water.

The reaction temperature is preferably room temperature to 90° C.

The reaction time is preferably 1 hour to 24 hours.

(Step D-3)

Step D-3 is the step of cyclizing compound (23) obtained in the step D-2 in the presence of a base to produce compound (24).

When $L^5$ is a silyl group, the compound (24) can be produced according to the Step B-3

When $L^5$ is a hydrogen atom, the compound (24) can be produced according to the Step A-2-1.

(Step D-4)

Step D-4 is the step of reacting the compound (24) obtained in the step D-3 with compound (7) in the presence of a base to produce compound (I).

When $L^1$ is a nitro group, the compound (I) can be produced according to the step A-4-1.

When $L^1$ is an amino group, the compound (I) can be produced according to the step A-4-1b.

When $L^1$ is a halogeno group, the compound (I) can be produced according to the step A-4-3.

(Step E-1)

Step E-1 is the step of reacting compound (1) with compound (25) and compound (22) to produce compound (26). The compound (25) is known in the art or is easily obtained from a compound known in the art.

The method for reacting a carboxylic acid with a primary amidine followed by reaction with a mono-substituted hydrazine to produce a 1,3,4-triazole is not particularly limited as long as the method does not influence the other parts of the compound. For example, this method can be carried out according to a method described in G. M. Castanedo, P. S. Seng, N. Blaquiere and S. T. Staben, Journal of Organic Chemistry, 76, 1177 (2011).

(Step E-2)

Step E-2 is the step of cyclizing compound (26) obtained in the step E-2 in the presence of a base to produce compound (27).

When $L^5$ is a silyl group, the compound (27) can be produced according to the Step B-3

When $L^5$ is a hydrogen atom, the compound (27) can be produced according to the Step A-2-1.

(Step E-3)

Step E-3 is the step of reacting the compound (27) obtained in the step E-2 with compound (7) in the presence of a base to produce compound (I).

When $L^1$ is a nitro group, the compound (I) can be produced according to the step A-4-1.

When $L^1$ is an amino group, the compound (I) can be produced according to the step A-4-1b.

When $L^1$ is a halogeno group, the compound (I) can be produced according to the step A-4-3.

(Step F-1)

Step F-1 is the step of condensing compound (1) with compound (29) to produce compound (30). The compound (1) and (29) are known in the art or is easily obtained from a compound known in the art.

The method for condensing a carboxylic acid with an amine differs depending on the type of the carboxylic acid and can be generally carried out by a method well known in the techniques of organic synthetic chemistry, for example, a method described in Comprehensive Organic Transformations (Second Edition, 1999, John Wiley & Sons, Inc., pp. 1929-1930, 1941-1949, and 1953-1954). A preferred method involves converting the carboxylic acid to a corresponding acid halide, which is then condensed with a corresponding amine. Thus, step F-1 comprises:

(step F-1-1): the step of reacting compound (1) with a halogenating agent; and (step F-1-2): the step of reacting the compound obtained in the step F-1-1 with compound (29) in the presence of a base.

(Step F-1-1)

Examples of the halogenating agent used can include: thionyl chloride, phosphorus trichloride, phosphorus oxychloride, phosphorus pentachloride, phosphorus tribromide, phosphorus pentabromide, oxalyl chloride, carbon tetrachloride-triphenylphosphine, hexachloroethane-triphenylphosphine, N-chlorosuccinimide-triphenylphosphine, carbon tetrabromide-triphenylphosphine, and N-bromosuccinimide-triphenylphosphine; and combinations of these halogenating agents with additives such as N,N-dimethylformamide. The halogenating agent is preferably a combination of thionyl chloride with an additive or a combination of oxalyl chloride with an additive, more preferably a combination of oxalyl chloride with N,N-dimethylformamide.

Examples of the solvent used can include aliphatic hydrocarbons, aromatic hydrocarbons, halogenated hydrocarbons, ethers, and esters. The solvent is preferably a halogenated hydrocarbon or an ether, more preferably methylene chloride or tetrahydrofuran.

The reaction temperature is preferably 0° C. to 100° C., more preferably room temperature.

The reaction time is preferably 15 minutes to 6 hours.

(Step F-1-2)

Examples of the base used can include alkali metal carbonates, alkali metal bicarbonates, alkali metal hydrides, lithium amides, alkali metal silylamides, alkyllithiums, and organic amines. The base is preferably an organic amine, more preferably triethylamine or diisopropylethylamine.

Examples of the solvent used can include aliphatic hydrocarbons, aromatic hydrocarbons, halogenated hydrocarbons, ethers, esters, and amides. The solvent is preferably an ether or an amide, more preferably tetrahydrofuran or N,N-dimethylformamide.

The reaction temperature is preferably −78° C. to 100° C., more preferably −20° C. to room temperature.

The reaction time is preferably 15 minutes to 24 hours.

(Step F-2)

Step F-2 is the step of intramolecularly cyclizing the compound (30) obtained in the step F-1-2 in the presence of a base to produce compound (31). The compound (31) of interest of this step can also be converted, if necessary, to another compound (31) of interest through chemical modification. The method for converting the obtained compound (31) of interest to another compound (31) of interest differs depending on the type of the functional group and can be generally carried out according to a routine method such as a method well known in the techniques of organic synthetic chemistry, for example, a method described in Comprehensive Organic Transformations, Second Edition, 1999, John Wiley & Sons, Inc.

Examples of the base used can include alkali metal carbonates, alkali metal bicarbonates, alkali metal hydrides, alkali metal hydroxides, alkaline earth metal hydroxides, alkali metal alkoxides, lithium amides, alkali metal silylamides, and organic amines. The base is preferably an alkali metal hydride, an alkali metal carbonate, an alkali metal silylamide, or an organic amine, more preferably sodium bistrimethylsilylamide, sodium hydride, potassium carbonate, or cesium carbonate.

Examples of the solvent used can include aliphatic hydrocarbons, aromatic hydrocarbons, halogenated hydrocarbons, alcohols, ethers, esters, nitriles, ketones, and amides. The solvent is preferably an ether, a nitrile, or an amide, more preferably tetrahydrofuran, acetonitrile, or N,N-dimethylformamide.

The reaction temperature is preferably −78° C. to 100° C.

The reaction time is preferably 15 minutes to 24 hours.

(Step F-3)

Step F-3 is the step of reacting the compound (31) obtained in the step F-2 with compound (32) in the presence of a base to produce compound (I). The compound (32) is known in the art or is easily obtained from a compound known in the art.

Hereinafter, this step is referred to as step F-3-1 when $L^1$ is a nitro group, as step F-3-2 when $L^1$ is an amino group, and as step F-3-3 when $L^1$ is a halogeno group.

(Step F-3-1)

When $L^1$ is a nitro group, step F-3-1 comprises:

(step F-3-1a): the step of selectively reducing the nitro group of the compound obtained in the step F-2 into an amino group; and (step F-3-1b): the step of reacting the compound obtained in the step F-3-1a with compound (32) in the presence of a base to produce compound (I).

(Step F-3-1a)

The method for selectively reducing the nitro group is not particularly limited as long as the method does not influence the other parts of the compound. This method can be generally carried out by a method well known in the techniques of organic synthetic chemistry, for example, a method described in Comprehensive Organic Transformations (Second Edition, 1999, John Wiley & Sons, Inc., pp. 821-828). The method is preferably a catalytic reduction method or a method using a combination of a reducing agent and an additive.

Examples of the metal catalyst for use in the catalytic reduction method can include: palladium catalysts such as palladium on carbon, palladium black, palladium hydroxide on carbon, and palladium on barium sulfate; platinum catalysts such as platinum oxide and platinum black, platinum on carbon; rhodium catalysts such as rhodium on aluminum oxide and chlorotris(triphenylphosphine)rhodium (I); and nickel catalysts such as Raney nickel. The metal catalyst is preferably a palladium catalyst, more preferably 10% palladium on carbon.

The hydrogen pressure in the catalytic reduction method is preferably 1 to 10 atm, more preferably 1 atm.

The solvent for use in the catalytic reduction method is not particularly limited as long as the solvent is inert to this reaction. Examples thereof can include aliphatic hydrocarbons, aromatic hydrocarbons, halogenated hydrocarbons, alcohols, ethers, esters, nitriles, ketones, amides, and mixtures thereof. The solvent is preferably an alcohol, an ether, an amide, or a mixture thereof, more preferably methanol or a mixture of tetrahydrofuran and ethanol.

The reaction temperature in the catalytic reduction method is preferably room temperature to 60° C.

The reaction time in the catalytic reduction method is preferably 1 hour to 24 hours.

The combination of the reagents for use in the reaction using the combination of the reducing agent and the additive is preferably a combination of sodium borohydride and nickel(II) chloride hexahydrate, a combination of zinc powder and acetic acid, a combination of iron powder and acetic acid, or a combination of tin(II) chloride and hydrochloric acid, more preferably a combination of sodium borohydride and nickel(II) chloride hexahydrate.

The solvent for use in the reaction using the combination of the reducing agent and the additive is preferably a mixture of an alcohol and an ether, more preferably a mixture of tetrahydrofuran and methanol.

The reaction temperature in the reaction using the combination of the reducing agent and the additive is preferably 0° C. to room temperature.

The reaction time in the reaction using the combination of the reducing agent and the additive is preferably 5 minutes to 2 hours.

(Step F-3-1b)

Examples of the base used can include alkali metal carbonates, alkali metal bicarbonates, alkali metal hydrides, alkali metal hydroxides, alkali metal alkoxides, lithium amides, alkali metal silylamides, and organic amines. The base is preferably an organic amine, more preferably pyridine.

Examples of the solvent used can include aliphatic hydrocarbons, aromatic hydrocarbons, halogenated hydrocarbons, ethers, esters, nitriles, ketones, and amides. Alternatively, the solvent may not be used. Preferably, the solvent is not used.

The reaction temperature is preferably 0° C. to 100° C., more preferably room temperature to 80° C.

The reaction time is preferably 5 minutes to 24 hours, more preferably 15 minutes to 3 hours.

The reaction for converting the obtained compound (I) of interest obtained in this step to another compound (I) of interest by the removal of the protective group is not particularly limited as long as the reaction does not influence the other parts of the compound. This reaction can be carried out according to a routine method, for example, a method described in T. W. Greene, P. G. M. Wuts, Protective Groups in Organic Synthesis, Fifth Edition, 2014, John Wiley & Sons, Inc.

(Step F-3-2)

When $L^1$ is an amino group, the compound (I) can be produced according to the step F-3-1b.

(Step F-3-3)

When $L^1$ is a halogeno group, step F-3-3 comprises:

(step F-3-3a): the step of converting the bromo group of the compound produced in the step F-2 to a N-Boc amide group using a metal catalyst in the presence of a base;

(step F-3-3b): the step of deprotecting the N-Boc group of the compound obtained in the step F-3-3a to form an amino group; and (step F-3-3c): the step of reacting the compound obtained in the step F-3-3b with compound (32) in the presence of a base to produce compound (I).

(Step F-3-3a)

The method for converting the bromo group on the aromatic ring to a N-Boc amide group is not particularly limited as long as the method does not influence the other parts of the compound. This method can be carried out according to a method well known in the techniques of organic synthetic chemistry, for example, a method described in A. P. Dishington, P. D. Johnson, J. G. Kettle, Tetrahedron Letters, 45, 3733 (2004) or S. Bhagwanth, A. G. Waterson, G. M. Adjabeng, K. R. Hornberger, Journal of Organic Chemistry, 74, 4634 (2009)

The metal catalyst used is preferably a combination of tris(dibenzylideneacetone)dipalladium(0) chloroform complex and 9,9-dimethyl-4,5-bis(diphenylphosphino)xanthene (Xantphos™) or a combination of tris(dibenzylideneacetone)dipalladium(0) chloroform complex and di-tert-butyl (2',4',6'-triisopropylbiphenyl-2-yl)phosphine (tBuXPhos™).

The base used is preferably an alkali metal carbonate, an alkali metal phosphate, or an alkali metal alkoxide, and more preferably potassium carbonate, cesium carbonate, potassium phosphate, or sodium tert-butoxide.

Examples of the solvent used can include aliphatic hydrocarbons, aromatic hydrocarbons, halogenated hydrocarbons, alcohols, ethers, esters, nitriles, ketones, amides, and mixtures thereof. The solvent is preferably an aromatic hydrocarbon, an ether, a nitrile, or an amide, more preferably toluene, 1,4-dioxane, acetonitrile, or N,N-dimethylformamide.

The reaction temperature is preferably room temperature to 100° C.

The reaction time is preferably 1 hour to 48 hours.

(Step F-3-3b)

The method for deprotecting the N-Boc group is not particularly limited as long as the method does not influence the other parts of the compound. This method can be carried out according to a routine method, for example, a method described in T. W. Greene, P. G. M. Wuts, Protective Groups in Organic Synthesis, Fifth Edition, 2014, John Wiley & Sons, Inc., pp. 930-946.

(Step F-3-3c)

The compound (I) can be produced according to the step F-3-1b.

When $L^1$ is a bromo group, the compound (I) can also be produced through the reaction of the compound (31) with the compound (32) using a metal catalyst in the presence of a base.

The method for converting the bromo group on the aromatic ring to an arylsulfonamide group is not particularly limited as long as the method does not influence the other parts of the compound. This method can be carried out according to a method well known in the techniques of organic synthetic chemistry, for example, a method described in X. Wang, A. Guram, M. Ronk, J. E. Milne, J. S. Tedrow and M. M. Faul, Tetrahedron Letters, 53, 7 (2012), W. Deng, L. Liu, C. Zhang, M. Liu, and Q.-X. Guo, Tetrahedron Letters, 46, 7295 (2005), or D. K. Luci, J. B. Jameson, A. Yasgar, G. Diaz, N. Joshi, A. Kantz, K. Markham, S. Perry, N. Kuhn, J. Yeung, E. H. Kerns, L. Schultz, M. Holinstat, J. Nadler, D. A. Taylor-Fishwick, A. Jadhav, A. Simeonov, T. R. Holman and D. J. Maloney, Journal of Medicinal Chemistry, 57, 495 (2014).

The metal catalyst used is preferably a combination of copper(I) iodide and N-methyl-2-(methylamino)ethylamine, or a combination of copper(I) iodide and trans-N,N'-dimethylcyclohexane-1,2-diamine.

The base used is preferably an alkali metal carbonate, an alkali metal phosphate, or an alkali metal alkoxide, more preferably potassium carbonate, cesium carbonate, or potassium phosphate.

Examples of the solvent used can include aliphatic hydrocarbons, aromatic hydrocarbons, halogenated hydrocarbons, alcohols, ethers, esters, nitriles, ketones, amides, and mixtures thereof. The solvent is preferably an aromatic hydrocarbon, an ether, a nitrile, or an amide, more preferably xylene, 1,4-dioxane, acetonitrile, or N,N-dimethylformamide.

The reaction temperature is preferably room temperature to 100° C.

The reaction time is preferably 1 hour to 48 hours.

When A is represented by the general formula (IIg) and (IIh), the compound represented by the general formula (I) of the present invention can be produced according to the methods A-F.

When the compound represented by the general formula (I) of the present invention or the pharmacologically acceptable salt thereof is used as a pharmaceutical, the compound or the salt can be administered alone (i.e., as a bulk) or can be administered orally as an appropriate pharmaceutically acceptable preparation such as a tablet, a capsule, granules, a powder, or a syrup or parenterally as an appropriate pharmaceutically acceptable preparation such as an injection, a suppository, or a patch (preferably orally).

These preparations are produced by well-known methods using additives such as excipients, binders, disintegrants, lubricants, emulsifiers, stabilizers, corrigents, diluents, solvents for injections, oleaginous bases, and water-soluble bases.

Examples of the excipients can include organic excipients and inorganic excipients. Examples of the organic excipients can include: sugar derivatives such as lactose, saccharose, glucose, mannitol, and sorbitol; starch derivatives such as corn starch, potato starch, α-starch, dextrin, and carboxymethyl starch; cellulose derivatives such as crystalline cellulose, low-substituted hydroxypropylcellulose, hydroxypropylmethylcellulose, carboxymethylcellulose, carboxymethylcellulose calcium, and internally cross-linked carboxymethylcellulose sodium; gum arabic; dextran; and pullulan. Examples of the inorganic excipients can include: light anhydrous silicic acid and silicate derivatives such as synthetic aluminum silicate and calcium silicate; phosphates such as calcium phosphate; and sulfates such as calcium sulfates.

Examples of the binders can include: the excipients listed above; gelatin; polyvinylpyrrolidone; and polyethylene glycol.

Examples of the disintegrants can include: the excipients listed above; chemically modified starch or cellulose derivatives such as croscarmellose sodium and carboxymethyl starch sodium; and cross-linked polyvinylpyrrolidone.

Examples of the lubricants can include: talc; stearic acid; stearic acid metal salts such as calcium stearate and magnesium stearate; colloidal silica; waxes such as bees wax and spermaceti; boric acid; glycol; D,L-leucine; carboxylic acids such as fumaric acid and adipic acid; carboxylic acid sodium salts such as sodium benzoate; sulfates such as sodium sulfate; lauryl sulfates such as sodium lauryl sulfate and magnesium lauryl sulfate; silicic acids such as silicic anhydride and silicic acid hydrate; and the starch derivatives listed as the excipients.

Examples of the emulsifiers can include: colloidal clay such as bentonite and veegum; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester.

Examples of the stabilizers can include: p-hydroxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

Examples of the corrigents can include sweeteners, acidulants, and flavors usually used.

Examples of the diluents can include: water, ethanol, propylene glycol, ethoxylated isostearyl alcohol, and polyoxyethylene sorbitan fatty acid esters.

Examples of the solvents for injections can include: water, ethanol, and glycerin.

Examples of the oleaginous bases can include: cacao butter, laurin butter, coconut oil, palm kernel oil, *Camellia* oil, liquid paraffin, white petrolatum, purified lanoline, glycerin monostearate, polyoxyethylene hydrogenated castor oil, sorbitan fatty acid ester, sucrose fatty acid ester, stearyl alcohol, and cetanol.

Examples of the water-soluble bases can include glycerin, polyethylene glycol, ethanol, and purified water.

The dose of the compound represented by the general formula (I) of the present invention or the pharmacologically acceptable salt thereof serving as an active ingredient differs depending on the symptoms and age of a patient, etc. The single dose thereof is 0.001 mg/kg (preferably 0.01 mg/kg) as the lower limit and 10 mg/kg (preferably 1 mg/kg) as the upper limit for oral administration and 0.001 mg/kg (preferably 0.01 mg/kg) as the lower limit and 10 mg/kg (preferably 1 mg/kg) as the upper limit for parenteral administration and can be administered once to six times a day according to the symptoms.

The compound of the present invention can be used in combination with any of various therapeutic or prophylactic agents for the aforementioned disease for which the compound of the present invention is probably effective. In this combined use, the compound of the present invention and the agent may be administered simultaneously, separately but continuously, or at the desired time interval. The preparations to be administered simultaneously may be formulated as a combination drug or formulated as separate preparations.

The sulfonamide compound or the pharmacologically acceptable salt thereof, which is the compound of the present invention, has an excellent TNAP inhibitory effect and is useful as a therapeutic or prophylactic agent for pseudoxanthoma elasticum (PXE), generalized arterial calcification of infancy (GACI), craniometaphyseal dysplasia (CMD), ossification of the yellow ligament (OYL), arterial calcification due to deficiency of CD73 (ACDC), arthrosis deformans, osteoarthritis, ankylosis of the joint, idiopathic infantile arterial calcification (IIAC), ankylosing spondylitis (AS), tumoral calcinosis (TC), progressive osseous heteroplasia (POH), Keutel syndrome, vascular calcification associated with chronic renal failure (including glomerulonephritis, IgA nephropathy, hypertensive nephropathy, and diabetic nephropathy) and secondary parathyroid hyperplasia, metastatic calcification, calciphylaxis, calcific tendinitis of the longus colli muscle, fibrodysplasia ossificans progressiva (FOP), calcific aortic stenosis, pericarditis calculosa, atherosclerotic vascular calcification, calcific uremic arteriopathy (CUA), Kawasaki disease, calcification due to obesity and aging, tibial arterial calcification, bone metastasis, prosthetic calcification, Paget's disease, or peritoneal calcification. Moreover, the compound of the present invention has low toxicity and excellent safety and as such, is very useful as a pharmaceutical.

DETAILED DESCRIPTION OF THE PREFERRED EMBODIMENTS

Hereinafter, the present invention will be described in more detail with reference to Examples, etc. However, the scope of the present invention is not intended to be limited by them.

The chemical structural formulas described in Examples represent the chemical structures of corresponding compounds in a free form.

Elution in column chromatography in Examples was carried out under observation by thin layer chromatography (TLC). In the TLC observation, silica gel $60F_{254}$ manufactured by Merck KGaA was used as a TLC plate; a solvent used as an eluting solvent in column chromatography was used as a developing solvent; and a UV detector or a chromogenic method using a coloring agent (e.g., a ninhydrin coloring solution, an anisaldehyde coloring solution, an ammonium phosphomolybdate coloring solution, a cerium ammonium nitrate (CAM) coloring solution, or an alkaline permanganate coloring solution) was used as a detection method. Silica gel SK-85 (230-400 mesh) also manufactured by Merck KGaA, silica gel 60 N (40-50 μm) manufactured by Kanto Chemical Co., Inc., or Chromatorex NH (200-350 mesh) manufactured by Fuji Silysia Chemical Ltd. was used as silica gel for columns. In addition to general column chromatography, an automatic chromatography apparatus (Purif-α2 or Purif-espoir2) manufactured by Shoko Scientific Co., Ltd., an automatic chromatography apparatus (W-Prep 2XY) manufactured by Yamazen Corp., an automatic chromatography apparatus (Isolera One) manufactured by Biotage Japan Ltd., or an automatic chromatography apparatus (CombiFlash Rf) manufactured by Teledyne Isco, Inc. was appropriately used. The eluting solvent was determined on the basis of the TLC observation.

In Examples, nuclear magnetic resonance ($^1$H NMR) spectra were indicated by chemical shift δ values (ppm) determined with tetramethylsilane as a standard. Splitting patterns were indicated by s for singlet, d for doublet, t for triplet, q for quartet, m for multiplet, and br for broad. Mass spectrometry (hereinafter, referred to as MS) was conducted by the electron ionization (EI), electron spray ionization (ESI), atmospheric pressure chemical ionization (APCI), electron spray atmospheric pressure chemical ionization (ES/APCI), or fast atom bombardment (FAB) method.

In each step of Examples, the adjustment of a reaction solution and reaction were carried out at room temperature unless the temperature is otherwise specified.

EXAMPLES (Example 1) 5-chloro-2-methoxy-N-(3-methyl-5,6-dihydropyrido[3,2-f][1,2,4]triazolo[4,3-d][1,4]oxazepin-10-yl)benzenesulfonamide

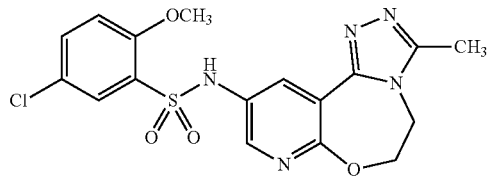 [SMILES: COc1ccc(Cl)cc1S(=O)(=O)Nc1cnc2c(c1)-c1nnc(C)n1CCO2]

(1a) 2-[(2,4-Dimethoxybenzyl)amino]ethanol

To a mixture of 2,4-dimethoxybenzaldehyde (16.20 g, 97.5 mmol) and 2-aminoethanol (5.98 g, 97.9 mmol) in methanol (120 mL), anhydrous sodium sulfate (6.23 g, 43.9 mmol) was added, and the mixture was stirred at room temperature for 20 hours. Subsequently, to the mixture, sodium borohydride (1.84 g, 48.6 mmol) was added over 15 minutes, and the mixture was stirred at 22° C. for 30 minutes. To the reaction mixture, acetic acid (2.8 mL, 49 mmol) was added, and the mixture was stirred for 10 minutes and concentrated into approximately ½ of the amount under reduced pressure. The concentrated mixture was diluted by addition of water and a saturated aqueous solution of sodium bicarbonate, followed by extraction with methylene chloride. The organic layer was washed with a saturated aqueous solution of sodium chloride and dried over anhydrous sodium sulfate. After filtration, the solvent was distilled off under reduced pressure. To the residue, n-hexane (100 mL) and ethyl acetate (4 mL) were added, and the precipitated solid was collected by filtration, washed with n-hexane, and then dried to obtain the title compound (18.44 g, yield: 90%).

$^1$H NMR spectrum (CDCl$_3$, 400 MHz) δ: 7.12 (1H, d, J=8.2 Hz), 6.47-6.42 (2H, m), 3.82 (3H, s), 3.80 (3H, s), 3.74 (2H, S), 3.65-3.63 (2H, m), 2.76-2.74 (2H, m).

(1b) 2-Chloro-N-(2,4-dimethoxybenzyl)-N-(2-hydroxyethyl)-5-nitropyridine-3-carboxamide To a suspension of 2-chloro-5-nitropyridine-3-carboxylic acid (4.91 g, 24.2 mmol) and oxalyl chloride (2.6 mL, 30 mmol) in methylene chloride (120 mL), N,N-dimethylformamide (0.10 mL, 1.3 mmol) was added at room temperature, and the mixture was stirred at the same temperature as above for 30 minutes. The reaction mixture was concentrated under reduced pressure to prepare a crude product of 2-chloro-5-nitropyridine-3-carboxylic acid chloride. To a solution of 2-[(2,4-dimethoxybenzyl)amino]ethanol (5.11 g, 24.2 mmol) obtained in Example (1a) and N,N-diisopropylethylamine (8.25 mL, 48.5 mmol) in tetrahydrofuran (50 mL), a solution of the crude product of 2-chloro-5-nitropyridine-3-carboxylic acid chloride in tetrahydrofuran (70 mL) was added over 20 minutes under ice cooling, and the reaction mixture was stirred at the same temperature as above for 90 minutes. To the reaction mixture, water (0.05 mL) was added, and then, the mixture was concentrated under reduced pressure. The concentrated mixture was diluted by addition of water, followed by extraction with ethyl acetate. The organic layer was washed with water and a saturated aqueous solution of sodium chloride, and anhydrous magnesium sulfate and charcoal were added thereto. After filtration through pad of Celite 545 ®, the solvent was distilled off under reduced pressure. To the residue, diisopropyl ether (50 mL) and ethyl acetate (10 mL) were added to precipitate a solid. The suspension was stirred at room temperature for 30 minutes. The precipitated solid was collected by filtration, washed with a mixed solvent of diisopropyl ether/ethyl acetate=5/1, and then dried to obtain the title compound (8.30 g, yield: 87%).

$^1$H NMR spectrum (CDCl$_3$, 400 MHz) δ: 9.24 (0.8H, d, J=2.7 Hz), 9.21 (0.2H, d, J=2.7 Hz), 8.57 (0.2H, d, J=2.7 Hz), 8.44 (0.8H, d, J=2.7 Hz), 7.38 (0.2H, d, J=8.2 Hz), 6.99 (0.8H, d, J=8.2 Hz), 6.54-6.48 (0.4H, m), 6.45-6.40 (1.6H, m), 5.13 (0.2H, d, J=14.9 Hz), 4.53 (0.2H, d, J=14.9 Hz), 4.38-3.54 (10.8H, m), 3.24-3.19 (0.4H, t, J=5.1 Hz), 2.42 (0.4H, t, J=5.1 Hz).

(1c) 4-(2,4-Dimethoxybenzyl)-7-nitro-3,4-dihydropyrido[3,2-f][1,4]oxazepin-5(2H)-one A solution of sodium bis(trimethylsilyl)amide in tetrahydrofuran (ca. 1.9 mol/L, 14.4 mL, 27.4 mmol) was diluted with tetrahydrofuran (450 mL). A solution of 2-chloro-N-(2,4-dimethoxybenzyl)-N-(2-hydroxyethyl)-5-nitropyridine-3-carboxamide (7.22 g, 18.2 mmol) obtained in Example (1b) in tetrahydrofuran (450 mL) was added thereto over 70 minutes under ice cooling, and the mixture was stirred at the same temperature as above for 10 minutes and further stirred at room temperature for 30 minutes. To the reaction mixture, a saturated aqueous solution of ammonium chloride (100 mL) was added, and then, the reaction mixture was concentrated into approximately ⅓ of the amount under reduced pressure. The concentrated mixture was diluted by addition of water, followed by extraction with ethyl acetate twice. The organic layer was washed with water and a saturated aqueous solution of sodium chloride and dried over anhydrous magnesium sulfate. After filtration, the solvent was distilled off under reduced pressure, and the residue was purified by silica gel column chromatography (ethyl acetate/n-hexane/methylene chloride=1/1/1-3/2/2). To the obtained solid, diisopropyl ether (20 mL) and ethyl acetate (10 mL) were added, and the suspension was stirred at room temperature for overnight. The precipitated solid was collected by filtration, washed with a mixed solvent of diisopropyl ether/ethyl acetate=2/1, and then dried to obtain the title compound (4.18 g, yield: 64%).

$^1$H NMR spectrum (CDCl$_3$, 400 MHz) δ: 9.34 (1H, d, J=2.7 Hz), 9.20 (1H, d, J=2.7 Hz), 7.34-7.32 (1H, m), 6.50-6.48 (2H, m), 4.76 (2H, s), 4.53-4.51 (2H, m), 3.84 (3H, s), 3.81 (3H, s), 3.78-3.76 (2H, m).

(1d) 7-nitro-3,4-dihydropyrido[3,2-f][1,4]oxazepine-5 (2H)-thione

To a solution of 4-(2,4-Dimethoxybenzyl)-7-nitro-3,4-dihydropyrido[3,2-f][1,4]oxazepin-5(2H)-one (2.4261 g, 6.75 mmol) obtained in Example (1c) and anisole (1.48 mL, 13.6 mmol) in chloroform (50 mL), trifluoroacetic acid (15 mL) and trifluoromethanesulfonic acid (1.78 mL, 20.3 mmol) were added, and the mixture was stirred at room temperature for 3 hour. The reaction mixture was concentrated under reduced pressure, and the concentrated mixture was diluted by addition of chloroform and a saturated aqueous solution of sodium bicarbonate, and the mixture was stirred at room temperature for further 30 minutes. A participated solid was collected by filtration to obtain a crude solid. The filtrate was extracted with chloroform and the organic layer dried over anhydrous sodium sulfate. After filtration, the solvent was distilled off under reduced pressure. The residue was combined with the above crude solid, diisopropyl ether was added thereto, and the precipitated solid was collected by filtration again, washed with diisopropyl ether, and then dried to obtain 7-nitro-3,4-dihydropyrido[3,2-f][1,4]oxazepin-5(2H)-one (971.1 mg, yield: 69%). To a suspension of 7-nitro-3,4-dihydropyrido[3,2-f][1,4]oxazepin-5(2H)-one (667 mg, 3.19 mmol) obtained in the above step in tetrahydrofuran (30 mL) was added Lawesson's reagent (785 mg, 1.94 mmol) at room temperature and the mixture was stirred at 50° C. for 3 hours in an oil bath. The reaction mixture was cooled and then concentrated under reduced pressure. The residue was suspended by addition of diisopropyl ether, and the suspension was stirred at room temperature for 3 hours. The precipitated solid was collected by filtration to obtain the title compound (630.5 mg). The filtrate was concentrated under reduced pressure, and the residue was purified in an automatic chromatography apparatus (n-hexane/ethyl acetate=100/0-0/100) to obtain the title compound (254.7 mg; total: 885.2 mg, yield: quantitative).

$^1$H NMR spectrum (CDCl$_3$, 400 MHz) δ: 9.48 (1H, t, J=2.4 Hz), 9.23 (1H, d, J=2.4 Hz), 8.70 (1H, br s), 4.78 (2H, t, J=4.6 Hz), 3.86-3.73 (3H, m).

(1e) 5-(methylsulfanyl)-7-nitro-2,3-dihydropyrido[3,2-f][1,4]oxazepine

To a solution of 7-nitro-3,4-dihydropyrido[3,2-f][1,4]oxazepine-5(2H)-thione (215 mg, 1.11 mmol) obtained in Example (1d) in tetrahydrofuran (15 mL) was added Sodium hydride (63% content, 73 mg, 1.92 mmol) under ice cooling, and the mixture was stirred at the same temperature as above for 15 minutes. Iodomethane (0.139 mL, 2.23 mmol) was added thereto under ice cooling, and the mixture was stirred at room temperature for 40 minutes. The mixture was cooled in ice water bath, and diluted by addition of a saturated aqueous solution of sodium chloride, followed by extraction with ethyl acetate. The organic layer was washed with a saturated aqueous solution of sodium chloride, and dried over anhydrous sodium sulfate. After filtration, the solvent was distilled off under reduced pressure, and the residue was purified in an automatic chromatography apparatus (n-hexane/ethyl acetate=100/0-50/50) to obtain the title compound (107.0 mg, yield: 40%).

$^1$H NMR spectrum (CDCl$_3$, 400 MHz) δ: 9.20 (1H, d, J=3.0 Hz), 8.96 (1H, d, J=3.0 Hz), 4.75 (2H, t, J=4.3 Hz), 4.09 (2H, t, J=4.3 Hz), 2.48 (3H, s).

(1f) 3-methyl-10-nitro-5,6-dihydropyrido[3,2-f][1,2,4]triazolo[4,3-d][1,4]oxazepine To a suspension of 5-(methylsulfanyl)-7-nitro-2,3-dihydropyrido[3,2-f][1,4]oxazepine (107.0 mg, 0.45 mmol) obtained in Example (1e) in ethanol (15 mL) was added acetohydrazide (134 mg, 1.81 mmol) at room temperature, and the mixture was heated to reflux for 23.5 hours in an oil bath. The reaction mixture was cooled and then concentrated under reduced pressure. The precipitated solid was collected by filtration, washed with minimum volume of ethanol to obtain the title compound (50.9 mg). The filtrate was concentrated under reduced pressure, and the residue was purified in an automatic chromatography apparatus (ethyl acetate/methanol=100/0-75/25) to obtain the title compound (34.1 mg; total: 85.0 mg, yield: 77%).

$^1$H NMR spectrum (DMSO-d6, 400 MHz) δ: 9.45 (1H, d, J=2.4 Hz), 9.13 (1H, d, J=2.4 Hz), 4.76-4.74 (3H, m), 4.45-4.43 (3H, m), 2.45 (5H, s).

(1g) 3-methyl-5,6-dihydropyrido[3,2-f][1,2,4]triazolo[4,3-d][1,4]oxazepin-10-amine To a mixture of 3-methyl-10-nitro-5,6-dihydropyrido[3,2-f][1,2,4]triazolo[4,3-d][1,4]oxazepine (85.0 mg, 0.34 mmol) obtained in Example (1f) in tetrahydrofuran (2 mL) and methanol (2 mL), nickel(II) chloride hexahydrate (164 mg, 0.69 mmol) was added. Subsequently, the mixture was cooled in an ice water bath. Sodium borohydride (56 mg, 1.48 mmol) was added thereto, the mixture was stirred at room temperature for 30 minutes. The reaction mixture was diluted by addition of acetone and a saturated aqueous solution of sodium bicarbonate, further Celite 545® (approximately 0.3 g) was added thereto, and the mixture was stirred at room temperature for further 30 minutes. The reaction mixture was filtered, and the filtrate was concentrated under reduced pressure. The residue was purified by reverse-phase silica gel column chromatography (Chromatorex ODS 100-200 mesh, water/methanol=100/0-70/30) to obtain the title compound (67.1 mg, yield: 90%).

$^1$H NMR spectrum (CD$_3$OD, 400 MHz) δ: 8.10 (1H, br d, J=2.4 Hz), 7.73 (1H, br d, J=2.4 Hz), 4.53 (2H, t, J=4.3 Hz), 4.37 (2H, t, J=4.3 Hz), 2.50 (3H, s).

(1h) 5-chloro-2-methoxy-N-(3-methyl-5,6-dihydropyrido[3,2-f][1,2,4]triazolo[4,3-d][1,4]oxazepin-10-yl)benzenesulfonamide To a mixture of 3-methyl-5,6-dihydropyrido[3,2-f][1,2,4]triazolo[4,3-d][1,4]oxazepin-10-amine (67.1 mg, 0.31 mmol) obtained in Example (1g) and pyridine (2 mL, 25 mmol), 5-chloro-2-methoxybenzenesulfonyl chloride (84 mg, 0.35 mmol) was added, and the mixture was stirred at 80° C. for 1.5 hours in an oil bath. The reaction mixture was cooled, and then concentrated under reduced pressure. The residue was diluted by addition of a 1N hydrochloric acid (1 mL) and purified by reverse-phase silica gel column chromatography (Chromatorex ODS 100-200 mesh, water/methanol/chloroform=100/0/0-50/50/0-0/100/0-0/50/50) to obtain the title compound (49.1 mg, yield: 38%).

$^1$H NMR spectrum (DMSO-$d_6$, 400 MHz) δ: 10.39 (1H, s), 8.58 (1H, d, J=2.4 Hz), 8.02 (1H, d, J=2.4 Hz), 7.67-7.64 (2H, m), 7.26 (1H, d, J=9.1 Hz), 4.50-4.49 (2H, m), 4.30-4.28 (2H, m), 3.90 (3H, s), 2.39 (3H, s).

MS spectrum (ES/APCI$^+$): 422 (M+H), 424 (M+2+H).

(Example 2) Potassium [(5-chloro-2-methoxyphenyl)sulfonyl](3-methyl-5,6-dihydropyrido[3,2-f][1,2,4]triazolo[4,3-d][1,4]oxazepin-10-yl)azanide (Potassium Salt of Example 1)

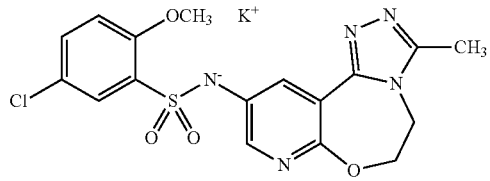 [SMILES: COc1ccc(Cl)cc1S(=O)(=O)[N-]c1cnc2c(c1)-c1nnc(C)n1CCO2 ; [K+]]

To a suspension of 5-chloro-2-methoxy-N-(3-methyl-5,6-dihydropyrido[3,2-f][1,2,4]triazolo[4,3-d][1,4]oxazepin-10-yl)benzenesulfonamide (33.5 mg, 0.079 mmol) obtained in Example (1h) in ethanol (1 mL), a solution of 0.5 N potassium hydroxide in ethanol (0.174 mL, 0.087 mmol) was added at room temperature, and the mixture was stirred at room temperature for 29 hours.

The precipitated solid was collected by filtration, and then dried to obtain the title compound (23.1 mg, yield: 63%).

$^1$H NMR spectrum (DMSO-d6, 400 MHz) δ: 8.25 (1H, d, J=2.4 Hz), 7.67-7.65 (2H, m), 7.34-7.32 (1H, m), 6.99 (1H, br d, J=9.1 Hz), 4.37-4.36 (2H, m), 4.23-4.22 (2H, m), 3.67 (3H, s), 2.37 (3H, s).

(Example 3) 5-chloro-N-(3-ethyl-5,6-dihydropyrido[3,2-f][1,2,4]triazolo[4,3-d][1,4]oxazepin-10-yl)-2-methoxybenzenesulfonamide

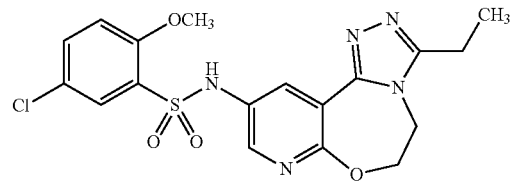 [SMILES: CCc1nnc2n1CCOc1ncc(NS(=O)(=O)c3cc(Cl)ccc3OC)cc1-2]

(3a) 3-ethyl-10-nitro-5,6-dihydropyrido[3,2-f][1,2,4]triazolo[4,3-d][1,4]oxazepine The title compound (140.1 mg, yield: quantitative) was obtained by production according to the method described in Examples (1f) using 5-(methylsulfanyl)-7-nitro-2,3-dihydropyrido[3,2-f][1,4]oxazepine (120 mg, 0.50 mmol) obtained in Example (1e) and propanoic acid hydrazide (90 mg, 1.02 mmol) as starting materials.

$^1$H NMR spectrum (CDCl$_3$, 400 MHz) δ: 9.46 (1H, d, J=3.0 Hz), 9.13 (1H, d, J=3.0 Hz), 4.76-4.74 (2H, m), 4.46-4.45 (2H, m), 2.81 (2H, q, J=7.5 Hz), 1.30 (3H, t, J=7.5 Hz).

(3b) 5-chloro-N-(3-ethyl-5,6-dihydropyrido[3,2-f][1,2,4]triazolo[4,3-d][1,4]oxazepin-10-yl)-2-methoxybenzenesulfonamide The title compound (28.4 mg, yield for 2 steps: 26%) was obtained by production according to the method described in Examples (1g) and (1h) using 3-ethyl-10-nitro-5,6-dihydropyrido[3,2-f][1,2,4]triazolo[4,3-d][1,4]oxazepine (131 mg, 0.50 mmol) obtained in Example (3a) and 5-chloro-2-methoxybenzenesulfonyl chloride (62.5 mg, 0.26 mmol) as starting materials.

$^1$H NMR spectrum (CDCl$_3$, 400 MHz) δ: 9.00-8.97 (1H, m), 8.41 (1H, t, J=3.0 Hz), 7.82 (1H, t, J=3.0 Hz), 7.42 (1H, dd, J=9.1, 2.4 Hz), 6.93-6.91 (1H, m), 4.55-4.54 (2H, m), 4.29-4.28 (2H, m), 3.95-3.92 (3H, m), 2.91-2.87 (2H, m), 1.43 (3H, t, J=7.6 Hz).

MS spectrum (ES/APCI$^+$): 436 (M+H), 438 (M+2+H).

(Example 4) Potassium [(5-chloro-2-methoxyphenyl)sulfonyl](3-ethyl-5,6-dihydropyrido[3,2-f][1,2,4]triazolo[4,3-d][1,4]oxazepin-10-yl)azanide (Potassium Salt of Example 3)

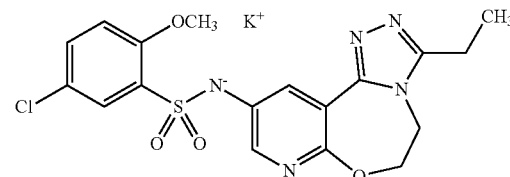

The title compound (16.7 mg, yield: 70%) was obtained by production according to the method described in Example 2 using 5-chloro-N-(3-ethyl-5,6-dihydropyrido[3,2-f][1,2,4]triazolo[4,3-d][1,4]oxazepin-10-yl)-2-methoxybenzenesulfonamide (22 mg, 0.050 mmol) obtained in Example (3b) and a solution of 0.5 N potassium hydroxide in ethanol (0.11 mL, 0.055 mmol).

$^1$H NMR spectrum (DMSO-d6, 400 MHz) δ: 8.26 (1H, s), 7.68-7.67 (2H, m), 7.35-7.33 (1H, m), 7.00 (1H, br d, J=8.5 Hz), 4.38-4.37 (2H, m), 4.25-4.24 (2H, m), 3.68 (3H, s), 2.73 (2H, q, J=7.6 Hz), 1.27 (3H, t, J=7.6 Hz).

(Example 5) 5-chloro-2-methoxy-N-[3-(propan-2-yl)-5,6-dihydropyrido[3,2-f][1,2,4]triazolo[4,3-d][1,4]oxazepin-10-yl]benzenesulfonamide

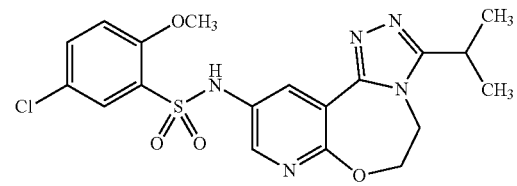 [SMILES: COc1ccc(Cl)cc1S(=O)(=O)Nc1cnc2c(c1)-c1nnc(C(C)C)n1CCO2]

(5a) 10-nitro-3-(propan-2-yl)-5,6-dihydropyrido[3,2-f][1,2,4]triazolo[4,3-d][1,4]oxazepine The title compound (61.2 mg, yield: 44%) was obtained by production according to the method described in Examples (1f) using 5-(methylsulfanyl)-7-nitro-2,3-dihydropyrido[3,2-f][1,4]oxazepine (120 mg, 0.50 mmol) obtained in Example (1e) and isobutyrohydrazide (111 mg, 1.09 mmol) as starting materials.

$^1$H NMR spectrum (CDCl$_3$, 400 MHz) δ: 9.46 (1H, d, J=3.0 Hz), 9.13 (1H, d, J=3.0 Hz), 4.76-4.74 (2H, m), 4.51-4.50 (2H, m), 3.21-3.15 (1H, m), 1.31 (6H, d, J=6.7 Hz).

(5b) 5-chloro-2-methoxy-N-[3-(propan-2-yl)-5,6-dihydropyrido[3,2-f][1,2,4]triazolo[4,3-d][1,4]oxazepin-10-yl]benzenesulfonamide The title compound (41.2 mg, yield for 2 steps: 41%) was obtained by production according to the method described in Examples (1g) and (1g) using 10-nitro-3-(propan-2-yl)-5,6-dihydropyrido[3,2-f][1,2,4]triazolo[4,3-d][1,4]oxazepine (61.2 mg, 0.22 mmol) obtained in Example (5a) and 5-chloro-2-methoxybenzenesulfonyl chloride (60.8 mg, 0.25 mmol) as starting materials.

$^1$H NMR spectrum (CDCl$_3$, 400 MHz) δ: 8.74-8.72 (1H, m), 8.39-8.38 (1H, m), 7.75-7.75 (1H, m), 7.43 (1H, dd, J=8.5, 2.7 Hz), 6.97 (1H, d, J=8.5 Hz), 4.55-4.54 (2H, m), 4.30-4.29 (2H, m), 4.05-4.04 (3H, m), 3.05-2.98 (1H, m), 1.44 (6H, d, J=6.7 Hz).

MS spectrum (ES/APCI$^+$): 450 (M+H), 452 (M+2+H)

(Example 6) 5-chloro-N-(5,6-dihydroimidazo[1,2-d]pyrido[3,2-f][1,4]oxazepin-10-yl)-2-methoxybenzenesulfonamide

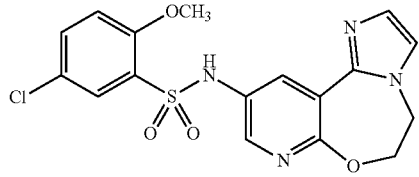 [SMILES: COc1ccc(Cl)cc1S(=O)(=O)Nc1cnc2c(c1)-c1nccn1CCO2]

(6a) 5-bromo-2-chloro-3-(1H-imidazol-2-yl)pyridine

To a solution of 5-bromo-2-chloro-pyridine-3-carbaldehyde (2.00 g, 9.07 mmol) in isopropanol (20 mL) and water (20 mL), ammonium acetate (6.29 g, 81.7 mmol) and an aqueous solution of glyoxal (39% content, 3.09 mL, 27.2 mmol) at room temperature and the mixture was stirred at the same temperature as above for 3 days. The mixture was concentrated under reduce pressure, and the residue was diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-0/100) to obtain the title compound (1.25 g, yield: 53%).

$^1$H NMR spectrum (CDCl$_3$, 400 MHz) δ: 8.86-8.78 (2H, m), 8.42-8.40 (2H, m).

(6b) 5-bromo-3-[1-(2-{[tert-butyl(dimethyl)silyl]oxy}ethyl)-1H-imidazol-2-yl]-2-chloropyridine To a solution of 5-bromo-2-chloro-3-(1H-imidazol-2-yl)pyridine (830 mg, 3.21 mmol) obtained in Example (6a) and (2-Bromoethoxy)-tert-butyldimethylsilane (1.92 g, 8.03 mmol) in N,N-dimethylformamide (30 mL), potassium carbonate (2.22 g, 16.1 mmol) at room temperature, the mixture was stirred at the same temperature as above for 24 hours, and subsequently stirred at 60° C. for 5 hours in an oil bath. The mixture was cooled to room temperature, and diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-40/60) to obtain the title compound (948 mg, yield: 71%).

$^1$H NMR spectrum (CDCl$_3$, 400 MHz) δ: 8.55 (1H, d, J=2.7 Hz), 8.01 (1H, d, J=2.7 Hz), 7.20 (1H, d, J=1.2 Hz), 7.18 (1H, d, J=1.2 Hz), 3.95 (2H, t, J=5.1 Hz), 3.78 (2H, t, J=5.3 Hz), 0.83 (9H, s), −0.03 (6H, s).

(6c) 10-bromo-5,6-dihydroimidazo[1,2-d]pyrido[3,2-f][1,4]oxazepine

To a solution of 5-bromo-3-[1-(2-{[tert-butyl(dimethyl)silyl]oxy}ethyl)-1H-imidazol-2-yl]-2-chloropyridine (948 mg, 2.27 mmol) obtained in Example (6b) in tetrahydrofuran (20 mL), a 1.0 mol/L solution of tetrabutyl ammonium fluoride in tetrahydrofuran (4.5 mL, 4.5 mmol) was added at room temperature, the mixture was stirred at the same temperature as above for 3 days, and subsequently stirred at 60° C. for 8 hours in an oil bath. The mixture was cooled in an ice water bath, diluted by addition of a saturated aqueous solution of ammonium chloride, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-90/10) to obtain the title compound (364 mg, yield: 60%).

$^1$H NMR spectrum (CDCl$_3$, 400 MHz) δ: 9.03-9.01 (1H, m), 8.26-8.24 (1H, m), 7.20-7.19 (1H, m), 7.04 (1H, s), 4.60-4.58 (2H, m), 4.46-4.44 (2H, m).

(6d) tert-butyl 5,6-dihydroimidazo[1,2-d]pyrido[3,2-f][1,4]oxazepin-10-ylcarbamate To a solution of 10-bromo-5,6-dihydroimidazo[1,2-d]pyrido[3,2-f][1,4]oxazepine (65.0 mg, 0.24 mmol) obtained in Example (6c) in 1,4-dioxane (5 mL), tert-butyl carbamate (34.3 mg, 0.29 mmol), palladium (II) acetate (6.0 mg, 0.027 mmol), dicyclohexyl[3,6-dimethoxy-2',4',6'-tris(1-methylethyl)[1,1'-biphenyl]-2-yl]phosphine (39.3 mg, 0.073 mmol) and cesium carbonate (111 mg, 0.34 mmol) was added at room temperature, and the mixture was stirred under nitrogen atmosphere at 100° C. for 10 hours in an oil bath. The mixture was cooled to room temperature, and diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-85/15) to obtain the title compound (42 mg, yield: 57%).

$^1$H NMR spectrum (CDCl$_3$, 400 MHz) δ: 8.77 (1H, d, J=2.7 Hz), 8.40 (1H, br s), 7.16 (1H, d, J=1.2 Hz), 7.01-6.92 (2H, m), 4.56-4.54 (2H, m), 4.44-4.42 (2H, m), 1.52 (9H, s).

(6e) 5-chloro-N-(5,6-dihydroimidazo[1,2-d]pyrido[3,2-f][1,4]oxazepin-10-yl)-2-methoxybenzenesulfonamide To a solution of tert-butyl 5,6-dihydroimidazo[1,2-d]pyrido[3,2-f][1,4]oxazepin-10-ylcarbamate (42.0 mg, 0.14 mmol) obtained in Example (6d) in methanol (3 mL), a 4.0 mol/L solution of hydrogen chloride in 1,4-dioxane (3 mL, 12 mmol) was added at room temperature, the mixture was stirred at room temperature for 2 hours. The mixture was concentrated under reduce pressure, and the residue was diluted by addition of a saturated aqueous solution of sodium bicarbonate. The solvent was distilled off under reduced pressure to obtain 5,6-dihydroimidazo[1,2-d]pyrido[3,2-f][1,4]oxazepin-10-amine as a mixture containing inorganic materials. To a mixture of 5,6-dihydroimidazo[1,2-d]pyrido[3,2-f][1,4]oxazepin-10-amine as a mixture containing inorganic materials in pyridine (0.224 mL, 2.78 mmol), 5-chloro-2-methoxybenzenesulfonyl chloride (40.2 mg, 0.17 mmol) was added, and the mixture was stirred at 80° C. for 3.5 hours in an oil bath. After cooling, the mixture was concentrated under reduced pressure, and the residue was purified in an automatic chromatography apparatus (ethyl acetate/methanol=100/0-90/10) to obtain the solid. The solid was dissolved into tetrahydrofuran (5 mL), a 1.0 mol/L solution of tetrabutyl ammonium fluoride in tetrahydrofuran (4.5 mL, 4.5 mmol) was added thereto at room temperature, and the mixture was stirred at room temperature for 1 hour. The mixture was diluted by addition of a saturated aqueous solution of ammonium chloride, and followed by extraction with ethyl acetate.

The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-85/15) to obtain the title compound (29 mg, yield for 3 steps: 51%).

$^1$H NMR spectrum (DMSO-d6, 400 MHz) δ: 10.28 (1H, br s), 8.57 (1H, d, J=2.7 Hz), 7.90 (1H, d, J=2.7 Hz), 7.67-7.64 (2H, m), 7.35 (1H, br s), 7.25 (1H, d, J=9.8 Hz), 7.07 (1H, br s), 4.48-4.46 (2H, m), 4.42-4.40 (2H, m), 3.91 (3H, s).

MS spectrum (ES/APCI$^+$): 407 (M+H), 409 (M+2+H)

(Example 7) 5-chloro-N-(5,6-dihydropyrazolo[1,5-d]pyrido[3,2-f][1,4]oxazepin-10-yl)-2-methoxybenzenesulfonamide

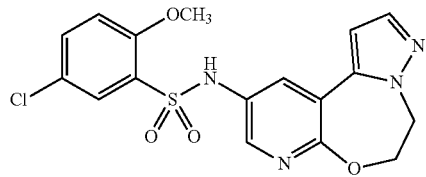 [SMILES: COc1ccc(Cl)cc1S(=O)(=O)Nc1cnc2c(c1)-c1ccnn1CCO2]

(7a) 10-bromo-5,6-dihydropyrazolo[1,5-d]pyrido[3,2-f][1,4]oxazepine

A mixture of 1-(5-bromo-2-chloropyridin-3-yl)ethanone (4.85 g, 0.85 mmol) and N,N-dimethylformamide dimethyl acetal (15 mL, 113 mmol) was stirred at 85° C. for 90 minutes in an oil bath. The mixture was cooled to room temperature, and concentrated under reduce pressure. The residue was diluted by addition of ethanol (30 mL) and water (15 mL), acetic acid (3.3 mL, 58 mmol) and 2-hydrazinoethanol (1.83 mL, 26.9 mmol) was added thereto at room temperature, and the mixture was stirred at 90° C. for 4 hours in an oil bath. The mixture was cooled to room temperature, and neutralized by addition of a 1.0 mol/L aqueous solution of sodium hydroxide, followed by extraction with chloroform. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-0/100) to obtain 2-[5-(5-bromo-2-chloropyridin-3-yl)-1H-pyrazol-1-yl]ethanol (3.62 g) as a mixture containing positional isomers. To a solution of 2-[5-(5-bromo-2-chloropyridin-3-yl)-1H-pyrazol-1-yl]ethanol (3.62 g) as a mixture containing positional isomers obtained in the above step in N,N-dimethylformamide (240 mL) was added potassium carbonate (3.31 g, 23.9 mmol) at room temperature, and the mixture was stirred at 120° C. for 2 hours in an oil bath. The reaction mixture was cooled, and an insoluble material was filtered off. The residue was washed with ethyl acetate, and the filtrate and the washes were combined. The solvent was distilled off under reduced pressure, and the residue was purified in an automatic chromatography apparatus (Yamazen Co. Ltd., High-Flash™ column Amino, n-hexane/ethyl acetate=100/0-30/70) to obtain the title compound (101 mg, yield for 2 steps: 57%).

$^1$H NMR spectrum (CDCl$_3$, 400 MHz) δ: 8.27 (1H, d, J=2.3 Hz), 8.18 (1H, d, J=2.3 Hz), 7.55 (1H, d, J=2.0 Hz), 6.69 (1H, d, J=2.0 Hz), 4.74-4.72 (2H, m), 4.62-4.60 (2H, m).

(7b) tert-butyl 5,6-dihydropyrazolo[1,5-d]pyrido[3,2-f][1,4]oxazepin-10-ylcarbamate To a mixture of 10-bromo-5,6-dihydropyrazolo[1,5-d]pyrido[3,2-f][1,4]oxazepine (3.15 g, 11.8 mmol) obtained in Example (7a) in toluene (130 mL), tert-butyl carbamate (1.66 g, 14.2 mmol), tris(dibenzylideneacetone)dipalladium (0)-chloroform adduct (613.5 mg, 0.59 mmol), 2-di-tert-butylphosphino-2',4',6'-triisopropylbiphenyl (1.01 g, 2.37 mmol) and sodium tert-butoxide (2.64 g, 27.5 mmol) was added at room temperature, and the mixture was stirred under nitrogen atmosphere at the same temperature as above for 15 hours. The mixture was diluted by addition of water, and an insoluble material was filtered off through pad of Celite 545®. The residue was washed with ethyl acetate, and the filtrate and the washes were combined. The organic layer was separated, washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-20/80) to obtain the title compound (2.07 g, yield: 58%).

¹H NMR spectrum (CDCl₃, 400 MHz) δ: 8.44 (1H, br s), 8.07 (1H, br d, J=2.7 Hz), 7.53 (1H, br d, J=2.7 Hz), 6.74-6.65 (2H, m), 4.72-4.71 (2H, m), 4.58-4.57 (2H, m), 1.54 (9H, s).

(7c) 5-chloro-N-(5,6-dihydropyrazolo[1,5-d]pyrido[3,2-f][1,4]oxazepin-10-yl)-2-methoxybenzenesulfonamide To a solution of tert-butyl 5,6-dihydropyrazolo[1,5-d]pyrido[3,2-f][1,4]oxazepin-10-ylcarbamate (53.0 mg, 0.18 mmol) obtained in Example (7b) in methanol (10 mL), a 4.0 mol/L solution of hydrogen chloride in 1,4-dioxane (5 mL, 20 mmol) was added at room temperature, the mixture was stirred at the same temperature as above for 1 hour. The mixture was concentrated under reduce pressure. The residue was diluted with pyridine (0.282 mL, 3.51 mmol), 5-chloro-2-methoxybenzenesulfonyl chloride (46.5 mg, 0.19 mmol) was added thereto at room temperature, and the mixture was stirred at 80° C. for 2 hours in an oil bath. After cooling, the mixture was concentrated under reduced pressure, and the residue was purified in an automatic chromatography apparatus (ethyl acetate/methanol=100/0-90/10) to obtain the title compound (36 mg, yield: 51%).

¹H NMR spectrum (DMSO-d6, 400 MHz) δ: 10.28 (1H, br s), 7.93 (1H, d, J=2.3 Hz), 7.87 (1H, d, J=2.3 Hz), 7.69-7.67 (2H, m), 7.54 (1H, d, J=2.0 Hz), 7.26 (1H, d, J=9.0 Hz), 6.67 (1H, d, J=2.0 Hz), 4.61-4.60 (2H, m), 4.49-4.48 (2H, m), 3.89 (3H, s).

MS spectrum (ES/APCI⁺): 407 (M+H), 409 (M+2+H).

(Example 8) Potassium [(5-chloro-2-methoxyphenyl) sulfonyl](5,6-dihydropyrazolo[1,5-d]pyrido[3,2-f][1,4]oxazepin-10-yl)azanide (Potassium Salt of Example 7)

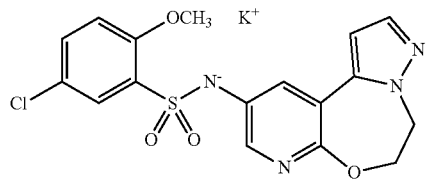 [SMILES: COc1ccc(Cl)cc1S(=O)(=O)[N-]c1cnc2c(c1)-c1ccnn1CCO2 ; [K+]]

To a suspension of 5-chloro-N-(5,6-dihydropyrazolo[1,5-d]pyrido[3,2-f][1,4]oxazepin-10-yl)-2-methoxybenzenesulfonamide (28 mg, 0.069 mmol) obtained in Example (7c) in ethanol (5 mL), a solution of 0.5 N potassium hydroxide in ethanol (0.137 mL, 0.069 mmol) was added at room temperature, and the mixture was stirred at the same temperature as above for 1 hour. The solvent was distillated off under reduce pressure to obtain the title compound (31 mg, yield: quantitative).

¹H NMR spectrum (DMSO-d6, 400 MHz) δ: 7.73 (1H, d, J=2.7 Hz), 7.62 (1H, d, J=2.7 Hz), 7.55 (1H, d, J=2.3 Hz), 7.47 (1H, d, J=2.0 Hz), 7.34 (1H, dd, J=8.6, 2.3 Hz), 6.99 (1H, d, J=8.6 Hz), 6.52 (1H, d, J=2.0 Hz), 4.53-4.52 (2H, m), 4.36-4.35 (3H, m), 3.65 (3H, s).

(Example 9) N-(5,6-dihydropyrazolo[1,5-d]pyrido[3,2-f][1,4]oxazepin-10-yl)-2-ethoxy-5-fluorobenzenesulfonamide

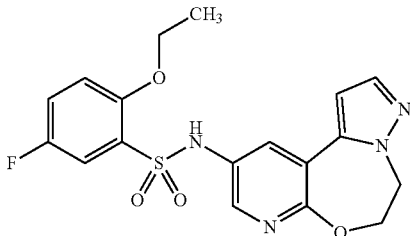

(9a) 5-Fluoro-2-ethoxybenzenesulfonyl chloride

To chlorosulfonic acid (30.0 mL, 451 mmol), 1-ethoxy-4-fluorobenzene (10.33 mL, 73.7 mmol) was added at −12° C. over 10 minutes, the mixture was stirred at the same temperature as above for 30 minutes, and subsequently stirred in an ice water bath for 1 hour. The reaction mixture was carefully poured into ice (approximately 300 mL), followed by extraction with ethyl acetate. The organic layer was washed with a saturated aqueous solution of sodium chloride and dried over anhydrous magnesium sulfate. After filtration, the solvent was distilled off under reduced pressure, and the residue was purified by silica gel column chromatography (n-hexane/ethyl acetate=4/1). To the obtained solid, n-hexane was added, and the suspension was cooled in ice water bath. The precipitated solid was collected by filtration, washed with n-hexane, and then dried to obtain the title compound (7.69 g, yield: 44%).

¹H NMR spectrum (CDCl₃, 400 MHz) δ: 7.70 (1H, dd, J=7.4, 3.1 Hz), 7.41-7.36 (1H, m), 7.07 (1H, dd, J=9.4, 3.9 Hz), 4.26 (2H, q, J=6.8 Hz), 1.55 (3H, t, J=6.8 Hz).

(9b) N-(5,6-dihydropyrazolo[1,5-d]pyrido[3,2-f][1,4]oxazepin-10-yl)-2-ethoxy-5-fluorobenzenesulfonamide To a solution of tert-butyl 5,6-dihydropyrazolo[1,5-d]pyrido[3,2-f][1,4]oxazepin-10-ylcarbamate (48.0 mg, 0.16 mmol) obtained in Example (7b) in methanol (10 mL), a 4.0 mol/L solution of hydrogen chloride in 1,4-dioxane (5 mL, 20 mmol) was added at room temperature, the mixture was stirred at the same temperature as above for 1 hour. The mixture was concentrated under reduce pressure. The residue was diluted with pyridine (0.256 mL, 3.18 mmol), 5-Fluoro-2-ethoxybenzenesulfonyl chloride (42.0 mg, 0.18 mmol) obtained in Example (9a) was added thereto at room temperature, and the mixture was stirred at 80° C. for 30 minutes in an oil bath. After cooling, the mixture was concentrated under reduced pressure, and the residue was purified in an automatic chromatography apparatus (ethyl acetate/methanol=100/0-95/5) to obtain the title compound (49 mg, yield: 76%).

¹H NMR spectrum (DMSO-d6, 400 MHz) δ: 10.13 (1H, br s), 7.92 (1H, d, J=2.3 Hz), 7.88 (1H, d, J=2.3 Hz), 7.58 (1H, dd, J=8.2, 3.1 Hz), 7.54 (1H, d, J=2.0 Hz), 7.49-7.44

(1H, m), 7.26-7.23 (1H, m), 6.64 (1H, d, J=2.0 Hz), 4.60 (2H, t, J=3.9 Hz), 4.48 (2H, t, J=3.9 Hz), 4.17 (2H, q, J=7.0 Hz), 1.27 (3H, t, J=7.0 Hz).

MS spectrum (ES/APCI⁺): 405 (M+H)

(Example 10) Potassium 5,6-dihydropyrazolo[1,5-d]pyrido[3,2-f][1,4]oxazepin-10-yl[(2-ethoxy-5-fluorophenyl)sulfonyl]azanide (Potassium Salt of Example 9)

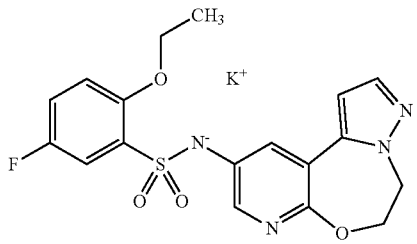 [SMILES: CCOc1ccc(F)cc1S(=O)(=O)[N-]c1cnc2c(c1)-c1ccnn1CCO2 ; [K+]]

To a suspension of N-(5,6-dihydropyrazolo[1,5-d]pyrido[3,2-f][1,4]oxazepin-10-yl)-2-ethoxy-5-fluorobenzenesulfonamide (37.0 mg, 0.092 mmol) obtained in Example (9b) in ethanol (3 mL), a solution of 0.5 N potassium hydroxide in ethanol (0.182 mL, 0.092 mmol) was added at room temperature, and the mixture was stirred at the same temperature as above for 1 hour. The solvent was distillated off under reduce pressure to obtain the title compound (44 mg, yield: quantitative) H NMR spectrum (DMSO-d6, 400 MHz) δ: δ: 7.65 (1H, d, J=2.7 Hz), 7.59 (1H, d, J=2.7 Hz), 7.50-7.47 (2H, m), 7.11-7.08 (1H, m), 6.96 (1H, dd, J=9.0, 4.3 Hz), 6.51 (1H, d, J=2.0 Hz), 4.53-4.52 (2H, m), 4.37-4.34 (2H, m), 3.91 (2H, q, J=7.0 Hz), 1.10 (3H, t, J=7.0 Hz).

(Example 11) N-(5,6-dihydropyrazolo[1,5-d]pyrido[3,2-f][1,4]oxazepin-10-yl)-5-fluoro-2-(2-methoxyethoxy)benzenesulfonamide

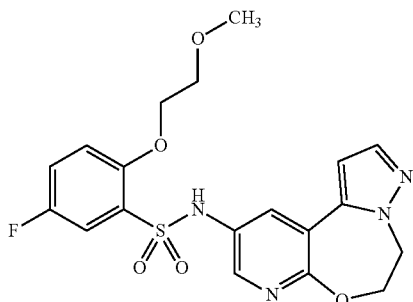

(11a) 2-bromo-4-fluoro-1-(2-methoxyethoxy)benzene

To a solution of 2-Bromo-4-fluorophenol (3.39 g, 17.7 mmol) and 2-Bromoethyl Methyl Ether (2.55 mL, 26.8 mmol) in N,N-dimethylformamide (35 mL), potassium carbonate (4.92 g, 35.6 mmol) was added at room temperature, the mixture was stirred at the same temperature as above for 2 hours, and subsequently stirred at 60° C. for 2 hours. The mixture was cooled to room temperature, and diluted by addition of water, followed by extraction with ethyl acetate. The organic layer was washed with water twice and a saturated aqueous solution of sodium chloride, and dried over anhydrous magnesium sulfate. After filtration, the solvent was distilled off under reduced pressure, and the residue was purified by silica gel column chromatography (n-hexane/ethyl acetate=4/1) to obtain the title compound (4.34 g, yield: 98%).

¹H NMR spectrum (CDCl₃, 400 MHz) δ: 7.29 (1H, dd, J=7.8, 2.7 Hz), 6.99-6.96 (1H, m), 6.89 (1H, dd, J=9.0, 4.7 Hz), 4.15-4.13 (2H, m), 3.80-3.79 (2H, m), 3.48 (3H, s).

(11b) 5-fluoro-2-(2-methoxyethoxy)benzenesulfonyl chloride

To a mixture of 2-bromo-4-fluoro-1-(2-methoxyethoxy)benzene (3.42 g, 13.7 mmol) obtained in Example (11a), phenylmethanethiol (1.62 mL, 13.8 mmol), Tris(dibenzylideneacetone)dipalladium(0) (0.3150 g, 0.34 mmol) and (9,9-dimethyl-9H-xanthene-4,5-diyl)bis(diphenylphosphane) (0.3930 g, 0.68 mmol) in 1,4-dioxane (70 mL), N,N-Diisopropylethylamine (4.8 mL, 28 mmol) was added at room temperature, the mixture was stirred under nitrogen atmosphere at 100° C. for 8 hours in an oil bath. The mixture was cooled, and concentrated under reduced pressure. The residue was diluted by addition of water, followed by extraction with ethyl acetate. The organic layer was washed with a saturated aqueous solution of sodium bicarbonate and a saturated aqueous solution of sodium chloride, and dried over anhydrous magnesium sulfate. After filtration, the solvent was distilled off under reduced pressure, and the residue was purified by silica gel column chromatography (n-hexane/ethyl acetate=6/1) to obtain 2-(benzylsulfanyl)-4-fluoro-1-(2-methoxyethoxy)benzene (5.02 g) as a mixture containing unknown materials. To a mixture of 2-(benzylsulfanyl)-4-fluoro-1-(2-methoxyethoxy)benzene (5.02 g) obtained the above step, acetic acid (7.8 mL, 140 mmol) and water (3.5 mL) in acetonitrile (70 mL), 1,3-dichloro-5,5-dimethylhydantoin (5.41 g, 27.5 mmol) was added under ice cooling over 5 minutes in several portions, and the mixture was stirred at the same temperature as above for 20 minutes. The mixture was concentrated under reduced pressure, diluted by addition of a saturated aqueous solution of sodium bicarbonate, extracted with ethyl acetate. The organic layer was washed with water and a saturated aqueous solution of sodium chloride and dried over anhydrous magnesium sulfate. After filtration, the solvent was distilled off under reduced pressure, and the residue was purified by column chromatography (n-hexane/ethyl acetate=4/1-2/1) to obtain the title compound (3.66 g, yield for 2 steps: 99%).

¹H NMR spectrum (CDCl₃, 400 MHz) δ: 7.69 (1H, dd, J=7.4, 3.1 Hz), 7.40-7.37 (1H, m), 7.16 (1H, dd, J=9.2, 4.1 Hz), 4.34-4.32 (2H, m), 3.87-3.85 (2H, m), 3.47 (3H, s).

(11c) N-(5,6-dihydropyrazolo[1,5-d]pyrido[3,2-f][1,4]oxazepin-10-yl)-5-fluoro-2-(2-methoxyethoxy)benzenesulfonamide The title compound (46 mg, yield: 46%) was obtained by production according to the method described in Examples (7c) using tert-butyl 5,6-dihydropyrazolo[1,5-d]pyrido[3,2-f][1,4]oxazepin-10-ylcarbamate (70.0 mg, 0.23 mmol) obtained in Example (7b) and 5-fluoro-2-(2-methoxyethoxy)benzenesulfonyl chloride (77.3 mg, 0.29 mmol) obtained in Example (11b) as starting materials.

¹H NMR spectrum (DMSO-d6, 400 MHz) δ: 9.83 (1H, br s), 7.95 (1H, d, J=2.3 Hz), 7.91 (1H, d, J=2.3 Hz), 7.56-7.46 (3H, m), 7.33 (1H, dd, J=9.2, 4.1 Hz), 6.70 (1H, d, J=2.0

Hz), 4.61-4.60 (2H, m), 4.49-4.48 (2H, m), 4.31 (2H, t, J=4.7 Hz), 3.73 (2H, t, J=4.7 Hz), 3.29 (3H, s).
MS spectrum (ES/APCI⁺): 435 (M+H).

(Example 12) 5-chloro-N-(5,6-dihydropyrazolo[1,5-d]pyrido[3,2-f][1,4]oxazepin-10-yl)-2-methoxypyridine-3-sulfonamide

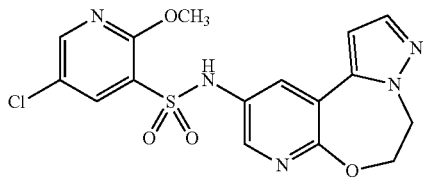 [SMILES: COc1ncc(Cl)cc1S(=O)(=O)Nc1cnc2c(c1)-c1ccnn1CCO2]

(12a) 5-chloro-2-methoxypyridine-3-sulfonyl chloride

To a mixture of 3-bromo-5-chloro-2-methoxypyridine (2.24 g, 10.1 mmol), phenylmethanethiol (1.18 mL, 10.1 mmol), Tris(dibenzylideneacetone)dipalladium(0) (0.2319 g, 0.25 mmol) and (9,9-dimethyl-9H-xanthene-4,5-diyl)bis (diphenylphosphane) (0.2955 g, 0.51 mmol) in 1,4-dioxane (100 mL), N,N-Diisopropylethylamine (3.5 mL, 20 mmol) was added at room temperature, the mixture was stirred under nitrogen atmosphere at 100° C. for 30 minutes in an oil bath. The mixture was cooled, and concentrated under reduced pressure. The residue was diluted by addition of water, followed by extraction with ethyl acetate. The organic layer was washed with a saturated aqueous solution of sodium bicarbonate and a saturated aqueous solution of sodium chloride, and dried over anhydrous magnesium sulfate. After filtration, the solvent was distilled off under reduced pressure, and the residue was purified by silica gel column chromatography (n-hexane/ethyl acetate=15/1) to obtain 3-(benzylsulfanyl)-5-chloro-2-methoxypyridine (2.76 g) as a mixture containing unknown materials. To a mixture of 3-(benzylsulfanyl)-5-chloro-2-methoxypyridine (2.76 g) obtained the above step, acetic acid (5.8 mL, 100 mmol) and water (2.5 mL, 139 mmol) in acetonitrile (50 mL), 1,3-dichloro-5,5-dimethylhydantoin (3.97 g, 20.2 mmol) was added under ice cooling over 5 minutes in several portions, and the mixture was stirred at the same temperature as above for 20 minutes. The mixture was concentrated under reduced pressure, and diluted by addition of a saturated aqueous solution of sodium bicarbonate, followed by extraction with ethyl acetate. The organic layer was washed with water and a saturated aqueous solution of sodium chloride and dried over anhydrous magnesium sulfate. After filtration, the solvent was distilled off under reduced pressure, and the residue was purified by column chromatography (n-hexane/ethyl acetate=4/1-2/1). To the obtained solid, n-hexane (4 mL) was added, the precipitated solid was collected by filtration, washed with n-hexane, and then dried to obtain the title compound (1.86 g, yield for 2 steps: 76%).
¹H NMR spectrum (CDCl₃, 400 MHz) δ: 8.43 (1H, d, J=2.7 Hz), 8.22 (1H, d, J=2.7 Hz), 4.19 (3H, s).

(12b) 5-chloro-N-(5,6-dihydropyrazolo[1,5-d]pyrido [3,2-f][1,4]oxazepin-10-yl)-2-methoxypyridine-3-sulfonamide The title compound (47 mg, yield: 57%) was obtained by production according to the method described in Examples (7c) using tert-butyl 5,6-dihydropyrazolo[1,5-d]pyrido[3,2-f][1,4]oxazepin-10-ylcarbamate (61.0 mg, 0.20 mmol) obtained in Example (7b) and 5-chloro-2-methoxypyridine-3-sulfonyl chloride (54.2 mg, 0.22 mmol) obtained in Example (12a) as starting materials.
¹H NMR spectrum (DMSO-d6, 400 MHz) δ: 10.55 (1H, br s), 8.49 (1H, d, J=2.3 Hz), 8.20 (1H, d, J=2.3 Hz), 7.96 (1H, d, J=2.3 Hz), 7.89 (1H, d, J=2.3 Hz), 7.54 (1H, d, J=2.0 Hz), 6.72 (1H, d, J=2.0 Hz), 4.63-4.61 (2H, m), 4.51-4.50 (2H, m), 3.96 (3H, s).
MS spectrum (ES/APCI⁺): 408 (M+H), 410 (M+2+H)

(Example 13) 5-chloro-N-(5,6-dihydropyrazolo[1,5-d]pyrido[3,2-f][1,4]oxazepin-10-yl)-2-ethoxypyridine-3-sulfonamide

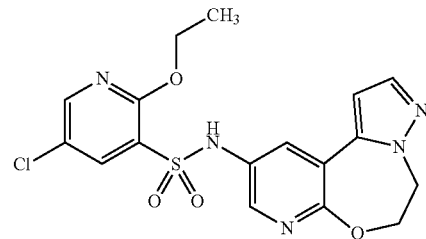 [SMILES: CCOc1ncc(Cl)cc1S(=O)(=O)Nc1cnc2c(c1)-c1ccnn1CCO2]

(13a) 3-bromo-5-chloro-2-ethoxypyridine

To a solution of 4-bromo-5-chloro-2-fluoro-pyridine (2.00 g, 9.50 mmol) in ethanol (50 mL), a 20% ethanol solution of sodium ethoxide (6.12 mL, 14.3 mmol) was added at room temperature, and the mixture was stirred at 80° C. for 1 hour in an oil bath. The mixture was cooled, and concentrated under reduced pressure. The residue was purified in an automatic chromatography apparatus (n-hexane/ethyl acetate=100/0-90/10) to obtain the title compound (2.155 g, yield: 96%).
¹H NMR spectrum (CDCl₃, 400 MHz) δ: 8.02 (1H, d, J=2.7 Hz), 7.48 (1H, d, J=2.7 Hz), 4.07 (2H, q, J=7.0 Hz), 1.44 (3H, t, J=7.0 Hz).

(13b) 5-chloro-2-ethoxypyridine-3-sulfonyl chloride

The title compound (1.39 g, yield for 2 steps: quantitative) was obtained by production according to the method described in Examples (12a) using 3-bromo-5-chloro-2-ethoxypyridine (1.04 g, 4.40 mmol) obtained in Example (13a) as a starting material.
¹H NMR spectrum (CDCl₃, 400 MHz) δ: 8.40 (1H, d, J=2.3 Hz), 8.20 (1H, d, J=2.3 Hz), 4.63 (2H, q, J=7.0 Hz), 1.50 (3H, t, J=7.0 Hz).

(13c) 5-chloro-N-(5,6-dihydropyrazolo[1,5-d]pyrido [3,2-f][1,4]oxazepin-10-yl)-2-ethoxypyridine-3-sulfonamide The title compound (91 mg, yield: 93%) was obtained by production according to the method described in Examples (7c) using tert-butyl 5,6-dihydropyrazolo[1,5-d]pyrido[3,2-f][1,4]oxazepin-10-ylcarbamate (70.0 mg, 0.23 mmol) obtained in Example (7b) and 5-chloro-2-ethoxypyridine-3-sulfonyl chloride (96.0 mg, 0.37 mmol) obtained in Example (13b) as starting materials.

¹H NMR spectrum (DMSO-d6, 400 MHz) δ: 10.49 (1H, br s), 8.47 (1H, d, J=2.7 Hz), 8.22 (1H, d, J=2.7 Hz), 7.96 (1H, d, J=2.7 Hz), 7.92 (1H, d, J=2.7 Hz), 7.54 (1H, d, J=2.0 Hz), 6.69 (1H, d, J=2.0 Hz), 4.62-4.61 (2H, m), 4.50-4.49 (2H, m), 4.44 (2H, q, J=7.0 Hz), 1.25 (3H, t, J=7.0 Hz).

MS spectrum (ES/APCI⁺): 422 (M+H), 424 (M+2+H)

(Example 14) N-(5,6-dihydropyrazolo[1,5-d]pyrido[3,2-f][1,4]oxazepin-10-yl)-2-ethoxy-5-fluoropyridine-3-sulfonamide

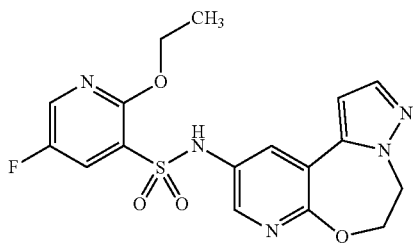 [SMILES: CCOc1ncc(F)cc1S(=O)(=O)Nc1cnc2c(c1)-c1ccnn1CCO2]

(14a) 3-bromo-2-ethoxy-5-fluoropyridine

To a mixture of 3-bromo-5-fluoro-pyridin-2-amine (1.50 g, 7.85 mmol) and hydrogen fluoride pyridine (4 mL, 44 mmol), sodium nitrite was added at −10° C. in a several portions, and the mixture was stirred at room temperature for 2 hours. The mixture was diluted by addition of a saturated aqueous solution of sodium bicarbonate until it became basic, followed by extraction with ethyl acetate. The organic layer was washed with a saturated aqueous solution of sodium chloride, and dried over anhydrous magnesium sulfate. After filtration, the solvent was distilled off under reduced pressure to obtain a crude product of 3-bromo-2,5-difluoro-pyridine (1.00 g). To a solution of a crude product of 3-bromo-2,5-difluoro-pyridine (1.00 g) obtained in the above step in ethanol (20 mL), a 20% ethanol solution of sodium ethoxide (2.84 mL, 6.61 mmol) was added at room temperature, and the mixture was stirred at 80° C. for 1 hour in an oil bath. The mixture was cooled, and concentrated under reduced pressure. The residue was purified in an automatic chromatography apparatus (n-hexane/ethyl acetate=100/0-90/10) to obtain the title compound (1.04 g, yield for 2 steps: 66%).

¹H NMR spectrum (CDCl₃, 400 MHz) δ: 8.02 (1H, d, J=2.3 Hz), 7.80 (1H, d, J=2.3 Hz), 4.41 (2H, q, J=7.0 Hz), 1.43 (3H, t, J=7.0 Hz).

(14b) 2-ethoxy-5-fluoropyridine-3-sulfonyl chloride 3-(benzylsulfanyl)-2-ethoxy-5-fluoropyridine To a mixture of 3-bromo-2-ethoxy-5-fluoropyridine (2.60 g, 11.8 mmol) obtained in Example (14a), phenylmethanethiol (1.39 mL, 11.8 mmol), Tris(dibenzylideneacetone)dipalladium(0) (0.2702 g, 0.30 mmol) and (9,9-dimethyl-9H-xanthene-4,5-diyl)bis(diphenylphosphane) (0.3415 g, 0.59 mmol) in 1,4-dioxane (120 mL), N,N-Diisopropylethylamine (4.11 mL, 23.6 mmol) was added at room temperature, the mixture was stirred under nitrogen atmosphere at 100° C. for 4 hours in an oil bath. The mixture was cooled, and concentrated under reduced pressure. The residue was diluted by addition of water, followed by extraction with ethyl acetate. The organic layer was washed with a saturated aqueous solution of sodium chloride, and dried over anhydrous sodium sulfate. After filtration, the solvent was distilled off under reduced pressure, and the residue was purified in an automatic chromatography apparatus (n-hexane/ethyl acetate=100/0-90/10) to obtain 3-(benzylsulfanyl)-2-ethoxy-5-fluoropyridine (3.11 g) as a mixture containing unknown materials. To a mixture of 3-(benzylsulfanyl)-2-ethoxy-5-fluoropyridine (3.11 g) obtained the above step, acetic acid (0.9 mL, 16 mmol) and water (0.6 mL, 33 mmol) in acetonitrile (60 mL), 1,3-dichloro-5,5-dimethylhydantoin (4.65 g, 23.6 mmol) was added under ice cooling in several portions, and the mixture was stirred at the same temperature as above for 3 hours. The mixture was allowed to warm up to room temperature, concentrated under reduced pressure, and the residue was purified in an automatic chromatography apparatus (n-hexane/ethyl acetate=100/0-80/20) to obtain the title compound (2.67 g, yield for 2 steps: 94%).

¹H NMR spectrum (CDCl₃, 400 MHz) δ: 8.34 (1H, d, J=3.1 Hz), 8.02 (1H, dd, J=6.6, 3.1 Hz), 4.61 (2H, q, J=7.0 Hz), 1.49 (3H, t, J=7.0 Hz).

(14c) N-(5,6-dihydropyrazolo[1,5-d]pyrido[3,2-f][1,4]oxazepin-10-yl)-2-ethoxy-5-fluoropyridine-3-sulfonamide To a solution of tert-butyl 5,6-dihydropyrazolo[1,5-d]pyrido[3,2-f][1,4]oxazepin-10-ylcarbamate (70.0 mg, 0.23 mmol) obtained in Example (7b) in methanol (10 mL), a 4.0 mol/L solution of hydrogen chloride in 1,4-dioxane (5 mL, 20 mmol) was added at room temperature, the mixture was stirred at the same temperature as above for 4 hours. The mixture was concentrated under reduce pressure. The residue was diluted with pyridine (0.373 mL, 4.63 mmol), 2-ethoxy-5-fluoropyridine-3-sulfonyl chloride (83.2 mg, 0.35 mmol) obtained in Example (14b) was added thereto at room temperature, and the mixture was stirred at 80° C. for 2 hours in an oil bath. After cooling, the mixture was concentrated under reduced pressure, and the residue was purified in an automatic chromatography apparatus (ethyl acetate/methanol=100/0-90/10) to obtain the title compound (86 mg, yield: 92%).

¹H NMR spectrum (DMSO-d6, 400 MHz) δ: 10.49 (1H, br s), 8.43 (1H, d, J=3.1 Hz), 8.17 (1H, dd, J=7.4, 3.1 Hz), 7.96 (1H, d, J=2.7 Hz), 7.92 (1H, d, J=2.7 Hz), 7.54 (1H, d, J=2.3 Hz), 6.69 (1H, d, J=2.3 Hz), 4.62-4.60 (2H, m), 4.50-4.48 (2H, m), 4.43 (2H, q, J=7.0 Hz), 1.25 (3H, t, J=7.0 Hz).

MS spectrum (ES/APCI⁺): 406 (M+H)

(Example 15) Potassium 5,6-dihydropyrazolo[1,5-d]pyrido[3,2-f][1,4]oxazepin-10-yl[(2-ethoxy-5-fluoropyridin-3-yl)sulfonyl]azanide (Potassium Salt of Example 14)

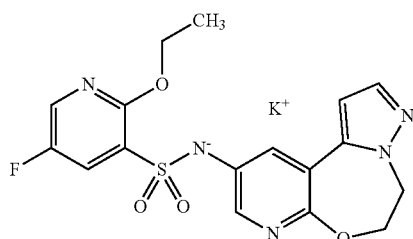

To a suspension of N-(5,6-dihydropyrazolo[1,5-d]pyrido[3,2-f][1,4]oxazepin-10-yl)-2-ethoxy-5-fluoropyridine-3-sulfonamide (66.0 mg, 0.16 mmol) obtained in Example (14c) in ethanol (5 mL), a solution of 0.5 N potassium hydroxide in ethanol (0.325 mL, 0.16 mmol) was added at room temperature, and the mixture was stirred at room temperature for 1 hour. The solvent was distillated off under reduce pressure to obtain the title compound (80 mg, yield: quantitative).

$^1$H NMR spectrum (DMSO-d6, 400 MHz) δ: 8.07 (1H, d, J=3.1 Hz), 7.87 (1H, dd, J=8.2, 3.1 Hz), 7.71 (1H, d, J=2.7 Hz), 7.64 (1H, d, J=2.7 Hz), 7.48 (1H, d, J=2.0 Hz), 6.57 (1H, d, J=2.0 Hz), 4.55-4.52 (2H, m), 4.38-4.35 (3H, m), 4.18 (2H, q, J=7.0 Hz), 1.05 (3H, t, J=7.0 Hz).

(Example 16) 5-chloro-2-methoxy-N-[(5S)-5-methyl-5,6-dihydropyrazolo[1,5-d]pyrido[3,2-f][1,4]oxazepin-10-yl]benzenesulfonamide

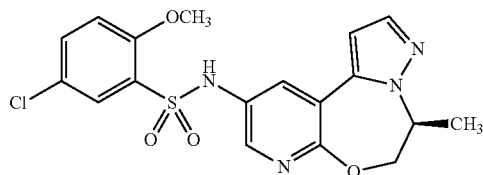

(16a) methyl (2S)-2-hydrazinylpropanoate hydrochloride

To a solution of methyl (2R)-2-hydroxypropanoate (4.14 g, 39.8 mmol) and 2.6-lutidine (10.5 mL, 85.8 mmol) in methylene chloride (55 mL), was added trifluoromethanesulfonic acid anhydride (7.4 mL, 44.1 mmol) under ice cooling, and the mixture was stirred at the same temperature as above for 15 minutes. To the mixture, a solution of tert-butyl carbazate (5.33 g, 40.3 mmol) under ice cooling over 25 minutes, and the mixture was stirred at the same temperature as above for 4 hours. The mixture was allowed to warm up to room temperature, and the solvent was distillated off under reduce pressure. The residue was diluted by addition of ether (70 mL), and the mixture was stored at −20° C. for 3 days. The mixture was allowed to warm up to room temperature, and the precipitated solid was filtered off through pad of celite 545®. The filtrate was washed with water and a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=65/35-40/60) to obtain tert-butyl 2-[(2S)-1-methoxy-1-oxopropan-2-yl]hydrazinecarboxylate (5.96 g) as a mixture containing some unknown materials. To a solution of tert-butyl 2-[(2S)-1-methoxy-1-oxopropan-2-yl]hydrazinecarboxylate (5.96 g) obtained in the above step in methanol (100 mL), a 1.0 mol/L aqueous solution of sodium hydroxide (55 mL, 55 mmol) was added at room temperature, and the mixture was stirred at room temperature for 2 days. Most of the organic solvent was distilled off under reduce pressure, ether was added thereto, the aqueous layer was separated. The aqueous layer was acidified by addition of 2.0 mol/L hydrochloric acid, followed by extraction with a mixed solvent of chloroform/isopropanol=4/1. The organic layer was dried over anhydrous sodium sulfate. After filtration, the solvent was distilled off under reduced pressure to obtain a crude product of (2S)-2-[2-(tert-butoxycarbonyl)hydrazinyl]propanoic acid (3.45 g). To a solution of the crude product of (2S)-2-[2-(tert-butoxycarbonyl)hydrazinyl]propanoic acid (3.45 g) obtained in the above step in methanol (35 mL), thionyl chloride (2.44 mL, 33.6 mmol) was added under ice cooling, and the mixture was stirred at room temperature for 14 hours. The solvent was distilled off under reduce pressure to obtain the title compound (2.55 g, yield for 3 steps: 42%)

$^1$H NMR spectrum (DMSO-d6, 400 MHz) δ: 3.82 (1H, q, J=7.3 Hz), 3.70 (3H, s), 1.26 (3H, d, J=7.3 Hz).

(16b) (5S)-10-bromo-5-methyl-5,6-dihydropyrazolo[1,5-d]pyrido[3,2-f][1,4]oxazepine A mixture of 1-(5-bromo-2-chloropyridin-3-yl)ethanone (980 mg, 3.97 mmol) and N,N-dimethylformamide dimethyl acetal (4.0 mL, 30 mmol) was stirred at 90° C. for 90 minutes in an oil bath. The mixture was cooled to room temperature, and concentrated under reduce pressure. The residue was diluted by addition of ethanol (13 mL) and water (6.5 mL), acetic acid (1.6 mL, 28 mmol) and methyl (2S)-2-hydrazinylpropanoate hydrochloride (0.859 g, 5.56 mmol) obtained in Example (16a) was added thereto at room temperature, and the mixture was stirred at 90° C. for 4 hours in an oil bath. The mixture was cooled to room temperature, and neutralized by addition of a 2.0 mol/L aqueous solution of sodium hydroxide, followed by extraction with chloroform. The organic layer was washed with a saturated aqueous solution of sodium chloride and dried over anhydrous sodium sulfate. After filtration, the solvent was distilled off under reduced pressure to obtain a crude product of (2S)-2-[5-(5-bromo-2-chloropyridin-3-yl)-1H-pyrazol-1-yl]propanoic acid (1.39 g) as a mixture containing a positional isomer. To a solution of the crude product of (2S)-2-[5-(5-bromo-2-chloropyridin-3-yl)-1H-pyrazol-1-yl]propanoic acid (1.31 g) obtained in the above step in tetrahydrofuran (10 mL), a 0.92 mol/L solution of borantetrahydrofuran complex in tetrahydrofuran (6.5 mL, 6.0 mmol) was added under ice cooling, the mixture was stirred at the same temperature as above for 10 minutes and subsequently stirred at room temperature for 20 hours. The mixture was cooled in an ice water bath, a 1.0 mol/L aqueous solution of sodium hydroxide was added thereto, followed by extraction with a mixed solvent of ethyl acetate/n-hexane=4/1. The organic layer was washed with water and a saturated aqueous solution of sodium chloride and dried over anhydrous sodium sulfate. After filtration, the solvent was distilled off under reduced pressure to obtain a crude product of (2S)-2-[5-(5-bromo-2-chloropyridin-3-yl)-1H-pyrazol-1-yl]propan-1-ol (760 mg) as a mixture containing a positional isomer. To a solution of the crude product of (2S)-2-[5-(5-bromo-2-chloropyridin-3-yl)-1H-pyrazol-1-yl]propan-1-ol (760 mg) as a mixture containing positional isomers obtained in the above step in N,N-dimethylformamide (50 mL) was added potassium carbonate (829 mg, 6.00 mmol) at room temperature, and the mixture was stirred at 120° C. for 2 hours in an oil bath. The reaction mixture was cooled, and diluted by addition of a saturated aqueous solution of ammonium chloride, followed by extraction with a mixed solvent of ethyl acetate/n-hexane=4/1. The organic layer was washed with a saturated aqueous solution of ammonium chloride and a saturated aqueous solution of sodium chloride and dried over anhydrous sodium sulfate. After filtration, the solvent was distilled off under reduced pressure, the residue was purified in an automatic chromatography apparatus (Yamazen Co. Ltd., High-Flash™ column Amino, n-hexane/ethyl acetate=96/4-66/34) to obtain the title compound (597 mg, yield for 3 steps: 54%).
¹H NMR spectrum (CDCl₃, 400 MHz) δ: 8.26 (1H, d, J=2.4 Hz), 8.19 (1H, d, J=2.4 Hz), 7.55 (1H, d, J=1.8 Hz), 6.66 (1H, d, J=1.8 Hz), 4.95-4.89 (1H, m), 4.59 (1H, dd, J=13.1, 4.6 Hz), 4.44-4.43 (1H, m), 1.64 (3H, d, J=7.3 Hz).

(16c) tert-butyl [(5S)-5-methyl-5,6-dihydropyrazolo[1,5-d]pyrido[3,2-f][1,4]oxazepin-10-yl]carbamate To a mixture of (5S)-10-bromo-5-methyl-5,6-dihydropyrazolo[1,5-d]pyrido[3,2-f][1,4]oxazepine (590 mg, 2.11 mmol) obtained in Example (16b) in toluene (10 mL), tert-butyl carbamate (321 mg, 2.74 mmol), Tris(dibenzylideneacetone)dipalladium(0)-chloroform adduct (109 mg, 0.11 mmol), 2-Di-tert-butylphosphino-2',4',6'-triisopropylbiphenyl (179 mg, 0.42 mmol) and sodium tert-butoxide (466 mg, 4.84 mmol) were added at room temperature, and the mixture was stirred under nitrogen atmosphere at the same temperature as above for 17 hours. The mixture was diluted by addition of ethyl acetate and a saturated aqueous solution of ammonium chloride, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=61/39-40/60). To the obtained solid, diisopropyl ether was added, the precipitated solid was collected by filtration, washed with diisopropyl ether, and then dried to obtain the title compound (493 mg, yield: 74%).
¹H NMR spectrum (CDCl₃, 400 MHz) δ: 8.43 (1H, br s), 8.06 (1H, d, J=2.4 Hz), 7.54 (1H, d, J=1.8 Hz), 6.71 (1H, d, J=1.8 Hz), 6.55 (1H, br s), 4.91-4.88 (1H, m), 4.55 (1H, dd, J=12.8, 4.3 Hz), 4.41 (1H, dd, J=12.8, 1.2 Hz), 1.64 (3H, d, J=6.7 Hz), 1.54 (9H, s).

(16d) 5-chloro-2-methoxy-N-[(5S)-5-methyl-5,6-dihydropyrazolo[1,5-d]pyrido[3,2-f][1,4]oxazepin-10-yl]benzenesulfonamide The title compound (108 mg, yield: 90%) was obtained by production according to the method described in Examples (7c) using tert-butyl [(5S)-5-methyl-5,6-dihydropyrazolo[1,5-d]pyrido[3,2-f][1,4]oxazepin-10-yl]carbamate (90.1 mg, 0.29 mmol) obtained in Example (16c) and 5-chloro-2-methoxybenzenesulfonyl chloride (72.8 mg, 0.30 mmol) as starting materials.
¹H NMR spectrum (DMSO-d6, 400 MHz) δ: 10.29 (1H, br s), 7.95 (1H, d, J=2.4 Hz), 7.87 (1H, d, J=2.4 Hz), 7.70-7.68 (2H, m), 7.56 (1H, d, J=1.8 Hz), 7.27 (1H, d, J=8.5 Hz), 6.63 (1H, d, J=1.8 Hz), 4.85-4.79 (1H, m), 4.49 (1H, dd, J=13.1, 4.6 Hz), 4.38 (1H, br d, J=13.1 Hz), 3.89 (3H, s), 1.44 (3H, d, J=6.7 Hz).
MS spectrum (ES/APCI⁺): 421 (M+H), 423 (M+2+H).

(Example 17) 5-chloro-2-methoxy-N-[(5R)-5-methyl-5,6-dihydropyrazolo[1,5-d]pyrido[3,2-f][1,4]oxazepin-10-yl]benzenesulfonamide

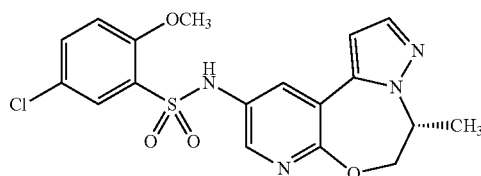

(17a) methyl (2R)-2-hydrazinylpropanoate hydrochloride

The title compound (6.82 g, yield for 3 steps: 92%) was obtained by production according to the method described in Examples (16a) using (2S)-2-hydroxypropanoate (5.00 g, 48.0 mmol) as a starting material.
¹H NMR spectrum (DMSO-d6, 400 MHz) δ: 3.82 (1H, q, J=7.3 Hz), 3.70 (3H, s), 1.26 (3H, d, J=7.3 Hz).

(17b) (5R)-10-bromo-5-methyl-5,6-dihydropyrazolo[1,5-d]pyrido[3,2-f][1,4]oxazepine The title compound (285 mg, yield for 3 steps: 31%) was obtained by production according to the method described in Examples (16b) using 1-(5-bromo-2-chloropyridin-3-yl)ethanone (825 mg, 3.34 mmol) and methyl (2R)-2-hydrazinylpropanoate hydrochloride (672 mg, 4.35 mmol) obtained in Example (17b) as starting materials.
¹H NMR spectrum (CDCl₃, 400 MHz) δ: 8.26 (1H, d, J=2.4 Hz), 8.19 (1H, d, J=2.4 Hz), 7.55 (1H, d, J=1.8 Hz), 6.66 (1H, d, J=1.8 Hz), 4.95-4.88 (1H, m), 4.60 (1H, dd, J=13.1, 4.6 Hz), 4.45-4.43 (1H, m), 1.64 (3H, d, J=6.7 Hz).

(17c) tert-butyl [(5R)-5-methyl-5,6-dihydropyrazolo[1,5-d]pyrido[3,2-f][1,4]oxazepin-10-yl]carbamate The title compound (290 mg, yield: 91%) was obtained by production according to the method described in Examples (7b) using (5R)-10-bromo-5-methyl-5,6-dihydropyrazolo[1,5-d]pyrido[3,2-f][1,4]oxazepine (282 mg, 1.01 mmol) obtained in Example (17b) as a starting material.
¹H NMR spectrum (CDCl₃, 400 MHz) δ: 8.43 (1H, br s), 8.05 (1H, d, J=2.4 Hz), 7.54 (1H, d, J=1.8 Hz), 6.71 (1H, d, J=1.8 Hz), 6.52 (1H, br s), 4.93-4.86 (1H, m), 4.55 (1H, dd, J=12.8, 4.6 Hz), 4.42 (1H, d, J=12.8 Hz), 1.64 (3H, d, J=6.7 Hz), 1.54 (9H, s).

(17d) 5-chloro-2-methoxy-N-[(5R)-5-methyl-5,6-dihydropyrazolo[1,5-d]pyrido[3,2-f][1,4]oxazepin-10-yl]benzenesulfonamide The title compound (104 mg, yield: 92%) was obtained by production according to the method described in Examples (7c) using tert-butyl [(5R)-5-methyl-5,6-dihydropyrazolo[1,5-d]pyrido[3,2-f][1,4]oxazepin-10-yl]carbamate (85.1 mg, 0.27 mmol) obtained in Example (17c) and 5-chloro-2-methoxybenzenesulfonyl chloride (69.2 mg, 0.27 mmol) as starting materials.
¹H NMR spectrum (DMSO-d6, 400 MHz) δ: 10.28 (1H, br s), 7.95 (1H, d, J=2.4 Hz), 7.87 (1H, d, J=2.4 Hz), 7.75-7.63 (2H, m), 7.56 (1H, d, J=1.8 Hz), 7.27 (1H, d, J=9.2 Hz), 6.63 (1H, d, J=1.8 Hz), 4.85-4.79 (1H, m), 4.49 (1H, dd, J=12.8, 4.6 Hz), 4.38 (1H, dd, J=12.8, 1.2 Hz), 3.89 (3H, s), 1.44 (3H, d, J=6.7 Hz).
MS spectrum (ES/APCI⁺): 421 (M+H), 423 (M+2+H).

(Example 18) 2-ethoxy-5-fluoro-N-[(5S)-5-methyl-5,6-dihydropyrazolo[1,5-d]pyrido[3,2-f][1,4]oxazepin-10-yl]benzenesulfonamide

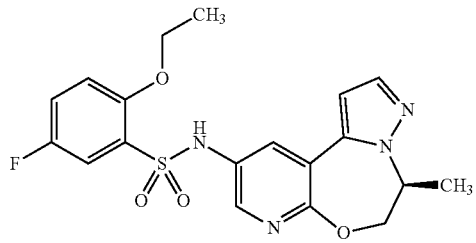 [SMILES: CCOc1ccc(F)cc1S(=O)(=O)Nc1cnc2c(c1)-c1ccnn1[C@@H](C)CO2]

The title compound (113 mg, yield: 93%) was obtained by production according to the method described in Examples (7c) using tert-butyl [(5S)-5-methyl-5,6-dihydropyrazolo[1,5-d]pyrido[3,2-f][1,4]oxazepin-10-yl]carbamate (90.9 mg, 0.29 mmol) obtained in Example (16c) and 5-Fluoro-2-ethoxybenzenesulfonyl chloride (74.2 mg, 0.31 mmol) obtained in Example (9a) as starting materials.

$^1$H NMR spectrum (DMSO-d6, 400 MHz) δ: 10.14 (1H, s), 7.94 (1H, d, J=2.4 Hz), 7.88 (1H, d, J=2.4 Hz), 7.60 (1H, dd, J=7.9, 3.1 Hz), 7.56 (1H, d, J=2.4 Hz), 7.50-7.45 (1H, m), 7.25 (1H, dd, J=9.2, 3.7 Hz), 6.61 (1H, d, J=2.4 Hz), 4.83-4.81 (1H, m), 4.49 (1H, dd, J=13.1, 4.6 Hz), 4.36 (1H, br d, J=13.1 Hz), 4.17 (2H, q, J=7.0 Hz), 1.44 (3H, d, J=6.7 Hz), 1.26 (3H, t, J=7.0 Hz).

MS spectrum (ES/APCI$^+$): 419 (M+H).

(Example 19) Potassium [(2-ethoxy-5-fluorophenyl)sulfonyl][(5S)-5-methyl-5,6-dihydropyrazolo[1,5-d]pyrido[3,2-f][1,4]oxazepin-10-yl]azanide (Potassium Salt of Example 18)

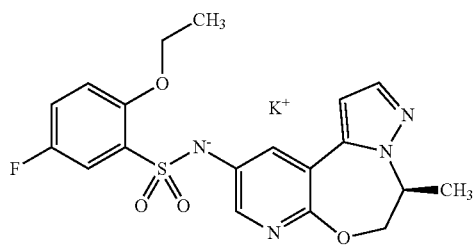 [SMILES: CCOc1ccc(F)cc1S(=O)(=O)[N-]c1cnc2c(c1)-c1ccnn1[C@@H](C)CO2 ; [K+]]

To a suspension of 2-ethoxy-5-fluoro-N-[(5S)-5-methyl-5,6-dihydropyrazolo[1,5-d]pyrido[3,2-f][1,4]oxazepin-10-yl]benzenesulfonamide (34.1 mg, 0.082 mmol) obtained in Example 18 in ethanol (0.8 mL), a solution of 0.5 N potassium hydroxide in ethanol (0.171 mL, 0.086 mmol) was added at room temperature, and the mixture was stirred at room temperature for 3.5 hours. The solvent was distillated off under reduce pressure to obtain a crude solid. To the crude solid, ethanol was added, the precipitated solid was collected by filtration, washed with ethyl acetate, and then dried to obtain the title compound (30.5 mg, yield: 82%).

$^1$H NMR spectrum (DMSO-d6, 400 MHz) δ: 7.66 (1H, d, J=2.4 Hz), 7.59 (1H, d, J=2.4 Hz), 7.51-7.48 (2H, m), 7.11-7.09 (1H, m), 6.96 (1H, dd, J=9.1, 4.3 Hz), 6.48 (1H, d, J=1.8 Hz), 4.75-4.72 (1H, m), 4.34 (1H, dd, J=13.4, 4.9 Hz), 4.23-4.20 (1H, m), 3.91 (2H, q, J=7.0 Hz), 1.44 (3H, d, J=6.7 Hz), 1.10 (3H, t, J=7.0 Hz).

(Example 20) 2-ethoxy-5-fluoro-N-[(5R)-5-methyl-5,6-dihydropyrazolo[1,5-d]pyrido[3,2-f][1,4]oxazepin-10-yl]benzenesulfonamide

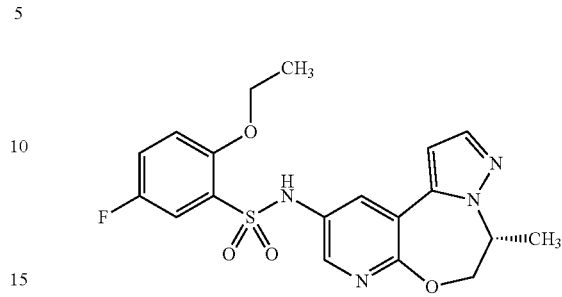

The title compound (110 mg, yield: 91%) was obtained by production according to the method described in Examples (7c) using tert-butyl [(5R)-5-methyl-5,6-dihydropyrazolo[1,5-d]pyrido[3,2-f][1,4]oxazepin-10-yl]carbamate (91.4 mg, 0.29 mmol) obtained in Example (17c) and 5-Fluoro-2-ethoxybenzenesulfonyl chloride (72.9 mg, 0.31 mmol) obtained in Example (9a) as starting materials.

$^1$H NMR spectrum (DMSO-d6, 400 MHz) δ: 10.14 (1H, s), 7.94 (1H, d, J=2.4 Hz), 7.88 (1H, d, J=2.4 Hz), 7.60 (1H, dd, J=7.9, 3.1 Hz), 7.56 (1H, d, J=2.4 Hz), 7.52-7.43 (1H, m), 7.25 (1H, dd, J=9.5, 4.0 Hz), 6.60 (1H, d, J=2.4 Hz), 4.85-4.79 (1H, m), 4.49 (1H, dd, J=13.4, 4.3 Hz), 4.36 (1H, dd, J=13.4, 1.2 Hz), 4.17 (2H, q, J=7.0 Hz), 1.44 (3H, d, J=6.7 Hz), 1.26 (3H, t, J=7.0 Hz).

MS spectrum (ES/APCI$^+$): 419 (M+H).

(Example 21) 5-chloro-2-methoxy-N-[(5S)-5-methyl-5,6-dihydropyrazolo[1,5-d]pyrido[3,2-f][1,4]oxazepin-10-yl]pyridine-3-sulfonamide

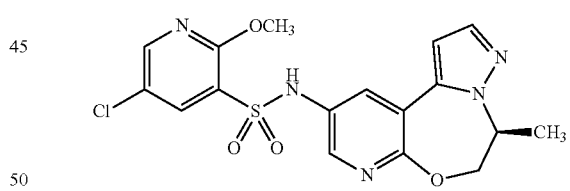

The title compound (104 mg, yield: 86%) was obtained by production according to the method described in Examples (7c) using tert-butyl [(5S)-5-methyl-5,6-dihydropyrazolo[1,5-d]pyrido[3,2-f][1,4]oxazepin-10-yl]carbamate (91.0 mg, 0.29 mmol) obtained in Example (16c) and 5-chloro-2-methoxypyridine-3-sulfonyl chloride (73.1 mg, 0.30 mmol) obtained in Example (12a) as starting materials.

$^1$H NMR spectrum (DMSO-d6, 400 MHz) δ:10.56 (1H, br s), 8.50 (1H, d, J=2.4 Hz), 8.21 (1H, d, J=2.4 Hz), 7.98 (1H, d, J=2.4 Hz), 7.89 (1H, d, J=2.4 Hz), 7.56 (1H, d, J=2.4 Hz), 6.69 (1H, d, J=2.4 Hz), 4.89-4.78 (1H, m), 4.50 (1H, dd, J=13.4, 4.3 Hz), 4.39 (1H, br d, J=13.4 Hz), 3.96 (3H, s), 1.45 (3H, d, J=6.7 Hz).

MS spectrum (ES/APCI$^+$): 422 (M+H), 424 (M+2+H).

(Example 22) potassium [(5-chloro-2-methoxypyridin-3-yl)sulfonyl][(5S)-5-methyl-5,6-dihydropyrazolo[1,5-d]pyrido[3,2-f][1,4]oxazepin-10-yl]azanide (potassium Salt of Example 21)

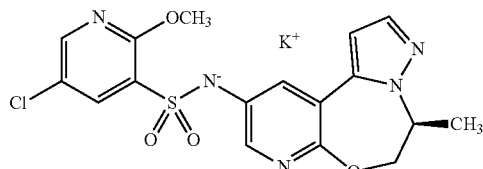

To a suspension of 5-chloro-2-methoxy-N-[(5S)-5-methyl-5,6-dihydropyrazolo[1,5-d]pyrido[3,2-f][1,4]oxazepin-10-yl]pyridine-3-sulfonamide (33.8 mg, 0.080 mmol) obtained in Example 21 in ethanol (0.8 mL), a solution of 0.5 N potassium hydroxide in ethanol (0.168 mL, 0.084 mmol) was added at room temperature, and the mixture was stirred at room temperature for 4 hours. The solvent was distillated off under reduce pressure, ethyl acetate was added thereto, and the solvent was distillated off under reduce pressure again to obtain a crude solid. To the crude solid, diisopropyl ether was added, the precipitated solid was collected by filtration, washed with diisopropyl ether, and then dried to obtain the title compound (34.7 mg, yield: 94%).

$^1$H NMR spectrum (DMSO-d6, 400 MHz) δ: 8.17 (1H, d, J=2.4 Hz), 8.01 (1H, d, J=2.4 Hz), 7.66 (1H, d, J=2.4 Hz), 7.59 (1H, d, J=2.4 Hz), 7.49 (1H, d, J=1.8 Hz), 6.54 (1H, d, J=1.8 Hz), 4.76-4.73 (1H, m), 4.36 (1H, dd, J=13.1, 4.6 Hz), 4.25 (1H, dd, J=13.1, 1.5 Hz), 3.76 (3H, s), 1.44 (3H, d, J=7.3 Hz).

(Example 23) 5-chloro-2-methoxy-N-[(5R)-5-methyl-5,6-dihydropyrazolo[1,5-d]pyrido[3,2-f][1,4]oxazepin-10-yl]pyridine-3-sulfonamide

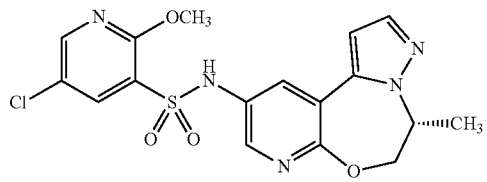 [SMILES: COc1ncc(Cl)cc1S(=O)(=O)Nc1cnc2c(c1)-c1ccnn1[C@H](C)CO2]

The title compound (107 mg, yield: 86%) was obtained by production according to the method described in Examples (7c) using tert-butyl [(5R)-5-methyl-5,6-dihydropyrazolo[1,5-d]pyrido[3,2-f][1,4]oxazepin-10-yl]carbamate (93.0 mg, 0.29 mmol) obtained in Example (17c) and 5-chloro-2-methoxypyridine-3-sulfonyl chloride (65.5 mg, 0.27 mmol) obtained in Example (12a) as starting materials.

$^1$H NMR spectrum (DMSO-d6, 400 MHz) δ: 10.56 (1H, br s), 8.50 (1H, d, J=3.1 Hz), 8.21 (1H, d, J=3.1 Hz), 7.98 (1H, d, J=2.4 Hz), 7.89 (1H, d, J=2.4 Hz), 7.56 (1H, d, J=2.4 Hz), 6.69 (1H, d, J=2.4 Hz), 4.87-4.78 (1H, m), 4.51 (1H, dd, J=13.4, 4.3 Hz), 4.39 (1H, dd, J=13.4, 1.2 Hz), 3.96 (3H, s), 1.45 (3H, d, J=6.7 Hz).

MS spectrum (ES/APCI$^+$): 422 (M+H), 424 (M+2+H).

(Example 24) 2-ethoxy-5-fluoro-N-[(5S)-5-methyl-5,6-dihydropyrazolo[1,5-d]pyrido[3,2-f][1,4]oxazepin-10-yl]pyridine-3-sulfonamide

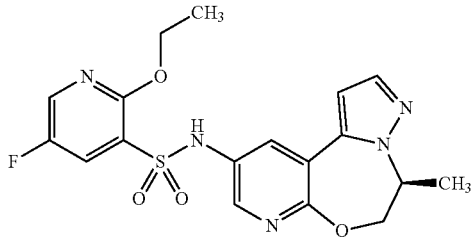

To a solution of tert-butyl [(5S)-5-methyl-5,6-dihydropyrazolo[1,5-d]pyrido[3,2-f][1,4]oxazepin-10-yl]carbamate (92.1 mg, 0.29 mmol) obtained in Example (16c) in methanol (1 mL), a 4.0 mol/L solution of hydrogen chloride in 1,4-dioxane (2 mL, 8 mmol) was added at room temperature, the mixture was stirred at the same temperature as above for 3 hour. The mixture was concentrated under reduce pressure. The residue was diluted with pyridine (1.0 mL, 12 mmol), 2-ethoxy-5-fluoropyridine-3-sulfonyl chloride (83.7 mg, 0.35 mmol) obtained in Example (14b) was added thereto at room temperature, and the mixture was stirred at 80° C. for 30 minutes in an oil bath. After cooling, the mixture was concentrated under reduced pressure, and the residue was purified in an automatic chromatography apparatus (methylene chloride/methanol=99/1-91/9, and Yamazen Co. Ltd., High-Flash™ column Amino, methylene chloride/methanol=95/5-88/12). To the obtained solid, diisopropyl ether was added, the precipitated solid was collected by filtration, washed with diisopropyl ether, and then dried to obtain the title compound (87.1 mg, yield: 71%).

$^1$H NMR spectrum (DMSO-d6, 400 MHz) δ: 10.48 (1H, br s), 8.43 (1H, d, J=3.1 Hz), 8.18 (1H, dd, J=7.3, 3.1 Hz), 7.98 (1H, d, J=2.4 Hz), 7.92 (1H, d, J=2.4 Hz), 7.56 (1H, d, J=1.8 Hz), 6.66 (1H, d, J=1.8 Hz), 4.88-4.79 (1H, m), 4.50 (1H, dd, J=12.8, 4.3 Hz), 4.44-4.36 (3H, m), 1.45 (3H, d, J=6.7 Hz), 1.24 (3H, t, J=7.0 Hz).

MS spectrum (ES/APCI$^+$): 420 (M+H).

(Example 25) potassium [(2-ethoxy-5-fluoropyridin-3-yl)sulfonyl][(5S)-5-methyl-5,6-dihydropyrazolo[1,5-d]pyrido[3,2-f][1,4]oxazepin-10-yl]azanide (potassium Salt of Example 24)

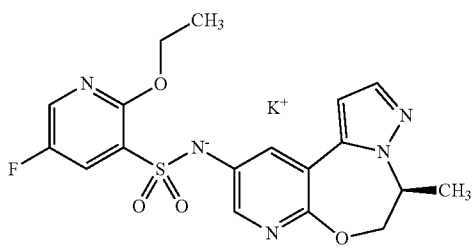

To a suspension of 2-ethoxy-5-fluoro-N-[(5S)-5-methyl-5,6-dihydropyrazolo[1,5-d]pyrido[3,2-f][1,4]oxazepin-10-yl]pyridine-3-sulfonamide (33.7 mg, 0.080 mmol) obtained in Example 24 in ethanol (0.8 mL), a solution of 0.5 N potassium hydroxide in ethanol (0.169 mL, 0.084 mmol)

was added at room temperature, and the mixture was stirred at the same temperature as above for 2 hours. The solvent was distillated off under reduce pressure, ethyl acetate was added thereto, and the solvent was distillated off under reduce pressure again to obtain a crude solid. To the crude solid, diisopropyl ether was added, the precipitated solid was collected by filtration, washed with diisopropyl ether, and then dried to obtain the title compound (40.3 mg, yield: quantitative).

$^1$H NMR spectrum (DMSO-d6, 400 MHz) δ: 8.07 (1H, d, J=3.0 Hz), 7.87 (1H, dd, J=7.9, 3.9 Hz), 7.72 (1H, d, J=2.4 Hz), 7.64 (1H, d, J=3.0 Hz), 7.49 (1H, d, J=1.8 Hz), 6.54 (1H, d, J=1.8 Hz), 4.77-4.73 (1H, m), 4.36 (1H, dd, J=13.1, 4.6 Hz), 4.25-4.15 (3H, m), 1.44 (3H, d, J=6.7 Hz), 1.04 (3H, t, J=7.0 Hz).

(Example 26) 5-chloro-N-(4,5-dihydropyrazolo[1,5-d]pyrido[2,3-b][1,4]oxazepin-9-yl)-2-methoxybenzenesulfonamide

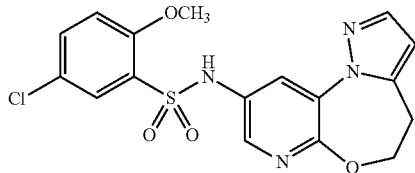 [SMILES: COc1ccc(Cl)cc1S(=O)(=O)Nc1cnc2c(c1)-n1nccc1CCO2]

(26a) 3-{[tert-butyl(diphenyl)silyl]oxy}-N-methoxy-N-methylpropanamide

To a solution of methyl 3-hydroxypropanoate (1.50 g, 14.4 mmol) in methylene chloride (70 mL), imidazole (1.96 g, 28.8 mmol) and tert-butyldiphenylchlorosilane (4.36 g, 15.8 mmol) was added at room temperature, and the mixture was stirred at the same temperature as above for 5 days. The mixture was diluted by addition of water, and followed by extraction with methylene chloride. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-40/60) to obtain methyl 3-{[tert-butyl(diphenyl)silyl]oxy}propanoate (5.54 g). To a solution of methyl 3-{[tert-butyl(diphenyl)silyl]oxy}propanoate (5.54 g) obtained in the above step in methanol (200 mL), a 1.0 mol/L aqueous solution of sodium hydroxide (40 mL, 40 mmol) was added at room temperature, and the mixture was stirred at the same temperature as above for 4 hours. The mixture was diluted by addition of a saturated aqueous ammonium chloride under ice cooling, and followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-40/60) to obtain 3-{[tert-butyl(diphenyl)silyl]oxy}propanoic acid (5.81 g). To a solution of 3-{[tert-butyl(diphenyl)silyl]oxy}propanoic acid (5.81 g) obtained in the above step in methylene chloride (100 mL), N,N'-carbonyldiimidazole (3.01 g, 18.6 mmol) was added at room temperature, and the mixture was stirred at the same temperature as above for 1 hour. Subsequently, N,O-dimethylhydroxylamine hydrochloride (1.81 g, 18.6 mmol) and triethylamine (2.94 mL, 21.2 mmol) was added thereto, and the mixture was stirred at room temperature for 19 hours. The mixture was diluted by addition of water, followed by extraction with methylene chloride. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-35/65) to obtain the title compound (4.80 g, yield for 3 steps: 73%).

$^1$H NMR spectrum (CDCl$_3$, 400 MHz) δ: 7.69-7.67 (4H, m), 7.44-7.36 (6H, m), 4.00 (2H, t, J=6.8 Hz), 3.66 (3H, s), 3.18 (3H, s), 2.71-2.70 (2H, m), 1.04 (9H, s).

(26b) (4E)-3,11,11-trimethyl-10,10-diphenyl-2,9-dioxa-3-aza-10-siladodec-4-en-6-one To 3-{[tert-butyl(diphenyl)silyl]oxy}-N-methoxy-N-methylpropanamide (1.50 g, 4.04 mmol) obtained in Example (26a), a 0.5 mol/L solution of ethynylmagnesium bromide in tetrahydrofuran (10.1 mL, 5.05 mmol) was added at room temperature, and the mixture was stirred at 50° C. for 40 minutes in an oil bath. The mixture was cooled to room temperature, a saturated aqueous solution of ammonium chloride (10 mL) was added thereto, and the mixture was stirred at 50° C. for further 40 minutes in an oil bath. The mixture was cooled to room temperature, and followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-40/60) to obtain the title compound (1.48 g, yield: 92%).

$^1$H NMR spectrum (CDCl$_3$, 400 MHz) δ: 7.69-7.66 (4H, m), 7.44-7.33 (7H, m), 5.48 (1H, d, J=12.9 Hz), 3.98 (2H, t, J=6.6 Hz), 3.64 (3H, s), 3.10 (3H, s), 2.65 (2H, t, J=6.6 Hz), 1.03 (9H, s).

(26c) 5-bromo-2-chloro-3-hydrazinylpyridine hydrochloride

To a mixture of 5-bromo-2-chloro-pyridin-3-amine (1.50 g, 7.23 mmol) in 35% hydrochloric acid (10 mL), a solution of sodium nitrite (500.1 mg, 7.23 mmol) in water (5 mL) was added under ice cooling. Subsequently, the mixture was added to a solution of tin (II) chloride dihydrate (3.26 g, 14.5 mmol) in 35% hydrochloric acid (4 mL) under ice cooling, and the mixture was stirred at room temperature for 1 hour. The precipitated solid was collected by filtration, washed with 35% hydrochloric acid, and then dried to obtain the title compound (1.465 g, yield: 78%).

$^1$H NMR spectrum (DMSO-d6, 400 MHz) δ: 10.07 (3H, br s), 8.63 (1H, br s), 8.12-8.11 (1H, m), 7.73-7.72 (1H, m).

(26d) 9-bromo-4,5-dihydropyrazolo[1,5-d]pyrido[2,3-b][1,4]oxazepine

To a solution of (4E)-3,11,11-trimethyl-10,10-diphenyl-2,9-dioxa-3-aza-10-siladodec-4-en-6-one (507 mg, 1.28 mmol) obtained in Example (26b) in methanol (1.5 mL), 5-bromo-2-chloro-3-hydrazinylpyridine hydrochloride (396.5 mg, 1.53 mmol) obtained in Example (26c) was added under ice cooling, and the mixture was heated in an oil bath until reflux. And then, a solution of sodium carbonate (257.9 mg, 2.42 mmol) in water (10 mL) was added thereto, and the mixture was stirred under reflux for 1.5 hours. The mixture was cooled to room temperature, and concentrated under reduce pressure. The residue was diluted by addition of water, followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-60/40) to obtain 5-bromo-3-[5-(2-{[tert-butyl(diphenyl)silyl]oxy}ethyl)-1H-pyrazol-1-yl]-2-chloropyridine (390 mg). To a solution of 5-bromo-3-[5-(2-{[tert-butyl(diphenyl)silyl]oxy}ethyl)-1H-pyrazol-1-yl]-2-chloropyridine (390 mg) obtained in the above step in tetrahydrofuran (10 mL), a 1.0 mol/L solution of tetrabutyl ammonium fluoride in tetrahydrofuran (1.08 mL, 1.08 mmol) was added under ice cooling, the mixture was stirred at room temperature for 16 hours.

The mixture was diluted by addition of a saturated aqueous solution of ammonium chloride, followed by extraction with a mixed solvent of chloroform/isopropanol=3/1. The organic layer was washed with a saturated aqueous solution of sodium chloride and dried over anhydrous sodium sulfate. After filtration, the solvent was distilled off under reduced pressure, and the residue was purified in an automatic chromatography apparatus (ethyl acetate/methanol=100/0-50/50) to obtain the title compound (60 mg, yield for 2 steps: 18%).

$^1$H NMR spectrum (CDCl$_3$, 400 MHz) δ: 8.75 (1H, d, J=2.0 Hz), 8.21 (1H, d, J=2.0 Hz), 7.66 (1H, d, J=2.0 Hz), 6.27 (1H, br s), 4.56 (2H, t, J=5.4 Hz), 3.31 (2H, t, J=5.4 Hz).

(26e) tert-butyl 4,5-dihydropyrazolo[1,5-d]pyrido[2,3-b][1,4]oxazepin-9-ylcarbamate The title compound (54 mg, yield: 79%) was obtained by production according to the method described in Examples (7b) using 9-bromo-4,5-dihydropyrazolo[1,5-d]pyrido[2,3-b][1,4]oxazepine (60.0 mg, 0.22 mmol) obtained in Example (26d) as a starting material.

$^1$H NMR spectrum (CDCl$_3$, 400 MHz) δ: 8.66 (1H, br s), 8.17 (1H, br d, J=2.7 Hz), 7.65 (1H, br d, J=1.6 Hz), 6.59 (1H, br s), 6.25-6.25 (1H, m), 4.55 (2H, t, J=5.5 Hz), 3.25 (2H, t, J=5.5 Hz), 1.53 (9H, s).

(26f) 5-chloro-N-(4,5-dihydropyrazolo[1,5-d]pyrido[2,3-b][1,4]oxazepin-9-yl)-2-methoxybenzenesulfonamide The title compound (51 mg, yield: 70%) was obtained by production according to the method described in Examples (7c) using tert-butyl 4,5-dihydropyrazolo[1,5-d]pyrido[2,3-b][1,4]oxazepin-9-ylcarbamate (54.0 mg, 0.18 mmol) obtained in Example (26e) and 5-chloro-2-methoxybenzenesulfonyl chloride (47.5 mg, 0.20 mmol) as starting materials.

$^1$H NMR spectrum (DMSO-d6, 400 MHz) δ: 10.46 (1H, br s), 8.28 (1H, d, J=2.7 Hz), 7.87 (1H, d, J=2.7 Hz), 7.71-7.66 (2H, m), 7.25 (1H, d, J=9.0 Hz), 6.38-6.37 (1H, m), 4.43 (2H, t, J=5.3 Hz), 3.89 (3H, s), 3.22 (2H, t, J=5.3 Hz).

MS spectrum (ES/APCI$^+$): 407 (M+H), 409 (M+2+H).

(Example 27) 5-chloro-2-methoxy-N-[(9aS)-5-oxo-8,9,9a,10-tetrahydro-5H,7H-pyrido[3,2-f]pyrrolo[2,1-c][1,4]oxazepin-3-yl]benzenesulfonamide

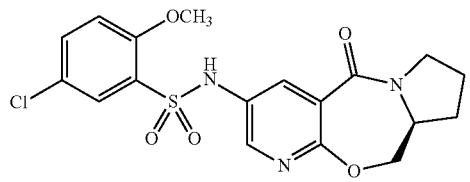 [SMILES: COc1ccc(Cl)cc1S(=O)(=O)Nc1cnc2c(c1)C(=O)N1CCC[C@H]1CO2]

(27a) (2-chloro-5-nitropyridin-3-yl) [(2S)-2-(hydroxymethyl)pyrrolidin-1-yl]methanone To a suspension of 2-chloro-5-nitropyridine-3-carboxylic acid (300 mg, 1.48 mmol) and oxalyl chloride (0.17 mL, 2.0 mmol) in methylene chloride (8 mL), N,N-dimethylformamide (0.05 mL) was added at room temperature, and the mixture was stirred at the same temperature as above for 1 hour. The reaction mixture was concentrated under reduced pressure to prepare a crude product of 2-chloro-5-nitropyridine-3-carbonyl chloride. To a solution of (2S)-pyrrolidin-2-ylmethanol (0.145 mL, 1.49 mmol) and N,N-diisopropylethylamine (0.5 mL, 3 mmol) in tetrahydrofuran (4 mL), a solution of the crude product of 2-chloro-5-nitropyridine-3-carbonyl chloride in tetrahydrofuran (4 mL) was added under ice cooling, and then the reaction mixture was stirred at room temperature for 40 minutes. The mixture was diluted by addition of ethyl acetate, the organic layer was washed with a saturated aqueous solution of sodium chloride, and dried over anhydrous sodium sulfate. After filtration, the solvent was distilled off under reduced pressure and the residue was purified in an automatic chromatography apparatus (n-hexane/ethyl acetate=100/0-0/100) to obtain the title compound (338 mg, yield: 80%).

$^1$H NMR spectrum (CDCl$_3$, 400 MHz) δ: 9.27-9.22 (1H, m), 8.54-8.52 (1H, m), 4.41-4.39 (1H, m), 3.91-3.78 (2H, m), 3.42-3.25 (2H, m), 2.25-2.19 (1H, m), 2.09-1.78 (4H, m).

(27b) (9aS)-3-nitro-8,9,9a,10-tetrahydro-5H,7H-pyrido[3,2-f]pyrrolo[2,1-c][1,4]oxazepin-5-one To a solution of (2-chloro-5-nitropyridin-3-yl) [(2S)-2-(hydroxymethyl)pyrrolidin-1-yl]methanone (338 mg, 1.18 mmol) obtained in Example (27a) in tetrahydrofuran (60 mL), sodium hydride (approximately 63% content, 102 mg, 2.68 mmol) was added at room temperature, and the mixture was stirred at the same temperature as above for 24 hours. Additional sodium hydride (approximately 63% content, 101 mg, 2.65 mmol) was added thereto at room temperature, and the mixture was stirred at the same temperature as above for further 24 hours. The reaction mixture was cooled with ice-water bath, a 2.0 mol/L aqueous solution of sodium hydroxide was added thereto, and stirred at room temperature for 30 minutes followed by extraction with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (n-hexane/ethyl acetate=100/0-0/100) to obtain the title compound (180 mg, yield: 61%).

¹H NMR spectrum (CDCl₃, 400 MHz) δ: 9.48 (1H, d, J=3.0 Hz), 9.21 (1H, d, J=3.0 Hz), 4.76 (1H, d, J=12.1 Hz), 4.25 (1H, dd, J=12.8, 7.9 Hz), 4.11-4.05 (1H, m), 3.89-3.84 (1H, m), 3.78-3.75 (1H, m), 2.39-2.32 (1H, m), 2.12-2.05 (1H, m), 2.00-1.88 (1H, m), 1.80-1.70 (1H, m).

(27c) (9aS)-3-amino-8,9,9a,10-tetrahydro-5H,7H-pyrido[3,2-f]pyrrolo[2,1-c][1,4]oxazepin-5-one To a mixture of (9aS)-3-nitro-8,9,9a,10-tetrahydro-5H,7H-pyrido[3,2-f]pyrrolo[2,1-c][1,4]oxazepin-5-one (180 mg, 0.72 mmol) obtained in Example (27b) in tetrahydrofuran (3 mL) and methanol (3 mL), nickel(II) chloride hexahydrate (358 mg, 1.51 mmol) was added. Subsequently, the mixture was cooled in an ice water bath. Sodium borohydride (107 mg, 2.83 mmol) was added thereto, the mixture was stirred at room temperature for 50 minutes. The reaction mixture was diluted by addition of acetone and a saturated aqueous solution of sodium bicarbonate, further Celite 545® (approximately 0.7 g) was added thereto, and the mixture was stirred at room temperature for further 30 minutes. The reaction mixture was filtered, the filtrate was extracted with a mixed solvent of ethyl acetate and tetrahydrofuran, and the organic layer was dried over anhydrous sodium sulfate. After filtration, the solvent was distilled off under reduced pressure, and the residue was purified in an automatic chromatography apparatus (ethyl acetate/methanol=100/0-80/20) to obtain the title compound (140 mg, yield: 89%).

¹H NMR spectrum (CDCl₃, 400 MHz) δ: 7.88-7.87 (2H, m), 4.55-4.52 (1H, m), 4.05-3.98 (2H, m), 3.77-3.73 (2H, m), 3.60 (2H, br s), 2.24-2.20 (1H, m), 2.04-1.88 (2H, m), 1.73-1.64 (1H, m).

(27d) 5-chloro-2-methoxy-N-[(9aS)-5-oxo-8,9,9a,10-tetrahydro-5H,7H-pyrido[3,2-f]pyrrolo[2,1-c][1,4]oxazepin-3-yl]benzenesulfonamide To a mixture of (9aS)-3-amino-8,9,9a,10-tetrahydro-5H,7H-pyrido[3,2-f]pyrrolo[2,1-c][1,4]oxazepin-5-one (140 mg, 0.64 mmol) obtained in Example (27c) and pyridine (3 mL, 37 mmol), 5-chloro-2-methoxybenzenesulfonyl chloride (170 mg, 0.70 mmol) was added, and the mixture was stirred at 80° C. for 1 hour in an oil bath. The reaction mixture was cooled, and then concentrated under reduced pressure. The residue was purified in an automatic chromatography apparatus (ethyl acetate/methanol=100/0-80/20). To the obtained solid, diisopropyl ether was added, the precipitated solid was collected by filtration, and then dried to obtain the title compound (172 mg, yield: 63%).

¹H NMR spectrum (CDCl₃, 400 MHz) δ: 8.32 (1H, d, J=3.0 Hz), 8.24 (1H, d, J=3.0 Hz), 7.73 (1H, d, J=2.7 Hz), 7.46 (1H, dd, J=8.8, 2.7 Hz), 7.03 (1H, br s), 7.00 (1H, d, J=8.8 Hz), 4.60 (1H, d, J=11.5 Hz), 4.04-3.98 (5H, m), 3.80-3.66 (2H, m), 2.29-2.23 (1H, m), 2.06-1.84 (2H, m), 1.70-1.65 (1H, m).

MS spectrum (ES/APCI⁺): 424 (M+H), 426 (M+2+H)

(Example 28) 5-chloro-2-methoxy-N-[(9aR)-5-oxo-8,9,9a,10-tetrahydro-5H,7H-pyrido[3,2-f]pyrrolo[2,1-c][1,4]oxazepin-3-yl]benzenesulfonamide

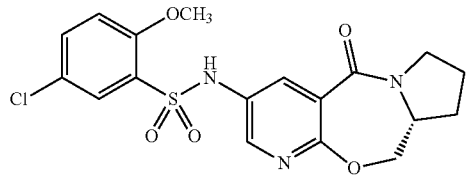 [SMILES: COc1ccc(Cl)cc1S(=O)(=O)Nc1cnc2c(c1)C(=O)N1CCC[C@@H]1CO2]

(28a) (2-chloro-5-nitropyridin-3-yl)[(2R)-2-(hydroxymethyl)pyrrolidin-1-yl]methanone The title compound (594 mg, yield: 71%) was obtained by production according to the method described in Example (27a) using 2-chloro-5-nitropyridine-3-carboxylic acid (500 mg, 2.49 mmol) and (2R)-pyrrolidin-2-ylmethanol (0.258 mg, 2.55 mmol) as starting materials.

¹H NMR spectrum (CDCl₃, 400 MHz) δ: 9.27-9.22 (1H, m), 8.54-8.52 (1H, m), 4.41-4.39 (1H, m), 3.91-3.78 (2H, m), 3.42-3.25 (2H, m), 2.25-2.19 (1H, m), 2.09-1.78 (4H, m).

(28b) (9aR)-3-nitro-8,9,9a,10-tetrahydro-5H,7H-pyrido[3,2-f]pyrrolo[2,1-c][1,4]oxazepin-5-one To a solution of (2-chloro-5-nitropyridin-3-yl)[(2R)-2-(hydroxymethyl)pyrrolidin-1-yl]methanone (594 mg, 2.08 mmol) obtained in Example (28a) in tetrahydrofuran (100 mL), a ca. 1.9 mol/L solution of sodium bis(trimethylsilyl)amide in tetrahydrofuran (1.6 mL, 3.0 mmol) was added under ice cooling, and the mixture was stirred at the same temperature for 1 hour. The mixture was diluted by addition of a saturated aqueous solution of sodium chloride followed by extraction with ethyl acetate. The organic layer was washed with a saturated aqueous solution of sodium chloride, dried over anhydrous sodium sulfate. After filtration, the solvent was distillated off under reduced pressure, and the residue was purified in an automatic chromatography apparatus (n-hexane/ethyl acetate=100/0-20/80) to obtain the title compound (385 mg, yield: 52%).

¹H NMR spectrum (CDCl₃, 400 MHz) δ: 9.48 (1H, d, J=3.0 Hz), 9.21 (1H, d, J=3.0 Hz), 4.76 (1H, d, J=12.1 Hz), 4.25 (1H, dd, J=12.8, 7.9 Hz), 4.11-4.05 (1H, m), 3.89-3.84 (1H, m), 3.78-3.75 (1H, m), 2.39-2.32 (1H, m), 2.12-2.05 (1H, m), 2.00-1.88 (1H, m), 1.80-1.70 (1H, m).

(28c) (9aR)-3-amino-8,9,9a,10-tetrahydro-5H,7H-pyrido[3,2-f]pyrrolo[2,1-c][1,4]oxazepin-5-one The title compound (341 mg, yield: quantitative) was obtained by production according to the method described in Example (27c) using (9aR)-3-nitro-8,9,9a,10-tetrahydro-5H,7H-pyrido[3,2-f]pyrrolo[2,1-c][1,4]oxazepin-5-one (385 mg, 1.54 mmol) obtained in Example (28b) as a starting material.

¹H NMR spectrum (CDCl₃, 400 MHz) δ: 7.88-7.87 (2H, m), 4.55-4.52 (1H, m), 4.05-3.98 (2H, m), 3.77-3.73 (2H, m), 3.60 (2H, br s), 2.24-2.20 (1H, m), 2.04-1.88 (2H, m), 1.73-1.64 (1H, m).

(28d) 5-chloro-2-methoxy-N-[(9aR)-5-oxo-8,9,9a,10-tetrahydro-5H,7H-pyrido[3,2-f]pyrrolo[2,1-c][1,4]oxazepin-3-yl]benzenesulfonamide The title compound (178 mg, yield: 58%) was obtained by production according to the method described in Example (27d) using (9aR)-3-amino-8,9,9a,10-tetrahydro-5H,7H-pyrido[3,2-f]pyrrolo[2,1-c][1,4]oxazepin-5-one (165 mg, 0.75 mmol) obtained in Example (28c) and 5-chloro-2-methoxybenzenesulfonyl chloride (60.8 mg, 0.25 mmol) as starting materials.

$^1$H NMR spectrum (CDCl$_3$, 400 MHz) δ: 8.32 (1H, d, J=3.0 Hz), 8.24 (1H, d, J=3.0 Hz), 7.73 (1H, d, J=2.7 Hz), 7.46 (1H, dd, J=8.8, 2.7 Hz), 7.03 (1H, br s), 7.00 (1H, d, J=8.8 Hz), 4.60 (1H, d, J=11.5 Hz), 4.04-3.98 (5H, m), 3.80-3.66 (2H, m), 2.29-2.23 (1H, m), 2.06-1.84 (2H, m), 1.70-1.65 (1H, m).

MS spectrum (ES/APCI$^+$): 424 (M+H), 426 (M+2+H).

(Example 29) 5-chloro-N-[(8R,9aS)-8-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide

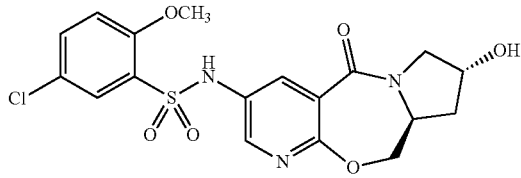 [SMILES: COc1ccc(Cl)cc1S(=O)(=O)Nc1cnc2c(c1)C(=O)N1C[C@H](O)C[C@H]1CO2]

(29a) (2-chloro-5-nitropyridin-3-yl)[(2S,4R)-4-hydroxy-2-(hydroxymethyl)pyrrolidin-1-yl]methanone The title compound (540 mg, yield: 77%) was obtained by production according to the method described in Example (27a) using 2-chloro-5-nitropyridine-3-carboxylic acid (470 mg, 2.32 mmol) and (3R,5S)-5-(hydroxymethyl)pyrrolidin-3-ol (0.354 mg, 2.30 mmol) as starting materials.

$^1$H NMR spectrum (DMSO-d6, 400 MHz) δ: 9.28 (1H, d, J=3.0 Hz), 8.79-8.74 (1H, m), 5.00-4.24 (4H, m), 3.79-2.96 (4H, m), 2.08-1.97 (2H, m).

(29b) (8R,9aS)-8-hydroxy-3-nitro-8,9,9a,10-tetrahydro-5H,7H-pyrido[3,2-f]pyrrolo[2,1-c][1,4]oxazepin-5-one The title compound (182 mg, yield: 78%) was obtained by production according to the method described in Example (28b) using (2-chloro-5-nitropyridin-3-yl) [(2S,4R)-4-hydroxy-2-(hydroxymethyl)pyrrolidin-1-yl]methanone (265 mg, 0.88 mmol) obtained in Example (29a) as a starting material.

$^1$H NMR spectrum (CDCl$_3$, 400 MHz) δ: 9.51 (1H, d, J=2.4 Hz), 9.23 (1H, d, J=2.4 Hz), 4.80 (1H, d, J=12.8 Hz), 4.63 (1H, d, J=3.6 Hz), 4.47-4.40 (1H, m), 4.27-4.24 (1H, m), 3.95 (1H, dd, J=13.7, 3.6 Hz), 3.83 (1H, dd, J=13.7, 2.1 Hz), 2.37-2.33 (1H, m), 1.90-1.81 (2H, m).

(29c) (8R,9aS)-3-amino-8-hydroxy-8,9,9a,10-tetrahydro-5H, 7H-pyrido[3,2-f]pyrrolo[2,1-c][1,4]oxazepin-5-one The title compound (134 mg, yield: 84%) was obtained by production according to the method described in Example (27c) using (8R,9aS)-8-hydroxy-3-nitro-8,9,9a,10-tetrahydro-5H,7H-pyrido[3,2-f]pyrrolo[2,1-c][1,4]oxazepin-5-one (180 mg, 0.68 mmol) obtained in Example (29b) as a starting material.

$^1$H NMR spectrum (CD$_3$OD, 400 MHz) δ: 7.84 (1H, d, J=3.0 Hz), 7.81 (1H, d, J=3.0 Hz), 4.55 (1H, dd, J=11.5, 1.8 Hz), 4.44 (1H, br s), 4.21-4.08 (2H, m), 3.77-3.73 (2H, m), 2.22-2.19 (1H, m), 1.91-1.85 (1H, m).

(29d) 5-chloro-N-[(8R,9aS)-8-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide The title compound (96 mg, yield: 78%) was obtained by production according to the method described in Example (27d) using (8R,9aS)-3-amino-8-hydroxy-8,9,9a,10-tetrahydro-5H,7H-pyrido[3,2-f]pyrrolo[2,1-c][1,4]oxazepin-5-one (66 mg, 0.28 mmol) obtained in Example (29c) and 5-chloro-2-methoxybenzenesulfonyl chloride (77 mg, 0.32 mmol) as starting materials.

$^1$H NMR spectrum (DMSO-d6, 400 MHz) δ: 10.28 (1H, br s), 8.23 (1H, br s), 8.08 (1H, br s), 7.64 (2H, br s), 7.25 (1H, br s), 5.07 (1H, br s), 4.53-4.52 (1H, m), 4.26 (1H, br s), 4.13-4.05 (2H, m), 3.89 (3H, s), 3.64-3.46 (2H, m), 2.04 (1H, br s), 1.72 (1H, br s).

MS spectrum (ES/APCI$^+$): 440 (M+H), 442 (M+2+H).

(Example 30) 5-chloro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide

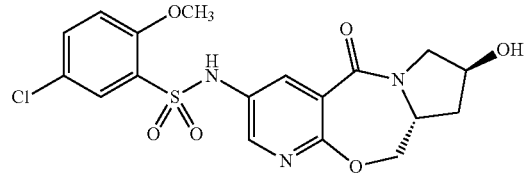 [SMILES: COc1ccc(Cl)cc1S(=O)(=O)Nc1cnc2c(c1)C(=O)N1C[C@@H](O)C[C@@H]1CO2]

(30a) (2-chloro-5-nitropyridin-3-yl)[(2R,4S)-4-hydroxy-2-(hydroxymethyl)pyrrolidin-1-yl]methanone To a suspension of 2-chloro-5-nitropyridine-3-carboxylic acid (280 mg, 1.38 mmol) and oxalyl chloride (0.154 mL, 1.80 mmol) in methylene chloride (8 mL), N,N-dimethylformamide (0.05 mL) was added at room temperature, and the mixture was stirred at the same temperature as above for 1 hour. The reaction mixture was concentrated under reduced pressure to prepare a crude product of 2-chloro-5-nitropyridine-3-carbonyl chloride. To a mixture of (3S,5R)-5-(hydroxymethyl)pyrrolidin-3-ol (212 mg, 1.38 mmol) and N,N-diisopropylethylamine (1 mL, 5.9 mmol) in tetrahydrofuran (4 mL), a solution of the crude product of 2-chloro-5-nitropyridine-3-carbonyl chloride in tetrahydrofuran (4 mL) was added under ice cooling, and then the reaction mixture was stirred at room temperature for 80 minutes. The mixture was concentrated under reduced pressure and the residue was purified in an automatic chromatography apparatus (ethyl acetate/methanol=100/0-85/15) to obtain the title compound (243 mg, yield: 80%).

$^1$H NMR spectrum (DMSO-d6, 400 MHz) δ: 9.28 (1H, d, J=3.0 Hz), 8.79-8.74 (1H, m), 5.00-4.24 (4H, m), 3.79-2.96 (4H, m), 2.08-1.97 (2H, m).

(30b) (8S,9aR)-8-hydroxy-3-nitro-8,9,9a,10-tetra-hydro-5H, 7H-pyrido[3,2-f]pyrrolo[2,1-c][1,4]oxazepin-5-one A 1.09 mol/L solution of sodium bis(trimethylsilyl)amide in tetrahydrofuran (1.7 mmol, 1.9 mmol) was diluted with tetrahydrofuran (50 mL), a solution of (2-chloro-5-nitropyridin-3-yl)[(2R,4S)-4-hydroxy-2-(hydroxymethyl)pyrrolidin-1-yl]methanone (243 mg, 0.80 mmol) obtained in Example (30a) in tetrahydrofuran (10 mL) was added thereto under ice cooling, and the mixture was stirred at the same temperature for 40 minutes. The mixture was diluted by addition of a saturated aqueous solution of sodium chloride followed by extraction with ethyl acetate. The organic layer was washed with a saturated aqueous solution of sodium chloride, dried over anhydrous sodium sulfate. After filtration, the solvent was distilled off under reduced pressure, and the residue was purified in an automatic chromatography apparatus (ethyl acetate/methanol=100/0-85/15) to obtain the title compound (77.4 mg, yield: 36%).

$^1$H NMR spectrum (CDCl$_3$, 400 MHz) δ: 9.51 (1H, d, J=2.4 Hz), 9.23 (1H, d, J=2.4 Hz), 4.80 (1H, d, J=12.8 Hz), 4.63 (1H, d, J=3.6 Hz), 4.47-4.40 (1H, m), 4.27-4.24 (1H, m), 3.95 (1H, dd, J=13.7, 3.6 Hz), 3.83 (1H, dd, J=13.7, 2.1 Hz), 2.37-2.33 (1H, m), 1.90-1.81 (2H, m).

(30c) (8S,9aR)-3-amino-8-hydroxy-8,9,9a,10-tetra-hydro-5H, 7H-pyrido[3,2-f]pyrrolo[2,1-c][1,4]oxazepin-5-one A mixture of (8S,9aR)-8-hydroxy-3-nitro-8,9,9a,10-tetrahydro-5H,7H-pyrido[3,2-f]pyrrolo[2,1-c][1,4]oxazepin-5-one (77.4 mg, 0.29 mmol) obtained in Example (30b) and 10% palladium carbon (water content: 54.6%, 20 mg) in methanol (6 mL) was stirred at room temperature for 1.5 hours at normal pressure under the hydrogen atmosphere. Hydrogen in the reaction container was replaced with nitrogen, and then, the reaction mixture was filtered through pad of Celite 545®. The solvent in the filtrate was distilled off under reduced pressure to obtain the title compound (64.2 mg, yield: 94%).

$^1$H NMR spectrum (CD$_3$OD, 400 MHz) δ: 7.84 (1H, d, J=3.0 Hz), 7.81 (1H, d, J=3.0 Hz), 4.55 (1H, dd, J=11.5, 1.8 Hz), 4.44 (1H, br s), 4.21-4.08 (2H, m), 3.77-3.73 (2H, m), 2.22-2.19 (1H, m), 1.91-1.85 (1H, m).

(30d) 5-chloro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide The title compound (83.7 mg, yield: 70%) was obtained by production according to the method described in Example (27d) using (8S,9aR)-3-amino-8-hydroxy-8,9,9a,10-tetrahydro-5H,7H-pyrido[3,2-f]pyrrolo[2,1-c][1,4]oxazepin-5-one (64.2 mg, 0.27 mmol) obtained in Example (30c) and 5-chloro-2-methoxybenzenesulfonyl chloride (70.5 mg, 0.29 mmol) as starting materials.

$^1$H NMR spectrum (DMSO-d6, 400 MHz) δ: 10.28 (1H, br s), 8.23 (1H, br s), 8.08 (1H, br s), 7.64 (2H, br s), 7.25 (1H, br s), 5.07 (1H, br s), 4.53-4.52 (1H, m), 4.26 (1H, br s), 4.13-4.05 (2H, m), 3.89 (3H, s), 3.64-3.46 (2H, m), 2.04 (1H, br s), 1.72 (1H, br s).

MS spectrum (ES/APCI$^+$): 440 (M+H), 442 (M+2+H).

(Example 31) 5-fluoro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide

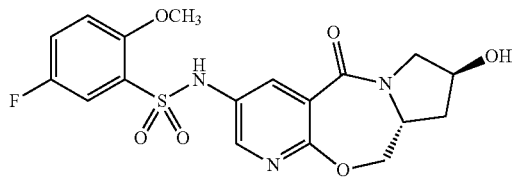

The title compound (211 mg, yield: 65%) was obtained by production according to the method described in Example (27d) using (8S,9aR)-3-amino-8-hydroxy-8,9,9a,10-tetrahydro-5H,7H-pyrido[3,2-f]pyrrolo[2,1-c][1,4]oxazepin-5-one (180 mg, 0.76 mmol) obtained in Example (30c) and 5-fluoro-2-methoxybenzenesulfonyl chloride (190 mg, 0.85 mmol) as starting materials.

$^1$H NMR spectrum (DMSO-d6, 400 MHz) δ: 10.25 (1H, br s), 8.23 (1H, d, J=2.4 Hz), 8.09 (1H, d, J=2.4 Hz), 7.51-7.46 (2H, m), 7.26-7.24 (1H, m), 5.06 (1H, br s), 4.52 (1H, d, J=11.5 Hz), 4.25 (1H, br s), 4.09-4.04 (2H, m), 3.88 (3H, s), 3.63 (1H, dd, J=13.1, 6.5 Hz), 3.45 (1H, d, J=12.8 Hz), 2.05 (1H, dd, J=13.1, 5.8 Hz), 1.75-1.68 (1H, m).

MS spectrum (ES/APCI$^+$): 424 (M+H).

(Example 32) 5-chloro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide

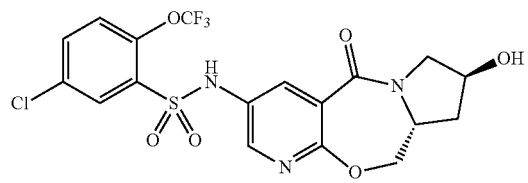 [SMILES: O=C1c2cc(NS(=O)(=O)c3cc(Cl)ccc3OC(F)(F)F)cnc2OC[C@H]2C[C@H](O)CN12]

(32a) 5-chloro-2-(trifluoromethoxy)benzenesulfonyl chloride

To a suspension of 5-chloro-2-(trifluoromethoxy)aniline (5.00 g, 23.6 mmol) and dibenzyl disulfide (4.66 g, 18.9 mmol) in acetonitrile (75 mL), isoamyl nitrite (3.46 mL, 26.0 mmol) was slowly added at 60° C. in an oil bath, and the mixture was stirred at the same temperature as above for 2 hours. The reaction mixture was cooled and then concentrated under reduced pressure, and the residue was purified in an automatic chromatography apparatus (n-hexane/ethyl acetate=100/0-95/5) to prepare 2-(benzylsulfanyl)-4-chlorophenyl trifluoromethyl ether (3.86 g, yield: 51%). To a mixture of 2-(benzylsulfanyl)-4-chlorophenyl trifluoromethyl ether (4.84 g, 15.2 mmol) obtained in the above step, acetic acid (4.5 mL) and water (3 mL) in acetonitrile (120 mL), 1,3-dichloro-5,5-dimethylhydantoin (5.98 g, 30.4 mmol) was added under ice cooling, and the mixture was stirred at the same temperature as above for 3 hours. The mixture was diluted by addition of a saturated aqueous solution of sodium bicarbonate, extracted with ethyl acetate. The organic layer was washed with a saturated aqueous solution of sodium chloride and dried over anhydrous sodium sulfate. After filtration, the solvent was distilled off under reduced pressure, and the residue was purified in an automatic chromatography apparatus (hexane/ethyl acetate=100/0-85/15) to obtain the title compound (3.64 g, yield: 81%).

$^1$H NMR spectrum (CDCl$_3$, 400 MHz) δ: 8.09 (1H, d, J=2.3 Hz), 7.75 (1H, dd, J=9.0, 2.7 Hz), 7.50-7.47 (1H, m).

(32b) 5-chloro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide To a mixture of (8S,9aR)-3-amino-8-hydroxy-8,9,9a,10-tetrahydro-5H,7H-pyrido[3,2-f]pyrrolo[2,1-c][1,4]oxazepin-5-one (562 mg, 2.39 mmol) obtained in Example (30c) and pyridine (3.86 mL, 47.8 mmol), 5-chloro-2-(trifluoromethoxy)benzenesulfonyl chloride (740 mg, 2.51 mmol) obtained in Example (32a) was added, and the mixture was stirred at 80° C. for 2 hours in an oil bath. After cooling, additional 5-chloro-2-(trifluoromethoxy)benzenesulfonyl chloride (141 mg, 0.48 mmol) was added thereto, and the mixture was stirred at 80° C. for further 2 hours in an oil bath. The reaction mixture was cooled, and then concentrated under reduced pressure. The residue was purified in an automatic chromatography apparatus (ethyl acetate/methanol=100/0-90/10). To the obtained solid, ethanol was added, the precipitated solid was collected by filtration, and then dried to obtain the title compound (844 mg, yield: 72%).

$^1$H NMR spectrum (DMSO-d6, 400 MHz) δ: 10.78 (1H, br s), 8.20 (1H, d, J=2.7 Hz), 8.13 (1H, d, J=2.7 Hz), 7.90-7.88 (2H, m), 7.64-7.61 (1H, m), 5.08 (1H, br s), 4.56 (1H, d, J=12.1 Hz), 4.26 (1H, br s), 4.14-4.06 (2H, m), 3.65 (1H, dd, J=12.9, 3.9 Hz), 3.45 (2H, d, J=12.9 Hz), 2.07 (1H, dd, J=12.9, 6.6 Hz), 1.77-1.70 (1H, m).

MS spectrum (ES/APCI$^+$): 494 (M+H), 496 (M+2+H).

(Example 33) Potassium {[5-chloro-2-(trifluoromethoxy)phenyl]sulfonyl}[(8S,9aR)-8-hydroxy-5-oxo-8,9,9a,10-tetrahydro-5H,7H-pyrido[3,2-f]pyrrolo[2,1-c][1,4]oxazepin-3-yl]azanide (Potassium Salt of Example 32)

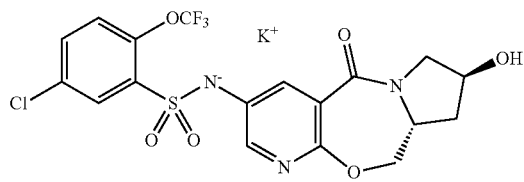 [SMILES: O=C1c2cc([N-]S(=O)(=O)c3cc(Cl)ccc3OC(F)(F)F)cnc2OC[C@H]2C[C@H](O)CN12 ; [K+]]

To a suspension of 5-chloro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide (26.8 mg, 0.054 mmol) obtained in Example (32b) in ethanol (0.5 mL), a 0.5 mol/L solution of potassium hydroxide in ethanol (0.119 mL, 0.060 mmol) was added at room temperature, and the mixture was stirred at room temperature for 3 hours. The mixture was concentered under reduced pressure, diisopropyl ether was added thereto, the precipitated solid was collected by filtration, and then dried to obtain the title compound (27.2 mg, yield: 94%).

$^1$H NMR spectrum (DMSO-d6, 400 MHz) δ: 7.79-7.78 (2H, m), 7.74 (1H, d, J=2.7 Hz), 7.51 (1H, dd, J=8.6, 2.7 Hz), 7.34 (1H, dd, J=8.6, 1.2 Hz), 5.03 (1H, d, J=3.5 Hz), 4.38 (1H, d, J=9.4 Hz), 4.25 (1H, br s), 3.96-3.95 (2H, m), 3.60-3.57 (1H, m), 3.48 (1H, d, J=12.1 Hz), 2.03-1.99 (1H, m), 1.74-1.67 (1H, m).

(Example 34) 5-fluoro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide

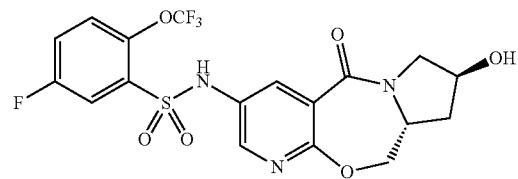 [SMILES: O=C1c2cc(NS(=O)(=O)c3cc(F)ccc3OC(F)(F)F)cnc2OC[C@H]2C[C@H](O)CN12]

(34a) 5-fluoro-2-(trifluoromethoxy)benzenesulfonyl chloride

The title compound (0.82 g, yield for 2 steps: 29%) was obtained by production according to the method described in Example (32a) using 5-fluoro-2-(trifluoromethoxy)aniline (2.00 g, 10.3 mmol).

$^1$H NMR spectrum (CDCl$_3$, 400 MHz) δ: 7.84 (1H, dd, J=6.8, 2.9 Hz), 7.56-7.47 (2H, m).

(34b) 5-fluoro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide The title compound (81 mg, yield: 67%) was obtained by production according to the method described in Example (27d) using (8S,9aR)-3-amino-8-hydroxy-8,9,9a,10-tetrahydro-5H,7H-pyrido[3,2-f]pyrrolo[2,1-c][1,4]oxazepin-5-one (60 mg, 0.26 mmol) obtained in Example (30c) and 5-fluoro-2-(trifluoromethoxy)benzenesulfonyl chloride (78 mg, 0.28 mmol) obtained in Example (34a) as starting materials.

$^1$H NMR spectrum (DMSO-d6, 400 MHz) δ: 10.75 (1H, br s), 8.20 (1H, d, J=2.9 Hz), 8.12 (1H, d, J=2.9 Hz), 7.74-7.73 (1H, m), 7.67-7.66 (2H, m), 5.06 (1H, d, J=3.4 Hz), 4.56 (1H, d, J=12.0 Hz), 4.26 (1H, d, J=3.4 Hz), 4.13 (1H, dd, J=12.0, 8.1 Hz), 4.08-4.05 (1H, m), 3.64 (1H, dd, J=12.7, 3.9 Hz), 3.45 (1H, dd, J=12.7, 1.5 Hz), 2.08-2.05 (1H, m), 1.75-1.72 (1H, m).

MS spectrum (ES/APCI$^+$): 478 (M+H)

(Example 35) 5-chloro-N-[(8R,9aR)-8-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide

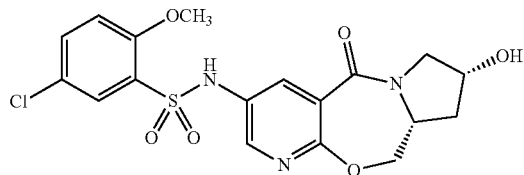 [SMILES: COc1ccc(Cl)cc1S(=O)(=O)Nc1cnc2c(c1)C(=O)N1C[C@H](O)C[C@@H]1CO2]

(35a) tert-butyl (2R,4R)-4-hydroxy-2-(hydroxymethyl) pyrrolidine-1-carboxylate

To a solution of (4R)-1-(tert-butoxycarbonyl)-4-hydroxy-D-proline (820 mg, 3.55 mmol) and triethylamine (0.516 mL, 3.72 mmol) in tetrahydrofuran (30 mL), isobutyl chloroformate (0.489 mL, 3.72 mmol) was added under ice cooling, and the mixture was stirred at the same temperature as above for 30 minutes. The insoluble matter was filtered off, and the residue was washed with tetrahydrofuran. The filtrate and washing were combined, sodium borohydride (268 mg, 7.09 mmol) was added thereto under ice cooling followed by addition of water (3 mL), and the mixture was stirred at the same temperature as above for 30 minutes. The mixture was diluted with addition of water, and followed by extraction with ethyl acetate. The organic layer was washed with a saturated aqueous solution of sodium chloride, and dried over anhydrous sodium sulfate. The solvent was distilled off under reduced pressure, the residue was purified in an automatic chromatography apparatus (n-hexane/ethyl acetate=100/0-0/100) to obtain the title compound (725 mg, yield: 94%).

$^1$H NMR spectrum (CDCl$_3$, 400 MHz) δ: 4.42-3.95 (4H, m), 3.59-3.47 (4H, m), 2.38-2.35 (1H, m), 1.94-1.83 (1H, m), 1.47 (9H, s).

(35b) (3R,5R)-5-(hydroxymethyl)pyrrolidin-3-ol hydrochloride

To a solution of tert-butyl (2R,4R)-4-hydroxy-2-(hydroxymethyl)pyrrolidine-1-carboxylate (725 mg, 3.34 mmol) obtained in Example (35a) in methanol (18 mL), a 4.0 mol/L solution of hydrochloric acid in 1,4-dioxane (12 mL, 48 mmol) was added at room temperature, and the mixture was stirred at the same temperature for 1 hour. The solvent was distilled off under reduced pressure to obtain a crude product of the title compound (513 mg, yield: quantitative).

$^1$H NMR spectrum (CD$_3$OD, 400 MHz) δ: 4.52-4.51 (1H, m), 3.84-3.70 (3H, m), 3.24-3.23 (2H, m), 2.37-2.30 (1H, m), 1.74-1.68 (1H, m).

(35c) (2-chloro-5-nitropyridin-3-yl)[(2R,4R)-4-hydroxy-2-(hydroxymethyl)pyrrolidin-1-yl]methanone To a suspension of 2-chloro-5-nitropyridine-3-carboxylic acid (676 mg, 3.34 mmol) in methylene chloride (15 mL), oxalyl chloride (0.358 mL, 4.17 mmol) and N,N-dimethylformamide (0.128 mL, 0.128 mmol) was added at room temperature, and the mixture was stirred at the same temperature as above for 1.5 hours. The reaction mixture was concentrated under reduced pressure to prepare a crude product of 2-chloro-5-nitropyridine-3-carbonyl chloride. To a mixture of (3R,5R)-5-(hydroxymethyl)pyrrolidin-3-ol hydrochloride (513 mg, 3.34 mmol) obtained in Example (35b) and N,N-diisopropylethylamine (2.91 mL, 16.7 mmol) in N,N-dimethylformamide (15 mL), a solution of the crude product of 2-chloro-5-nitropyridine-3-carbonyl chloride in N,N-dimethylformamide (5 mL) was added under ice cooling, and then the reaction mixture was stirred at room temperature for 1 hour. The mixture was concentrated under reduced pressure and the residue was purified in an automatic chromatography apparatus (ethyl acetate/methanol=100/0-90/10) to obtain the title compound (966 mg, yield: 96%).

$^1$H NMR spectrum (CDCl$_3$, 400 MHz) δ: 9.25-9.24 (1H, m), 8.59 (1H, br s), 5.27 (1H, br s), 4.76-4.33 (4H, m), 4.06-3.30 (3H, m), 2.53-2.48 (1H, m), 2.07-2.01 (1H, m).

(35d) (8R,9aR)-8-hydroxy-3-nitro-8,9,9a,10-tetrahydro-5H, 7H-pyrido[3,2-f]pyrrolo[2,1-c][1,4]oxazepin-5-one To a solution of (2-chloro-5-nitropyridin-3-yl)[(2R,4R)-4-hydroxy-2-(hydroxymethyl)pyrrolidin-1-yl]methanone (966 mg, 3.20 mmol) obtained in Example (35c) in N,N-dimethylformamide (160 mL), potassium carbonate (1.33 g, 9.61 mmol) was added at room temperature, and the mixture was stirred at the same temperature for 3 days. The insoluble matter was filtered off, and the residue was washed with ethyl acetate. The filtrate and the washes were combined, the solvent was distilled off under reduced pressure, and the residue was purified in an automatic chromatography apparatus (ethyl acetate/methanol=100/0-85/15) to obtain the title compound (626 mg, yield: 74%).

$^1$H NMR spectrum (CDCl$_3$, 400 MHz) δ: 9.38 (1H, d, J=2.7 Hz), 9.23 (1H, d, J=2.7 Hz), 4.73-4.68 (2H, m), 4.59-4.57 (1H, m), 4.16-4.12 (2H, m), 3.74 (1H, dd, J=13.3, 4.3 Hz), 2.62-2.55 (1H, m), 2.04-2.01 (2H, m).

(35e) (8R,9aR)-3-amino-8-hydroxy-8,9,9a,10-tetrahydro-5H, 7H-pyrido[3,2-f]pyrrolo[2,1-c][1,4]oxazepin-5-one A mixture of (8R,9aR)-8-hydroxy-3-nitro-8,9,9a,10-tetrahydro-5H,7H-pyrido[3,2-f]pyrrolo[2,1-c][1,4]oxazepin-5-one (243 mg, 0.92 mmol) obtained in Example (35d) and 10% palladium carbon (water content: 54.6%, 100 mg) in methanol (15 mL) was stirred at room temperature for 5 hours at normal pressure under the hydrogen atmosphere. Hydrogen in the reaction container was replaced with nitrogen, and then, the reaction mixture was filtered through pad of Celite 545®. The solvent in the filtrate was distilled off under reduced pressure to obtain the title compound (208 mg, yield: 97%).

$^1$H NMR spectrum (CD$_3$OD, 400 MHz) δ: 7.79 (1H, d, J=3.1 Hz), 7.61 (1H, d, J=3.1 Hz), 4.55-4.53 (1H, m), 4.47-4.45 (1H, m), 4.41 (1H, dd, J=11.0, 3.1 Hz), 4.08-4.01 (1H, m), 3.79-3.75 (1H, m), 3.70 (1H, dd, J=12.9, 4.7 Hz), 2.43-2.36 (1H, m), 1.85-1.80 (1H, m).

(35f) 5-chloro-N-[(8R,9aR)-8-hydroxy-5-oxo-8,9,9a, 10-tetrahydro-5H,7H-pyrido[3,2-f]pyrrolo[2,1-c][1, 4]oxazepin-3-yl]-2-methoxybenzenesulfonamide The title compound (165 mg, yield: 74%) was obtained by production according to the method described in Example (27d) using (8R,9aR)-3-amino-8-hydroxy-8,9,9a,10-tetrahydro-5H,7H-pyrido[3,2-f]pyrrolo[2,1-c][1,4]oxazepin-5-one (120 mg, 0.51 mmol) obtained in Example (35e) and 5-chloro-2-methoxybenzenesulfonyl chloride (135 mg, 0.56 mmol) as starting materials.

$^1$H NMR spectrum (DMSO-d6, 400 MHz) δ: 10.30 (1H, br s), 7.67 (1H, dd, J=9.0, 2.3 Hz), 7.64 (1H, d, J=2.3 Hz), 7.26 (1H, d, J=9.0 Hz), 5.21 (1H, d, J=3.5 Hz), 4.47-4.44 (1H, m), 4.34 (1H, t, J=10.2 Hz), 4.27-4.25 (1H, m), 3.97-3.93 (1H, m), 3.88 (3H, s), 3.55-3.54 (2H, m), 2.31-2.26 (1H, m), 1.71-1.65 (1H, m).

MS spectrum (ES/APCI$^+$): 440 (M+H), 442 (M+2+H).

(Example 36) 5-fluoro-N-[(8R,9aR)-8-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide

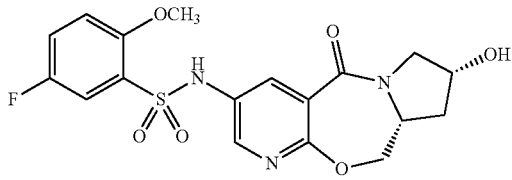 [SMILES: COc1ccc(F)cc1S(=O)(=O)Nc1cnc2c(c1)C(=O)N1C[C@H](O)C[C@@H]1CO2]

The title compound (135 mg, yield: 85%) was obtained by production according to the method described in Example (27d) using (8R,9aR)-3-amino-8-hydroxy-8,9,9a,10-tetrahydro-5H,7H-pyrido[3,2-f]pyrrolo[2,1-c][1,4]oxazepin-5-one (88 mg, 0.37 mmol) obtained in Example (35e) and 5-fluoro-2-methoxybenzenesulfonyl chloride (92.4 mg, 0.41 mmol) as starting materials.

$^1$H NMR spectrum (DMSO-d6, 400 MHz) δ: 10.28 (1H, br s), 8.09-8.08 (2H, m), 7.51-7.47 (2H, m), 7.26-7.23 (1H, m), 5.20 (1H, d, J=3.1 Hz), 4.46-4.44 (1H, m), 4.33-4.26 (2H, m), 3.94 (1H, dd, J=12.5, 9.4 Hz), 3.87 (3H, s), 3.55-3.54 (2H, m), 2.32-2.28 (1H, m), 1.69-1.65 (1H, m).

MS spectrum (ES/APCI$^+$): 424 (M+H).

(Example 37) 5-chloro-N-[(8R,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide

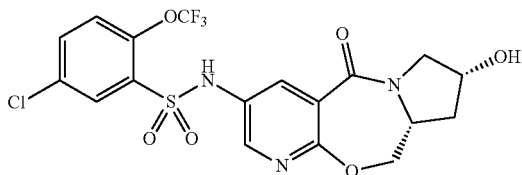

To a mixture of (8R,9aR)-3-amino-8-hydroxy-8,9,9a,10-tetrahydro-5H,7H-pyrido[3,2-f]pyrrolo[2,1-c][1,4]oxazepin-5-one (44.0 mg, 0.19 mmol) obtained in Example (35e) and pyridine (2 mL, 25 mmol), 5-chloro-2-(trifluoromethoxy)benzenesulfonyl chloride (60 mg, 0.20 mmol) obtained in Example (32a) was added, and the mixture was stirred at 80° C. for 4.5 hours in an oil bath. The reaction mixture was cooled, and then concentrated under reduced pressure. The residue was purified in an automatic chromatography apparatus (ethyl acetate/methanol=100/0-90/10) to obtain the title compound (49.2 mg, yield: 53%).

$^1$H NMR spectrum (DMSO-d6, 400 MHz) δ: 10.80 (1H, br s), 8.12 (1H, d, J=2.4 Hz), 8.06 (1H, d, J=2.4 Hz), 7.90-7.88 (2H, m), 7.63-7.62 (1H, m), 5.22 (1H, d, J=3.0 Hz), 4.49 (1H, dd, J=11.8, 1.8 Hz), 4.36 (1H, dd, J=11.8, 5.9 Hz), 4.27-4.25 (1H, m), 3.97-3.94 (1H, m), 3.63-3.50 (3H, m), 2.34-2.30 (1H, m), 1.73-1.67 (1H, m).

MS spectrum (ES/APCI$^+$): 494 (M+H), 496 (M+2+H)

(Example 38) Potassium {[5-chloro-2-(trifluoromethoxy)phenyl]sulfonyl}[(8R,9aR)-8-hydroxy-5-oxo-8,9,9a,10-tetrahydro-5H,7H-pyrido[3,2-f]pyrrolo[2,1-c][1,4]oxazepin-3-yl]azanide (Potassium Salt of Example 37)

To a suspension of 5-chloro-N-[(8R,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide (807 mg, 1.63 mmol) obtained in Example 37 in ethanol (20 mL), a 0.5 mol/L solution of potassium hydroxide in ethanol (3.26 mL, 1.63 mmol) was added at room temperature, and the mixture was stirred at room temperature for 1.5 hour. The mixture was concentered under reduced pressure, diisopropyl ether (10 mL) and ethyl acetate (5 mL) were added thereto, the precipitated solid was collected by filtration to obtain the title compound (743 mg, yield: 86%).

$^1$H NMR spectrum (DMSO-d6, 400 MHz) δ: 7.78-7.76 (2H, m), 7.63 (1H, br s), 7.54 (1H, br d, J=7.8 Hz), 7.36 (1H, br d, J=7.8 Hz), 5.15 (1H, d, J=2.7 Hz), 4.33-4.26 (3H, m), 3.86-3.82 (1H, m), 3.53-3.52 (2H, m), 2.27-2.20 (1H, m), 1.65-1.62 (1H, m).

(Example 39) 5-fluoro-N-[(8R,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide The title compound (92 mg, yield: 91%) was obtained by production according to the method described in Example (27d) using (8R,9aR)-3-amino-8-hydroxy-8,9,9a,10-tetrahydro-5H,7H-pyrido[3,2-f]pyrrolo[2,1-c][1,4]oxazepin-5-one (50 mg, 0.21 mmol) obtained in Example (35e) and 5-fluoro-2-(trifluoromethoxy)benzenesulfonyl chloride (71 mg, 0.26 mmol) obtained in Example (34a) as starting materials.

$^1$H NMR spectrum (DMSO-d6, 400 MHz) δ: 10.79 (1H, br s), 8.12 (1H, d, J=2.4 Hz), 8.05 (1H, d, J=2.4 Hz), 7.75-7.73 (1H, m), 7.68-7.67 (2H, m), 5.21 (1H, d, J=3.4 Hz), 4.49 (1H, dd, J=11.7, 2.0 Hz), 4.35 (1H, dd, J=11.7, 8.8 Hz), 4.26 (1H, br s), 3.97-3.96 (1H, m), 3.55-3.52 (2H, m), 2.34-2.29 (1H, m), 1.70-1.68 (1H, m).

MS spectrum (ES/APCI$^+$): 478 (M+H).

(Example 40) 5-chloro-N-[(9R,9aS)-9-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide (40a) (3R)-1-(tert-butoxycarbonyl)-3-hydroxy-D-proline To a solution of (3R)-3-hydroxy-D-proline (2.0 g, 15 mmol) in tetrahydrofuran (50 mL), a saturated aqueous solution of sodium bicacrbonate (30 mL) was added at room temperature, followed by addition of di-tert-butyl dicarbonate (4.9 g, 22 mmol), and the mixture was stirred at the same temperature as above for 24 hours. Most of the organic solvent was distilled off under reduced pressure, the concentrated mixture was washed with ethyl acetate. The aqueous layer was diluted by addition of a 1.0 mol/L hydrochloric acid until it became acidic, followed by extraction with ethyl acetate four times. The organic layer was dried over anhydrous sodium sulfate. After filtration, the solvent was distilled off under reduced pressure to obtain the title compound (3 g, yield: 85%).

$^1$H NMR spectrum (DMSO-d6, 400 MHz) δ: 12.66 (1H, br s), 5.44 (1H, br s), 4.24-4.20 (1H, m), 3.95 (0.4H, s), 3.90 (0.6H, s), 3.45-3.31 (2H, m), 1.90-1.84 (1H, m), 1.77-1.70 (1H, m), 1.40 (3.6H, s), 1.34 (5.4H, s).

(40b) (2S,3R)-2-(hydroxymethyl) pyrrolidin-3-ol hydrochloride

A crude product of the title compound (247 mg, yield: 36% for 2 steps) was obtained by production according to the method described in Examples (35a) and (35b) using (3R)-1-(tert-butoxycarbonyl)-3-hydroxy-D-proline (1 g, 4.3 mmol) obtained in Example (40a) as a starting material.

(40c) (9R,9aS)-9-hydroxy-3-nitro-8,9,9a,10-tetrahydro-5H, 7H-pyrido[3,2-f]pyrrolo[2,1-c][1,4]oxazepin-5-one The title compound (253 mg, yield: 63% for 2 steps) was obtained by production according to the method described in Examples (35c) and (35d) using 2-chloro-5-nitropyridine-3-carboxylic acid (305 mg, 1.51 mmol) and (2S,3R)-2-(hydroxymethyl)pyrrolidin-3-ol hydrochloride (0.24 g, 1.57 mmol) obtained in Example (40b) as starting materials.

$^1$H NMR spectrum (CDCl$_3$, 400 MHz) δ: 9.50 (1H, d, J=3.0 Hz), 9.22 (1H, d, J=3.0 Hz), 5.02 (1H, br d, J=12.1 Hz), 4.24 (1H, dd, J=12.1, 8.5 Hz), 4.16-4.12 (1H, m), 3.89-3.78 (3H, m), 3.06 (1H, d, J=5.5 Hz), 2.38-2.31 (1H, m), 2.03-1.99 (1H, m).

(40d) (9R,9aS)-3-amino-9-hydroxy-8,9,9a,10-tetrahydro-5H, 7H-pyrido[3,2-f]pyrrolo[2,1-c][1,4]oxazepin-5-one A crude product of the title compound (120 mg, yield: 53%) was obtained by production according to the method described in Example (30c) using (9R,9aS)-9-hydroxy-3-nitro-8,9,9a,10-tetrahydro-5H,7H-pyrido[3,2-f]pyrrolo[2,1-c][1,4]oxazepin-5-one (253 mg, 0.95 mmol) obtained in Example (40c) as a starting material.

$^1$H NMR spectrum (DMSO-d6, 400 MHz) δ: 7.70 (1H, d, J=3.0 Hz), 7.51 (1H, d, J=3.0 Hz), 5.37 (1H, d, J=4.3 Hz), 5.21 (2H, br s), 4.45 (1H, dd, J=11.5, 3.0 Hz), 3.97-3.93 (2H, m), 3.62-3.48 (3H, m), 2.11-2.08 (1H, m), 1.80-1.77 (1H, m).

(40e) 5-chloro-N-[(9R,9aS)-9-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide The title compound (49.6 mg, yield: 49%) was obtained by production according to the method described in Example (27d) using (9R,9aS)-3-amino-9-hydroxy-8,9,9a,10-tetrahydro-5H,7H-pyrido[3,2-f]pyrrolo[2,1-c][1,4]oxazepin-5-one (54.1 mg, 0.23 mmol) obtained in Example (40d) and 5-chloro-2-methoxybenzenesulfonyl chloride (70 mg, 0.29 mmol) as starting materials.

$^1$H NMR spectrum (DMSO-d6, 400 MHz) δ: 10.29 (1H, br s), 8.22 (1H, d, J=2.4 Hz), 8.08 (1H, d, J=2.4 Hz), 7.67-7.64 (2H, m), 7.26 (1H, d, J=9.1 Hz), 5.56 (1H, br s), 4.61 (1H, dd, J=12.1, 1.2 Hz), 4.11 (1H, dd, J=12.1, 9.1 Hz), 3.90-3.88 (4H, m), 3.57-3.47 (3H, m), 3.37 (1H, br s), 2.09-2.06 (1H, m), 1.77-1.72 (1H, m).

MS spectrum (ES/APCI$^+$): 440 (M+H), 442 (M+2+H).

(Example 41) 5-chloro-N-[(9S,9aS)-9-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide (41a) tert-butyl (2S,3S)-3-hydroxy-2-(hydroxymethyl) pyrrolidine-1-carboxylate To a solution of (3S)-1-(tert-butoxycarbonyl)-3-hydroxy-D-proline (988 mg, 4.27 mmol) in a mixed solvent of tetrahydrofuran (20 mL) and methanol (20 mL), a ca. 0.60 mol/L solution of trimethylsiliydiazomethane (14 mL, 8.6 mmol) was added under ice cooling, and the mixture was stirred at room temperature for 2 hours. The solvent was distilled off under reduced pressure, and the residue was purified in an automatic chromatography apparatus (n-hexane/ethyl acetate=100/0-0/100) to obtain 1-tert-butyl 2-methyl (2R,3S)-3-hydroxypyrrolidine-1,2-dicarboxylate (1.117 g). To a solution of 1-tert-butyl 2-methyl (2R,3S)-3-hydroxypyrrolidine-1,2-dicarboxylate (1.117 g) obtained in the above step in tetrahydrofuran (40 mL), a 2.0 mol/L solution of lithium borohydride in tetrahydrofuran (2.7 mL, 5.5 mmol) was added under ice cooling, and the mixture was stirred at room temperature for 4 days. The mixture was diluted by addition of a saturated aqueous solution of ammonium chloride followed by extraction with ethyl acetate. The organic layer was washed with a saturated aqueous solution of sodium chloride, and dried over anhydrous sodium sulfate. After filtration, the solvent was distilled off under reduced pressure, and the residue was purified in an automatic chromatography apparatus (n-hexane/ethyl acetate=100/0-0/100) to obtain the title compound (793 mg, yield: 80% for 2 steps).

$^1$H NMR spectrum (CDCl$_3$, 400 MHz) δ: 4.50 (1H, br s), 4.00-3.78 (4H, m), 3.48-3.46 (2H, m), 2.30-1.87 (2H, m), 1.47 (9H, s).

(41b) (2S,3S)-2-(hydroxymethyl)pyrrolidin-3-ol hydrochloride

A crude product of the title compound (561 mg, yield: quantitative) was obtained by production according to the method described in Example (35b) using tert-butyl (2S,3S)-3-hydroxy-2-(hydroxymethyl)pyrrolidine-1-carboxylate (793 mg, 3.65 mmol) obtained in Example (41a) as a starting material.

$^1$H NMR spectrum (CD$_3$OD, 400 MHz) δ: 4.44-4.43 (1H, m), 3.94 (1H, dd, J=11.7, 4.3 Hz), 3.84 (1H, dd, J=11.7, 8.6 Hz), 3.66 (1H, s), 3.52-3.30 (2H, m), 2.22-2.13 (1H, m), 2.08-2.02 (1H, m).

(41c) (9S,9aS)-9-hydroxy-3-nitro-8,9,9a,10-tetrahydro-5H, 7H-pyrido[3,2-f]pyrrolo[2,1-c][1,4]oxazepin-5-one The title compound (43.0 mg, yield: 66% for 2 steps) was obtained by production according to the method described in Examples (35c) and (35d) using 2-chloro-5-nitropyridine-3-carboxylic acid (50 mg, 0.25 mmol) and (2S,3S)-2-(hydroxymethyl)pyrrolidin-3-ol hydrochloride (38.5 mg, 0.25 mmol) obtained in Example (41b) as starting materials.

¹H NMR spectrum (CDCl₃, 400 MHz) δ: 9.56 (1H, d, J=3.0 Hz), 9.21 (1H, d, J=3.0 Hz), 5.04 (1H, d, J=13.4 Hz), 4.76 (1H, br s), 4.36 (1H, dd, J=13.4, 7.3 Hz), 4.08-4.04 (2H, m), 3.92-3.89 (1H, m), 2.10-2.07 (2H, m).

(41d) (9S,9aS)-3-amino-9-hydroxy-8,9,9a,10-tetrahydro-5H, 7H-pyrido[3,2-f]pyrrolo[2,1-c][1,4]oxazepin-5-one A crude product of the title compound (28.3 mg, yield: 74%) was obtained by production according to the method described in Example (27c) using (9S,9aS)-9-hydroxy-3-nitro-8,9,9a,10-tetrahydro-5H,7H-pyrido[3,2-f]pyrrolo[2,1-c][1,4]oxazepin-5-one (43.0 mg, 0.16 mmol) obtained in Example (41c) as a starting material.

(41e) 5-chloro-N-[(9S,9aS)-9-hydroxy-5-oxo-8,9,9a,10-tetrahydro-5H,7H-pyrido[3,2-f]pyrrolo[2,1-c][1,4]oxazepin-3-yl]-2-methoxybenzenesulfonamide The title compound (36.1 mg, yield: 68%) was obtained by production according to the method described in Example (27d) using (9S,9aS)-3-amino-9-hydroxy-8,9,9a,10-tetrahydro-5H,7H-pyrido[3,2-f]pyrrolo[2,1-c][1,4]oxazepin-5-one (28.3 mg, 0.12 mmol) obtained in Example (41d) and 5-chloro-2-methoxybenzenesulfonyl chloride (32 mg, 0.13 mmol) as starting materials.

¹H NMR spectrum (DMSO-d6, 400 MHz) δ: 10.25 (1H, br s), 8.30 (1H, d, J=3.0 Hz), 8.07 (1H, d, J=3.0 Hz), 7.67-7.63 (2H, m), 7.26 (1H, d, J=9.1 Hz), 5.24 (1H, br s), 4.71 (1H, d, J=12.8 Hz), 4.43 (1H, br s), 4.01 (1H, dd, J=12.8, 7.9 Hz), 3.90 (4H, s), 3.72-3.68 (1H, m), 3.57-3.55 (1H, m), 1.92-1.77 (2H, m).

MS spectrum (ES/APCI⁺): 440 (M+H), 442 (M+2+H)

(Example 42) 5-chloro-N-[(9S,9aS)-9-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide The title compound (70 mg, yield: 63%) was obtained by production according to the method described in Example (27d) using (9S,9aS)-3-amino-9-hydroxy-8,9,9a,10-tetrahydro-5H,7H-pyrido[3,2-f]pyrrolo[2,1-c][1,4]oxazepin-5-one (53 mg, 0.23 mmol) obtained in Example (41d) and 5-chloro-2-(trifluoromethoxy)benzenesulfonyl chloride (73.1 mg, 0.25 mmol) obtained in Example (32a) as starting materials.

¹H NMR spectrum (DMSO-d6, 400 MHz) δ: 10.75 (1H, br s), 8.26 (1H, d, J=2.7 Hz), 8.11 (1H, d, J=2.7 Hz), 7.89-7.87 (2H, m), 7.64-7.61 (1H, m), 5.25 (1H, d, J=4.3 Hz), 4.75 (1H, d, J=12.9 Hz), 4.46-4.44 (1H, m), 4.05-3.99 (1H, m), 3.91-3.89 (1H, m), 3.73-3.67 (1H, m), 3.59-3.53 (1H, m), 1.95-1.78 (2H, m).

MS spectrum (ES/APCI⁺): 494 (M+H), 496 (M+2+H)

(Example 43) Potassium {[5-chloro-2-(trifluoromethoxy)phenyl]sulfonyl}[(9S,9aS)-9-hydroxy-5-oxo-8,9,9a,10-tetrahydro-5H,7H-pyrido[3,2-f]pyrrolo[2,1-c][1,4]oxazepin-3-yl]azanide (Potassium Salt of Example 42)

The title compound (49 mg, yield: 84%) was obtained by production according to the method described in Example 33 using 5-chloro-N-[(9S,9aS)-9-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide (54 mg, 0.11 mmol) obtained in Example 42 as a starting material.

¹H NMR spectrum (DMSO-d6, 400 MHz) δ: 7.84 (1H, d, J=2.7 Hz), 7.78 (1H, d, J=2.7 Hz), 7.73 (1H, d, J=2.7 Hz), 7.50 (1H, dd, J=9.0, 2.7 Hz), 7.35-7.32 (1H, m), 4.52 (1H, dd, J=12.5, 2.0 Hz), 4.43-4.40 (1H, m), 3.94 (1H, dd, J=12.3, 8.8 Hz), 3.80-3.76 (1H, m), 3.65-3.62 (1H, m), 3.53-3.51 (1H, m), 1.95-1.76 (2H, m)

(Example 44) 5-chloro-N-[(8S,9aR)-8-fluoro-5-oxo-8,9,9a,10-tetrahydro-5H,7H-pyrido[3,2-f]pyrrolo[2,1-c][1,4]oxazepin-3-yl]-2-methoxybenzenesulfonamide (44a) [(2R,4S)-4-fluoropyrrolidin-2-yl]methanol hydrochloride A crude product of the title compound (218 mg, yield: 65% for 2 steps) was obtained by production according to the method described in Examples (35a) and (35b) using (4S)-1-(tert-butoxycarbonyl)-4-fluoro-D-proline (500 mg, 2.14 mmol) as a starting material.

¹H NMR spectrum (CD₃OD, 400 MHz) δ: 5.45 (1H, dt, J=52.0, 3.4 Hz), 3.99-3.96 (1H, m), 3.90 (1H, dd, J=11.7, 3.5 Hz), 3.65 (1H, dd, J=11.9, 6.1 Hz), 3.59-3.45 (2H, m), 2.46-2.40 (1H, m), 2.19-2.02 (1H, m).

(44b) (8S,9aR)-8-fluoro-3-nitro-8,9,9a,10-tetrahydro-5H, 7H-pyrido[3,2-f]pyrrolo[2,1-c][1,4]oxazepin-5-one The title compound (144 mg, yield: 28% for 2 steps) was obtained by production according to the method described in Examples (35c) and (35d) using 2-chloro-5-nitropyridine-3-carboxylic acid (400 mg, 1.97 mmol) and [(2R,4S)-4-fluoropyrrolidin-2-yl]methanol hydrochloride (218 mg, 1.4 mmol) obtained in Example (44a) as starting materials.

¹H NMR spectrum (CDCl₃, 400 MHz) δ: 9.53 (1H, d, J=2.7 Hz), 9.23 (1H, d, J=2.7 Hz), 5.33 (1H, dt, J=51.5, 3.5 Hz), 4.83 (1H, d, J=13.3 Hz), 4.44-4.40 (1H, m), 4.27-4.24 (1H, m), 4.13-4.00 (2H, m), 2.70-2.58 (1H, m), 2.00-1.88 (1H, m).

(44c) (8S,9aR)-3-amino-8-fluoro-8,9,9a,10-tetrahydro-5H, 7H-pyrido[3,2-f]pyrrolo[2,1-c][1,4]oxazepin-5-one A crude product of the title compound (109 mg, yield: 85%) was obtained by production according to the method described in Example (30c) using (8S,9aR)-8-fluoro-3-nitro-8,9,9a,10-tetrahydro-5H,7H-pyrido[3,2-f]pyrrolo[2,1-c][1,4]oxazepin-5-one (144 mg, 0.54 mmol) obtained in Example (44b) as a starting material.

¹H NMR spectrum (CDCl₃, 400 MHz) δ: 7.98 (1H, d, J=2.7 Hz), 7.89 (1H, d, J=2.7 Hz), 5.27 (1H, dt, J=52.2, 3.3 Hz), 4.61 (1H, dd, J=12.5, 1.2 Hz), 4.32-4.28 (1H, m), 4.10-3.87 (4H, m), 3.60 (2H, br s), 2.55-2.49 (1H, m), 1.91-1.73 (1H, m).

(44d) 5-chloro-N-[(8S,9aR)-8-fluoro-5-oxo-8,9,9a, 10-tetrahydro-5H,7H-pyrido[3,2-f]pyrrolo[2,1-c][1,4]oxazepin-3-yl]-2-methoxybenzenesulfonamide The title compound (91 mg, yield: 80%) was obtained by production according to the method described in Example (27d) using (8S,9aR)-3-amino-8-fluoro-8,9,9a,10-tetrahydro-5H,7H-pyrido[3,2-f]pyrrolo[2,1-c][1,4]oxazepin-5- one (61 mg, 0.26 mmol) obtained in Example (44c) and 5-chloro-2-methoxybenzenesulfonyl chloride (68.2 mg, 0.26 mmol) as starting materials.

$^1$H NMR spectrum (DMSO-d6, 400 MHz) δ: 10.27 (1H, br s), 8.27 (1H, d, J=2.7 Hz), 8.11 (1H, d, J=2.7 Hz), 7.66-7.64 (2H, m), 7.26 (1H, d, J=8.6 Hz), 5.39-5.26 (1H, m), 4.58 (1H, d, J=11.0 Hz), 4.18-4.12 (2H, m), 3.89 (3H, s), 3.77-3.71 (2H, m), 2.44-2.36 (2H, m).

MS spectrum (ES/APCI$^+$): 442 (M+H), 444 (M+2+H).

(Example 45) 5-chloro-N-[(9aR)-8,8-difluoro-5-oxo-8,9,9a,10-tetrahydro-5H,7H-pyrido[3,2-f]pyrrolo[2,1-c][1,4]oxazepin-3-yl]-2-methoxybenzenesulfonamide (45a) [(2R)-4,4-difluoropyrrolidin-2-yl]methanol hydrochloride A crude product of the title compound (332 mg, yield: quantitative for 2 steps) was obtained by production according to the method described in Examples (35a) and (35b) using 1-(tert-butoxycarbonyl)-4,4-difluoro-D-proline (500 mg, 1.89 mmol) as a starting material.

$^1$H NMR spectrum (CD$_3$OD, 400 MHz) δ: 4.07-4.00 (1H, m), 3.88 (1H, dd, J=11.7, 3.1 Hz), 3.78-3.68 (3H, m), 2.72-2.61 (1H, m), 2.52-2.38 (1H, m).

(45b) (9aR)-8,8-difluoro-3-nitro-8,9,9a,10-tetrahydro-5H, 7H-pyrido[3,2-f]pyrrolo[2,1-c][1,4]oxazepin-5-one The title compound (223 mg, yield: 41% for 2 steps) was obtained by production according to the method described in Examples (35c) and (35d) using 2-chloro-5-nitropyridine-3-carboxylic acid (387 mg, 1.91 mmol) and [(2R)-4,4-difluoropyrrolidin-2-yl]methanol hydrochloride (332 mg, 1.91 mmol) obtained in Example (45a) as starting materials.

$^1$H NMR spectrum (CDCl$_3$, 400 MHz) δ: 9.47 (1H, dd, J=2.7, 1.2 Hz), 9.25 (1H, d, J=2.7 Hz), 4.83-4.77 (1H, m), 4.46-4.34 (2H, m), 4.27-4.22 (1H, m), 4.07-4.03 (1H, m), 2.84-2.74 (1H, m), 2.39-2.25 (1H, m).

(45c) (9aR)-3-amino-8,8-difluoro-8,9,9a,10-tetrahydro-5H, 7H-pyrido[3,2-f]pyrrolo[2,1-c][1,4]oxazepin-5-one A crude product of the title compound (150 mg, yield: 75%) was obtained by production according to the method described in Example (30c) using (9aR)-8,8-difluoro-3-nitro-8,9,9a,10-tetrahydro-5H,7H-pyrido[3,2-f]pyrrolo[2,1-c][1,4]oxazepin-5-one (223 mg, 0.78 mmol) obtained in Example (45b) as a starting material.

$^1$H NMR spectrum (CDCl$_3$, 400 MHz) δ: 7.91 (1H, d, J=3.1 Hz), 7.86 (1H, d, J=3.1 Hz), 4.57 (1H, dd, J=11.7, 2.0 Hz), 4.32-4.30 (1H, m), 4.23-4.11 (2H, m), 4.05-4.02 (1H, m), 3.66 (2H, br s), 2.73-2.62 (1H, m), 2.27-2.19 (1H, m).

(45d) 5-chloro-N-[(9aR)-8,8-difluoro-5-oxo-8,9,9a, 10-tetrahydro-5H,7H-pyrido[3,2-f]pyrrolo[2,1-c][1,4]oxazepin-3-yl]-2-methoxybenzenesulfonamide The title compound (106 mg, yield: 75%) was obtained by production according to the method described in Example (27d) using (9aR)-3-amino-8,8-difluoro-8,9,9a,10-tetrahydro-5H,7H-pyrido[3,2-f]pyrrolo[2,1-c][1,4]oxazepin-5-one (78 mg, 0.31 mmol) obtained in Example (45c) and 5-chloro-2-methoxybenzenesulfonyl chloride (81.1 mg, 0.34 mmol) as starting materials.

$^1$H NMR spectrum (DMSO-d6, 400 MHz) δ: 10.34 (1H, br s), 8.20 (1H, d, J=2.7 Hz), 8.12 (1H, d, J=2.7 Hz), 7.68-7.64 (2H, m), 7.27-7.25 (1H, m), 4.57-4.54 (1H, m), 4.28-4.27 (2H, m), 4.12-3.99 (1H, m), 3.90-3.87 (4H, m), 2.49-2.42 (2H, m).

MS spectrum (ES/APCI$^+$): 460 (M+H), 462 (M+2+H)

(Example 46) 5-chloro-2-methoxy-N-[(8S,9aR)-8-methoxy-5-oxo-8,9,9a,10-tetrahydro-5H,7H-pyrido[3,2-f]pyrrolo[2,1-c][1,4]oxazepin-3-yl]benzenesulfonamide (46a) (8S,9aR)-8-methoxy-3-nitro-8,9,9a,10-tetrahydro-5H, 7H-pyrido[3,2-f]pyrrolo[2,1-c][1,4]oxazepin-5-one To a solution of (8S,9aR)-8-hydroxy-3-nitro-8,9,9a,10-tetrahydro-5H,7H-pyrido[3,2-f]pyrrolo[2,1-c][1,4]oxazepin-5-one (150 mg, 0.57 mmol) obtained in Example (30b) in N,N-dimethylformamide (5 mL), sodium hydride (approximately 63% content, 25.9 mg, 0.68 mmol) was added under ice cooling, and the mixture was stirred at the same temperature as above for 30 minutes. Subsequently, methyl iodide (0.070 mL, 1.13 mmol) was added thereto under ice cooling, and the mixture was stirred at room temperature for 18 hours. The mixture was diluted by addition of water followed by extraction with ethyl acetate. The organic layer was washed with a saturated aqueous solution of sodium chloride, and dried over anhydrous sodium sulfate. After filtration, the solvent was distilled off under reduced pressure, and the residue was purified in an automatic chromatography apparatus (ethyl acetate/methanol=100/0-85/15) to obtain the title compound (66 mg, yield: 42%).

$^1$H NMR spectrum (CDCl$_3$, 400 MHz) δ: 9.50 (1H, d, J=2.7 Hz), 9.21 (1H, d, J=2.7 Hz), 4.78 (1H, d, J=11.7 Hz), 4.30-4.26 (2H, m), 4.04-4.03 (1H, m), 3.95 (1H, br d, J=13.9 Hz), 3.82 (1H, dd, J=13.9, 3.7 Hz), 3.36 (3H, s), 2.46-2.44 (1H, m), 1.80-1.77 (1H, m).

(46b) (8S,9aR)-3-amino-8-methoxy-8,9,9a,10-tetrahydro-5H, 7H-pyrido[3,2-f]pyrrolo[2,1-c][1,4]oxazepin-5-one The title compound (41 mg, yield: 70%) was obtained by production according to the method described in Example (30c) using (8S,9aR)-8-methoxy-3-nitro-8,9,9a,10-tetrahydro-5H,7H-pyrido[3,2-f]pyrrolo[2,1-c][1,4]oxazepin-5-one (66 mg, 0.24 mmol) obtained in Example (46a) as a starting material.

$^1$H NMR spectrum (CDCl$_3$, 400 MHz) δ: 7.96 (1H, d, J=3.1 Hz), 7.89 (1H, d, J=3.1 Hz), 4.57 (1H, dd, J=12.1, 1.6 Hz), 4.23-4.17 (1H, m), 4.04-3.99 (2H, m), 3.93 (1H, dd, J=13.7, 2.0 Hz), 3.78 (1H, dd, J=13.7, 4.3 Hz), 3.62 (2H, br s), 2.37-2.34 (1H, m), 1.74-1.70 (1H, m).

(46c) 5-chloro-2-methoxy-N-[(8S,9aR)-8-methoxy-5-oxo-8,9,9a,10-tetrahydro-5H,7H-pyrido[3,2-f]pyrrolo[2,1-c][1,4]oxazepin-3-yl]benzenesulfonamide The title compound (58 mg, yield: 78%) was obtained by production according to the method described in Example (27d) using (8S,9aR)-3-amino-8-methoxy-8,9,9a,10-tetrahydro-5H,7H-pyrido[3,2-f]pyrrolo[2,1-c][1,4]oxazepin-5-one (41 mg, 0.16 mmol) obtained in Example (46b) and 5-chloro-2-methoxybenzenesulfonyl chloride (43.6 mg, 0.18 mmol) as starting materials.

$^1$H NMR spectrum (DMSO-d6, 400 MHz) δ: 10.27 (1H, br s), 8.23 (1H, d, J=2.7 Hz), 8.09 (1H, d, J=2.7 Hz), 7.67-7.64 (2H, m), 7.26 (1H, d, J=9.0 Hz), 4.52 (1H, br d, J=12.1 Hz), 4.12 (1H, dd, J=12.1, 8.2 Hz), 4.00-3.94 (2H, m), 3.89 (3H, s), 3.66-3.61 (2H, m), 2.46-2.44 (1H, m), 2.31-2.25 (1H, m).

MS spectrum (ES/APCI$^+$): 454 (M+H), 456 (M+2+H)

(Example 47) (8S,9aR)-3-({[5-chloro-2-(trifluoromethoxy)phenyl]sulfonyl}amino)-5-oxo-8,9,9a,10-tetrahydro-5H,7H-pyrido[3,2-f]pyrrolo[2,1-c][1,4]oxazepin-8-yl acetate (47a) (8S,9aR)-3-nitro-5-oxo-8,9,9a,10-tetrahydro-5H,7H-pyrido[3,2-f]pyrrolo[2,1-c][1,4]oxazepin-8-yl acetate To a solution of (8S,9aR)-8-hydroxy-3-nitro-8,9,9a,10-tetrahydro-5H,7H-pyrido[3,2-f]pyrrolo[2,1-c][1,4]oxazepin-5-one (200 mg, 0.75 mmol) obtained in Example (30b) in pyridine (8 mL), acetic anhydride (0.143 mL, 1.51 mmol) and 4-dimethylaminopyridine (18.4 mg, 0.15 mmol) was added at room temperature, and the mixture was stirred at the same temperature as above for 18 hours. The mixture was concentrated under reduced pressure, and the residue was purified in an automatic chromatography apparatus (ethyl acetate/methanol=100/0-90/10) to obtain the title compound (229 mg, yield: 99%).

$^1$H NMR spectrum (CDCl$_3$, 400 MHz) δ: 9.52 (1H, d, J=2.7 Hz), 9.23 (1H, d, J=2.7 Hz), 5.41 (1H, t, J=4.3 Hz), 4.80 (1H, d, J=12.1 Hz), 4.37-4.33 (1H, m), 4.27 (1H, dd, J=12.1, 7.8 Hz), 4.05 (1H, dd, J=14.5, 4.3 Hz), 3.90 (1H, dd, J=14.5, 2.0 Hz), 2.48-2.45 (1H, m), 2.07 (3H, s), 1.99-1.96 (1H, m).

(47b) (8S,9aR)-3-amino-5-oxo-8,9,9a,10-tetrahydro-5H,7H-pyrido[3,2-f]pyrrolo[2,1-c][1,4]oxazepin-8-yl acetate The title compound (169 mg, yield: 82%) was obtained by production according to the method described in Example (30c) using (8S,9aR)-3-nitro-5-oxo-8,9,9a,10-tetrahydro-5H,7H-pyrido[3,2-f]pyrrolo[2,1-c][1,4]oxazepin-8-yl acetate (229 mg, 0.75 mmol) obtained in Example (47a) as a starting material.

$^1$H NMR spectrum (CDCl$_3$, 400 MHz) δ: 8.03 (1H, d, J=3.1 Hz), 7.94 (1H, d, J=3.1 Hz), 5.40 (1H, t, J=4.3 Hz), 4.63 (1H, dd, J=12.5, 1.2 Hz), 4.30-4.26 (1H, m), 4.08-4.02 (2H, m), 3.91 (1H, br d, J=14.1 Hz), 3.66 (2H, br s), 2.41-2.38 (1H, m), 2.10 (3H, s), 1.95-1.92 (1H, m).

(47c) (8S,9aR)-3-({[5-chloro-2-(trifluoromethoxy)phenyl]sulfonyl}amino)-5-oxo-8,9,9a,10-tetrahydro-5H,7H-pyrido[3,2-f]pyrrolo[2,1-c][1,4]oxazepin-8-yl acetate The title compound (95 mg, yield: 61%) was obtained by production according to the method described in Example (27d) using (8S,9aR)-3-amino-5-oxo-8,9,9a,10-tetrahydro-5H,7H-pyrido[3,2-f]pyrrolo[2,1-c][1,4]oxazepin-8-yl acetate (80 mg, 0.29 mmol) obtained in Example (47b) and 5-chloro-2-(trifluoromethoxy)benzenesulfonyl chloride (102 mg, 0.35 mmol) obtained in Example (32a) as starting materials.

$^1$H NMR spectrum (CDCl$_3$, 400 MHz) δ: 8.47 (1H, br s), 8.36 (1H, d, J=2.7 Hz), 7.91 (1H, d, J=2.7 Hz), 7.57 (1H, dd, J=8.8, 2.5 Hz), 7.36 (1H, br d, J=9.4 Hz), 5.37 (1H, t, J=4.3 Hz), 4.65 (1H, d, J=12.1 Hz), 4.27-4.24 (1H, m), 4.08-4.01 (2H, m), 3.87 (1H, br d, J=14.3 Hz), 2.41-2.36 (1H, m), 2.05 (3H, s), 1.92-1.88 (1H, m).

MS spectrum (ES/APCI$^+$): 536 (M+H), 538 (M+2+H)

(Example 48) (8S,9aR)-3-{[(5-chloro-2-methoxyphenyl)sulfonyl]amino}-5-oxo-8,9,9a,10-tetrahydro-5H, 7H-pyrido[3,2-f]pyrrolo[2,1-c][1,4]oxazepin-8-yl methylcarbamate (48a) (8S,9aR)-3-nitro-5-oxo-8,9,9a,10-tetrahydro-5H,7H-pyrido[3,2-f]pyrrolo[2,1-c][1,4]oxazepin-8-yl methylcarbamate To a solution of (8S,9aR)-8-hydroxy-3-nitro-8,9,9a,10-tetrahydro-5H,7H-pyrido[3,2-f]pyrrolo[2,1-c][1,4]oxazepin-5-one (200 mg, 0.75 mmol) obtained in Example (30b) in tetrahydrofuran (10 mL), N,N'-carbonyldiimizazole (135 mg, 0.83 mmol) was added at room temperature, and the mixture was stirred at the same temperature as above for 18 hours. Subsequently, a 2.0 mol/L solution of methylamine in tetrahydrofuran (0.829 mL, 2.00 mmol) was added thereto under ice cooling, and the mixture was stirred at the same temperature as above for 2 hours. The mixture was diluted by addition of water followed by extraction with ethyl acetate. The organic layer was washed with a saturated aqueous solution of sodium chloride, and dried over anhydrous sodium sulfate. After filtration, the solvent was distilled off under reduced pressure, and the residue was purified in an automatic chromatography apparatus (ethyl acetate/methanol=100/0-95/5) to obtain the title compound (154 mg, yield: 63%).

$^1$H NMR spectrum (CDCl$_3$, 400 MHz) δ: 9.51 (1H, br s), 9.22 (1H, d, J=2.7 Hz), 5.33-3.11 (5H, m), 2.81-2.74 (4H, m), 2.49-1.91 (2H, m).

(48b) (8S,9aR)-3-amino-5-oxo-8,9,9a,10-tetrahydro-5H,7H-pyrido[3,2-f]pyrrolo[2,1-c][1,4]oxazepin-8-yl methylcarbamate A crude product of the title compound (156 mg, yield: quantitative) was obtained by production according to the method described in Example (30c) using (8S,9aR)-3-nitro-5-oxo-8,9,9a,10-tetrahydro-5H,7H-pyrido[3,2-f]pyrrolo[2,1-c][1,4]oxazepin-8-yl methylcarbamate (154 mg, 0.48 mmol) obtained in Example (48a) as a starting material.

$^1$H NMR spectrum (CD$_3$OD, 400 MHz) δ: 7.84 (1H, d, J=2.7 Hz), 7.81 (1H, d, J=2.7 Hz), 5.22 (1H, t, J=3.7 Hz), 4.57 (1H, d, J=11.3 Hz), 4.18-4.11 (2H, m), 3.89-3.85 (2H, m), 2.68 (3H, s), 2.38-2.34 (1H, m), 2.04-1.97 (1H, m).

(48c) (8S,9aR)-3-{[(5-chloro-2-methoxyphenyl)sulfonyl]amino}-5-oxo-8,9,9a,10-tetrahydro-5H, 7H-pyrido[3,2-f]pyrrolo[2,1-c][1,4]oxazepin-8-yl methylcarbamate The title compound (43 mg, yield: 87%) was obtained by production according to the method described in Example (27d) using (8S,9aR)-3-amino-5-oxo-8,9,9a,10-tetrahydro-5H,7H-pyrido[3,2-f]pyrrolo[2,1-c][1,4]oxazepin-8-yl methylcarbamate (29 mg, 0.10 mmol) obtained in Example (48b) and 5-chloro-2-methoxybenzenesulfonyl chloride (28.7 mg, 0.12 mmol) as starting materials.

¹H NMR spectrum (DMSO-d6, 400 MHz) δ: 10.26 (1H, br s), 8.23 (1H, d, J=2.9 Hz), 8.10 (1H, d, J=2.9 Hz), 7.67-7.64 (2H, m), 7.26 (1H, d, J=8.8 Hz), 7.06 (1H, br q, J=4.4 Hz), 5.09 (1H, t, J=3.9 Hz), 4.55 (1H, d, J=12.2 Hz), 4.15 (1H, dd, J=12.2, 7.8 Hz), 4.03-3.98 (1H, m), 3.89 (3H, s), 3.81 (1H, dd, J=13.9, 4.1 Hz), 3.57 (1H, d, J=13.9 Hz), 2.54 (3H, d, J=4.4 Hz), 2.25-2.22 (1H, m), 1.95-1.89 (1H, m).

MS spectrum (ES/APCI⁺): 497 (M+H), 499 (M+2+H).

(Example 49) Potassium [(5-chloro-2-methoxyphenyl)sulfonyl]{(8S,9aR)-8-[(methylcarbamoyl)oxy]-5-oxo-8,9,9a,10-tetrahydro-5H,7H-pyrido[3,2-f]pyrrolo[2,1-c][1,4]oxazepin-3-yl}azanide (Potassium Salt of Example 48)

The title compound (23 mg, yield: 67%) was obtained by production according to the method described in Example 33 using (8S,9aR)-3-{[(5-chloro-2-methoxyphenyl)sulfonyl]amino}-5-oxo-8,9,9a,10-tetrahydro-5H, 7H-pyrido[3,2-f]pyrrolo[2,1-c][1,4]oxazepin-8-yl methylcarbamate (32.0 mg, 0.064 mmol) obtained in Example (48c) as a starting material.

¹H NMR spectrum (DMSO-d6, 400 MHz) δ: 7.76 (1H, d, J=2.9 Hz), 7.71 (1H, d, J=2.9 Hz), 7.64 (1H, d, J=2.9 Hz), 7.32 (1H, dd, J=9.0, 3.2 Hz), 7.12 (1H, br q, J=4.4 Hz), 6.98 (1H, d, J=8.8 Hz), 5.09 (1H, br s), 4.40 (1H, dd, J=11.7, 2.0 Hz), 4.02-3.90 (2H, m), 3.71-3.67 (5H, m), 2.53 (4H, d, J=4.4 Hz), 2.21-2.19 (1H, m), 1.94-1.89 (1H, m).

(Example 50) methyl [(8R,9aR)-3-{[(5-chloro-2-methoxyphenyl)sulfonyl]amino}-5-oxo-8,9,9a,10-tetrahydro-5H, 7H-pyrido[3,2-f]pyrrolo[2,1-c][1,4]oxazepin-8-yl]carbamate (50a) tert-butyl (2R,4R)-4-{[(benzyloxy) carbonyl]amino}-2-(hydroxymethyl)pyrrolidine-1-carboxylate To a solution of 1-tert-butyl 2-methyl (2R,4R)-4-aminopyrrolidine-1,2-dicarboxylate (2.53 g, 10.4 mmol) in tetrahydrofuran (50 mL), a saturated aqueous solution of sodium carbonate (25 mL) was added at room temperature, followed by addition of benzyl chloroformate (1.77 mL, 12.4 mmol) under ice cooling, and the mixture was stirred at room temperature for 24 hours. The mixture was diluted by addition of water followed by extraction with ethyl acetate. The organic layer was washed with a saturated aqueous solution of sodium chloride, and dried over anhydrous sodium sulfate. After filtration, the solvent was distilled off under reduced pressure, and the residue was purified in an automatic chromatography apparatus (n-hexane/ethyl acetate=100/0-50/50) to obtain 1-tert-butyl 2-methyl (2R,4R)-4-{[(benzyloxy)carbonyl]amino}pyrrolidine-1,2-dicarboxylate (3.82 g, yield: 98%). To a solution of 1-tert-butyl 2-methyl (2R,4R)-4-{[(benzyloxy)carbonyl]amino}pyrrolidine-1,2-dicarboxylate (3.28 g, 10.1 mmol) obtained in the above step in tetrahydrofuran (100 mL), a 2.0 mol/L solution of lithium borohydride in tetrahydrofuran (10.1 mL, 20.2 mmol) was added under ice cooling, and the mixture was stirred at room temperature for 4 days. The mixture was diluted by addition of water and a saturated aqueous solution of ammonium chloride under ice cooling followed by extraction with ethyl acetate. The organic layer was washed with a saturated aqueous solution of sodium chloride, and dried over anhydrous sodium sulfate. After filtration, the solvent was distilled off under reduced pressure, and the residue was purified in an automatic chromatography apparatus (n-hexane/ethyl acetate=100/0-30/70) to obtain the title compound (2.99 g, yield: 85%).

¹H NMR spectrum (CDCl₃, 400 MHz) δ: 7.36-7.30 (5H, m), 5.61-3.56 (9H, m), 3.19 (1H, br s), 2.41 (1H, br s), 1.46 (9H, s).

(50b) benzyl [(3R,5R)-5-(hydroxymethyl)pyrrolidin-3-yl]carbamate hydrochloride

A crude product of the title compound (2.45 g, yield: quantitative) was obtained by production according to the method described in Example (35b) using tert-butyl (2R,4R)-4-{[(benzyloxy)carbonyl]amino}-2-(hydroxymethyl)pyrrolidine-1-carboxylate (2.99 g, 8.54 mmol) obtained in Example (50a) as a starting material.

¹H NMR spectrum (CD₃OD, 400 MHz) δ: 7.34-7.31 (5H, m), 5.09 (2H, br s), 4.31-4.30 (1H, m), 3.86-3.83 (1H, m), 3.76-3.70 (2H, m), 3.51-3.48 (1H, m), 3.21-3.18 (1H, m), 2.45-2.42 (1H, m), 1.82-1.78 (1H, m).

(50c) benzyl [(8R,9aR)-3-nitro-5-oxo-8,9,9a,10-tetrahydro-5H,7H-pyrido[3,2-f]pyrrolo[2,1-c][1,4]oxazepin-8-yl]carbamate The title compound (2.74 g, yield: 81% for 2 steps) was obtained by production according to the method described in Examples (35c) and (35d) using 2-chloro-5-nitropyridine-3-carboxylic acid (1.73 g, 8.54 mmol) and (benzyl [(3R, 5R)-5-(hydroxymethyl)pyrrolidin-3-yl]carbamate hydrochloride (2.45 g, 8.54 mmol) obtained in Example (50b) as starting materials.

¹H NMR spectrum (CDCl₃, 400 MHz) δ: 9.46 (1H, d, J=2.7 Hz), 9.21 (1H, d, J=3.1 Hz), 7.40-7.33 (5H, m), 5.13 (2H, br s), 4.94 (1H, br s), 4.74 (1H, d, J=12.5 Hz), 4.34-4.31 (2H, m), 4.16-4.11 (2H, m), 3.63-3.60 (1H, m), 2.68-2.66 (1H, m), 1.79-1.76 (1H, m).

(50d) methyl [(8R,9aR)-3-nitro-5-oxo-8,9,9a,10-tetrahydro-5H,7H-pyrido[3,2-f]pyrrolo[2,1-c][1,4]oxazepin-8-yl]carbamate To benzyl [(8R,9aR)-3-nitro-5-oxo-8,9,9a,10-tetrahydro-5H,7H-pyrido[3,2-f]pyrrolo[2,1-c][1,4]oxazepin-8-yl]carbamate (484 mg, 1.21 mmol) obtained in Example (50c), a 30% solution of hydrogen bromide in acetic acid (approximately 5.1 mol/L, 12 mL, 61 mmol) was added under ice cooling, the mixture was stirred at room temperature for 1 hour. The mixture was concentrated under reduced pressure, the residue was diluted with methylene chloride (20 mL), triethylamine (0.505 mL, 3.64 mmol) and methyl chloroformate (0.140 mL, 1.82 mL) was added thereto under ice cooling, and the mixture was stirred at room temperature for 20 hours. The mixture was diluted by addition of water followed by extraction with methylene chloride. The organic layer was washed with a saturated aqueous solution of sodium chloride, and dried over anhydrous sodium sulfate. After filtration, the solvent was distilled off under reduced pressure, and the residue was purified in an automatic chromatography apparatus (ethyl acetate/methanol=100/0-90/10) to obtain the title compound (242 mg, yield: 62%).

¹H NMR spectrum (CDCl₃, 400 MHz) δ: 9.47 (1H, d, J=2.7 Hz), 9.22 (1H, d, J=2.7 Hz), 4.77-4.74 (2H, m), 4.33-4.30 (2H, m), 4.17-4.12 (2H, m), 3.72 (3H, s), 3.59-3.53 (1H, m), 2.70-2.64 (1H, m), 1.81-1.73 (1H, m).

(50e) methyl [(8R,9aR)-3-amino-5-oxo-8,9,9a,10-tetrahydro-5H,7H-pyrido[3,2-f]pyrrolo[2,1-c][1,4]oxazepin-8-yl]carbamate A crude product of the title compound (293 mg, yield: quantitative) was obtained by production according to the method described in Example (30c) using methyl [(8R,9aR)-3-nitro-5-oxo-8,9,9a,10-tetrahydro-5H,7H-pyrido[3,2-f]pyrrolo[2,1-c][1,4]oxazepin-8-yl]carbamate (322 mg, 1.00 mmol) obtained in Example (50d) as a starting material.

$^1$H NMR spectrum (CD$_3$OD, 400 MHz) δ: 7.80 (1H, d, J=2.7 Hz), 7.78 (1H, d, J=2.7 Hz), 4.51 (1H, dd, J=11.5, 2.2 Hz), 4.22-4.19 (2H, m), 4.12-4.09 (1H, m), 4.00 (1H, dd, J=12.1, 7.4 Hz), 3.50-3.45 (1H, m), 2.52-2.45 (1H, m), 1.75-1.71 (1H, m).

(50f) methyl [(8R,9aR)-3-{[(5-chloro-2-methoxyphenyl)sulfonyl]amino}-5-oxo-8,9,9a,10-tetrahydro-5H, 7H-pyrido[3,2-f]pyrrolo[2,1-c][1,4]oxazepin-8-yl]carbamate The title compound (80 mg, yield: 94%) was obtained by production according to the method described in Example (27d) using methyl [(8R,9aR)-3-amino-5-oxo-8,9,9a,10-tetrahydro-5H,7H-pyrido[3,2-f]pyrrolo[2,1-c][1,4]oxazepin-8-yl]carbamate (50 mg, 0.17 mmol) obtained in Example (50e) and 5-chloro-2-methoxybenzenesulfonyl chloride (49.5 mg, 0.21 mmol) as starting materials.

$^1$H NMR spectrum (DMSO-d6, 400 MHz) δ: 10.26 (1H, br s), 8.22 (1H, d, J=2.9 Hz), 8.08 (1H, d, J=2.9 Hz), 7.67-7.62 (2H, m), 7.49 (1H, br d, J=6.8 Hz), 7.26 (1H, d, J=8.8 Hz), 4.51 (1H, d, J=12.2 Hz), 4.16 (1H, dd, J=12.2, 8.3 Hz), 4.09-3.99 (2H, m), 3.89 (3H, s), 3.76-3.74 (1H, m), 3.55 (4H, br s), 2.39-2.35 (1H, m), 1.58-1.55 (1H, m).

MS spectrum (ES/APCI$^+$): 497 (M+H), 499 (M+2+H).

(Example 51) Potassium [(5-chloro-2-methoxyphenyl)sulfonyl]{(8R,9aR)-8-[(methoxycarbonyl)amino]-5-oxo-8,9,9a,10-tetrahydro-5H, 7H-pyrido[3,2-f]pyrrolo[2,1-c][1,4]oxazepin-3-yl}azanide (Potassium Salt of Example 50)

The title compound (59 mg, yield: quantitative) was obtained by production according to the method described in Example 33 using methyl [(8R,9aR)-3-{[(5-chloro-2-methoxyphenyl)sulfonyl]amino}-5-oxo-8,9,9a,10-tetrahydro-5H, 7H-pyrido[3,2-f]pyrrolo[2,1-c][1,4]oxazepin-8-yl]carbamate (55.0 mg, 0.11 mmol) obtained in Example (50f) as a starting material.

$^1$H NMR spectrum (DMSO-d6, 400 MHz) δ: 7.76 (1H, d, J=2.9 Hz), 7.71 (1H, d, J=2.9 Hz), 7.64 (1H, d, J=2.9 Hz), 7.49 (1H, br d, J=5.4 Hz), 7.33-7.31 (1H, m), 6.98 (1H, d, J=8.8 Hz), 4.36-4.33 (2H, m), 4.05-4.00 (2H, m), 3.93-3.89 (1H, m), 3.80-3.77 (1H, m), 3.65 (3H, s), 3.54 (3H, br s), 3.45-3.43 (2H, m), 2.34-2.32 (1H, m), 1.58-1.56 (1H, m).

(Example 52) 5-chloro-2-methoxy-N-[(9aS)-7-oxo-8,9,9a,10-tetrahydro-5H,7H-pyrido[3,2-f]pyrrolo[2,1-c][1,4]oxazepin-3-yl]benzenesulfonamide (52a) (5S)-5-({[tert-butyl(dimethyl)silyl]oxy}methyl)pyrrolidin-2-one To a solution of (5S)-5-(hydroxymethyl)pyrrolidin-2-one (1.00 g, 8.69 mmol) and imidazole (0.710 g, 10.4 mmol) in N,N-dimethylformamide (15 mL), tert-butyldimethylchlorosilane (1.44 g, 9.55 mmol) was added under ice cooling, and the mixture was stirred at room temperature for 3 days. The mixture was diluted by addition of water followed by extraction with ethyl acetate. The organic layer was washed with water, a 1.0 mol/L hydrochloric acid and a saturated aqueous solution of sodium chloride, and dried over anhydrous sodium sulfate. After filtration, the solvent was distilled off under reduced pressure and the residue was purified in an automatic chromatography apparatus (n-hexane/ethyl acetate=27/73-6/94) to obtain the title compound (1.66 g, yield: 83%).

$^1$H NMR spectrum (CDCl$_3$, 400 MHz) δ: 5.75 (1H, br s), 3.79-3.73 (1H, m), 3.63 (1H, dd, J=9.8, 4.0 Hz), 3.44 (1H, dd, J=9.8, 7.9 Hz), 2.37-2.34 (2H, m), 2.20-2.16 (1H, m), 1.78-1.69 (1H, m), 0.89 (9H, s), 0.06 (6H, s).

(52b) (5-bromo-2-chloropyridin-3-yl)methyl methanesulfonate

To a solution of 5-bromo-2-chloro-pyridine-3-carboxylic acid (6.50 g, 27.5 mmol) and triethylamine (4.19 mL, 30.2 mmol) in tetrahydrofuran (70 mL), isobutyl chloroformate (3.79 mL, 28.9 mmol) was added under ice cooling, and the mixture was stirred at the same temperature as above for 1.5 hours. The insoluble matter was filtered off, and the residue was washed with tetrahydrofuran. The filtrate and washing were combined, water (14 mL) was added thereto under ice cooling followed by addition of sodium borohydride (1.56 g, 41.2 mmol), and the mixture was stirred at the same temperature as above for 1 hour, and then stirred at room temperature for 19 hours. The mixture was concentrated under reduced pressure up to approximately ⅓ volume, diluted by addition of a 1.0 mol/L hydrochloric acid followed by extraction with ethyl acetate. The organic layer was washed with water, a saturated aqueous solution of sodium bicarbonate and a saturated aqueous solution of sodium chloride, and dried over anhydrous sodium sulfate. The solvent was distilled off under reduced pressure to obtain a crude product of (5-bromo-2-chloropyridin-3-yl)methanol (5.29 g).

To a solution of (5-bromo-2-chloropyridin-3-yl)methanol (5.29 g) obtained in the above step and triethylamine (8.3 mL, 59.4 mmol) in methylene chloride (82 mL), methanesulfonyl chloride (3.7 mL, 47.6 mmol) was added under ice cooling, and the mixture was stirred at the same temperature as above for 1 hour. The mixture was concentrated under reduced pressure, and the residue was diluted by addition of water followed by extraction with ethyl acetate. The organic layer was washed with water and a saturated aqueous solution of sodium chloride, and dried over anhydrous sodium sulfate. The solvent was distilled off under reduced pressure, and the residue was purified in an automatic chromatography apparatus (n-hexane/ethyl acetate=90/10-65/35) to obtain the title compound (5.03 g, yield: 61% for 2 steps).

$^1$H NMR spectrum (CDCl$_3$, 400 MHz) δ: 8.48 (1H, d, J=2.4 Hz), 7.98 (1H, d, J=2.4 Hz), 5.29 (2H, s), 3.14 (3H, s).

(52c) (5S)-1-[(5-bromo-2-chloropyridin-3-yl)methyl]-5-({[tert-butyl(dimethyl)silyl]oxy}methyl)pyrrolidin-2-one To a suspension of sodium hydride (approximately 63% content, 160 mg, 3.99 mmol) in N,N-dimethylformamide (11 mL), a solution of (5S)-5-({[tert-butyl(dimethyl)silyl]oxy}methyl)pyrrolidin-2-one (840 mg, 3.66 mmol) obtained in Example (52a) in N,N-dimethylformamide (5.5 mL) was added under ice cooling, and the mixture was stirred at the same temperature for 20 minutes. Subsequently, (5-bromo-2-chloropyridin-3-yl)methyl methanesulfonate (1.00 g, 3.33 mmol) obtained in Example (52b) was added thereto under ice cooling, the mixture was stirred at the same temperature as above for 10 minutes, and then stirred at room temperature for 30 minutes. The mixture was poured into ice-water followed by extraction with ethyl acetate. The organic layer was washed with a saturated aqueous solution of ammonium chloride and a saturated aqueous solution of sodium chloride, and dried over anhydrous sodium sulfate. The solvent was distilled off under reduced pressure, and the residue was purified in an automatic chromatography apparatus (n-hexane/ethyl acetate=92/8-68/32) to obtain the title compound (786 mg, yield: 55%).

$^1$H NMR spectrum (CDCl$_3$, 400 MHz) δ: 8.36 (1H, d, J=2.4 Hz), 7.73 (1H, d, J=1.8 Hz), 4.74 (1H, d, J=16.5 Hz), 4.45 (1H, d, J=16.5 Hz), 3.74 (1H, dd, J=10.7, 2.7 Hz), 3.70-3.62 (1H, m), 3.58 (1H, dd, J=10.4, 4.3 Hz), 2.62-2.54 (1H, m), 2.47-2.35 (1H, m), 2.24-2.12 (1H, m), 2.00-1.89 (1H, m), 0.85 (9H, s), 0.01 (6H, s).

(52d) (9aS)-3-bromo-8,9,9a,10-tetrahydro-5H,7H-pyrido[3,2-f]pyrrolo[2,1-c][1,4]oxazepin-7-one To a suspension of (5S)-1-[(5-bromo-2-chloropyridin-3-yl)methyl]-5-({[tert-butyl(dimethyl)silyl]oxy}methyl)pyrrolidin-2-one (783 mg, 1.80 mmol) in tetrahydrofuran (30 mL), a 1.0 mol/L solution of tetra-n-butylammonium fluoride in tetrahydrofuran (3.6 mL, 3.6 mmol) was added at room temperature, and the mixture was stirred at 65-70° C. for 6.5 hours in an oil bath. The mixture was cooled to room temperature, and diluted by addition of water followed by extraction with ethyl acetate. The organic layer was washed with a saturated aqueous solution of sodium chloride, and dried over anhydrous sodium sulfate. The solvent was distilled off under reduced pressure, and the residue was purified in an automatic chromatography apparatus (ethyl acetate/methanol=93/7-68/32) to obtain the title compound (393 mg, yield: 77%).

$^1$H NMR spectrum (CDCl$_3$, 400 MHz) δ: 8.24 (1H, d, J=2.4 Hz), 7.80 (1H, d, J=2.4 Hz), 4.95 (1H, d, J=15.3 Hz), 4.50 (1H, dd, J=12.2, 3.1 Hz), 4.19-4.03 (2H, m), 3.77 (1H, dd, J=12.8, 7.9 Hz), 2.53-2.36 (2H, m), 2.28-2.19 (1H, m), 1.77-1.71 (1H, m).

(52e) (9aS)-3-amino-8,9,9a,10-tetrahydro-5H,7H-pyrido[3,2-f]pyrrolo[2,1-c][1,4]oxazepin-7-one trifluoroacetate To a mixture of (9aS)-3-bromo-8,9,9a,10-tetrahydro-5H,7H-pyrido[3,2-f]pyrrolo[2,1-c][1,4]oxazepin-7-one (389 mg, 1.37 mmol) obtained in Example (52d), tert-butyl carbamate (209 mg, 1.79 mmol), 2-di-tert-butylphosphino-2',4',6'-triisopropylbiphenyl (117 mg, 0.28 mmol) and sodium tert-butoxide (198 mg, 2.06 mmol) in toluene (120 mL), tris(dibenzylideneacetone)dipalladium(0)-chloroform adduct (72 mg, 0.068 mmol) was added at room temperature, the mixture was stirred under nitrogen atmosphere at the same temperature as above for 1 hour, and then stirred at 80-90° C. for 5.5 hours in an oil bath. The mixture was cooled to room temperature, and diluted by addition of ethyl acetate. An insoluble matter was filtered off through pad of Celite 545®, the filtrate was concentrated under reduced pressure, and the residue was purified in an automatic chromatography apparatus (methylene chloride/methanol=99/1-91/9) to obtain tert-butyl [(9aS)-7-oxo-8,9,9a,10-tetrahydro-5H,7H-pyrido[3,2-f]pyrrolo[2,1-c][1,4]oxazepin-3-yl]carbamate (214 mg) as a mixture containing a small amount of unknown materials.

To a mixture of tert-butyl [(9aS)-7-oxo-8,9,9a,10-tetrahydro-5H,7H-pyrido[3,2-f]pyrrolo[2,1-c][1,4]oxazepin-3-yl]carbamate (214 mg) obtained in the above step in methylene chloride (3 mL), trifluoroacetic acid (1.5 mL, 20 mmol) was added at room temperature, and the mixture was stirred at the same temperature as above for 12 hours. The solvent was distilled off under reduced pressure, the residue was diluted by addition of toluene, and the solvent was distilled off under reduced pressure again. The residue was purified in an automatic chromatography apparatus (methylene chloride/methanol=99/1-89/11) to obtain the title compound (86.2 mg, yield: 39% for 2 steps).

$^1$H NMR spectrum (DMSO-d$_6$, 400 MHz) δ: 7.41 (1H, d, J=3.1 Hz), 6.91 (1H, d, J=2.4 Hz), 5.10 (2H, s), 4.57 (1H, d, J=15.3 Hz), 4.27 (1H, dd, J=12.8, 3.1 Hz), 4.04-3.95 (2H, m), 3.56-3.42 (1H, m), 2.29-2.20 (2H, m), 2.11-2.02 (1H, m), 1.58-1.45 (1H, m).

(52f) 5-chloro-2-methoxy-N-[(9aS)-7-oxo-8,9,9a,10-tetrahydro-5H,7H-pyrido[3,2-f]pyrrolo[2,1-c][1,4]oxazepin-3-yl]benzenesulfonamide The title compound (31.8 mg, yield: 31%) was obtained by production according to the method described in Example (27d) using (9aS)-3-amino-8,9,9a,10-tetrahydro-5H,7H-pyrido[3,2-f]pyrrolo[2,1-c][1,4]oxazepin-7-one trifluoroacetate (80.6 mg, 0.24 mmol) obtained in Example (52e) and 5-chloro-2-methoxybenzenesulfonyl chloride (71 mg, 0.29 mmol) as starting materials.

$^1$H NMR spectrum (DMSO-d6, 400 MHz) δ: 10.28 (1H, br s), 7.78 (1H, d, J=2.4 Hz), 7.72-7.61 (2H, m), 7.45 (1H, d, J=2.4 Hz), 7.25 (1H, d, J=9.2 Hz), 4.68 (1H, d, J=15.9 Hz), 4.41 (1H, dd, J=12.5, 2.7 Hz), 4.13 (1H, d, J=15.3 Hz), 4.04-3.96 (1H, m), 3.86 (3H, s), 3.74 (1H, dd, J=12.8, 6.7 Hz), 2.36-2.02 (3H, m), 1.68-1.55 (1H, m).

MS spectrum (ES/APCI$^+$): 424 (M+H), 426 (M+2+H).

(Example 53) 5-chloro-N-[(8R,9aS)-8-hydroxy-7-oxo-8,9,9a,10-tetrahydro-5H,7H-pyrido[3,2-f]pyrrolo[2,1-c][1,4]oxazepin-3-yl]-2-methoxybenzenesulfonamide (53a) tert-butyl (2S,4R)-4-hydroxy-2-(hydroxymethyl) pyrrolidine-1-carboxylate To a solution of 1-tert-butyl 2-methyl (2S,4R)-4-hydroxy-pyrrolidine-1,2-dicarboxylate (5.20 g, 21.2 mmol) in tetrahydrofuran (53 mL), lithium chloride (2.70 g, 63.6 mmol) and sodium borohydride (2.41 g, 63.6 mmol) at room temperature followed by addition of ethanol (106 mL), and the mixture was stirred at the same temperature as above for 24 hours. Water (40 mL) was carefully added thereto, and the mixture was concentrated under reduced pressure. The residue was diluted by addition of water (80 mL) followed by extraction with ethyl acetate four times. The organic layer was washed with a saturated aqueous solution of sodium chloride, and dried over anhydrous sodium sulfate. The solvent was distilled off under reduced pressure to obtain a crude product of the title compound (5.11 g, yield: quantitative).

$^1$H NMR spectrum (CDCl$_3$, 400 MHz) δ:5.03 (1H, d, J=6.1 Hz), 4.38 (1H, s), 4.25-4.01 (1H, m), 3.78-3.65 (1H, m), 3.63-3.48 (2H, m), 3.44 (1H, dd, J=12.1, 3.6 Hz), 1.48 (9H, s).

(53b) tert-butyl (3R,5S)-3-{[tert-butyl(dimethyl) silyl]oxy}-5-({[tert-butyl(dimethyl)silyl] oxy}methyl)-2-oxopyrrolidine-1-carboxylate To a solution of tert-butyl (2S,4R)-4-hydroxy-2-(hydroxymethyl)pyrrolidine-1-carboxylate (4.61 g, 21.2 mmol) obtained in Example (53a) and imidazole (5.05 g, 74.2 mmol) in N,N-dimethylformamide (45 mL), tert-butyldimethylchlorosilane (9.59 g, 63.6 mmol) was added under ice cooling, the mixture was stirred at room temperature for 23.5 hours. The mixture was diluted by addition of n-hexane, ethyl acetate and a saturated aqueous solution of ammonium chloride, followed by extraction with ethyl acetate. The organic layer was washed with a saturated aqueous solution of sodium chloride, and dried over anhydrous sodium sulfate. After filtration, the solvent was distilled off under reduced pressure and the residue was purified in an automatic chromatography apparatus (n-hexane/ethyl acetate=99/1-95/5) to obtain (tert-butyl (2S,4R)-4-{[tert-butyl(dimethyl)silyl]oxy}-2-({[tert-butyl(dimethyl)silyl]oxy}methyl)pyrrolidine-1-carboxylate) (9.55 g).

To a solution of sodium periodate (11.3 g, 53.0 mmol) in water (140 mL), ruthenium (IV) oxide hydrate (0.480 g, 3.18 mmol) was added at room temperature, and the mixture was stirred at the same temperature as above for 10 minutes. The mixture was cooled in an ice-water bath, then a solution of (tert-butyl (2S,4R)-4-{[tert-butyl(dimethyl)silyl]oxy}-2-({[tert-butyl(dimethyl)silyl]oxy}methyl)pyrrolidine-1-carboxylate) (9.55 g) obtained in the above step in ethyl acetate (85 mL) was added thereto over 25 minutes period, and the mixture was stirred at room temperature for 15 hours. The mixture was diluted by addition of ethyl acetate, the insoluble matter was filtered off through pad of Celite 545®, and the filtrate was extracted with ethyl acetate. The organic layer was washed with a saturated aqueous solution of sodium bicarbonate and a saturated aqueous solution of sodium chloride, and dried over anhydrous sodium sulfate. After filtration, the solvent was distilled off under reduced pressure and the residue was purified in an automatic chromatography apparatus (n-hexane/ethyl acetate=99/1-88/12) to obtain the title compound (6.85 g, yield: 70% for 2 steps).

$^1$H NMR spectrum (CDCl$_3$, 400 MHz) δ: 4.66 (1H, t, J=9.2 Hz), 4.13 (1H, d, J=9.2 Hz), 3.96 (1H, dd, J=10.4, 2.4 Hz), 3.61 (1H, d, J=10.4 Hz), 2.32 (1H, dd, J=12.2, 8.5 Hz), 2.11-2.00 (1H, m), 1.53 (9H, s), 0.91 (9H, s), 0.87 (9H, s), 0.16 (3H, s), 0.12 (3H, s), 0.04 (3H, s), 0.01 (3H, s).

(53c) (3R,5S)-3-{[tert-butyl(dimethyl)silyl]oxy}-5-({[tert-butyl(dimethyl)silyl]oxy}methyl)pyrrolidin-2-one To a solution of tert-butyl (3R,5S)-3-{[tert-butyl(dimethyl)silyl]oxy}-5-({[tert-butyl(dimethyl)silyl]oxy}methyl)-2-oxopyrrolidine-1-carboxylate (6.85 g, 14.9 mmol) obtained in Example (53b) in methylene chloride (150 mL), trifluoroacetic acid (11.4 mL, 149 mmol) was added at room temperature, and the mixture was stirred at the same temperature as above for 30 minutes. The mixture was cooled in an ice-water bath, diluted by addition of a saturated aqueous solution of sodium bicarbonate (180 mL) followed by extraction with methylene chloride. The organic layer was washed with a saturated aqueous solution of sodium chloride, and dried over anhydrous sodium sulfate. After filtration, the solvent was distilled off under reduced pressure and the residue was purified in an automatic chromatography apparatus (n-hexane/ethyl acetate=95/5-65/35) to obtain the title compound (5.28 g, yield: 99%).

$^1$H NMR spectrum (CDCl$_3$, 400 MHz) δ: 4.35 (1H, t, J=7.0 Hz), 5.71 (1H, br s), 3.79-3.69 (1H, m), 3.60 (1H, dd, J=10.4, 3.7 Hz), 3.44 (1H, dd, J=10.1, 6.4 Hz), 2.09 (2H, t, J=6.4 Hz), 0.91 (9H, s), 0.89 (9H, s), 0.16 (3H, s), 0.14 (3H, s), 0.06 (3H, s), 0.05 (3H, s).

(53d) (3R,5S)-1-[(5-bromo-2-chloropyridin-3-yl)methyl]-3-hydroxy-5-(hydroxymethyl)pyrrolidin-2-one To a suspension of sodium hydride (approximately 63% content, 56 mg, 1.42 mmol) in tetrahydrofuran (5 mL), a solution of (3R,5S)-3-{[tert-butyl(dimethyl)silyl]oxy}-5-({[tert-butyl(dimethyl)silyl]oxy}methyl)pyrrolidin-2-one (500 mg, 1.39 mmol) obtained in Example (53c) was added at room temperature, and the mixture was stirred at the same temperature for 30 minutes. Subsequently, a solution of (5-bromo-2-chloropyridin-3-yl)methyl methanesulfonate (422 mg, 1.40 mmol) obtained in Example (52b) in teterahydrofuran (2.5 mL) was added thereto, the mixture was stirred under reflux for 1.5 hours. After cooling, the mixture was poured into a mixture of ice and a saturated aqueous solution of ammonium chloride followed by extraction with ethyl acetate. The organic layer was washed with a saturated aqueous solution of sodium chloride, and dried over anhydrous sodium sulfate. The solvent was distilled off under reduced pressure, and the residue was purified in an automatic chromatography apparatus (n-hexane/ethyl acetate=99/1-78/22) to obtain ((3R,5S)-1-[(5-bromo-2-chloropyridin-3-yl)methyl]-3-{[tert-butyl(dimethyl)silyl]oxy}-5-({[tert-butyl(dimethyl)silyl]oxy}methyl)pyrrolidin-2-one) (753 mg yield: 96%).

To a solution of ((3R,5S)-1-[(5-bromo-2-chloropyridin-3-yl)methyl]-3-{[tert-butyl(dimethyl)silyl]oxy}-5-({[tert-butyl(dimethyl)silyl]oxy}methyl)pyrrolidin-2-one) (751 mg, 1.33 mmol) obtained in the above step in tetrahydrofuran (22 mL), a 1.0 mol/L solution of tetra-n-butylammonium fluoride in tetrahydrofuran (3.3 mL, 3.3 mmol) was added at room temperature, and the mixture was stirred at the same temperature as above for 20 minutes. The mixture was diluted by addition of a saturated aqueous solution of ammonium chloride followed by extraction with ethyl acetate twice. The organic layer was washed with a saturated aqueous solution of sodium chloride, and dried over anhydrous sodium sulfate. The solvent was distilled off under reduced pressure, and the residue was purified in an automatic chromatography apparatus (ethyl acetate/methanol=99/1-89/11) to obtain the title compound (331 mg, yield: 74%).

$^1$H NMR spectrum (DMSO-d$_6$, 400 MHz) δ: 8.51 (1H, d, J=2.4 Hz), 7.85 (1H, d, J=2.4 Hz), 5.74-5.45 (1H, m), 4.96 (1H, br s), 4.59 (1H, d, J=16.5 Hz), 4.37-4.28 (2H, m), 3.61-3.51 (2H, m), 3.42-3.36 (1H, m), 2.22 (1H, ddd, J=12.8, 8.2, 1.8 Hz), 1.97-1.85 (1H, m)

(53e) (8R,9aS)-3-bromo-8-hydroxy-8,9,9a,10-tetrahydro-5H, 7H-pyrido[3,2-f]pyrrolo[2,1-c][1,4]oxazepin-7-one To a solution of (3R,5S)-1-[(5-bromo-2-chloropyridin-3-yl)methyl]-3-hydroxy-5-(hydroxymethyl)pyrrolidin-2-one (335 mg, 1.00 mmol) obtained in Example (53d) in N,N-dimethylformamide (20 mL), potassium carbonate (414 mg, 2.99 mmol) was added at room temperature, and the mixture was stirred at 120-125° C. for 4 hours in an oil bath. After cooling, the mixture was poured into a mixture of ethyl acetate and a saturated aqueous solution of ammonium chloride followed by extraction with a mixed solvent of methylene chloride/isopropanol=3/1 three times. The organic layer was dried over anhydrous sodium sulfate. The solvent was distilled off under reduced pressure, isopropanol was added to the residue, and the suspension was stirred at room temperature for a while. The precipitated solid was collected by filtration to obtain the title compound (284 mg, yield: 95%).

$^1$H NMR spectrum (DMSO-$d_6$, 400 MHz) δ: 8.23 (1H, d, J=2.4 Hz), 8.11 (1H, d, J=2.4 Hz), 5.73 (1H, br s), 4.81 (1H, d, J=15.9 Hz), 4.48 (1H, dd, J=12.8, 3.1 Hz), 4.26 (1H, d, J=15.9 Hz), 4.16-4.05 (2H, m), 3.84 (1H, dd, J=12.5, 7.0 Hz), 2.04-1.87 (2H, m) (53f) 5-chloro-2-methoxybenzenesulfonamide To a solution of 5-chloro-2-methoxybenzenesulfonyl chloride (3 g, 12.4 mmol) in tetrahydrofuran (20 mL), a 28% aqueous ammonia solution (20 mL, 295 mmol) was added, and the mixture was stirred at room temperature for 19 hours. The reaction mixture was diluted by addition of 1 mol/L hydrochloric acid, followed by extraction with ethyl acetate. The organic layer was washed with water and a saturated aqueous solution of sodium chloride and dried over anhydrous sodium sulfate. After filtration, the solvent was distilled off under reduced pressure to obtain the title compound (2.74 g, yield: quantitative).

$^1$H NMR spectrum (CDCl3, 400 MHz) δ: 7.91 (1H, d, J=3.0 Hz), 7.56-7.46 (1H, m), 7.00 (1H, d, J=8.5 Hz), 5.06 (2H, br s), 4.02 (3H, s).

(53g) 5-chloro-N-[(8R,9aS)-8-hydroxy-7-oxo-8,9,9a,10-tetrahydro-5H,7H-pyrido[3,2-f]pyrrolo[2,1-c][1,4]oxazepin-3-yl]-2-methoxybenzenesulfonamide To a mixture of (8R,9aS)-3-bromo-8-hydroxy-8,9,9a,10-tetrahydro-5H,7H-pyrido[3,2-f]pyrrolo[2,1-c][1,4]oxazepin-7-one (120 mg, 0.40 mmol) obtained in Example (53e), 5-chloro-2-methoxybenzenesulfonamide (116 mg, 0.52 mmol) obtained in Example (53f), N,N-dimethylglycine (20.7 mg, 0.20 mmol) and tripotassium phosphate (255 mg, 1.20 mmol) in dimethylsulfoxide (1.2 mL), copper (I) iodide (31 mg, 0.12 mmol) was added at room temperature, and the mixture was stirred under nitrogen atmosphere at 120-125° C. for 3.5 hours in an oil bath. After cooling, the mixture was diluted by addition of a saturated aqueous solution of ammonium chloride, and the insoluble matter was filtered off. The filtrate was diluted by addition of a 2.0 mol/L hydrochloric acid (5 mL) and a saturated aqueous solution of sodium chloride followed by extraction with a mixed solvent of methylene chloride/isopropanol=3/1. The organic layer was dried over anhydrous sodium sulfate. The solvent was distilled off under reduced pressure, and the residue was purified in an automatic chromatography apparatus (methylene chloride/methanol=98/2-91/9) to obtain a solid. To the solid, isopropanol was added, and the suspension was stirred at room temperature for a while. The precipitated solid was collected by filtration to obtain the title compound (57.3 mg, yield: 33%).

$^1$H NMR spectrum (DMSO-$d_6$, 400 MHz) δ: 10.31 (1H, br s), 7.79 (1H, d, J=2.4 Hz), 7.71-7.65 (2H, m), 7.47 (1H, d, J=3.1 Hz), 7.24 (1H, d, J=8.5 Hz), 5.69 (1H, d, J=4.9 Hz), 4.67 (1H, d, J=15.3 Hz), 4.38 (1H, dd, J=12.8, 3.1 Hz), 4.17 (1H, d, J=15.3 Hz), 4.09-4.00 (2H, m), 3.85 (3H, s), 3.68 (1H, dd, J=12.8, 7.9 Hz), 1.98-1.84 (2H, m).

MS spectrum (ES/APCI$^+$): 440 (M+H), 442 (M+2+H)

(Example 54) 5-chloro-N-[(8S,9aS)-8-hydroxy-7-oxo-8,9,9a,10-tetrahydro-5H,7H-pyrido[3,2-f]pyrrolo[2,1-c][1,4]oxazepin-3-yl]-2-methoxybenzenesulfonamide (54a) tert-butyl (2S,4S)-4-hydroxy-2-(hydroxymethyl) pyrrolidine-1-carboxylate The title compound (8.02 g, yield: quantitative) was obtained by production according to the method described in Example (53a) using (4S)-1-(tert-butoxycarbonyl)-4-hydroxy-L-proline (9.00 g, 36.7 mmol) as a starting material.

$^1$H NMR spectrum (CDCl3, 400 MHz) δ: 4.31 (1H, br s), 4.07-4.00 (3H, m), 3.60-3.44 (4H, m), 2.36-2.32 (1H, m), 1.94-1.83 (1H, m), 1.47 (9H, s).

(54b) tert-butyl (3S,5S)-3-{[tert-butyl(dimethyl)silyl]oxy}-5-({[tert-butyl(dimethyl)silyl]oxy}methyl)-2-oxopyrrolidine-1-carboxylate The title compound (4.73 g, yield: 63% for 2 steps) was obtained by production according to the method described in Example (53b) using tert-butyl (2S,4S)-4-hydroxy-2-(hydroxymethyl)pyrrolidine-1-carboxylate (3.6 g, 17 mmol) obtained in Example (54a) as a starting material.

$^1$H NMR spectrum (CDCl3, 400 MHz) δ: 4.24 (1H, dd, J=8.2, 5.5 Hz), 4.03-3.99 (1H, m), 3.85-3.80 (2H, m), 2.25-2.21 (1H, m), 2.06-2.00 (1H, m), 1.53 (9H, s), 0.90 (9H, s), 0.88 (9H, s), 0.15 (3H, s), 0.13 (3H, s), 0.05 (3H, s), 0.04 (3H, s).

(54c) (3S,5S)-3-{[tert-butyl(dimethyl)silyl]oxy}-5-({[tert-butyl(dimethyl)silyl]oxy}methyl)pyrrolidin-2-one The title compound (2.32 g, yield: 63%) was obtained by production according to the method described in Example (53c) using tert-butyl (3S,5S)-3-{[tert-butyl(dimethyl)silyl]oxy}-5-({[tert-butyl(dimethyl)silyl]oxy}methyl)-2-oxopyrrolidine-1-carboxylate (4.73 g, 10.3 mmol) obtained in Example (54b) as a starting material.

$^1$H NMR spectrum (CDCl3, 400 MHz) δ: 5.85 (1H, br s), 4.30 (1H, t, J=7.8 Hz), 3.68-3.43 (3H, m), 2.43-2.39 (1H, m), 1.59-1.56 (2H, m), 0.91 (9H, s), 0.89 (9H, s), 0.17 (3H, s), 0.14 (3H, s), 0.06 (6H, s).

(54d) (8S,9aS)-3-bromo-8-hydroxy-8,9,9a,10-tetrahydro-5H, 7H-pyrido[3,2-f]pyrrolo[2,1-c][1,4]oxazepin-7-one The title compound (734 mg, yield: 45% for 3 steps) was obtained by production according to the method described in Examples (53d) and (53e) using (3S,5S)-3-{[tert-butyl(dimethyl)silyl]oxy}-5-({[tert-butyl(dimethyl)silyl]oxy}methyl)pyrrolidin-2-one (1.976 g, 5.51 mmol) obtained in Example (54c) and (5-bromo-2-chloropyridin-3-yl)methyl methanesulfonate (1.74 g, 5.78 mmol) obtained in Example (52b) as starting materials.

$^1$H NMR spectrum (DMSO-$d_6$, 400 MHz) δ: 8.20 (1H, d, J=2.4 Hz), 8.10 (1H, d, J=2.4 Hz), 4.80 (1H, d, J=16.4 Hz), 4.62 (1H, dd, J=13.4, 3.0 Hz), 4.33 (1H, d, J=15.8 Hz), 4.24 (1H, t, J=8.8 Hz), 3.99 (1H, dd, J=13.1, 3.9 Hz), 3.92-3.83 (1H, m), 2.48-2.38 (1H, m), 1.64-1.54 (1H, m).

(54e) 5-chloro-N-[(8S,9aS)-8-hydroxy-7-oxo-8,9,9a, 10-tetrahydro-5H,7H-pyrido[3,2-f]pyrrolo[2,1-c][1, 4]oxazepin-3-yl]-2-methoxybenzenesulfonamide The title compound (550 mg, yield: 43%) was obtained by production according to the method described in Example (53g) using (8S,9aS)-3-bromo-8-hydroxy-8,9,9a,10-tetrahydro-5H,7H-pyrido[3,2-f]pyrrolo[2,1-c][1,4]oxazepin-7-one (870 mg, 2.91 mmol) obtained in Example (54d) and 5-chloro-2-methoxybenzenesulfonamide (838 mg, 3.78 mmol) obtained in Example (53f) as starting materials.

$^1$H NMR spectrum (DMSO-d$_6$, 400 MHz) δ: 10.25 (1H, br s), 7.76 (1H, d, J=2.4 Hz), 7.71-7.64 (2H, m), 7.47 (1H, d, J=2.4 Hz), 7.25 (1H, dd, J=7.3, 2.4 Hz), 5.57 (1H, d, J=6.1 Hz), 4.68 (1H, d, J=15.8 Hz), 4.51 (1H, dd, J=14.6, 4.3 Hz), 4.28-4.16 (2H, m), 3.89-3.79 (5H, m), 2.44-2.35 (1H, m), 1.56-1.46 (1H, m).

MS spectrum (ES/APCI$^+$): 440 (M+H), 442 (M+2+H).

(Example 55) Potassium [(5-chloro-2-methoxyphenyl)sulfonyl][(8S,9aS)-8-hydroxy-7-oxo-8,9,9a,10-tetrahydro-5H,7H-pyrido[3,2-f]pyrrolo[2,1-c][1,4]oxazepin-3-yl]azanide (Potassium Salt of Example 54)

The title compound (23.2 mg, yield: 95%) was obtained by production according to the method described in Example 33 using 5-chloro-N-[(8S,9aS)-8-hydroxy-7-oxo-8,9,9a,10-tetrahydro-5H,7H-pyrido[3,2-f]pyrrolo[2,1-c][1,4]oxazepin-3-yl]-2-methoxybenzenesulfonamide (22.4 mg, 0.051 mmol) obtained in Example (54e) as a starting material.

$^1$H NMR spectrum (DMSO-d6, 400 MHz) δ: 7.65 (1H, d, J=3.1 Hz), 7.41 (1H, d, J=2.4 Hz), 7.33 (1H, dd, J=8.9, 2.7 Hz), 7.18 (1H, d, J=3.1 Hz), 6.98 (1H, d, J=9.2 Hz), 5.57 (1H, br s), 4.51 (1H, d, J=15.3 Hz), 4.31 (1H, dd, J=12.8, 3.1 Hz), 4.15 (1H, t, J=8.2 Hz), 4.07-3.98 (1H, m), 3.84-3.74 (1H, m), 3.65 (3H, s), 3.53 (1H, dd, J=12.5, 7.0 Hz), 2.43-2.32 (1H, m), 1.41-1.30 (1H, m).

(Example 56) 5-chloro-N-[(8S,9aS)-8-hydroxy-7-oxo-8,9,9a,10-tetrahydro-5H,7H-pyrido[3,2-f]pyrrolo[2,1-c][1,4]oxazepin-3-yl]-2-(trifluoromethoxy)benzenesulfonamide

(56a) 5-chloro-2-(trifluoromethoxy)benzenesulfonamide

The title compound (2.44 g, yield: 74%) was obtained by production according to the method described in Example (53f) using 5-chloro-2-(trifluoromethoxy)benzenesulfonyl chloride (3.52 g, 11.9 mmol) obtained in Example (32a) as a starting material.

$^1$H NMR spectrum (DMSO-d6, 400 MHz) δ: 7.92 (1H, d, J=2.4 Hz), 7.89-7.80 (3H, m), 7.62 (1H, dd, J=8.8, 1.5 Hz).

(56b) 5-chloro-N-[(8S,9aS)-8-hydroxy-7-oxo-8,9,9a, 10-tetrahydro-5H,7H-pyrido[3,2-f]pyrrolo[2,1-c][1, 4]oxazepin-3-yl]-2-(trifluoromethoxy)benzenesulfonamide The title compound (28 mg, yield: 11%) was obtained by production according to the method described in Example (53g) using (8S,9aS)-3-bromo-8-hydroxy-8,9,9a,10-tetrahydro-5H,7H-pyrido[3,2-f]pyrrolo[2,1-c][1,4]oxazepin-7-one (150 mg, 0.50 mmol) obtained in Example (54d) and 5-chloro-2-(trifluoromethoxy)benzenesulfonamide (838 mg, 3.78 mmol) obtained in Example (56a) as starting materials.

$^1$H NMR spectrum (DMSO-d$_6$, 400 MHz) δ: 10.75 (1H, br s), 7.93 (1H, d, J=2.3 Hz), 7.85 (1H, dd, J=8.6, 2.3 Hz), 7.75 (1H, d, J=2.3 Hz), 7.61 (1H, d, J=9.4 Hz), 7.48 (1H, d, J=2.3 Hz), 5.58 (1H, d, J=6.3 Hz), 4.70 (1H, d, J=16.0 Hz), 4.52-4.49 (1H, m), 4.24-4.18 (2H, m), 3.85-3.83 (2H, m), 2.44-2.37 (1H, m), 1.52-1.49 (1H, m).

MS spectrum (ES/APCI$^+$): 494 (M+H), 496 (M+2+H).

(Example 57) Potassium {[5-chloro-2-(trifluoromethoxy)phenyl]sulfonyl}[(8S,9aS)-8-hydroxy-7-oxo-8,9,9a,10-tetrahydro-5H,7H-pyrido[3,2-f]pyrrolo[2,1-c][1,4]oxazepin-3-yl]azanide (Potassium Salt of Example 56)

The title compound (23 mg, yield: 97%) was obtained by production according to the method described in Example 33 using 5-chloro-N-[(8S,9aS)-8-hydroxy-7-oxo-8,9,9a,10-tetrahydro-5H,7H-pyrido[3,2-f]pyrrolo[2,1-c][1,4]oxazepin-3-yl]-2-(trifluoromethoxy)benzenesulfonamide (22 mg, 0.045 mmol) obtained in Example (56b) as a starting material.

$^1$H NMR spectrum (DMSO-d6, 400 MHz) δ: 7.79 (1H, d, J=2.7 Hz), 7.51 (1H, dd, J=8.6, 2.7 Hz), 7.45 (1H, d, J=2.7 Hz), 7.34 (1H, d, J=8.6 Hz), 7.15 (1H, d, J=2.7 Hz), 4.52 (1H, d, J=14.9 Hz), 4.33-4.31 (1H, m), 4.16-4.14 (1H, m), 4.03 (1H, d, J=14.9 Hz), 3.80-3.77 (1H, m), 3.56 (1H, dd, J=12.7, 6.8 Hz), 2.40-2.33 (1H, m), 1.40-1.33 (1H, m).

(Example 58) 5-chloro-2-methoxy-N-[(9aR)-7-oxo-9a,10-dihydro-5H, 9H-[1,3]oxazolo[4,3-c]pyrido[3,2-f][1,4]oxazepin-3-yl]benzenesulfonamide

(58a) (4S)-4-({[tert-butyl(dimethyl)silyl]oxy}methyl)-1,3-oxazolidin-2-one

The title compound (426 mg, yield: 79%) was obtained by production according to the method described in Example (52a) using (4R)-4-(hydroxymethyl)-1,3-oxazolidin-2-one (272 mg, 2.32 mmol) as a starting material.

$^1$H NMR spectrum (CDCl$_3$, 400 MHz) δ: 5.19 (1H, br s), 4.46 (1H, t, J=8.5 Hz), 4.14 (1H, dd, J=9.1, 4.9 Hz), 3.97-3.91 (1H, m), 3.66-3.58 (2H, m), 0.89 (9H, s), 0.07 (6H, s).

(58b) (9aR)-3-bromo-9a,10-dihydro-5H,9H-[1,3]oxazolo[4,3-c]pyrido[3,2-f][1,4]oxazepin-7-one The title compound (248 mg, yield: 49% for 3 steps) was obtained by production according to the method described in Examples (53d) and (53e) using (4S)-4-({[tert-butyl(dimethyl)silyl]oxy}methyl)-1,3-oxazolidin-2-one (428 mg, 1.85 mmol) obtained in Example (58a) and (5-bromo-2-chloropyridin-3-yl)methyl methanesulfonate (530 mg, 1.76 mmol) obtained in Example (52b) as starting materials.

$^1$H NMR spectrum (CDCl$_3$, 400 MHz) δ: 8.28 (1H, d, J=2.4 Hz), 7.80 (1H, d, J=2.4 Hz), 4.71 (1H, d, J=15.8 Hz), 4.54-4.45 (2H, m), 4.38-4.27 (2H, m), 4.02 (1H, dd, J=9.1, 5.5 Hz), 3.90 (1H, dd, J=12.8, 8.5 Hz).

(58c) (9aR)-3-amino-9a, 10-dihydro-5H, 9H-[1,3]oxazolo[4,3-c]pyrido[3,2-f][1,4]oxazepin-7-one The title compound (43.3 mg, yield: 23% for 2 steps) was obtained by production according to the method described in Example (52e) using (9aR)-3-bromo-9a,10-dihydro-5H, 9H-[1,3]oxazolo[4,3-c]pyrido[3,2-f][1,4]oxazepin-7-one (246 mg, 0.86 mmol) obtained in Example (58b) as a starting material.

¹H NMR spectrum (CDCl₃, 400 MHz) δ: 7.65 (1H, d, J=3.1 Hz), 7.01 (1H, d, J=3.1 Hz), 4.60 (1H, d, J=15.3 Hz), 4.47-4.38 (2H, m), 4.34-4.24 (2H, m), 3.92 (1H, dd, J=9.2, 5.5 Hz), 3.76 (1H, dd, J=12.5, 9.5 Hz), 3.65-3.57 (2H, m).

(58d) 5-chloro-2-methoxy-N-[(9aR)-7-oxo-9a,10-dihydro-5H, 9H-[1,3]oxazolo[4,3-c]pyrido[3,2-f][1, 4]oxazepin-3-yl]benzenesulfonamide The title compound (76.2 mg, yield: 93%) was obtained by production according to the method described in Example (27d) using (9aR)-3-amino-9a,10-dihydro-5H,9H-[1,3]oxazolo[4,3-c]pyrido[3,2-f][1,4]oxazepin-7-one (42.8 mg, 0.19 mmol) obtained in Example (58c) and 5-chloro-2-methoxybenzenesulfonyl chloride (51 mg, 0.21 mmol) as starting materials.

¹H NMR spectrum (DMSO-d₆, 400 MHz) δ: 10.29 (1H, br s), 7.78 (1H, d, J=2.4 Hz), 7.70-7.65 (2H, m), 7.48 (1H, d, J=3.1 Hz), 7.28-7.21 (1H, m), 4.53-4.38 (4H, m), 4.28-4.18 (1H, m), 4.04 (1H, dd, J=9.2, 5.5 Hz) 3.94 (1H, dd, J=13.1, 5.2 Hz), 3.84 (3H, s).

MS spectrum (ES/APCI⁺): 426 (M+H), 428 (M+2+H).

(Example 59) 5-chloro-2-methoxy-N-[(10aS)-7-oxo-7,8,9,10,10a, 11-hexahydro-5H-dipyrido[2,1-c:3',2'-f][1,4]oxazepin-3-yl]benzenesulfonamide (59a) (6S)-6-({[tert-butyl(dimethyl)silyl]oxy}methyl)piperidin-2-one The title compound (318 mg, yield: 40%) was obtained by production according to the method described in Example (52a) using (6S)-6-(hydroxymethyl)piperidin-2-one (421 mg, 3.26 mmol) as a starting material.

¹H NMR spectrum (CDCl₃, 400 MHz) δ: 6.12 (1H, br s), 3.63 (1H, dd, J=9.4, 3.3 Hz), 3.53-3.43 (1H, m), 3.37 (1H, t, J=9.4 Hz), 2.49-2.36 (1H, m), 2.35-2.22 (1H, m), 1.94-1.87 (1H, m), 1.86-1.77 (1H, m), 1.76-1.66 (1H, m), 1.33-1.23 (1H, m), 0.89 (9H, s), 0.06 (6H, s).

(59b) (10aS)-3-bromo-9,10,10a,11-tetrahydro-5H-dipyrido[2,1-c:3',2'-f][1,4]oxazepin-7(8H)-one The title compound (178 mg, yield: 60% for 2 steps) was obtained by production according to the method described in Examples (52c) and (52d) using (6S)-6-({[tert-butyl(dimethyl)silyl]oxy}methyl)piperidin-2-one (260 mg, 1.05 mmol) obtained in Example (59a) and (5-bromo-2-chloropyridin-3-yl)methyl methanesulfonate (300 mg, 1.00 mmol) obtained in Example (52b) as starting materials.

¹H NMR spectrum (CDCl₃, 400 MHz) δ: 8.19 (1H, d, J=2.4 Hz), 7.82 (1H, d, J=2.4 Hz), 5.33 (1H, d, J=14.6 Hz), 4.50 (1H, dd, J=15.3, 5.5 Hz), 4.03-3.93 (3H, m), 2.53-2.43 (1H, m), 2.36-2.28 (1H, m), 2.08-1.98 (1H, m), 1.90-1.73 (3H, m).

(59c) 5-chloro-2-methoxy-N-[(10aS)-7-oxo-7,8,9,10,10a,11-hexahydro-5H-dipyrido[2,1-c:3',2'-f][1,4]oxazepin-3-yl]benzenesulfonamide The title compound (7.5 mg, yield: 3% for 3 steps) was obtained by production according to the method described in Examples (52e) and (27d) using (10aS)-3-bromo-9,10,10a,11-tetrahydro-5H-dipyrido[2,1-c:3',2'-f][1,4]oxazepin-7(8H)-one (178 mg, 0.60 mmol) obtained in Example (59b) and 5-chloro-2-methoxybenzenesulfonyl chloride (45 mg, 0.19 mmol) as starting materials.

¹H NMR spectrum (DMSO-d₆, 400 MHz) δ: 10.19 (1H, br s), 7.73 (1H, d, J=2.4 Hz), 7.67-7.66 (2H, m), 7.40 (1H, d, J=2.4 Hz), 7.24 (1H, d, J=9.8 Hz), 5.00 (1H, d, J=15.3 Hz), 4.51 (1H, dd, J=12.8, 2.4 Hz), 4.15 (1H, d, J=15.3 Hz), 3.92-3.87 (5H, m), 2.33-2.12 (2H, m), 1.92 (1H, s), 1.71-1.66 (3H, m).

MS spectrum (ES/APCI⁺): 438 (M+H), 440 (M+2+H)

(Example 60) 5-chloro-2-methoxy-N-[(10aS)-7-oxo-7,8,10a,11-tetrahydro-5H,10H-[1,4]oxazino[3,4-c]pyrido[3,2-f][1,4]oxazepin-3-yl]benzenesulfonamide (60a) tert-butyl (3S)-3-({[tert-butyl(dimethyl)silyl]oxy}methyl)-5-oxomorpholine-4-carboxylate The title compound (753 mg, yield: 56% for 3 steps) was obtained by production according to the method described in Examples (53a) and (53b) using 4-tert-butyl 3-methyl (3S)-5-oxomorpholine-3,4-dicarboxylate (1.67 g, 6.81 mmol) as a starting material.

¹H NMR spectrum (CDCl3, 400 MHz) δ: 4.29-4.10 (3H, m), 4.10-4.04 (1H, m), 3.79 (1H, t, J=9.1 Hz), 3.73-3.65 (2H, m), 1.55 (9H, s), 0.89 (9H, s), 0.08 (6H, s)

(60b) (5S)-5-({[tert-butyl(dimethyl)silyl]oxy}methyl)morpholin-3-one

The title compound (371 mg, yield: 70%) was obtained by production according to the method described in Example (53c) using tert-butyl (3S)-3-({[tert-butyl(dimethyl)silyl]oxy}methyl)-5-oxomorpholine-4-carboxylate (750 mg, 2.17 mmol) obtained in Example (60a) as a starting material.

¹H NMR spectrum (CDCl3, 400 MHz) δ: 6.23 (1H, br s), 4.24-4.08 (2H, m), 3.88-3.83 (1H, m), 3.70-3.52 (4H, m), 0.90 (9H, s), 0.08 (6H, s).

(60c) (10aS)-3-bromo-10a,11-dihydro-5H,10H-[1,4]oxazino[3,4-c]pyrido[3,2-f][1,4]oxazepin-7(8H)-one The title compound (117 mg, yield: 50% for 3 steps) was obtained by production according to the method described in Examples (53d) and (53e) using (5S)-5-({[tert-butyl(dimethyl)silyl]oxy}methyl)morpholin-3-one (190 mg, 0.77 mmol) obtained in Example (60b) and (5-bromo-2-chloropyridin-3-yl)methyl methanesulfonate (256 mg, 0.85 mmol) obtained in Example (52b) as starting materials.

¹H NMR spectrum (CDCl₃, 400 MHz) δ: 8.19 (1H, d, J=2.4 Hz), 8.07 (1H, d, J=2.4 Hz), 5.12 (1H, d, J=15.8 Hz), 4.67 (1H, dd, J=14.0, 4.3 Hz), 4.38 (1H, d, J=15.8 Hz), 4.17-3.98 (5H, m), 3.79-3.70 (1H, m).

(60d) 5-chloro-2-methoxy-N-[(10aS)-7-oxo-7,8,10a,11-tetrahydro-5H,10H-[1,4]oxazino[3,4-c]pyrido[3,2-f][1,4]oxazepin-3-yl]benzenesulfonamide The title compound (68.6 mg, yield: 41%) was obtained by production according to the method described in Example (53g) using 5-chloro-2-methoxy-N-[(10aS)-7-oxo-7,8,10a,11-tetrahydro-5H,10H-[1,4]oxazino[3,4-c]pyrido[3,2-f][1,4]oxazepin-3-yl]benzenesulfonamide (115 mg, 0.38 mmol) obtained in Example (60c) and 5-chloro-2-methoxybenzenesulfonamide (119 mg, 0.54 mmol) obtained in Example (53f) as starting materials.

¹H NMR spectrum (DMSO-d₆, 400 MHz) δ: 10.24 (1H, br s), 7.75 (1H, d, J=3.0 Hz), 7.69-7.64 (2H, m), 7.44 (1H, d, J=3.0 Hz), 7.27-7.21 (1H, m), 5.00 (1H, d, J=15.8 Hz), 4.56 (1H, dd, J=13.1, 2.7 Hz), 4.27 (1H, d, J=15.2 Hz), 4.11-3.93 (5H, m), 3.86 (3H, s), 3.71 (1H, dd, J=13.1, 8.8 Hz).

MS spectrum (ES/APCI⁺): 440 (M+H), 442 (M+2+H)

(Example 61) 2-ethoxy-5-fluoro-N-[(10aS)-7-oxo-7, 8,10a,11-tetrahydro-5H,10H-[1,4]oxazino[3,4-c] pyrido[3,2-f][1,4]oxazepin-3-yl]benzenesulfonamide (61a) (10aS)-3-amino-10a,11-dihydro-5H,10H-[1,4] oxazino[3,4-c]pyrido[3,2-f][1,4]oxazepin-7 (8H)-one The title compound (114.5 mg, yield: 69% for 2 steps) was obtained by production according to the method described in Example (52e) using (10aS)-3-bromo-10a,11-dihydro-5H,10H-[1,4]oxazino[3,4-c]pyrido[3,2-f][1,4]oxazepin-7(8H)-one (210 mg, 0.70 mmol) obtained in Example (60c) as a starting material.

¹H NMR spectrum (CDCl₃, 400 MHz) δ: 7.63 (1H, d, J=3.0 Hz), 7.07 (1H, d, J=3.0 Hz), 5.23 (1H, d, J=14.6 Hz), 4.42 (1H, dd, J=12.1, 2.4 Hz), 4.21-4.08 (2H, m), 4.06-3.92 (4H, m), 3.86 (1H, dd, J=11.5, 3.6 Hz), 3.58 (2H, br s).

(61b) 5-fluoro-2-ethoxybenzenesulfonyl chloride

To chlorosulfonic acid (30.0 mL, 451 mmol), 1-ethoxy-4-fluorobenzene (10.33 mL, 73.7 mmol) was added at −12° C. over 10 minutes, the mixture was stirred at the same temperature as above for 30 minutes, and subsequently stirred in an ice water bath for 1 hour. The reaction mixture was carefully poured into ice water (approximately 300 mL), followed by extraction with ethyl acetate. The organic layer was washed with a saturated aqueous solution of sodium chloride and dried over anhydrous magnesium sulfate. After filtration, the solvent was distilled off under reduced pressure, and the residue was purified by silica gel column chromatography (n-hexane/ethyl acetate=4/1). To the obtained solid, n-hexane was added, and the suspension was cooled in ice water bath. The precipitated solid was collected by filtration, washed with n-hexane, and then dried to obtain the title compound (7.69 g, yield: 44%).

¹H NMR spectrum (CDCl₃, 400 MHz) δ: 7.70 (1H, dd, J=7.4, 3.1 Hz), 7.41-7.36 (1H, m), 7.07 (1H, dd, J=9.4, 3.9 Hz), 4.26 (2H, q, J=6.8 Hz), 1.55 (3H, t, J=6.8 Hz).

(61c) 2-ethoxy-5-fluoro-N-[(10aS)-7-oxo-7,8,10a, 11-tetrahydro-5H,10H-[1,4]oxazino[3,4-c]pyrido[3, 2-f][1,4]oxazepin-3-yl]benzenesulfonamide The title compound (50.9 mg, yield: 66%) was obtained by production according to the method described in Example (27d) using (10aS)-3-amino-10a,11-dihydro-5H, 10H-[1,4]oxazino[3,4-c]pyrido[3,2-f][1,4]oxazepin-7(8H)-one (41.5 mg, 0.18 mmol) obtained in Example (61a) and 5-fluoro-2-ethoxybenzenesulfonyl chloride (48.3 mg, 0.19 mmol) obtained in Example (61b) as starting materials.

¹H NMR spectrum (DMSO-d₆, 400 MHz) δ: 10.11 (1H, br s), 7.77 (1H, d, J=2.4 Hz), 7.54 (1H, dd, J=7.9, 3.0 Hz), 7.50-7.41 (2H, m), 7.23 (1H, dd, J=9.1, 4.3 Hz), 4.99 (1H, d, J=15.8 Hz), 4.54 (1H, dd, J=13.4, 3.0 Hz), 4.25 (1H, d, J=15.8 Hz), 4.14 (2H, q, J=6.9 Hz), 4.10-3.98 (4H, m), 3.97-3.93 (1H, m), 3.72 (1H, dd, J=12.8, 8.5 Hz), 1.22 (3H, t, J=7.0 Hz).

MS spectrum (ES/APCI⁺): 438 (M+H).

(Example 62) Potassium [(2-ethoxy-5-fluorophenyl) sulfonyl][(10aS)-7-oxo-7,8,10a,11-tetrahydro-5H, 10H-[1,4]oxazino[3,4-c]pyrido[3,2-f][1,4]oxazepin-3-yl]azanide (Potassium Salt of Example 61)

The title compound (32.1 mg, yield: 99%) was obtained by production according to the method described in Example 33 using 2-ethoxy-5-fluoro-N-[(10aS)-7-oxo-7,8, 10a,11-tetrahydro-5H,10H-[1,4]oxazino[3,4-c]pyrido[3,2-f] [1,4]oxazepin-3-yl]benzenesulfonamide (29.8 mg, 0.068 mmol) obtained in Example (61c) as a starting material.

¹H NMR spectrum (DMSO-d6, 400 MHz) δ: 7.45-7.40 (2H, m), 7.19 (1H, d, J=3.0 Hz), 7.08 (1H, td, J=8.5, 3.2 Hz), 6.94 (1H, dd, J=9.1, 4.3 Hz), 4.90 (1H, d, J=14.6 Hz), 4.33 (1H, dd, J=12.5, 2.1 Hz), 4.08-3.86 (7H, m), 3.78-3.71 (2H, m), 1.09 (3H, t, J=7.0 Hz).

Example 63

The title compound (38.0 mg, yield: 52%) was obtained by production according to the method described in Example (27d) using (10aS)-3-amino-10a,11-dihydro-5H, 10H-[1,4]oxazino[3,4-c]pyrido[3,2-f][1,4]oxazepin-7(8H)-one (35.1 mg, 0.15 mmol) obtained in Example (61a) and 5-chloro-2-(trifluoromethoxy)benzenesulfonyl chloride (49.5 mg, 0.16 mmol) obtained in Example (32a) as starting materials.

¹H NMR spectrum (DMSO-d₆, 400 MHz) δ: 10.72 (1H, br s), 7.91 (1H, d, J=2.4 Hz), 7.87 (1H, dd, J=8.5, 2.4 Hz), 7.77 (1H, d, J=2.4 Hz), 7.61 (1H, dd, J=8.8, 1.5 Hz), 7.46 (1H, d, J=3.0 Hz), 5.03 (1H, d, J=15.2 Hz), 4.56 (1H, dd, J=13.4, 2.4 Hz), 4.25 (1H, d, J=15.2 Hz), 4.12-3.92 (5H, m), 3.73 (1H, dd, J=12.8, 8.5 Hz).

MS spectrum (ES/APCI⁺): 494 (M+H), 496 (M+2+H)

(Example 64) 5-chloro-2-methoxy-N-[(10aS)-9-methyl-7-oxo-7,8,9,10,10a, 11-hexahydro-5H-pyrazino[2,1-c]pyrido[3,2-f][1,4]oxazepin-3-yl]benzenesulfonamide (64a) (6S)-4-benzyl-6-(hydroxymethyl)piperazin-2-one To a mixture of tert-butyl (4R)-4-formyl-2,2-dimethyl-1, 3-oxazolidine-3-carboxylate (4.00 g, 17.4 mmol), ethyl N-benzylglycinate (6.42 mL, 34.9 mmol) and acetic acid (2.00 mL, 34.9 mmol) in methanol (60 mL), sodium cyanoborohydride (1.64 g, 26.2 mmol) was added in portion-wise manner over 10 minutes under ice cooling, the mixture was stirred at the same temperature as above for 30 minutes, and then stirred at room temperature for 18 hours. Potassium carbonate was added thereto until gas generation stopped, and the mixture was stirred at room temperature for a while. The mixture was concentrated under reduced pressure, diluted by addition of water (50 mL), a saturated aqueous solution of sodium bicarbonate (50 mL) and a saturated aqueous solution of sodium chloride (50 mL), and followed by extraction with methylene chloride three times. The organic layers were combined, and dried over anhydride sodium sulfate. After filtration, the solvent was distilled off under reduced pressure, and the residue was purified in an automatic chromatography apparatus (n-hexane/ethyl acetate=90/10-70/30) to obtain tert-butyl (4S)-4-{[benzyl(2-ethoxy-2-oxoethyl)amino]methyl}-2,2-dimethyl-1,3-oxazolidine-3-carboxylate (4.56 g, yield: 64%).

To a solution of tert-butyl (4S)-4-{[benzyl(2-ethoxy-2-oxoethyl)amino]methyl}-2,2-dimethyl-1,3-oxazolidine-3-carboxylate (4.40 g, 10.8 mmol) obtained in the above step in methanol (50 mL), a 5.0 mol/L hydrochloric acid (5 mL, 25 mmol) was added at room temperature, and the mixture was stirred at 100° C. for 26.5 hours in an oil bath. After cooling, the mixture was concentrated under reduced pressure up to approximately ⅓ volume, and diluted by addition of a saturated aqueous solution of sodium bicarbonate until it became weak basic, followed by extraction with methylene chloride four times. The organic layers were combined, and dried over anhydrous sodium sulfate. The solvent was distilled off under reduced pressure, and the residue was purified in an automatic chromatography apparatus (methylene chloride/methanol=100/0-90/10) to obtain the title compound (1.47 g, yield: 62%).

$^1$H NMR spectrum (CDCl3, 400 MHz) δ: 7.37-7.28 (5H, m), 6.70 (1H, br s), 3.65-3.61 (2H, m), 3.55-3.51 (2H, m), 3.41 (1H, br s), 3.21 (1H, d, J=16.4 Hz), 3.09 (1H, d, J=16.4 Hz), 2.72 (1H, dd, J=12.1, 4.3 Hz), 2.61 (1H, dd, J=12.1, 5.1 Hz).

(64b) tert-butyl (3S)-3-({[tert-butyl(dimethyl)silyl]oxy}methyl)-5-oxopiperazine-1-carboxylate A mixture of (6S)-4-benzyl-6-(hydroxymethyl)piperazin-2-one (1.42 g, 6.45 mmol) obtained in Example (64a), di-tert-butyl dicarbonate (1.69 g, 7.74 mmol) and 20% palladium hydroxide on carbon (water content: 50%, 500 mg) in methanol (30 mL) was stirred at room temperature for 20 hours at normal pressure under the hydrogen atmosphere. Hydrogen in the reaction container was replaced with nitrogen, and then, the reaction mixture was filtered through pad of Celite 545®. The solvent in the filtrate was distilled off under reduced pressure, the residue was purified in an automatic chromatography apparatus (methylene chloride/methanol=100/0-95/5) to obtain tert-butyl (3S)-3-(hydroxymethyl)-5-oxopiperazine-1-carboxylate (1.31 g, yield: 88%).

To a solution of tert-butyl (3S)-3-(hydroxymethyl)-5-oxopiperazine-1-carboxylate (1.30 g, 5.65 mmol) obtained in the above step in N,N-dimethylformamide (15 mL), imidazole (0.846 g, 12.4 mmol) and tert-butyldimethylchlorosilane (0.936 g, 6.21 mmol) was added at room temperature, and the mixture was stirred at the same temperature as above for 23 hours. The mixture was concentrated under reduced pressure, diluted by addition of a saturated aqueous solution of ammonium chloride followed by extraction with ethyl acetate three times. The organic layers were combined, washed with water, and dried over anhydrous sodium sulfate. After filtration, the solvent was distilled off under reduced pressure and the residue was purified in an automatic chromatography apparatus (methylene chloride/methanol=100/0-97/3) to obtain the title compound (1.91 g, yield: 98%).

$^1$H NMR spectrum (CDCl3, 400 MHz) δ: 6.26 (1H, br s), 4.23-3.55 (5H, m), 3.45 (1H, t, J=8.8 Hz), 3.23-3.10 (1H, m), 1.47 (9H, s), 0.90 (9H, s), 0.07 (6H, s).

(64c) tert-butyl (10aS)-3-bromo-7-oxo-7,8,10a,11-tetrahydro-5H-pyrazino[2,1-c]pyrido[3,2-f][1,4]oxazepine-9(10H)-carboxylate The title compound (396 mg, yield: 19% for 2 steps) was obtained by production according to the method described in Examples (52c) and (52d) using tert-butyl (3S)-3-({[tert-butyl(dimethyl)silyl]oxy}methyl)-5-oxopiperazine-1-carboxylate (1.20 g, 3.49 mmol) obtained in Example (64b) and (5-bromo-2-chloropyridin-3-yl)methyl methanesulfonate (1.00 g, 3.33 mmol) obtained in Example (52b) as starting materials.

$^1$H NMR spectrum (CDCl$_3$, 400 MHz) δ: 8.22 (1H, d, J=2.3 Hz), 7.81 (1H, d, J=2.3 Hz), 5.29 (1H, d, J=15.3 Hz), 4.62-4.56 (1H, m), 4.17-4.01 (5H, m), 3.90-3.70 (2H, m), 1.45 (9H, s).

(64d) (10aS)-3-bromo-9-methyl-9,10,10a,11-tetrahydro-5H-pyrazino[2,1-c]pyrido[3,2-f][1,4]oxazepin-7(8H)-one To a solution of tert-butyl (10aS)-3-bromo-7-oxo-7,8,10a,11-tetrahydro-5H-pyrazino[2,1-c]pyrido[3,2-f][1,4]oxazepine-9(10H)-carboxylate (335 mg, 0.84 mmol) obtained in Example (64c) in methanol (2 mL), a 4.0 mol/L solution of hydrochloric acid in 1,4-dioxane (4 mL, 16 mmol) was added at room temperature, and the mixture was stirred at the same temperature as above for 3 hours. The mixture was poured into a saturated aqueous solution of sodium bicarbonate under ice cooling, followed by extraction with a mixed solvent of methylene chloride/methanol=5/1 six times. The organic layers were combined, and dried over anhydride sodium sulfate. After filtration, the solvent was distilled off under reduced pressure to obtain (10aS)-3-bromo-9,10,10a,11-tetrahydro-5H-pyrazino[2,1-c]pyrido[3,2-f][1,4]oxazepin-7(8H)-one (201 mg, 80%).

To a solution of (10aS)-3-bromo-9,10,10a,11-tetrahydro-5H-pyrazino[2,1-c]pyrido[3,2-f][1,4]oxazepin-7(8H)-one (158 mg, 0.53 mmol) obtained in the above step in a mixed solvent of 1,2-dichloroethane (10 mL) and methanol (1 mL), a 37% aqueous solution of formaldehyde (0.047 mL, 2.65 mmol) and acetic acid (0.036 mL, 0.63 mmol) was added under ice cooling followed by addition of sodium triacetoxyborohydride (449 mg, 2.12 mmol), and the mixture was stirred at the same temperature as above for 5 hours. The mixture was diluted by addition of a saturated aqueous solution of sodium bicarbonate followed by extraction with methylene chloride three times. The organic layers were combined, and dried over anhydride sodium sulfate. After filtration, the solvent was distilled off under reduced pressure to obtain the title compound (159 mg, 96%).

$^1$H NMR spectrum (CDCl3, 400 MHz) δ: 8.21 (1H, d, J=2.3 Hz), 7.82 (1H, d, J=2.3 Hz), 5.28 (2H, d, J=15.3 Hz), 4.49 (1H, dd, J=12.9, 2.7 Hz), 4.10 (1H, dd, J=12.9, 6.7 Hz), 4.02-3.97 (2H, m), 3.08 (2H, s), 2.79 (1H, dd, J=12.1, 4.7 Hz), 2.66 (1H, dd, J=12.1, 5.9 Hz), 2.29 (3H, s).

(64e) 5-chloro-2-methoxy-N-[(10aS)-9-methyl-7-oxo-7,8,9,10,10a, 11-hexahydro-5H-pyrazino[2,1-c]pyrido[3,2-f][1,4]oxazepin-3-yl]benzenesulfonamide The title compound (36 mg, yield: 28%) was obtained by production according to the method described in Example (53g) using (10aS)-3-bromo-9-methyl-9,10,10a,11-tetrahydro-5H-pyrazino[2,1-c]pyrido[3,2-f][1,4]oxazepin-7(8H)-one (90 mg, 0.29 mmol) obtained in Example (64d) and 5-chloro-2-methoxybenzenesulfonamide (77 mg, 0.35 mmol) obtained in Example (53f) as starting materials.

$^1$H NMR spectrum (CD$_3$OD, 400 MHz) δ: 7.81 (1H, d, J=2.7 Hz), 7.70 (1H, d, J=2.7 Hz), 7.55-7.53 (2H, m), 7.15 (1H, d, J=9.0 Hz), 5.12 (1H, d, J=15.3 Hz), 4.58-4.54 (1H, m), 4.22 (1H, d, J=15.3 Hz), 4.03-4.01 (2H, m), 3.93 (3H, s), 3.14 (1H, d, J=16.8 Hz), 2.97 (1H, d, J=16.8 Hz), 2.91-2.88 (1H, m), 2.65-2.62 (1H, m), 2.30 (3H, s).

MS spectrum (ES/APCI+): 453 (M+H), 455 (M+2+H).

(Example 65) Potassium [(5-chloro-2-methoxyphenyl)sulfonyl][(10aS)-9-methyl-7-oxo-7,8,9,10,10a,11-hexahydro-5H-pyrazino[2,1-c]pyrido[3,2-f][1,4]oxazepin-3-yl]azanide (Potassium Salt of Example 64)

The title compound (12.5 mg, yield: 77%) was obtained by production according to the method described in Example 33 using 5-chloro-2-methoxy-N-[(10aS)-9-methyl-7-oxo-7,8,9,10,10a,11-hexahydro-5H-pyrazino[2,1-c]pyrido[3,2-f][1,4]oxazepin-3-yl]benzenesulfonamide (15 mg, 0.033 mmol) obtained in Example (64e) as a starting material.

$^1$H NMR spectrum (DMSO-d6, 400 MHz) δ: 7.64 (1H, d, J=2.7 Hz), 7.39 (1H, d, J=2.7 Hz), 7.32 (1H, dd, J=9.0, 2.7 Hz), 7.15 (1H, d, J=2.7 Hz), 6.97 (1H, d, J=9.0 Hz), 4.88 (1H, d, J=14.9 Hz), 4.38-4.31 (2H, m), 3.96 (1H, d, J=14.9 Hz), 3.86 (1H, s), 3.74 (1H, dd, J=12.3, 6.8 Hz), 3.65 (3H, s), 2.88-2.85 (2H, m), 2.72-2.69 (1H, m), 2.16 (3H, s)

TEST EXAMPLES (Test Example 1) Inhibitory Test of TNAP Activity

COS1 cells (DS Pharma Biomedical Co., Ltd.) were transfected with human TNAP (OriGene Technologies, Inc.) using Lipofectamine LTX & Plus reagent (Invitrogen Corp.). On the next day, the medium was replaced with a fresh medium, and the cells were cultured in an incubator for 3 days. After 3 days, the culture supernatant was collected and concentrated by centrifugation at 5000 G for 30 minutes using Amicon 14, $10^4$ cut (Merck Millipore). The concentrated culture supernatant was dialyzed against 5 L of 50 mM Tris/200 mM NaCl/1 mM MgCl$_2$/20 µM ZnCl$_2$ twice and used as an enzyme source (enzyme solution). The substrate pNPP (ProteoChem Inc.) was adjusted to 3.1 mM with Milli-Q water, and a solution of each test compound dissolved in dimethyl sulfoxide (DMSO; Wako Pure Chemical Industries, Ltd.) by 6 serial dilutions at a 5-fold common ratio from 100 µM, or DMSO was added thereto at a final concentration of 1% by volume. The enzyme solution adjusted to 2 µg/mL with an assay buffer (200 mM Tris/2 mM MgCl$_2$/0.04 mM ZnCl$_2$/0.01% Tween 20) was added in the same amount of the substrate solution and incubated at room temperature for 60 minutes. Then, the absorbance (ABS: 405 nm) was measured using a microplate reader (model plus 384, Molecular Devices, LLC), and the concentration of produced p-nitrophenol was calculated. The inhibition of human TNAP activity by the test compound was evaluated on the basis of the concentration IC$_{50}$ at which each test compound suppressed 50% of p-nitrophenol production.

The results are shown in Table 1.

TABLE 1

| Example compound No. | IC$_{50}$ (nM) |
| --- | --- |
| 1 | 2.6 |
| 3 | 2.4 |
| 5 | 2.8 |
| 6 | 5.9 |
| 7 | 6.5 |
| 9 | 3.4 |

TABLE 1-continued

| Example compound No. | IC$_{50}$ (nM) |
| --- | --- |
| 11 | 12.6 |
| 12 | 8.5 |
| 13 | 5.1 |
| 14 | 3.6 |
| 16 | 3.5 |
| 17 | 6.9 |
| 18 | 2.8 |
| 20 | 4.2 |
| 21 | 3.0 |
| 23 | 5.7 |
| 24 | 2.3 |
| 26 | 29.4 |
| 27 | 13.2 |
| 28 | 1.2 |
| 29 | 7.1 |
| 30 | 0.9 |
| 31 | 1.2 |
| 32 | 0.9 |
| 34 | 1.6 |
| 35 | 0.9 |
| 36 | 1.5 |
| 37 | 1.4 |
| 39 | 2.4 |
| 40 | 5.8 |
| 41 | 0.4 |
| 42 | 0.4 |
| 44 | 0.8 |
| 45 | 2.0 |
| 46 | 0.5 |
| 47 | 1.5 |
| 48 | 0.6 |
| 50 | 0.5 |
| 52 | 2.2 |
| 53 | 4.3 |
| 54 | 1.1 |
| 56 | 1.4 |
| 58 | 3.8 |
| 59 | 1.4 |
| 60 | 3.3 |
| 61 | 0.6 |
| 63 | 1.4 |
| 64 | 1.8 |

The compound of the present invention exhibits the excellent inhibition of human TNAP activity and is useful as a pharmaceutical agent for the treatment or prophylaxis of ectopic calcification.

(Test Example 2) Specific Inhibitory Test of TNAP Activity

COS1 cells (DS Pharma Biomedical Co., Ltd.) were transfected with human IAP (small-intestinal alkaline phosphatase, purchased from OriGene Technologies, Inc.) or human PLAP (placental alkaline phosphatase, purchased from OriGene Technologies, Inc.) using Lipofectamine LTX & Plus reagent (Invitrogen Corp.). On the next day, the medium was replaced with a fresh medium, and the cells were cultured in an incubator for 3 days. After 3 days, the culture supernatant was collected and concentrated by centrifugation at 5000 G for 30 minutes using Amicon 14, $10^4$ cut (Merck Millipore). The concentrated culture supernatant was dialyzed against 5 L of 50 mM Tris/200 mM NaCl/1 mM MgCl$_2$/20 µM ZnCl$_2$ twice and used as an enzyme source (enzyme solution). The substrate pNPP (ProteoChem Inc.) was adjusted to 3.1 mM with Milli-Q water, and a solution of each test compound dissolved in dimethyl sulfoxide (DMSO; Wako Pure Chemical Industries, Ltd.) by 6 serial dilutions at a 5-fold common ratio from 100 µM, or DMSO was added thereto at a final concentration of 1% by volume. The enzyme solution of human IAP or human PLAP adjusted to 2 μg/mL with an assay buffer (200 mM Tris/2 mM $MgCl_2$/0.04 mM $ZnCl_2$/0.01% Tween 20) was added in the same amount of the substrate solution and incubated at room temperature for 60 minutes. Then, the absorbance (ABS: 405 nm) was measured using a microplate reader (model plus 384, Molecular Devices, LLC), and the concentration of produced p-nitrophenol was calculated. The inhibition of human IAP or PLAP activity by the test compound was evaluated on the basis of the concentration $IC_{50}$ at which each test compound suppressed 50% of p-nitrophenol production.

The compound of the present invention exhibits the excellent specific inhibition of TNAP activity and is useful as a pharmaceutical drug for the treatment or prevention of ectopic calcification.

(Test Example 3) Inhibitory Test of Plasma TNAP Activity in B6 Mouse (Charles River Laboratories Japan, Inc.)

After blood sampling from the tail vein using a heparin-treated hematocrit capillary tube (EM Meister Hematocrit Capillary Tube, AS ONE Corp.) (as the sample before compound administration), each test compound suspended in a 0.5% methylcellulose solution (powder purchased from Wako Pure Chemical Industries, Ltd. was adjusted to 0.5% with Otsuka distilled water) was administered orally to the mouse. 1, 2, 4, 6, and 24 hours after the administration, blood was collected from the tail vein using a heparin-treated hematocrit capillary tube to obtain a plasma sample. The plasma sample was added to an assay buffer (1 M Tris, 1 M $MgCl_2$, 20 mM $ZnCl_2$, and water, pH 7.5), and the mixture was left standing for 5 minutes. Then, the absorbance at 405 nm was measured and used as a blank. The substrate pNPP was added to the plasma sample and incubated at room temperature for 180 minutes. Then, the absorbance (ABS: 405 nm) was measured using a microplate reader (model plus 384, Molecular Devices, LLC), and the concentration of produced p-nitrophenol was calculated. The blank was subtracted from all measurement values to calculate TNAP activity at each time point with the TNAP activity of the sample before compound administration defined as 100%. The pharmaceutical effect of the test compound was evaluated by the average inhibition of plasma ALP (80-90% containing TNAP) activity for 6 hours from 0 hour to 6 hour after the administration of the test compound. It was calculated according to the following expression:

100−((plasma ALP activity at 0 hr+plasma ALP activity at 1 hr)*½+(plasma ALP activity at 1 hr+plasma ALP activity at 2 hr)*½+(plasma ALP activity at 2 hr+plasma ALP activity at 4 hr)*2/2+(plasma ALP activity at 4 hr+plasma ALP activity at 6 hr)*2/2)/6 The results are shown in Table 2.

TABLE 2

| Example compound No. | Dose (mg/kg) | Plasma ALP inhibition (6 h ave. inhibition %) |
| --- | --- | --- |
| 2 | 1 | 34.4 |
| 4 | 1 | 40.7 |
| 8 | 3 | 29.4 |
| 10 | 3 | 43.3 |
| 15 | 3 | 61.4 |
| 19 | 3 | 27.5 |

TABLE 2-continued

| Example compound No. | Dose (mg/kg) | Plasma ALP inhibition (6 h ave. inhibition %) |
| --- | --- | --- |
| 22 | 3 | 28.4 |
| 25 | 3 | 55.5 |
| 33 | 0.3 | 59.0 |
| 38 | 0.3 | 65.5 |
| 43 | 0.3 | 65.5 |
| 49 | 1 | 52.8 |
| 51 | 1 | 59.7 |
| 55 | 1 | 65.7 |
| 62 | 1 | 76.0 |

The compound of the present invention exhibits an excellent in vivo TNAP inhibitory effect and is useful as a pharmaceutical agent for the treatment or prophylaxis of ectopic calcification.

(Test Example 4) In Vivo Anti-Calcification Test in Vitamin D-Induced Calcification Model A DBA/2 mouse (male, 6 weeks old when used, Charles River Laboratories Japan, Inc.) is given powder feed (FR-2 powder feed, Funabashi Farm Co., Ltd.) containing each test compound. 3.75 mg/kg cholecalciferol (Sigma-Aldrich Corp.) is intraperitoneally administered for 3 days from the next day. Seven days after the final cholecalciferol administration, the animal is sacrificed, and the thoracic aorta and the kidney are sampled. The tissue samples are freeze-dried (FREEZE DRYER, FRD-50M, Iwaki Asahi Techno Glass Corp.). Then, 10% formic acid (undiluted solution purchased from Kishida Chemical Co., Ltd. is adjusted to 10% with Milli-Q water) is added to each tissue sample, which is then homogenized using QIAGEN Retsch MM300 TissueLyser (Qiagen N. V.). The homogenate is centrifuged, and the supernatant is used as a sample. The calcium concentration in the sample is measured as absorbance (ABS 612 nm, Microplate reader, model plus 384, Molecular Devices, LLC) using Calcium assay kit (Wako Pure Chemical Industries, Ltd.) to calculate the amount of calcium in the tissue.

The compound of the present invention exhibits an excellent anti-calcification effect and is useful as a therapeutic agent for the treatment or prevention of ectopic calcification.

(Test Example 5) In Vivo Anti-Calcification Test in Nephrectomized Mouse

A 5/6 nephrectomized DBA/2 mouse (male, 8 weeks old) is purchased from CLEA Japan, Inc. This mouse is loaded with 1.2% high-phosphorus diet (Oriental Yeast Co., Ltd.). Each test compound suspended in a 0.5% methylcellulose solution (powder purchased from Wako Pure Chemical Industries, Ltd. is adjusted to 0.5% with Otsuka distilled water) is administered orally twice daily for three months. After three months, the animal is sacrificed, and the kidney is sampled. The tissue sample is freeze-dried (FREEZE DRYER, FRD-50M, Iwaki Asahi Techno Glass Corp.). Then, 10% formic acid (undiluted solution purchased from Kishida Chemical Co., Ltd. is adjusted to 10% with Milli-Q water) is added to the tissue sample, which is then homogenized using QIAGEN Retsch MM300 TissueLyser (Qiagen N. V.). The homogenate is centrifuged, and the supernatant is used as a sample. The calcium concentration in the sample is measured as absorbance (ABS 612 nm, Microplate reader, model plus 384, Molecular Devices, LLC) using Calcium assay kit (Wako Pure Chemical Industries, Ltd.) to calculate the amount of calcium in the tissue.

The compound of the present invention exhibits an excellent anti-calcification effect and is useful as a pharmaceutical drug for the treatment or prophylaxis of ectopic calcification.

(Test Example 6) Pharmacokinetic Test

The pharmacokinetic test can be conducted according to a method well-known in the field of pharmacodynamics.

Each test compound was suspended in a 0.5% aqueous methylcellulose solution. The obtained suspension was orally administered at a dose in an appropriate range (e.g., 0.01 mg/kg to 10 mg/kg) to an animal (e.g., a mouse, a rat, a dog, or a cynomolgus monkey) generally used in the pharmacokinetic test. Also, the test compound was dissolved in saline. The obtained solution was intravenously (e.g., through the tail vein, the cephalic vein, or the saphenous vein) administered at a dose in an appropriate range (e.g., 0.1 mg/kg to 10 mg/kg) to an animal (e.g., a mouse, a rat, a dog, or a cynomolgus monkey) generally used in the pharmacokinetic test. After given times (e.g., 0.08, 0.25, 0.5, 1, 2, 4, 6, 8, and 24 hours) from the administration, blood was collected from an appropriate blood collection site (e.g., the jugular vein, the cephalic vein, or the saphenous vein). The obtained blood was centrifuged to prepare a plasma sample. The concentration of the test compound contained in the plasma sample was measured by quantitative analysis using a liquid chromatography-mass spectrometer (LC-MS/MS).

The pharmacokinetics of the test compound were evaluated on the basis of maximum plasma concentration (Cmax), area under the plasma drug concentration-time curve (AUC), total clearance (CL), and bioavailability and analyzed using software (Phoenix, etc.). Cmax represents the maximum plasma concentration of the orally administered test compound. AUC was calculated according to the trapezium rule from the plasma concentrations of the test compound from the time when the test compound was administered up to the final time when the test compound was quantifiable. The bioavailability was calculated according to the following expression:

[(AUC after oral administration/Dose of the oral administration)/(AUC after intravenous administration/Dose of the intravenous administration)].

The compound of the present invention exhibits excellent pharmacokinetics (Cmax, AUC, CL, or bioavailability) and is useful as a pharmaceutical (particularly, a pharmaceutical for the treatment or prevention of ectopic calcification).

PREPARATION EXAMPLES

| (Preparation Example 1) Capsule | |
|---|---|
| Compound of Example 1 | 50 mg |
| Lactose | 128 mg |
| Corn starch | 70 mg |
| Magnesium stearate | 2 mg |
| | 250 mg |

A powder having the formulation mentioned above is mixed and sifted through a 60-mesh sieve. Then, this powder is put in a gelatin capsule shell to prepare a capsule.

| (Preparation Example 2) Tablet | |
|---|---|
| Compound of Example 1 | 50 mg |
| Lactose | 126 mg |
| Corn starch | 23 mg |
| Magnesium stearate | 1 mg |
| | 200 mg |

A powder having the formulation mentioned above is mixed, granulated using corn starch paste, and dried, followed by compression in a tableting machine to prepare tablets (200 mg each). This tablet can be coated, if necessary.

The novel pyridine compound represented by the general formula (I) of the present invention or the pharmacologically acceptable salt thereof has an excellent TNAP inhibitory effect and is useful as a pharmaceutical.

What is claimed is:
1. A compound represented by formula (I):

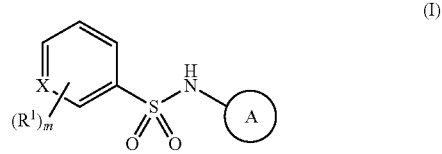

wherein

X represents —CH=, —C(—$R^1$)=, or —N=, each substituent $R^1$ may be the same or different and each represents a C1-6 alkyl group wherein the alkyl group is optionally substituted by one to three groups, which may be the same or different, selected from substituent group $A^B$, a C1-6 alkoxy group wherein the alkoxy group is optionally substituted by one to three groups, which may be the same or different, selected from substituent group $A^B$, a halogeno group, a C6-10 aryl group wherein the aryl group is optionally substituted by one or two groups, which may be the same or different, selected from substituent group $A^C$, a 3- to 10-membered heterocyclyl group containing one to four heteroatoms, which may be the same or different, selected from nitrogen, oxygen, and sulfur wherein the heterocyclyl group is optionally substituted by one or two groups, which may be the same or different, selected from substituent group $A^C$, a hydroxy group, an amino group wherein the amino group is optionally substituted by one or two groups, which may be the same or different C1-6 alkyl groups each optionally substituted by one to three groups, which may be the same or different, selected from substituent group $A^D$, a carboxyl group, a C1-6 alkoxycarbonyl group wherein the alkoxycarbonyl group is optionally substituted by one to three groups, which may be the same or different, selected from substituent group $A^D$, an aminocarbonyl group wherein the aminocarbonyl group is optionally substituted by one or two groups, which may be the same or different C1-6 alkyl groups each optionally substituted by one to three groups, which may be the same or different, selected from substituent group $A^D$, or a cyano group, m represents an integer selected from 1 to 4, A represents one of formula (IIa) to (IIh)

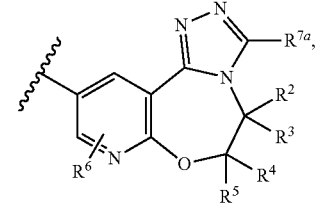 (IIa)

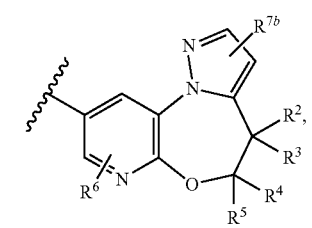 (IIb)

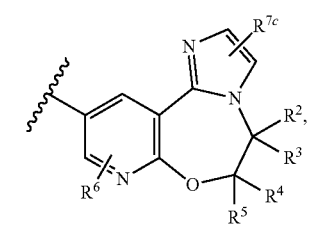 (IIc)

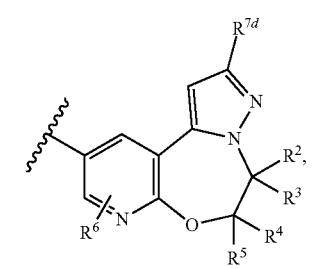 (IId)

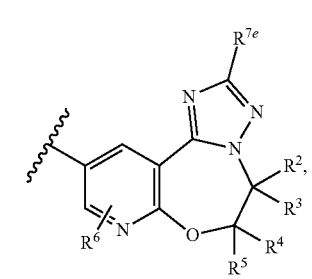 (IIe)

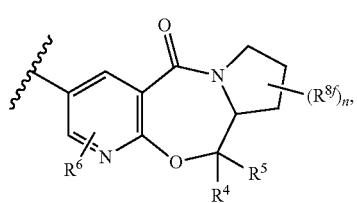 (IIf)

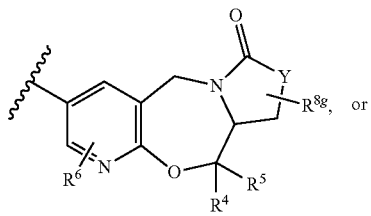 (IIg)

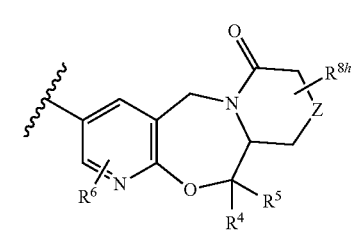 (IIh)

Y represents —CH$_2$—, —CH(—R$^{8g}$)—, —O—, or —N(—R$^{8g}$)—,

Z represents —CH$_2$—, —CH(—R$^{8h}$)—, —O—, or —N(—R$^{8h}$)—,

R$^2$ and R$^3$ are the same or different and each represent
a hydrogen atom;
a C1-6 alkyl group wherein the alkyl group is optionally substituted by one to three groups, which may be the same or different, selected from the following substituents:
a hydroxy group,
a C1-6 alkoxy group optionally substituted by one group selected from substituent group $A^E$,
a C3-8 cycloalkyl group optionally substituted by one group selected from substituent group $A^F$,
a C6-10 aryl group optionally substituted by one or two groups selected from substituent group $A^F$,
a 3- to 10-membered heterocyclyl group containing one to four heteroatoms, which may be the same or different, selected from nitrogen, oxygen, and sulfur and optionally substituted by one or two groups selected from substituent group $A^F$,
a carboxyl group,
a C1-6 alkylcarbonyl group,
a C1-6 alkoxycarbonyl group,
an amino group optionally substituted by one or two groups, which may be the same or different C1-6 alkyl groups,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur,
an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group;
a C6-10 aryl group wherein the aryl group is optionally substituted by one or two groups, which may be the same or different, selected from the following substituents:

a hydroxy group,
a C1-6 alkoxy group optionally substituted by one to three groups, which may be the same or different halogeno groups,
a C1-6 alkyl group optionally substituted by one group selected from substituent group $A^G$,
a C3-8 cycloalkyl group optionally substituted by one group selected from substituent group $A^G$,
a C6-10 aryl group optionally substituted by one group selected from substituent group $A^G$,
a 3- to 10-membered heterocyclyl group containing one to four heteroatoms, which may be the same or different, selected from nitrogen, oxygen, and sulfur and optionally substituted by one group selected from substituent group $A^G$,
an amino group optionally substituted by one or two groups, which may be the same or different C1-6 alkyl groups,
a carboxyl group,
a C1-6 alkylcarbonyl group,
a C1-6 alkoxycarbonyl group,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur,
an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group;
a 3- to 10-membered heterocyclyl group containing one to four heteroatoms, which may be the same or different, selected from nitrogen, oxygen, and sulfur wherein the heterocyclyl group is optionally substituted by one or two groups, which may be the same or different, selected from the following substituents:
a hydroxy group,
a C1-6 alkoxy group optionally substituted by one to three groups, which may be the same or different halogeno groups,
a C1-6 alkyl group optionally substituted by one group selected from substituent group $A^G$,
a C3-8 cycloalkyl group optionally substituted by one group selected from substituent group $A^G$,
a C6-10 aryl group optionally substituted by one group selected from substituent group $A^G$,
a 3- to 10-membered heterocyclyl group containing one to four heteroatoms, which may be the same or different, selected from nitrogen, oxygen, and sulfur, and optionally substituted by one group selected from substituent group $A^G$,
an amino group optionally substituted by one or two groups, which may be the same or different C1-6 alkyl groups,
a carboxyl group,
a C1-6 alkylcarbonyl group,
a C1-6 alkoxycarbonyl group,
an aminocarbonyl group optionally substituted by one or two groups, which may be the same or different C1-6 alkyl groups,
a 4- to 7-membered saturated heterocyclylcarbonyl group containing one or two heteroatoms, which may be the same or different, selected from nitrogen, oxygen, and sulfur, an aminocarbonyloxy group optionally substituted by one or two groups, which may be the same or different C1-6 alkyl groups,
a 4- to 7-membered saturated heterocyclylcarbonyloxy group containing one or two heteroatoms, which may be the same or different, selected from nitrogen, oxygen, and sulfur,
a halogeno group, and
a cyano group;
a C1-6 alkylcarbonyl group wherein the alkylcarbonyl group is optionally substituted by one to three groups, which may be the same or different, selected from substituent group $A^H$;
a C6-10 arylcarbonyl group wherein the arylcarbonyl group is optionally substituted by one or two groups, which may be the same or different, selected from substituent group $A^H$ and a C1-6 halogenoalkyl group;
a 3- to 10-membered heterocyclylcarbonyl group containing one to four heteroatoms, which may be the same or different, selected from nitrogen, oxygen, and sulfur wherein the heterocyclylcarbonyl group is optionally substituted by one or two groups, which may be the same or different, selected from substituent group $A^H$ and
a C1-6 halogenoalkyl group;
a carboxyl group;
a C1-6 alkoxycarbonyl group wherein the alkoxycarbonyl group is optionally substituted by one to three groups, which may be the same or different, selected from substituent group $A^J$;
an aminocarbonyl group wherein the aminocarbonyl group is optionally substituted by one or two groups, which may be the same or different C1-6 alkyl groups each optionally substituted by one to three groups, which may be the same or different, selected from substituent group $A^J$;
a C6-10 arylaminocarbonyl group wherein the arylaminocarbonyl group is optionally substituted by one or two groups, which may be the same or different, selected from substituent group $A^H$ and
a C1-6 halogenoalkyl group;
a 4- to 7-membered saturated heterocyclylcarbonyl group containing one or two heteroatoms, which may be the same or different, selected from nitrogen, oxygen, and sulfur wherein the heterocyclylcarbonyl group is optionally substituted by one to three groups, which may be the same or different, selected from substituent group $A^J$; or
a 3- to 10-membered heterocyclylaminocarbonyl group containing one to four heteroatoms, which may be the same or different, selected from nitrogen, oxygen, and sulfur wherein the heterocyclylaminocarbonyl group is optionally substituted by one or two groups, which may be the same or different, selected from substituent group $A^H$ and
a C1-6 halogenoalkyl group,
or
the C1-6 alkyl groups of $R^2$ and $R^3$ are optionally bonded to each other to form a 3- to 6-membered saturated carbocyclic ring or to form a 4- to 6-membered saturated heterocyclic ring via one nitrogen or oxygen atom wherein one nitrogen atom in the 4- to 6-membered saturated heterocyclic ring is optionally replaced with a hydrogen atom, a C1-6 alkyl group, a C1-6 alkylcarbonyl group, a C1-6 alkoxycarbonyl group, $R^4$ and $R^5$ are the same or different and each represent a hydrogen atom, a C1-6 alkyl group wherein the alkyl group is optionally substituted by one to three groups, which may be the same or different, selected from substituent group $A^C$, a C6-10 aryl group wherein the aryl group is optionally substituted by one or two groups, which may be the same or different, selected from substituent group $A^C$, or a 3- to 10-membered heterocyclyl group containing one to four heteroatoms, which may be the same or different, selected from nitrogen, oxygen, and sulfur wherein the heterocyclyl group is optionally substituted by one or two groups, which may be the same or different, selected from substituent group $A^C$, $R^6$ represents a hydrogen atom, a C1-6 alkyl group wherein $R^6$ is a carbon substituent of the pyridinyl ring, not a nitrogen substituent, or a hydroxy group, each substituent $R^{7a}$-$R^{7e}$ may be the same or different and each represents a hydrogen atom, a C1-6 alkyl group wherein the alkyl group is optionally substituted by one to three groups, which may be the same or different, selected from substituent group $A^B$, a C6-10 aryl group wherein the aryl group is optionally substituted by one or two groups, which may be the same or different, selected from substituent group $A^B$, a 3- to 10-membered heterocyclyl group containing one to four heteroatoms, which may be the same or different, selected from nitrogen, oxygen, and sulfur wherein the heterocyclyl group is optionally substituted by one or two groups, which may be the same or different, selected from substituent group $A^B$, or a hydroxy group, each substituent $R^{8f}$-$R^{8h}$ may be the same or different and each represents a hydrogen atom, a C1-6 alkyl group wherein the alkyl group is optionally substituted by one to three groups, which may be the same or different, selected from substituent group $A^B$, a C3-8 cycloalkyl group wherein the cycloalkyl group is optionally substituted by one group selected from substituent group $A^B$, a C6-10 aryl group wherein the aryl group is optionally substituted by one or two groups, which may be the same or different, selected from substituent group $A^K$, a 3- to 10-membered heterocyclyl group containing one to four heteroatoms, which may be the same or different, selected from nitrogen, oxygen, and sulfur wherein the heterocyclyl group is optionally substituted by one or two groups, which may be the same or different, selected from substituent group $A^K$, a hydroxy group, a C1-6 alkoxy group wherein the alkoxy group is optionally substituted by one group selected from substituent group $A^D$, a C3-8 cycloalkyloxy group wherein the cycloalkyloxy group is optionally substituted by one group selected from substituent group $A^D$, a C6-10 aryloxy group wherein the a C6-10 aryloxy group is optionally substituted by one or two groups selected from substituent group $A^D$, a carboxyl group, a C1-6 alkylcarbonyl group wherein the alkylcarbonyl group is optionally substituted by one or two groups selected from substituent group $A^B$, a C1-6 alkoxycarbonyl group wherein the alkoxycarbonyl group is optionally substituted by one or two groups selected from substituent group $A^D$, an aminocarbonyl group wherein the aminocarbonyl group is optionally substituted by one or two groups, which may be the same or different C1-6 alkyl groups, a 4- to 7-membered saturated heterocyclylcarbonyl group containing one or two heteroatoms, which may be the same or different, selected from nitrogen, oxygen, and sulfur, a C1-6 alkylcarbonyloxy group wherein the alkylcarbonyloxy group is optionally substituted by one to three halogeno groups, an aminocarbonyloxy group wherein the aminocarbonyloxy group is optionally substituted by one or two groups, which may be the same or different C1-6 alkyl groups, a 4- to 7-membered saturated heterocyclylcarbonyloxy group containing one or two heteroatoms, which may be the same or different, selected from nitrogen, oxygen, and sulfur, an amino group wherein the amino group is optionally substituted by one or two groups, which may be the same or different, selected from the following substituents:

a C1-6 alkyl group optionally substituted by one to three groups, which may be the same or different, selected from substituent group $A^C$, a C3-8 cycloalkyl group optionally substituted by one group selected from substituent group $A^C$, a C6-10 aryl group optionally substituted by one or two groups, which may be the same or different, selected from substituent group $A^K$, a 3- to 10-membered heterocyclyl group containing one to four heteroatoms, which may be the same or different, selected from nitrogen, oxygen, and sulfur optionally substituted by one or two groups, which may be the same or different, selected from substituent group $A^K$, a C1-6 alkoxycarbonyl group optionally substituted by one or two groups, selected from substituent group $A^D$, and an aminocarbonyl group optionally substituted by one or two groups, which may be the same or different C1-6 alkyl groups, a halogeno group, or a cyano group, n represents an integer selected from 1 to 4, and the substituent groups represent $A^B$: a hydroxy group, a C1-6 alkoxy group, a C3-8 cycloalkyl group, a C6-10 aryl group, a 3- to 10-membered heterocyclyl group containing one to four heteroatoms, which may be the same or different, selected from nitrogen, oxygen, and sulfur, a carboxyl group, a C1-6 alkoxycarbonyl group, an aminocarbonyl group wherein the aminocarbonyl group is optionally substituted by one or two groups, which may be the same or different C1-6 alkyl groups, an amino group wherein the amino group is optionally substituted by one or two groups, which may be the same or different C1-6 alkyl groups, a halogeno group, and
a cyano group;
A$^C$: a hydroxy group,
a C1-6 alkoxy group,
an amino group wherein the amino group is optionally substituted by one or two groups, which may be the same or different C1-6 alkyl groups,
a halogeno group, and
a cyano group;
A$^D$: a C1-6 alkyl group,
a C1-6 alkoxy group,
a carboxyl group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
a carboxyl group,
a C1-6 alkoxycarbonyl group,
an aminocarbonyl group wherein the aminocarbonyl group is optionally substituted by one or two groups, which may be the same or different C1-6 alkyl groups,
a halogeno group, and
a cyano group;
A$^E$: a C6-10 aryl group,
a 3- to 10-membered heterocyclyl group containing one to four heteroatoms, which may be the same or different, selected from nitrogen, oxygen, and sulfur, and
a halogeno group;
A$^F$: a hydroxy group,
a C1-6 alkyl group wherein the alkyl group is optionally substituted by one to three halogeno groups,
a C1-6 alkoxy group wherein the alkoxy group is optionally substituted by one to three halogeno groups,
a halogeno group,
an amino group, and
a cyano group;
A$^G$: a hydroxy group,
a C1-6 alkoxy group,
an amino group,
a halogeno group, and
a cyano group;
A$^H$: a hydroxy group,
a C1-6 alkoxy group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
an amino group wherein the amino group is optionally substituted by one or two groups, which may be the same or different C1-6 alkyl groups,
a halogeno group, and
a cyano group;
A$^J$: a C1-6 alkoxy group,
a C3-8 cycloalkyl group,
a C6-10 aryl group,
a 3- to 10-membered heterocyclyl group containing one to four heteroatoms, which may be the same or different, selected from nitrogen, oxygen, and sulfur,
a halogeno group, and
a cyano group,
A$^K$: a hydroxy group,
a C1-6 alkyl group wherein the alkyl group is optionally substituted by one to three halogeno groups,
a C1-6 alkoxy group wherein the alkoxy group is optionally substituted by one to three halogeno groups,
a carboxyl group,
a C1-6 alkoxycarbonyl group,
an aminocarbonyl group wherein the aminocarbonyl group is optionally substituted by one or two groups, which may be the same or different C1-6 alkyl groups,
an amino group wherein the amino group is optionally substituted by one or two groups, which may be the same or different C1-6 alkyl groups,
a halogeno group, and
a cyano group;
or a pharmacologically acceptable salt thereof.

2. A compound represented by formula (I):

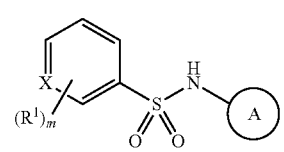

(I)

wherein

X represents —CH= or —N=, each substituent R$^1$ may be the same or different and each represents a C1-6 alkoxy group or a halogeno group, m represents an integer selected from 1 to 2, A represents one of formula (IIIa) to (IIId)

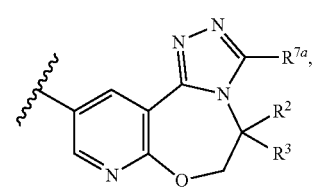

(IIIa)

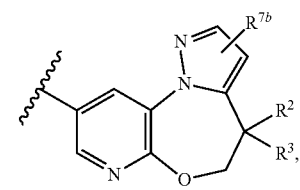

(IIIb)

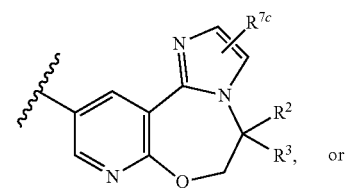

(IIIc)

or

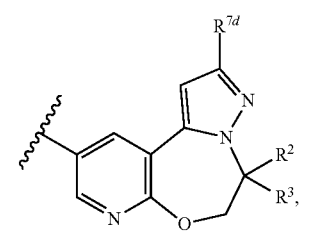

(IIId)

R$^2$ and R$^3$ are the same or different and each represents a hydrogen atom or a C1-6 alkyl group, each substituent $R^{7a}$-$R^{7d}$ may be the same or different and each represents a hydrogen atom or a C1-6 alkoxy group;

or a pharmacologically acceptable salt thereof.

3. The compound according to claim 2, wherein A is formula (IIId)

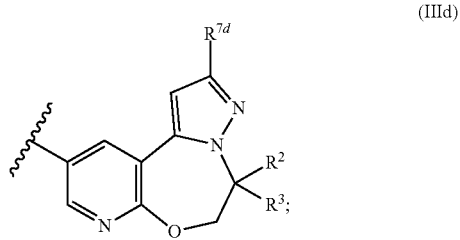

(IIId)

or a pharmacologically acceptable salt thereof.

4. The compound according to claim 2, wherein each substituent $R^1$ may be the same or different and represents an ethoxy group or a fluoro group;

or a pharmacologically acceptable salt thereof.

5. The compound according to claim 2, wherein $R^2$ and $R^3$ are the same or different and each represents a hydrogen atom or a methyl group;

or a pharmacologically acceptable salt thereof.

6. The compound according to claim 2, wherein $R^{7d}$ is a hydrogen atom;

or a pharmacologically acceptable salt thereof.

7. The compound according to claim 1, wherein the compound is 5-Chloro-N-(5,6-dihydropyrazolo[1,5-d]pyrido[3,2-f][1,4]oxazepin-10-yl)-2-methoxybenzenesulfonamide, 2-ethoxy-5-fluoro-N-[(5S)-5-methyl-5,6-dihydropyrazolo[1,5-d]pyrido[3,2-f][1,4]oxazepin-10-yl]benzenesulfonamide, 5-chloro-2-methoxy-N-[(5S)-5-methyl-5,6-dihydropyrazolo[1,5-d]pyrido[3,2-f][1,4]oxazepin-10-yl]pyridine-3-sulfonamide;

or a pharmacologically acceptable salt thereof.

8. The compound according to claim 1, wherein the compound is 5-Chloro-2-methoxy-N-(3-methyl-5,6-dihydropyrido[3,2-j][1,2,4]triazolo[4,3-d][1,4]oxazepin-10-yl)benzenesulfonamide, 5-chloro-N-(3-ethyl-5,6-dihydropyrido[3,2-f][1,2,4]triazolo[4,3-d][1,4]oxazepin-10-yl)-2-methoxybenzenesulfonamide;

or a pharmacologically acceptable salt thereof.

9. The compound according to claim 1, wherein the compound is N-(5,6-Dihydropyrazolo[1,5-d]pyrido[3,2-f][1,4]oxazepin-10-yl)-2-ethoxy-5-fluoropyridine-3-sulfonamide or a pharmacologically acceptable salt thereof.

10. The compound according to claim 1, wherein the compound is N-(5,6-Dihydropyrazolo[1,5-d]pyrido[3,2-f][1,4]oxazepin-10-yl)-2-ethoxy-5-fluorobenzenesulfonamide or a pharmacologically acceptable salt thereof.

11. The compound according to claim 1, wherein the compound is 2-Ethoxy-5-fluoro-N-[(5S)-5-methyl-5,6-dihydropyrazolo[1,5-d]pyrido[3,2-f][1,4]oxazepin-10-yl]pyridine-3-sulfonamide or a pharmacologically acceptable salt thereof.

12. The compound according to claim 1, wherein the compound is 5-Chloro-N-[(8S,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide or a pharmacologically acceptable salt thereof.

13. The compound according to claim 1, wherein the compound is 5-Chloro-N-[(8R,9aR)-8-hydroxy-5-oxo-8,9,9a,10-tetrahydro-5H,7H-pyrido[3,2-f]pyrrolo[2,1-c][1,4]oxazepin-3-yl]-2-(trifluoromethoxy)benzenesulfonamide or a pharmacologically acceptable salt thereof.

14. A compound according to claim 1, wherein the pharmacologically acceptable salt is sodium salt.

15. A compound according to claim 1, wherein the pharmacologically acceptable salt is potassium salt.

16. A pharmaceutical composition comprising a compound according to claim 1, or a pharmacologically acceptable salt thereof, as an active ingredient, and a pharmaceutically acceptable carrier.

17. A method for the treatment of a disease or condition selected from the group consisting of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis, comprising administering a therapeutically effective amount of a compound according to claim 1, or a pharmacologically acceptable salt thereof, to a subject in need thereof.

18. A method according to claim 17, wherein the disease or condition is pseudoxanthoma elasticum (PXE).

19. A method according to claim 17, wherein the subject is a human.

20. A compound according to claim 2, wherein the pharmacologically acceptable salt is sodium salt.

21. A compound according to claim 2, wherein the pharmacologically acceptable salt is potassium salt.

22. A pharmaceutical composition comprising a compound according to claim 2, or a pharmacologically acceptable salt thereof, as an active ingredient, and a pharmaceutically acceptable carrier.

23. A method for the treatment of a disease or condition selected from the group consisting of ectopic calcification, pseudoxanthoma elasticum (PXE), generalized arterial calcification of infancy (GACI), calcification of joints and arteries (CALJA), vascular calcification in CKD/ESRD, calciphylaxis, ossification of posterior longitudinal ligaments (OPLL), ossification of yellow ligaments (OYLL), and aortic stenosis, comprising administering a therapeutically effective amount of a compound according to claim 2, or a pharmacologically acceptable salt thereof, to a subject in need thereof.

24. A method according to claim 23, wherein the disease or condition is pseudoxanthoma elasticum (PXE).

25. A method according to claim 23, wherein the subject is a human.

* * * * *

UNITED STATES PATENT AND TRADEMARK OFFICE
CERTIFICATE OF CORRECTION

Page 1 of 1

PATENT NO. : 11,046,710 B2
APPLICATION NO. : 16/472109
DATED : June 29, 2021
INVENTOR(S) : S. Miyazaki et al.

It is certified that error appears in the above-identified patent and that said Letters Patent is hereby corrected as shown below:

In the Specification

| Column | Line | |
|---|---|---|
| 12 | 45 | Please change "alkoxy" to -- alkyl --. |

In the Claims

| Column | Line | |
|---|---|---|
| 129 | 2 | Please change "alkoxy" to -- alkyl --. |

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*